(12) United States Patent
Nakamura et al.

(10) Patent No.: US 9,062,100 B2
(45) Date of Patent: Jun. 23, 2015

(54) ANTI-HUMAN TROP-2 ANTIBODY HAVING ANTI-TUMOR ACTIVITY IN VIVO

(75) Inventors: Koji Nakamura, Tokyo (JP); Kentaro Okamura, Kanagawa (JP); Maki Tamura, Kanagawa (JP); Hiroyuki Yanai, Kanagawa (JP); Toru Kanke, Kanagawa (JP)

(73) Assignee: LIVTECH, INC., Kanagawa (JP)

( * ) Notice: Subject to any disclaimer, the term of this patent is extended or adjusted under 35 U.S.C. 154(b) by 0 days.

(21) Appl. No.: 13/698,201

(22) PCT Filed: May 17, 2011

(86) PCT No.: PCT/JP2011/061709
§ 371 (c)(1),
(2), (4) Date: Nov. 15, 2012

(87) PCT Pub. No.: WO2011/145744
PCT Pub. Date: Nov. 24, 2011

(65) Prior Publication Data
US 2013/0089872 A1    Apr. 11, 2013

(30) Foreign Application Priority Data
May 17, 2010  (JP) ................. 2010-113302

(51) Int. Cl.
| C07K 16/18 | (2006.01) |
| A61K 45/06 | (2006.01) |
| C07K 16/30 | (2006.01) |
| G01N 33/574 | (2006.01) |
| A61K 39/00 | (2006.01) |

(52) U.S. Cl.
CPC ............... *C07K 16/18* (2013.01); *A61K 45/06* (2013.01); *A61K 2039/505* (2013.01); *C07K 16/30* (2013.01); *C07K 2317/33* (2013.01); *C07K 2317/34* (2013.01); *C07K 2317/565* (2013.01); *C07K 2317/92* (2013.01); *G01N 33/57415* (2013.01); *G01N 33/57419* (2013.01); *G01N 33/57434* (2013.01); *G01N 33/57438* (2013.01)

(58) Field of Classification Search
None
See application file for complete search history.

(56) References Cited

U.S. PATENT DOCUMENTS

| 5,840,854 | A | 11/1998 | Hellstrom et al. |
| 6,653,104 | B2 | 11/2003 | Goldenberg |
| 7,420,040 | B2 | 9/2008 | Young et al. |
| 7,420,041 | B2 | 9/2008 | Young et al. |
| 2004/0001825 | A1 | 1/2004 | Govindan et al. |
| 2007/0202043 | A1* | 8/2007 | Young et al. ........... 424/1.49 |
| 2007/0202113 | A1 | 8/2007 | Young et al. |
| 2008/0131428 | A1 | 6/2008 | Young et al. |
| 2013/0089872 | A1 | 4/2013 | Nakamura et al. |

FOREIGN PATENT DOCUMENTS

| EP | 2573120 | A1 | 3/2013 |
| JP | 2001-501801 | A | 2/2001 |
| JP | 2006-502698 | A | 1/2006 |
| JP | 2009-527230 | A | 7/2009 |
| JP | 2009-528995 | A | 8/2009 |
| JP | 2010-528056 | A | 8/2010 |
| WO | 97/14796 | A1 | 4/1997 |
| WO | 03074566 | A2 | 9/2003 |
| WO | 2007095748 | A1 | 8/2007 |
| WO | 2007095749 | A1 | 8/2007 |
| WO | 2008144891 | A1 | 12/2008 |
| WO | 2010089782 | A1 | 8/2010 |
| WO | 2011145744 | A1 | 11/2011 |

OTHER PUBLICATIONS

Wang et al, Mole Cancer Therapeutics, 7:280-285, 2008.*
Cubas et al (BBA 1796:3009-314, 2009.*
Govindan et al (Cancer Research 70: (8 suppl), abstract 2438, Apr. 2010.*
An International Search Report, dated Mar. 12, 2013, which issued during the prosecution of International Application No. PCT/JP2012/080800, which is related to the present application.
An International Search Report, mailed Jun. 21, 2011, which issued during the prosecution of International Application No. PCT/JP2011/061709, which corresponds to the present application.
W. P. Faulk, et al., Antigens of human trophoblasts: A working hypothesis for their role in normal and abnormal pregnancies, Proc. Natl. Acad. Sci. USA, vol. 75, No. 4, pp. 1947-1951, Apr. 1978.
M. Lipinski, et al., Human trophoblast cell-surface antigens defined by monolonal antibodies, Proc. Natl. Acad. Sci. USA, vol. 78, No. 8, pp. 5147-5150, Aug. 1981.
A. J. Linnenbach, et al., Sequence investigation of the major gastrointestinal tumor-associated antigen gene family, GA733, Proc. Natl. Acad. Sci. USA, vol. 86, pp. 27-31, Jan. 1989.
A. Basu, et al., The epithelial/carcinoma antigen EGP-1, recognized by monoclonal antibody RS7-3G11, is phosphorylated on Serine 303, Int. J. Cancer: 62, pp. 472-479, 1995.
M. Fornaro, et al., Cloning of the gene encoding TROP-2, a cell-surface glycoprotein expressed by human carcinomas, Intl. J. Cancer: 62, pp. 610-618, 1995.
E. Ripani, et al., Human TROP-2 is a tumor-associated calcium signal transducer, Intl. J. Cancer: 76, pp. 671-676, 1998.
G. Calabrese, et al., Assignment of TACSTD1 (alias TROP1, M4S1) to human chromosome 2p21 and refinement of mapping of TACSTD2 (alias TROP2, M1S1) to human chromosome 1p32 by in situ hybridization, Cytogenet Cell Genet 92: pp. 164-165, 2001.

(Continued)

*Primary Examiner* — Lei Yao
(74) *Attorney, Agent, or Firm* — McDermott Will & Emery LLP

(57) ABSTRACT

The present invention provides: an antibody, which specifically reacts with hTROP-2 and has anti-tumor activity in vivo; a hybridoma, which produces the aforementioned antibody; a complex of the aforementioned antibody and a drug; a pharmaceutical composition for diagnosing or treating a tumor; a method for detecting a tumor; and a kit for detecting or diagnosing a tumor.

45 Claims, 40 Drawing Sheets

(56) References Cited

OTHER PUBLICATIONS

T. E. Sewedy, et al., Cloning of the murine TROP2 gene: conservation of a PIP2- binding sequence in the cytoplasmic domain of TROP-2, Intl. J. Cancer: 75, pp. 324-330, 1998.

R. Cubas, et al., Trop2: A possible therapeutic target for late stage epithelial carcinomas, Biochimica et Biophysica Acta, 1796, pp. 309-314, 2009.

T. Ohmachi, et al., Clinical Significance of TROP2 Expression in Colorectal Cancer, Clin. Cancer Res., 12, pp. 3057-3063, 2006.

Y. J. Fang, et al., Elevated expressions of MMP7, TROP2, and survivin are associated with survival, disease recurrence, and liver metastasis of colon cancer, Int. J. Colorectal Dis., 24, pp. 875-884, 2009.

D. Fong., et al., High expression of TROP2 correlates with poor prognosis in pancreatic cancer, British Journal of Cancer, 99, pp. 1290-1295, 2008.

D. Fong, et al., TROP2: a novel prognostic marker in squamous cell carcinoma of the oral cavity, Modern Pathology, 21, pp. 186-191, 2008.

A. D. Santin, et al., Gene expression profiles in primary ovarian serous papillary tumors and normal ovarian epithelium: identification of candidate molecular markers for ovarian cancer diagnosis and therapy, Intl. J. Cancer: 112, pp. 14-25, 2004.

J. Wang, et al., Identification of TROP-2 as an oncogene and an attractive therapeutic target in colon cancers, Mol. Cancer Ther., 7(2), pp. 280-285, Feb. 2008.

A Supplementary European Search Report, mailed Sep. 12, 2013, which issued during the prosecution of European Application No. 11 78 3675.9, which corresponds to the present application.

Truong et al., "520 Poster, A monoclonal antibody targeting Trop-2 exhibits anti-tumor efficacy in human cancer models as a monotherapy and demonstrates efficacy in combination therapy", European Journal of Cancer, Supplement, Pergamon, Oxford, GB, vol. 6, No. 12, Oct. 1, 2008, pp. 165, XP025534584.

Truong et al., "AR47A6.4.2, a naked monoclonal antibody targeting Trop-2, exhibits anti-tumor efficacy in multiple human cancer models as a monotherapeutic agent and demonstrates efficacy in combination therapy", American Association for Cancer Research, Proceedings of the Annual Meeting, vol. 49, Apr. 1, 2008, pp. 948, XP001539271.

Truong et al., "Functional antibodies targeting Trop-2 demonstrate in vivo efficacy in human pancreatic and other solid tumor xenograft models", Americal Association for Cancer Research, Proceedings of the Annual Meeting, vol. 48, Apr. 1, 2007, pp. 217, XP001539272.

Hahn et al., "Antibodies targeting the tumor-associated antigen TROP-2 demonstrate anti-tumor effects in human pancreatic cancer models", Proceedings of the American Association for Cancer Research Annual Meeting & 97th Annual Meeting of the American-Association-for-Cancer-Research (AACR), vol. 47, Apr. 1, 2006, pp. 877, XP001525503.

Communication pursuant to Article 94(3) EPC, mailed Jun. 25, 2014, which issued during the prosecution of European Patent Application No. 11 783 675.9, which corresponds to the present application.

Holt et al., "Domain antibodies: proteins for therapy," Trends in Biotechnology vol. 21, No. 11, Nov. 2003, pp. 484-490.

Office Action, mailed May 12, 2014, which issued during the prosecution of U.S. Appl. No. 13/682,319, which is related to the present application.

W. E. Paul, Fundamental Immunology 3rd Edition, 1993. pp. 292-295.

M. M. Bendig, Humanization of Rodent Monoclonal Antibodies by CDR Grafting, Methods: A Companion to Methods in Enzymology 8, pp. 83-93 (1995).

Office Action, mailed Feb. 12, 2015, which issued during the prosecution of U.S. Appl. No. 13/682,319, which is related to the present application.

* cited by examiner

Affinity

BxPC-3

Other cancer cell lines

Fig.6 Other cancer cell lines

Reactivity with mouse TROP-2

Fig. 10
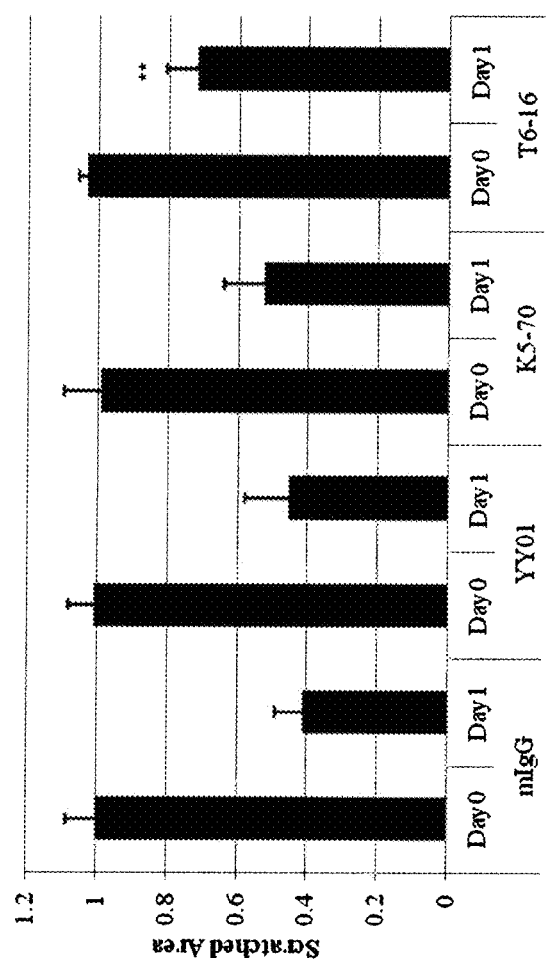
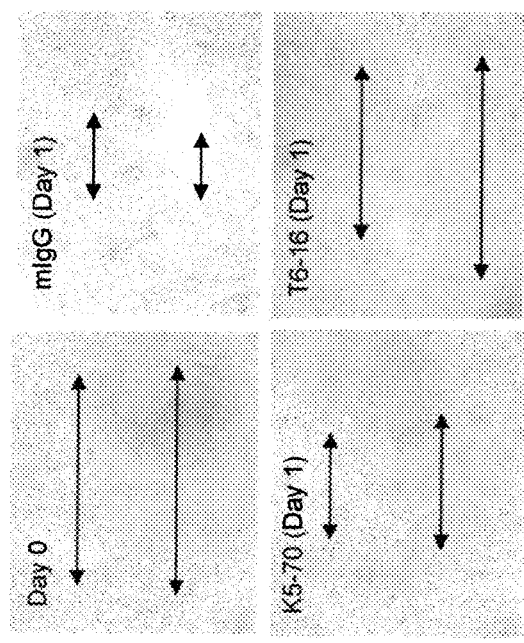

Fig.12 K5-70 / Treatment

Fig.14
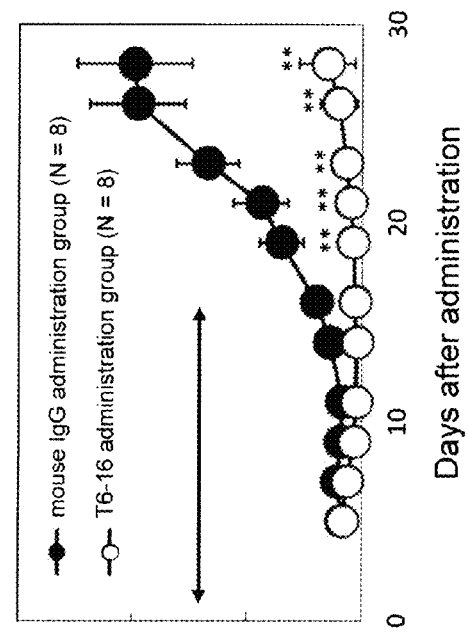
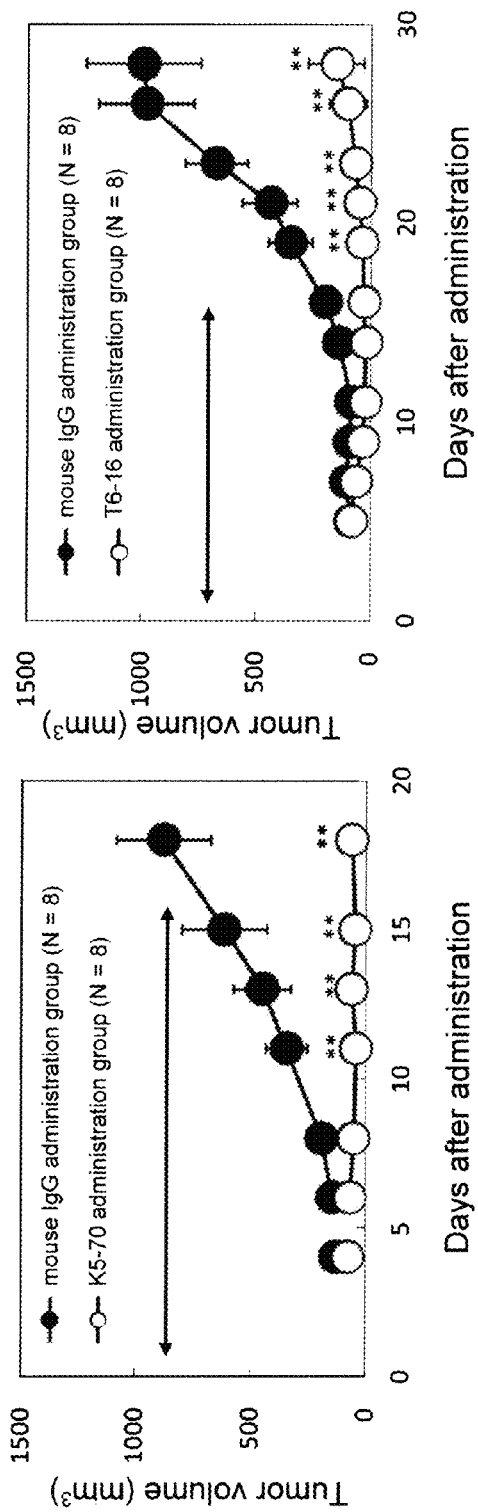
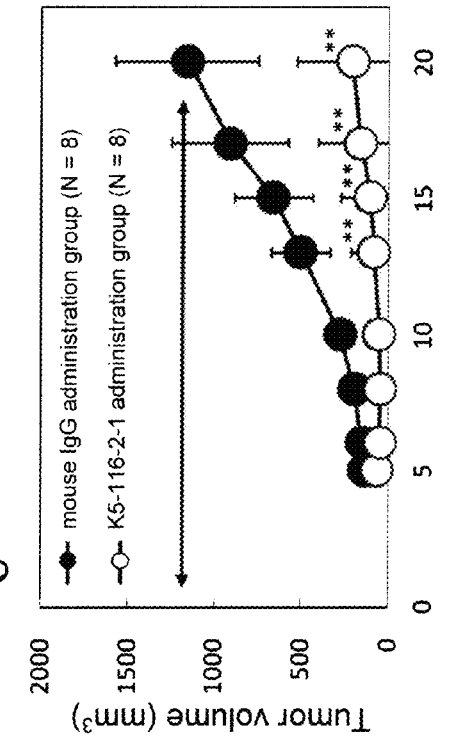

Fig.16 K5-70/dose-dependent prevention

Fig. 28
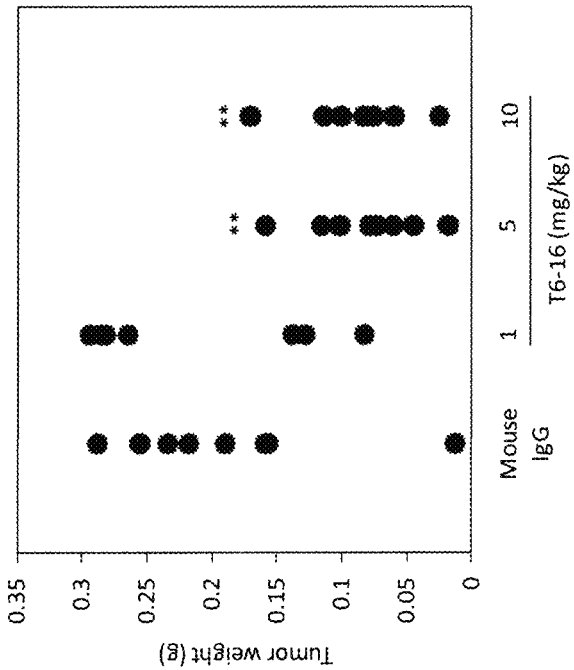
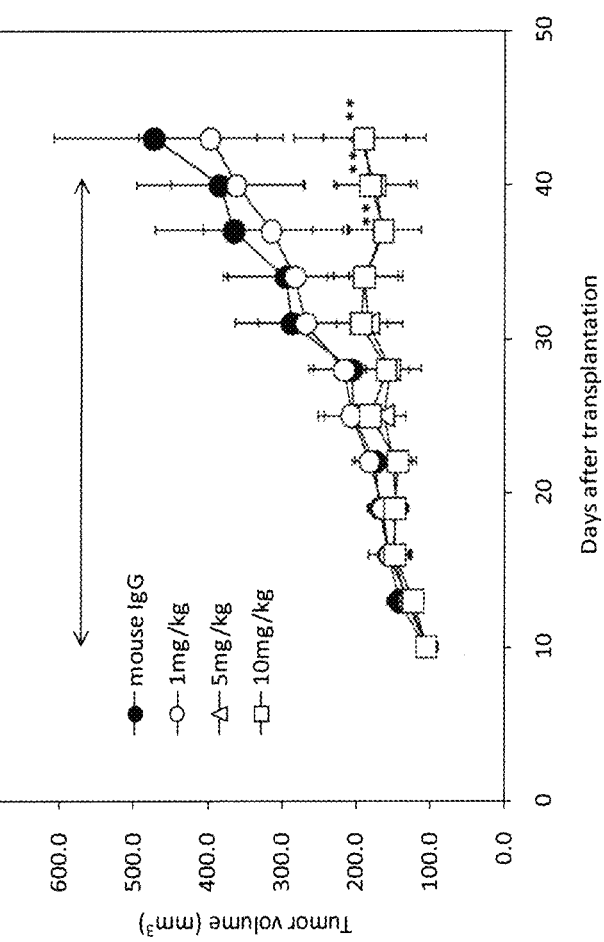

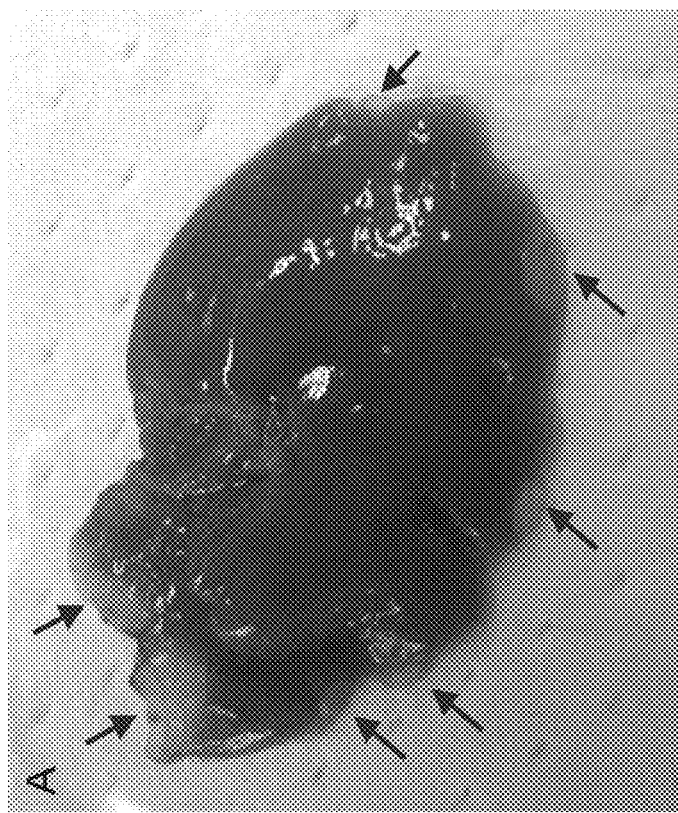
Fig.31

ATGGGATGGAGCTGTATCATCCTCTTCTTGGTAGCAACAGGTGTCCACTCCCAG
 M  G  W  S  C  I  I  L  F  L  V  A  T  *A  T  G  V  H  S  Q*
GTCCAACTGCAGCAGCCTGGGGCTGAGCTGGTGAGGCCTGGGGCTTCAGTGAAGCTGTCC
 V  Q  L  Q  Q  P  G  A  E  L  V  R  P  G  A  S  V  K  L  S
TGCAAGGCTTCTGGCTACACCTTCACCATCTACTGGATAAACTGGGTGAAACAGAGGCCT
 C  K  A  S  G  Y  T  F  T  I  *Y  W  I  N*  W  V  K  Q  R  P
GGACAAGGCCTTGAGTGGATTGGAAATATTTATCCTTCTGATAGTTATACTAACTACAAT
 G  Q  G  L  E  W  I  G  *N  I  Y  P  S  D  S  Y  T  N  Y  N*
CAAAAGTTCAAGGACAAGGCCACATTGACTGTAGACAAATCCTCCAGCACAGCCTACATG
 *Q  K  F  K  D*  K  A  T  L  T  V  D  K  S  S  S  T  A  Y  M
CAGCTCAGCAGCCCGACATCTGAGGACTCTGCGGTCTATTACTGTACAAGAACGTCTATG
 Q  L  S  S  P  T  S  E  D  S  A  V  Y  Y  C  T  R  *T  S  M*
GCGGACTACTGGGGCCAAGGCACCACTCTCACAGTCTCCTCA
 *A  D  Y*  W  G  Q  G  T  T  L  T  V  S  S

Fig.34
K5-70
VL

ATGGTATCCACACCTCAGTTCCTTGTATTTTTGCTTTTCTGGATTCCAGCCTTCCAGAGGT
 M  V  S  T  P  Q  F  L  V  F  L  L  F  W  I  P  A  S  R  G
GACATCTTGCTGACTCAGTCTCCAGCCATCCTGTCTGTGAGTCCAGGAGAAAGAGTCAGT
 D  I  L  L  T  Q  S  P  A  I  L  S  V  S  P  G  E  R  V  S
 =
TTCTCCTGCAGGGCCAGTCAGAGCATTGGCACAAGCATACACTGGTATCAGCAAAGAACA
 F  S  C  R  A  S  Q  S  I  G  T  S  I  H  W  Y  Q  Q  R  T
AATGGGTTCTCCAAGGCTTCTCATAAAGTATGCTTCTGAGTCTATCTCTGGGATCCCTTCC
 N  G  S  P  R  L  L  I  K  Y  A  S  E  S  I  S  G  I  P  S
AGGTTTAGTGGCAGTGGATCAGGGACAGATTTTACTCTTAGCATCAACAGTGTGGAGTCT
 R  F  S  G  S  G  S  G  T  D  F  T  L  S  I  N  S  V  E  S
GAAGATATTGCAGATTATTACTGTCAACAAAGTAATAGCTGGCCATTCACGTTCGGCTCG
 E  D  I  A  D  Y  Y  C  Q  Q  S  N  S  W  P  F  T  F  G  S
GGGACAAAGTTGGAAATAAAA
 G  T  K  L  E  I  K

Fig.35
K5-107
VH

```
ATGGGATGGAGCTGTATCATCCTCTTCTTGGTAGCAACAGTATACAGGTGTCCACTCCCAG
 M  G  W  S  C  I  I  L  F  L  V  A  T  A  T  G  V  H  S  Q
GTCCAACTGCAGCAACCTGGGTCTGAGCTGGTGAGGCCTGGAGCTTCAGTGAAGCTGTCC
 V  Q  L  Q  Q  P  G  S  E  L  V  R  P  G  A  S  V  K  L  S
TGCAAGGCTTCTGGCTACACATTCACCAGCTACTGGATGCACTGGGTGAAGCAGAGGCAT
 C  K  A  S  G  Y  T  F  T  S  Y  W  M  H  W  V  K  Q  R  H
GGACAAGGCCTTGAGTGGATTGGAAATATTTATCCTGGTGGTTATACTAACTACGAT
 G  Q  G  L  E  W  I  G  N  I  Y  P  G  G  Y  T  N  Y  D
GAGAAGTTCAAGAGCAAGGCCACATCTGAGGACTCTGCGGTCTATTACTGTACAAGATCATCCGTT
 E  K  F  K  S  K  G  T  L  T  V  D  T  S  S  S  T  A  Y  M
CACCTCAGCAGCCTGACATCTGAGGACTCTGCGGTCTATTACTGTACAAGATCATCCGTT
 H  L  S  S  L  T  S  E  D  S  A  V  Y  Y  C  T  R  S  S  V
TTTGACTACTGGGGCCAAGGCACCACTCTCACAGTCTCCTCA
 F  D  Y  W  G  Q  G  T  T  L  T  V  S  S
```

Fig.36
K5-107
VL

ATGGTATCCACACCTCAGTTCCTTGTATTTTGCTTTTCTGGATTCCAGCCTCCAGAGT
M  V  S  T  P  Q  F  L  V  F  L  L  F  W  I  P  A  S  R  G
GACATCTTGCTGACTCAGTCCTCCAGCCATCCTGTCTGTGAGTCCAGGAGAAAGAGTCAGT
D  I  L  L  T  Q  S  P  A  I  L  S  V  S  P  G  E  R  V  S
TTCTCCTGCAGGGCCAGTCAGAACATTGGCACAAGCATACACTGGTTTCAGCAAAGAACA
F  S  C  R  A  S  Q  N  I  G  T  S  I  H  W  F  Q  Q  R  T
AATGGTTCTCCAAGGCTTCTCATAAAGTATGCTTCTGAGTCTATCTCTGGGATCCCCTTCC
N  G  S  P  R  L  L  I  K  Y  A  S  E  S  I  S  G  I  P  S
AGGTTTAGTGGCAGTGGATCAGGGACAGATTTTACTCTCTTAGCATCAACAGTGTGGAGTCT
R  F  S  G  S  G  S  G  T  D  F  T  L  S  I  N  S  V  E  S
GAAGATATTGCAGATTATTACTGTCAACAAAGTAATAGCTGGCCATTCACGTTCGGCTCG
E  D  I  A  D  Y  Y  C  Q  Q  S  N  S  W  P  F  T  F  G  S
GGGACAAAGTTGGAAATAAAA
G  T  K  L  E  I  K

```
ATGGGGATGGAGCTGTATCATCCTCTTCTTGGTAGCAACAGCTACAGGTGTCCACTCCCAG
 M  G  W  S  C  I  I  L  F  L  V  A  T  A  T  G  V  H  S  Q
GTCCAACTGCAGCAGCCTGGGGCTGAGCTGGTGAGGCCTGGGGCTTCAGTGAAGCTGTCC
 V  Q  L  Q  Q  P  G  A  E  L  V  R  P  G  A  S  V  K  L  S
TGCAAGGCTTCTGGCTACACCTTCACCAGCTACTGGATAACCTGGGTGAAGCAGAGGCCT
 C  K  A  S  G  Y  T  F  T  S  Y  W  I  T  W  V  K  Q  R  P
GGACAAGGCCTTGAGTGGATCGGAAATATTTATCCTTCTGATAGTTATACTAACTACAAT
 G  Q  G  L  E  W  I  G  N  I  Y  P  S  D  S  Y  T  N  Y  N
CAAAAGTTCAGGGACAAGGCCACACTGACTGTAGACAAATCCTCCAGTACAGCCTACATG
 Q  K  F  R  D  K  A  T  L  T  V  D  K  S  S  S  T  A  Y  M
CAGCTCAGCAGCCCGACATCTGAGGACTCTGCGGTCTATTACTGTTCAGCCCTCTTTGAC
 Q  L  S  S  P  T  S  E  D  S  A  V  Y  Y  C  S  A  L  F  D
TACTGGGGCCAAGGCACCACTCTCACAGTCTCCTCA
 Y  W  G  Q  G  T  T  L  T  V  S  S
```

```
ATGGTATCCACACCTCAGTTCCTTGTATTTTTGCTTTTCTGGATTCCAGCCTCCAGAGGT
 M  V  S  T  P  Q  F  L  V  F  L  L  F  W  I  P  A  S  R  G
GACATCTTGCTGACTCAGTCTCCAGCCATCCTGTCTGTGAGTCCAGGAGAAAGAGTCAGT
 D  I  L  L  T  Q  S  P  A  I  L  S  V  S  P  G  E  R  V  S
TTCTCCTGCAGGGCCAGTCAGAGCATTGGCACAAGCATACACTGGTATCAGCAGAAACA
 F  S  C  R  A  S  Q  S  I  G  T  S  I  H  W  Y  Q  Q  R  T
AATGGTTCTCCAAGGCTTCTCATAAAGTATGCTTCTGAGTCTATCTCTGGGATCCCTTCC
 N  G  S  P  R  L  L  I  K  Y  A  S  E  S  I  S  G  I  P  S
AGGTTTAGTGGCAGTGGATCAGGGACAGATTTTATTCTTAGCATCAACAGTGTGGAGTCT
 R  F  S  G  S  G  S  G  T  D  F  I  L  S  I  N  S  V  E  S
GAAGATATTGCAGATTATTACTGTCAACAAAGTAATAGCTGGCCATTCACGTTCGGCTCG
 E  D  I  A  D  Y  Y  C  Q  Q  S  N  S  W  P  F  T  F  G  S
GGGACAAAGTTGGAAATAAAA
 G  T  K  L  E  I  K
```

ATGGGATGGAGCTGGATCTTTCTCTTCCTCCTGTCAGGAACTGCAGGCGTCCACTCTGAG
 M  G  W  S  W  I  F  L  F  L  L  S  G  T  A  G  V  H  S  E
GTCCAGCTTCAGCAGTCAGGACCTGAGCTGGTGAAACCTGGGGCCTCAGTGAAGATTTCC
 V  Q  L  Q  Q  S  G  P  E  L  V  K  P  G  A  S  V  K  I  S
TGCAAGGCTTCTGGATACACATTCACTGACTACAATATGCACTGGGTGAAGCAGAGCCAT
 C  K  A  S  G  Y  T  F  T  D  Y  N  M  H  W  V  K  Q  S  H
GGAAAGAACCTTGAATGGATTGGATATATTTATCCTTACAATGGTGGTACTGGCTACAAC
 G  K  N  L  E  W  I  G  Y  I  Y  P  Y  N  G  G  T  G  Y  N
CAGAGGTTCAAGAGCAGGGCCACAATGACTGTAGACAAATCCTCCAGCACAGCCTACATG
 Q  R  F  K  S  R  A  T  M  T  V  D  K  S  S  S  T  A  Y  M
GAGCTCCGCAGCCTGACATCTGATGACTCTGCAGTCTATTACTGTGCAAGAGAAGACTAC
 E  L  R  S  L  T  S  D  D  S  A  V  Y  Y  C  A  R  E  D  Y
GGTAGTAGCCCCTCTTATGCTATGGACTATTGGGGTCAAGGAACCTCAGTCATCGTCTCC
 G  S  S  P  S  Y  A  M  D  Y  W  G  Q  G  T  S  V  I  V  S
TCA
 S

Fig.40
T6-16
VL

```
ATGAAGTTGCCTGTTGTTAGGCTGTGTTGGTGCTGATGTTTCTGGATTCCTGCTTCCAGCAGTGAT
 M   K   L   P   V   R   L   L   V   L   M   F   W   I   P   A   S   S   S   D
GTTGTGATGACCCAAACTCCACTCTCCCTGCCTGTCACTCAGGTCTTGGAGAGATCAGGCCTCCATC
 V   V   M   T   Q   T   P   L   S   L   P   V   T   Q   V   L   E   R   S   I
TCTTGCAGATCTAGTCAGAGCCTTGTACACGGTAATGGAAACACCTATTTACATTGGTAC
 S   C   R   S   S   Q   S   L   V   H   G   N   G   N   T   Y   L   H   W   Y
CTGCAGAAGCCAGGCCAGTCTCCAAAGCTCCTGATCTACAAAGTTTCCAACCGATTTTCT
 L   Q   K   P   G   Q   S   P   K   L   L   I   Y   K   V   S   N   R   F   S
GGGGTCCCAGACAGGTTCAGTGGCAGTGGATCAGGGACGGATTTCACACTCAAGATCAGC
 G   V   P   D   R   F   S   G   S   G   S   G   T   D   F   T   L   K   I   S
AGAGTGGAGGCTGAGGATCTGGGAGTTTATTTCTGCTCTCAAACTACACATGTTCCACG
 R   V   E   A   E   D   L   G   V   Y   F   C   S   Q   T   T   H   V   P   T
TTCGGCTCGGGGACAAAGTTGGAAATAAAA
 F   G   S   G   T   K   L   E   I   K
```

ANTI-HUMAN TROP-2 ANTIBODY HAVING ANTI-TUMOR ACTIVITY IN VIVO

CROSS REFERENCE TO PRIOR APPLICATIONS

This application is a U.S. National Phase application under 35 U.S.C. §371 of International Application No. PCT/JP2011/061709, filed on May 17, 2011 and claims benefit of priority to Japanese Patent Application No. 2010-113302, filed on May 17, 2010. The International Application was published in Japanese on Nov. 24, 2011 as WO 2011/145744 A1 under PCT Article 21(2). All of these applications are herein incorporated by reference.

SEQUENCE LISTING

The instant application contains a Sequence Listing which has been submitted electronically in ASCII format and is hereby incorporated by reference in its entirety. Said ASCII copy, created on Jan. 22, 2015, is named 086268-0139_SL.txt and is 90,204 bytes in size.

TECHNICAL FIELD

The present invention relates to an anti-human TROP-2 antibody having anti-tumor activity, and particularly, to an anti-human TROP-2 antibody having anti-tumor activity in vivo. In addition, the present invention relates to a hybridoma, which produces the aforementioned antibody, and a use of the aforementioned antibody.

BACKGROUND ART

Human TROP-2 (Tacstd2, GA733-1 and EGP-1) (hereinafter also referred to as "hTROP-2") is a single transmembrane, type 1 cell membrane protein consisting of 323 amino acid residues (see SEQ ID NO: 2), and this protein has been known to be overexpressed in various types of epidermal cell carcinomas. The presence of a cell membrane protein associated with immunological resistance, which is commonly expressed in both human trophoblasts and cancer cells, had been long suggested (Non-Patent Document 1). An antigen molecule recognized by mouse monoclonal antibodies (162-25.3, 162-46.2) reacting with the cell membrane protein of a human choriocarcinoma cell line BeWo was identified. This antigen molecule was considered as one of the molecules expressed in human trophoblasts, and was named as Trop-2 (Non-Patent Document 2). Thereafter, the same molecule was discovered by other researchers. That is to say, a tumor antigen recognized by a mouse monoclonal antibody GA733 which is obtained by immunization with stomach cancer cells SW948 was named as GA733-1 (Non-Patent Document 3), and an epithelial glycoprotein recognized by a mouse monoclonal antibody RS7-3G11 which is obtained by immunization with non-small cell lung cancer cells was named as an epithelial/carcinoma antigen, EGP-1 (Non-Patent Document 4). In 1995, the Trop-2 gene was cloned, and as a result, it was confirmed that these are the same molecules (Non-Patent Document 5). Moreover, it was clarified that the molecule has a function to amplify intracellular calcium signals in cancer cells (Non-Patent Document 6), and therefore, it is also referred to as a tumor-associated calcium signal transducer 2 (TACSTD2).

The hTROP-2 gene is mapped on chromosome 1p32, and it constitutes a TACSTD gene family together with GA733-2 having a homology of approximately 50% therewith (which has been known as "TACSTD1," "epithelial glycoprotein EGP-2," "EpCAM" or "Trop-1") (Non-Patent Document 7). The hTROP-2 protein (323 amino acid residues; SEQ ID NO: 2) has a molecular weight of approximately 36K Dalton, and this protein consists of a hydrophilic signal peptide ($1^{st}$ to $26^{th}$ amino acids), an extracellular domain ($27^{th}$ to $274^{th}$ amino acids), a transmembrane domain ($275^{th}$ to $297^{th}$ amino acids) and an intracellular domain ($298^{th}$ to $323^{rd}$ amino acids). The extracellular domain has four heterogeneous N-linked glycosylation sites, and its apparent molecular weight is increased by 11 to 13K Dalton due to addition of sugar chains (Non-Patent Document 5). It is considered that TACSTD gene family has a characteristic thyroglobulin (TY) repeat sequence in the extracellular domain and is associated with the proliferation, invasion and metastasis of cancer cells.

To date, a physiological ligand of hTROP-2 has not been identified, and the molecular function thereof has not been clarified. However, it has been described that hTROP-2 transmits a calcium signal in tumor cells (Non-Patent Document 6). In addition, from the facts that intracellular serine 303 is phosphorylated by $Ca^{2+}$-dependent protein kinase C (Non-Patent Document 4) and that hTROP-2 has a PIP2-binding sequence in its intracellular domain, it has been suggested that hTROP-2 has a signaling function in tumor cells (Non-Patent Document 8).

As a result of in vitro diagnostic studies such as immunohistochemistry (IHC) and flow cytometry analysis, overexpression of hTROP-2 in many types of epithelium-derived carcinomas such as stomach cancer, lung cancer, colon cancer, ovary cancer, breast cancer, prostate cancer, pancreatic cancer, liver cancer and esophagus cancer has been reported. In contrast, the expression of hTROP-2 in normal tissues is limited to cells in the epithelial region, and the expression level of hTROP-2 in normal cells is lower than that in cancer cells. Thus, the association of TROP-2 with tumor formation is suggested (Patent Documents 1-3 and 9).

Moreover, in the analysis of an hTROP-2 expression level used as a biomarker in clinical samples, it has been demonstrated that, when hTROP-2 is highly expressed, correlating with the malignancy of colon cancer (Non-Patent Documents 10 and 11), pancreatic cancer (Non-Patent Document 12) or oral cancer (Non-Patent Document 13), the possibility of metastasis or recurrence of such cancer is significantly high. Furthermore, in a large-scale gene expression analysis using a cDNA microarray technique, hTROP-2 has been identified as a gene cluster, which is overexpressed at the highest level in severe papillary carcinoma of the ovary, in comparison with in normal ovary epithelium (Non-Patent Document 14).

Still further, in recent years, an important role of hTROP-2 in tumor formation has been demonstrated in the models by using colon cancer cells (Non-Patent Document 15). Since the expression of hTROP-2 promotes the anchorage-independent cell proliferation of tumor cells and is required for the tumor formation and proliferation of cancer cells subcutaneously transplanted in immunodeficient mice, it raised the possibility that hTROP-2 would act as a functional tumor antigen and would be used as a new therapeutic target.

To date, studies regarding the anti-tumor effects of several anti-hTROP-2 antibodies have been reported. An RS7 antibody (Patent Document 1) has been examined by employing in vivo models, in which radiolabeled antibodies were used, and anti-tumor activity was demonstrated in nude mouse xenograft models. However, the anti-tumor effects by antibody alone (a naked antibody) have not been reported.

In addition, the cytotoxicity of a cytotoxin-attached anti-hTROP-2 monoclonal antibody BR110 (Patent Document 2) on human cancer cell lines H3619, H2987, MCF-7, H3396 and H2981 in in vitro experiments has been reported. However, the cytotoxicity of a naked antibody or an immune conjugate of BR110 in vivo has not been disclosed.

In recent years, it has been reported that an isolated monoclonal antibody, which was produced from a hybridoma cell line AR47A6.4.2 or AR52A301.5 obtained by immunizing mice with human ovary cancer tissues, bound to hTROP-2, and that, for the first time, it exhibited, as a naked antibody, anti-tumor activity on nude mouse xenograft models, as well as cytotoxicity in vitro (Patent Documents 3 and 4). In these patent documents, the aforementioned antibody exhibited anti-tumor effects by treatment with antibody alone in mouse xenograft models, into which pancreatic cancer cell lines BxPC-3 and PL45, a prostate cancer cell line PC-3, a breast cancer cell line MCF-7 and a colon cancer cell line Colo205 had been transplanted. The therapeutic effects of the antibody have appeared in the models, into which BxPC-3 cells had been transplanted. Other than this, tumor formation and proliferation were only partially (approximately 40% to 60%) suppressed by the preventive administration of the antibody, and an extremely large amount (approximately 20 mg/kg) of the antibody was necessary for such suppression of tumor formation and proliferation.

Based on the above-mentioned previous findings, the potential use of the anti-hTROP-2 antibody as an anti-tumor antibody has been suggested. However, not all of the anti-hTROP-2 antibodies exhibit anti-tumor effects by treatment with antibody alone as naked antibodies in vivo. The antibodies exhibit different functions to hTROP-2, depending on a binding site, affinity and the profile of a monoclonal antibody.

Patent Document 1: U.S. Pat. No. 6,653,104
Patent Document 2: U.S. Pat. No. 5,840,854
Patent Document 3: U.S. Pat. No. 7,420,040
Patent Document 4: U.S. Pat. No. 7,420,041
Non-Patent Document 1: Faulk W P, et al., Proc. Natl. Acad. Sci. U.S.A., 75(4), pp. 1947-1951 (1978)
Non-Patent Document 2: Lipinski M, et al., Proc. Natl. Acad. Sci. U.S.A., 78(8), pp. 5147-5150 (1981)
Non-Patent Document 3: Linnenbach A J, et al., Proc. Natl. Acad. Sci. U.S.A., 86(1), pp. 27-31 (1989)
Non-Patent Document 4: Basu A, et al., Int. J. Cancer, 62(4), pp. 472-479 (1995)
Non-Patent Document 5: Fornaro M, et al., Int. J. Cancer, 62(5), pp. 610-618 (1995)
Non-Patent Document 6: Ripani E, et al., Int. J. Cancer, 76(5), pp. 671-676 (1998)
Non-Patent Document 7: Calabrese G, et al., Cell Genet., 92(1-2), pp. 164-165 (2001)
Non-Patent Document 8: El Sewedy T et al., Int. J. Cancer, 75(2), pp. 324-330 (1998)
Non-Patent Document 9: Cubas R, et al., Biochim. Biophys. Acta., 1796(2), pp. 309-314 (2009)
Non-Patent Document 10: Ohmachi T et al., Clin. Cancer Res., 12(10), pp. 3057-3063 (2006)
Non-Patent Document 11: Fang Y J, et al., Int. J. Colorectal Dis., 24(8), pp. 875-884 (2009)
Non-Patent Document 12: Fong D, et al., Br. J. Cancer, 99(8), pp. 1290-1295 (2008)
Non-Patent Document 13: Fong D, et al., Mod. Pathol., 21(2), pp. 186-191 (2008)
Non-Patent Document 14: Santin A D, et al., Int. J. Cancer, 112(1), pp. 14-25 (2004)
Non-Patent Document 15: Wang J, et al., Mol. Cancer Ther., 7(2), pp. 280-285 (2008)

SUMMARY OF THE INVENTION

Under the aforementioned circumstances, it has been desired to develop an anti-hTROP-2 antibody (an anti-hTROP-2 monoclonal antibody) having high anti-tumor activity in vivo, and particularly, an anti-hTROP-2 antibody or the like, which has an anti-tumor effect as a naked antibody alone in vivo and further, which has the anti-tumor effect at a low dose.

The present invention has been completed, while taking into consideration the aforementioned circumstances. The present invention provides an anti-hTROP-2 antibody (an anti-hTROP-2 monoclonal antibody), a hybridoma, which produces the antibody, a fragment of the antibody, a complex (an immunoconjugate) of the antibody or the like and a drug, a pharmaceutical composition for diagnosing or treating a tumor, a method for detecting a tumor, a kit for detecting or diagnosing a tumor, and the like, which will be described below.

(1) An antibody against human TROP-2, which has anti-tumor activity in vivo.

Examples of the antibody according to (1) above include: an antibody exhibiting tumor growth inhibitory activity of 50% or more at a dosage of 5 to 20 mg/kg body weight; an antibody whose frequency of administration for exhibiting the tumor growth inhibitory activity is at most once a week; an antibody exhibiting tumor growth inhibitory activity of 50% or more by a single administration of 10 mg/kg body weight; an antibody having anti-tumor activity on two or more types of human tumor cell lines; and an antibody having a dissociation constant (Kd value) of $1.0 \times 10^{-10}$ M or less. Herein, the tumor is, for example, at least one type selected from the group consisting of human pancreatic cancer, human prostate cancer, human colon cancer and human breast cancer, and particularly, human pancreatic cancer. In addition, the tumor also includes a recurrent cancer and a metastatic cancer. Moreover, the tumor cell line is, for example, at least two types selected from the group consisting of a human pancreatic cancer cell line PK-59, a human pancreatic cancer cell line BxPC-3, a human pancreatic cancer cell line KP-3L, a human pancreatic cancer cell line KP-2, a human pancreatic cancer cell line PK-1, a human pancreatic cancer cell line PK-45H, a human pancreatic cancer cell line PK-45P, a human pancreatic cancer cell line TCC-PAN2, a human pancreatic cancer cell line SUIT-2, a human colon cancer cell line CACO-2, a human colon cancer cell line SW480, a human colon cancer cell line DLD-1, a human colon cancer cell line HCT 116, a human breast cancer cell line JIMT-1, a human breast cancer cell line HCC1143, a human breast cancer cell line MCF-7, a human prostate cancer cell line DU145 and a human prostate cancer cell line PC-3; and particularly, a human pancreatic cancer cell line PK-59 and a human pancreatic cancer cell line BxPC-3.

Examples of the antibody according to (1) above include:
an antibody in which the amino acid sequences of CDR 1 to 3 of the H chain V region of the antibody are shown in SEQ ID NOS: 36 to 38, respectively, and/or the amino acid sequences of CDR 1 to 3 of the L chain V region of the antibody are shown in SEQ ID NOS: 41 to 43, respectively;
an antibody in which the amino acid sequences of CDR 1 to 3 of the H chain V region of the antibody are shown in SEQ ID NOS: 46 to 48, respectively, and/or the amino acid sequences of CDR 1 to 3 of the L chain V region of the antibody are shown in SEQ ID NOS: 51 to 53, respectively;
an antibody in which the amino acid sequences of CDR 1 to 3 of the H chain V region of the antibody are shown in SEQ ID NOS: 56 to 58, respectively, and/or the amino acid sequences of CDR 1 to 3 of the L chain V region of the antibody are shown in SEQ ID NOS: 61 to 63, respectively; and an antibody in which the amino acid sequences of CDR 1 to 3 of the H chain V region of the antibody are shown in SEQ ID NOS: 66 to 68, respectively, and/or the amino acid sequences of CDR 1 to 3 of the L chain V region of the antibody are shown in SEQ ID NOS: 71 to 73, respectively.

An example of the antibody according to (1) above is a monoclonal antibody.

An example of the antibody according to (1) above is a genetically recombinant antibody, and more specific examples include a chimeric antibody, a humanized antibody and a human antibody.

Herein, examples of the above-described chimeric antibody include:

an antibody in which the H chain V region of the chimeric antibody consists of the amino acid sequence shown in SEQ ID NO: 35, and/or the L chain V region thereof consists of the amino acid sequence shown in SEQ ID NO: 40;

an antibody in which the H chain V region of the chimeric antibody consists of the amino acid sequence shown in SEQ ID NO: 45, and/or the L chain V region thereof consists of the amino acid sequence shown in SEQ ID NO: 50;

an antibody in which the H chain V region of the chimeric antibody consists of the amino acid sequence shown in SEQ ID NO: 55, and/or the L chain V region thereof consists of the amino acid sequence shown in SEQ ID NO: 60; and an antibody in which the H chain V region of the chimeric antibody consists of the amino acid sequence shown in SEQ ID NO: 65, and/or the L chain V region thereof consists of the amino acid sequence shown in SEQ ID NO: 70.

(2) A monoclonal antibody against human TROP-2, which is produced by a hybridoma having accession No. FERM BP-11251, FERM BP-11252, FERM BP-11253, FERM BP-11346 or FERM BP-11254.

Examples of the antibody according to (1) and (2) above include: an antibody, which binds to a site, to which a monoclonal antibody produced by a hybridoma having accession No. FERM BP-11251, FERM BP-11252, FERM BP-11253, FERM BP-11346 or FERM BP-11254; and an antibody, which binds to a portion comprising at least one region (for example, any one region) selected from the group consisting of a region consisting of amino acids at positions 43 to 65, a region consisting of amino acids at positions 152 to 165, a region consisting of amino acids at positions 171 to 183, a region consisting of amino acids at positions 109 to 120, a region consisting of amino acids at positions 43 to 56, and a region consisting of amino acids at positions 194 to 207, in the amino acid sequence of human TROP-2 shown in SEQ ID NO: 2.

(3) An antibody fragment derived from the antibody according to (1) or (2) above.

Examples of the antibody fragment according to (3) above include:

an antibody fragment comprising the amino acid sequences shown in SEQ ID NOS: 36 to 38 and/or the amino acid sequences shown in SEQ ID NOS: 41 to 43, for example, an antibody fragment comprising the amino acid sequence shown in SEQ ID NO: 35 and/or the amino acid sequence shown in SEQ ID NO: 40;

an antibody fragment comprising the amino acid sequences shown in SEQ ID NOS: 46 to 48 and/or the amino acid sequences shown in SEQ ID NOS: 51 to 53, for example, an antibody fragment comprising the amino acid sequence shown in SEQ ID NO: 45 and/or the amino acid sequence shown in SEQ ID NO: 50;

an antibody fragment comprising the amino acid sequences shown in SEQ ID NOS: 56 to 58 and/or the amino acid sequences shown in SEQ ID NOS: 61 to 63, for example, an antibody fragment comprising the amino acid sequence shown in SEQ ID NO: 55 and/or the amino acid sequence shown in SEQ ID NO: 60; and an antibody fragment comprising the amino acid sequences shown in SEQ ID NOS: 66 to 68 and/or the amino acid sequences shown in SEQ ID NOS: 71 to 73, for example, an antibody fragment comprising the amino acid sequence shown in SEQ ID NO: 65 and/or the amino acid sequence shown in SEQ ID NO: 70.

(4) A hybridoma, which produces the antibody according to (1) or (2) above.

(5) A hybridoma producing a monoclonal antibody against human TROP-2, which has accession No. FERM BP-11251, FERM BP-11252, FERM BP-11253, FERM BP-11346 or FERM ABP-11254.

(6) An antibody-drug conjugate, which comprises the antibody according to (1) or (2) above and a substance having anti-tumor activity and/or cell-killing activity.

(7) An antibody-drug conjugate, which comprises the antibody according to (3) above and a substance having anti-tumor activity and/or cell-killing activity.

With regard to the conjugate according to (6) and (7) above, the tumor is, for example, at least one type selected from the group consisting of human pancreatic cancer, human prostate cancer, human colon cancer and human breast cancer, and particularly, human pancreatic cancer. In addition, the tumor also includes a recurrent cancer and a metastatic cancer.

(8) A pharmaceutical composition, which comprises at least one type selected from the group consisting of the antibody according to (1) and (2) above, the antibody fragment according to (3) above and the conjugate according to (6) and (7) above.

An example of the composition according to (8) above is a composition used in the treatment of tumor, and particularly, a composition, which does not cause weight reduction as a side effect. Another example of the composition is a composition used in the diagnosis of tumor. Herein, the tumor is, for example, at least one type selected from the group consisting of human pancreatic cancer, human prostate cancer, human colon cancer and human breast cancer, and particularly, human pancreatic cancer. In addition, the tumor also includes a recurrent cancer and a metastatic cancer.

(9) A tumor therapeutic agent, which comprises at least one type selected from the group consisting of the antibody according to (1) and (2) above, the antibody fragment according to (3) above and the conjugate according to (6) and (7) above.

An example of the therapeutic agent according to (9) above is a therapeutic agent, which does not cause weight reduction as a side effect.

(10) A tumor diagnostic agent, which comprises at least one type selected from the group consisting of the antibody according to (1) and (2) above, the antibody fragment according to (3) above and the conjugate according to (6) and (7) above.

With regard to the therapeutic agent according to (9) above and the diagnostic agent according to (10) above, the tumor is, for example, at least one type selected from the group consisting of human pancreatic cancer, human prostate cancer, human colon cancer and human breast cancer, and particularly, human pancreatic cancer. In addition, the tumor also includes a recurrent cancer and a metastatic cancer.

(11) A method for detecting a tumor, which comprises: allowing at least one type selected from the group consisting of the antibody according to (1) and (2) above, the antibody fragment according to (3) above and the conjugate according to (6) and (7) above, to react with a sample collected from a living body; and then detecting a signal(s) of the reacted antibody and/or antibody fragment.

With regard to the method according to (11) above, the tumor is, for example, at least one type selected from the group consisting of human pancreatic cancer, human prostate cancer, human colon cancer and human breast cancer, and particularly, human pancreatic cancer. In addition, the tumor also includes a recurrent cancer and a metastatic cancer.

(12) A kit for treating, diagnosing or detecting a tumor, which comprises at least one type selected from the group consisting of the antibody according to (1) and (2) above, the antibody fragment according to (3) above and the conjugate according to (6) and (7) above.

With regard to the kit according to (12) above, the tumor is, for example, at least one type selected from the group consisting of human pancreatic cancer, human prostate cancer, human colon cancer and human breast cancer, and particularly, human pancreatic cancer. In addition, the tumor also includes a recurrent cancer and a metastatic cancer.

BRIEF DESCRIPTION OF THE DRAWINGS

FIG. 10 shows a scratch assay of a human pancreatic cancer cell line (PK-59 cells) in the presence of anti-hTROP-2 antibodies (T6-16 and K5-70).

FIG. 10A shows representative examples of photographs of the scratch regions of PK-59 cells. Day 0 shows a representative example immediately after scratching. mIgG (Day 1) shows a photograph taken 1 day (24 hours) after scratching and then adding a control antibody (mouse IgG, 1 µg/mL) to the medium. K5-70 (Day 1) shows a photograph taken 1 day (24 hours) after scratching and then adding a K5-70 antibody (1 µg/mL) to the medium. T6-16 (Day 1) shows a photograph taken 1 day (24 hours) after scratching and then adding a T6-16 antibody (1 µg/mL) to the medium. Each arrow in each photograph indicates the width of a scratch region.

FIG. 10B. The area of a scratch region was analyzed using image analysis software (Scion Image), and based on the obtained value, the values of various types of other samples were calculated using Day 0 of the control mIgG addition group as a standard value of 1.
*P<0.05, **P<0.01 (by Student's t-test).

FIG. 11A is a view illustrating FACS showing the expression of EpCAM in the PK-59 cells. The filled histogram indicates the reaction of the cells only with a secondary antibody (PE-labeled anti-mouse IgG), and the open histogram indicates the reaction of the cells with an anti-human EpCAM antibody (Becton, Dickinson and Company). FIGS. 11B and C are views illustrating FACS showing the expression of P-glycoprotein/MCR1 of the PK-59 cells (FIG. 11B), or the expression of ABCG2 in the PK-59 cells (FIG. 11C). The blue histogram indicates the reaction of the cells only with a secondary antibody, and the red histogram indicates the reaction of the cells with an anti-human P-glycoprotein/ MDR1 antibody (BD Biosciences Pharmingen) (FIG. 11B), or with an anti-human ABCG2 antibody (BD Biosciences Pharmingen) (FIG. 11C). FIG. 11D shows FACS analysis, in which the PK-59 cells were double stained with pancreatic cancer stem cell markers, an FITC-labeled anti-human CD24 antibody (BD Biosciences Pharmingen) and a PE-labeled anti-human CD44 antibody (BD Biosciences Pharmingen). Each number in FIG. 11D indicates the existing ratio of the cells in each fraction.

FIG. 12A shows the time course of tumor growth of a control group (mouse IgG) and a K5-70 administration group (a mean value±standard deviation). The arrow indicates an antibody administration period. * P<0.05, ** P<0.01 (by Student's t-test).

FIG. 12B shows the plotted tumor weight of each mouse at the time of the 21$^{st}$ day (Day 21) (the final day of experiment) in the test of FIG. 12A. The numerical value on each plot indicates a mean value±standard deviation. ** P<0.01 (by Student's t-test).

FIG. 14 shows the evaluation of the anti-tumor activity of a clone K5-70 (A), a clone T6-16 (B) and a clone K5-116-2-1 (C) in xenograft prevention models using PK-59 cells. The symbol "●" indicates a control group (mouse IgG), and the symbol "○" indicates an anti-hTROP-2 antibody administration group. The arrow in the graph indicates an antibody administration period, and the numerical value on each plot indicates a mean value±standard deviation. ** P<0.01 (by Student's t-test).

FIG. 15A shows the time course of tumor growth of a control group (mouse IgG) and a K5-70 administration group in prevention models (a mean value±standard deviation). The arrow indicates an antibody administration period. ** P<0.01 (by Student's t-test). FIG. 15B shows the time course of tumor growth of a control group (mouse IgG) and a K5-70 administration group in treatment models (a mean value±standard deviation). The arrow indicates an antibody administration period. * P<0.05 (by Student's t-test).

FIG. 16A shows the time course of tumor growth of a control group and K5-70 administration groups at different doses (a mean value±standard deviation). The arrow indicates an antibody administration period. * P<0.05 (by Student's t-test), ** P<0.01 (by Student's t-test).

FIG. 16B shows the plotted tumor weight of each mouse at the time of the 17$^{th}$ day (Day 17) (the final day of experiment) in the test of FIG. 16A. The numerical number on each plot indicates a mean value±standard deviation. ** P<0.01 (by Student's t-test).

An hTROP-2 gene and each human/mouse chimeric TROP-2 gene were introduced into HEK293 cells, and FACS analysis was then carried out using the cells, in which the genes were transiently expressed. In FIG. 19(A), the reactivity of K5-70, K5-107, T5-86 and K5-116-2-1 antibodies with hTROP-2 (upper case), with hmTROP-2-A (middle case) and with hmTROP-2-B (lower case) was studied. As a negative control, mouse IgG2b was used. In FIG. 19(B), the reactivity of T6-4 and T6-16 antibodies with hTROP-2 (upper case), with mhTROP-2-E (middle case) and with mhTROP-2-F (lower case) was studied. As a negative control, mouse IgG2b was used.

FIG. 22A shows time course of tumor formation in a control group (mouse IgG ●) and in a K5-70 administration group (○) (a mean value±standard deviation). The arrow indicates antibody administration. * P<0.05 (by Student's t-test), ** P<0.01 (by Student's t-test).

FIG. 22B shows the plotted tumor weight of each mouse at the time of the 28$^{th}$ day (Day 28) (the final day of experiment) in the test of FIG. 22A. ** P<0.01 (by Student's t-test).

FIG. 22C shows time course of tumor formation in each mouse in a control group (mouse IgG ●) and in a K5-70 administration group (○). The arrow indicates antibody administration.

FIG. 23A shows time course of tumor formation in a control group (mouse IgG ●) and in a K5-70 administration group (○) (a mean value±standard deviation). The arrow indicates an antibody administration period. ** P<0.01 (by Student's t-test).

FIG. 23B shows the plotted tumor weight of each mouse at the time of the 44$^{th}$ day (Day 44) (the final day of experiment) in the test of FIG. 23A. ** P<0.01 (by Student's t-test).

FIG. 24A shows time course of tumor formation in a control group (mouse IgG ●) and in a T6-16 administration group (○) (a mean value±standard deviation). The arrow indicates an antibody administration period. ** P<0.01 (by Student's t-test).

FIG. 24B shows the plotted tumor weight of each mouse at the time of the 42$^{nd}$ day (Day 42) (the final day of experiment) in the test of FIG. 24A. ** P<0.01 (by Student's t-test).

FIG. 25A shows time course of tumor formation in a control group (mouse IgG ●) and in a T6-16 administration group (○) (a mean value±standard deviation). The arrow indicates an antibody administration period. * P<0.05 (by Student's t-test).

FIG. 25B shows the plotted tumor weight of each mouse at the time of the 42$^{nd}$ day (Day 42) (the final day of experiment) in the test of FIG. 25A. * P<0.05 (by Student's t-test).

FIG. 26A shows time course of tumor formation in a control group (mouse IgG ●) and in a K5-70 administration group (○: 1 mg/kg, Δ: 5 mg/kg, □: 10 mg/kg) (a mean value±standard deviation). The arrow indicates an antibody administration period. * P<0.05 (by Student's t-test).

FIG. 26B shows the plotted tumor weight of each mouse at the time of the 42$^{nd}$ day (Day 42) (the final day of experiment) in the test of FIG. 26A. * P<0.05 (by Student's t-test).

FIG. 27A shows the anti-tumor activity of a K5-70 antibody at administration intervals of once a week. Time course of tumor formation in a control group (●: mouse IgG) and in a K5-70 administration group (○: 10 mg/kg) is shown (a mean value±standard deviation). The arrow heads (Days 10, 17, 24, 31, and 38) indicate administration of a K5-70 antibody. * P<0.05 by Student's t-test.

FIG. 27B shows time course of tumor formation by administration of a K5-70 antibody at administration intervals of once every ten days (○: q10d) or once every two weeks (Δ: q14d). The closed circle (●) indicates a control group (Mouse IgG, 10 mg/kg) (a mean value±standard deviation). The filled arrowheads (▼: Days 9, 19, and 29) and the open arrowheads (7: Days 9, 23, and 37) indicate administration of a K5-70 antibody. * P<0.05, ** P<0.01 by Student's t-test.

FIG. 28 shows the dose-dependent anti-tumor activity of a clone T6-16 on xenograft treatment models using SW480 cells.

FIG. 28A shows time course of tumor formation in a control group (●: mouse IgG) and in a T6-16 administration group (○: 1 mg/kg, Δ: 5 mg/kg, □: 10 mg/kg) is shown (a mean value±standard deviation). The arrow indicates an antibody administration period. ** P<0.01 (by Student's t-test).

FIG. 28B shows the plotted tumor weight of each mouse at the time of the 43$^{rd}$ day (Day 43) (the final day of experiment) in the test of FIG. 28A. ** P<0.01 (by Student's t-test).

FIG. 30A shows time course of tumor formation in a control group (●: mouse IgG) and in a K5-70 administration group (○) (a mean value±standard deviation). The arrow indicates an antibody administration period. * P<0.05 (by Student's t-test).

FIG. 30B shows the plotted tumor weight of each mouse at the time of the 40$^{th}$ day (Day 40) (the final day of experiment) in the test of FIG. 30A. * P<0.05 (by Student's t-test).

FIG. 31 shows the metastasis-inhibitory activity of a clone K5-70 on liver metastatic models using PK-59 cells.

FIGS. 31A and 31B show the excised liver image of a control group (mouse IgG) (A) and a K5-70 administration group (B), which were taken 6 weeks after the cell transplantation. The arrows indicate liver metastatic foci.

FIG. 33 shows the cDNA nucleotide sequence of a clone K5-70 H chain variable region (VH) (SEQ ID NO: 34) and the deduced amino acid sequence (SEQ ID NO: 35). A signal peptide is shown in italics. The double-underlined glutamine (Q) indicates the N-terminal amino acid residue of a mature peptide. The CDR sequences (underlined; IYWIN (SEQ ID NO: 36), NIYPSDSYTNYNQKFKD (SEQ ID NO: 37), and TSMADY (SEQ ID NO: 38)) were determined in accordance with the definitions of Kabat et al. (Sequences of Proteins of Immunological Interests, Fifth edition, NIH Publication No. 91-3242, U.S. Department of Health and Human Services, 1991). The amino acid sequences of CDR 1 to 3 of the clone K5-70 VH are shown in SEQ ID NOS: 36 to 38, respectively.

FIG. 34 shows the cDNA nucleotide sequence of a clone K5-70 L chain variable region (VL) (SEQ ID NO: 39) and the deduced amino acid sequence (SEQ ID NO: 40). A signal peptide is shown in italics. The double-underlined aspartic acid (D) indicates the N-terminal amino acid residue of a mature peptide. The CDR sequences (underlined; RASQSIGTSIH (SEQ ID NO: 41), YASESIS (SEQ ID NO: 42), and QQSNSWPFT (SEQ ID NO: 43)) were determined in accordance with the definitions of Kabat et al. (Sequences of Proteins of Immunological Interests, Fifth edition, NIH Publication No. 91-3242, U.S. Department of Health and Human Services, 1991). The amino acid sequences of CDR 1 to 3 of the clone K5-70 VL are shown in SEQ ID NOS: 41 to 43, respectively.

FIG. 35 shows the cDNA nucleotide sequence of a clone K5-107 H chain variable region (VH) (SEQ ID NO: 44) and the deuced amino acid sequence (SEQ ID NO: 45). A signal peptide is shown in italics. The double-underlined glutamine (Q) indicates the N-terminal amino acid residue of a mature peptide. The CDR sequences (underlined; SYWMH (SEQ ID NO: 46), NIYPGGGYTNYDEKFKS (SEQ ID NO: 47), and SSVFDY (SEQ ID NO: 48)) were determined in accordance with the definitions of Kabat et al. (Sequences of Proteins of Immunological Interests, Fifth edition, NIH Publication No. 91-3242, U.S. Department of Health and Human Services, 1991). The amino acid sequences of CDR 1 to 3 of the clone K5-107 VH are shown in SEQ ID NOS: 46 to 48, respectively.

FIG. 36 shows the cDNA nucleotide sequence of a clone K5-107 L chain variable region (VL) (SEQ ID NO: 49) and the deduced amino acid sequence (SEQ ID NO: 50). A signal peptide is shown in italics. The double-underlined aspartic acid (D) indicates the N-terminal amino acid residue of a mature peptide. The CDR sequences (underlined; RASQNIGTSIH (SEQ ID NO: 51), YASESIS (SEQ ID NO: 52), and QQSNSWPFT (SEQ ID NO: 53)) were determined in accordance with the definitions of Kabat et al. (Sequences of Proteins of Immunological Interests, Fifth edition, NIH Publication No. 91-3242, U.S. Department of Health and Human Services, 1991). The amino acid sequences of CDR 1 to 3 of the clone K5-107 VL are shown in SEQ ID NOS: 51 to 53, respectively.

FIG. 37 shows the cDNA nucleotide sequence of a clone K5-116-2-1 H chain variable region (VH) (SEQ ID NO: 54) and the deduced amino acid sequence (SEQ ID NO: 55). A signal peptide is shown in italics. The double-underlined glutamine (Q) indicates the N-terminal amino acid residue of a mature peptide. The CDR sequences (underlined; SYWIT (SEQ ID NO: 56), NIYPSDSYTNYNQKFRD (SEQ ID NO: 57), and LFDY (SEQ ID NO: 58)) were determined in accordance with the definitions of Kabat et al. (Sequences of Proteins of Immunological Interests, Fifth edition, NIH Publication No. 91-3242, U.S. Department of Health and Human Services, 1991). The amino acid sequences of CDR 1 to 3 of the clone K5-116-2-1 VH are shown in SEQ ID NOS: 56 to 58, respectively.

FIG. 38 shows the cDNA nucleotide sequence of a clone K5-116-2-1 L chain variable region (VL) (SEQ ID NO: 59) and the deduced amino acid sequence (SEQ ID NO: 60). A signal peptide is shown in italics. The double-underlined aspartic acid (D) indicates the N-terminal amino acid residue of a mature peptide. The CDR sequences (underlined; RASQSIGTSIH (SEQ ID NO: 61), YASESIS (SEQ ID NO: 62), and QQSNSWPFT (SEQ ID NO: 63)) were determined in accordance with the definitions of Kabat et al. (Sequences of Proteins of Immunological Interests, Fifth edition, NIH Publication No. 91-3242, U.S. Department of Health and Human Services, 1991). The amino acid sequences of CDR 1 to 3 of the clone K5-116-2-1 VL are shown in SEQ ID NOS: 61 to 63, respectively.

FIG. 39 shows the cDNA nucleotide sequence of a clone T6-16 H chain variable region (VH) (SEQ ID NO: 64) and the deduced amino acid sequence (SEQ ID NO: 65). A signal peptide is shown in italics. The double-underlined glutamic acid (E) indicates the N-terminal amino acid residue of a mature peptide. The CDR sequences (underlined; DYNMH (SEQ ID NO: 66), YIYPYNGGTGYNQRFKS (SEQ ID NO: 67), and EDYGSSPSYAMDY (SEQ ID NO: 68)) were determined in accordance with the definitions of Kabat et al. (Sequences of Proteins of Immunological Interests, Fifth edition, NIH Publication No. 91-3242, U.S. Department of Health and Human Services, 1991). The amino acid sequences of CDR 1 to 3 of the clone T6-16 VH are shown in SEQ ID NOS: 66 to 68, respectively.

FIG. 40 shows the cDNA nucleotide sequence of a clone T6-16 L chain variable region (VL) (SEQ ID NO: 69) and the deduced amino acid sequence (SEQ ID NO: 70). A signal peptide is shown in italics. The double-underlined aspartic acid (D) indicates the N-terminal amino acid residue of a mature peptide. The CDR sequences (underlined; RSSQSLVHGNGNTYLH (SEQ ID NO: 71), KVSNRFS (SEQ ID NO: 72), and SQTTHVPT (SEQ ID NO: 73)) were determined in accordance with the definitions of Kabat et al. (Sequences of Proteins of Immunological Interests, Fifth edition, NIH Publication No. 91-3242, U.S. Department of Health and Human Services, 1991). The amino acid sequences of CDR 1 to 3 of the clone T6-16 VL are shown in SEQ ID NOS: 71 to 73, respectively.

MODE FOR CARRYING OUT THE INVENTION

Figure 1:
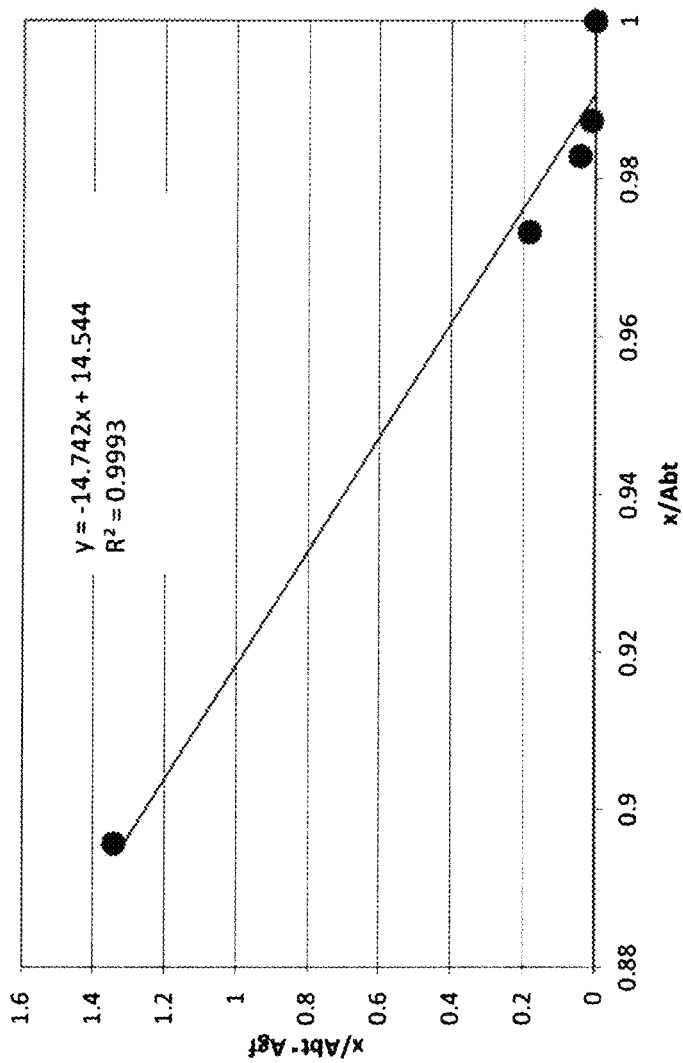
FIG. 1 shows the measurement of the antigen binding affinity (Kd: dissociation constant) of an anti-hTROP-2 monoclonal antibody (K5-70). Abt: Antibody (total); Agf: Antigen (free).

Hereinafter, the present invention will be described in detail. The following descriptions are not intended to limit the scope of the present invention. Other than the following examples, the present invention may be modified and may be carried out, as appropriate, within a range that does not impair the intention of the present invention The present specification includes all of the contents as disclosed in the specification of Japanese Patent Application No. 2010-113302 (filed on May 17, 2010), which is a priority document of the present application.

In addition, all publications cited in the present specification, which include prior art documents and patent documents such as laid-open application publications and patent publications, are incorporated herein by reference in their entirety.

1. Summary of the Present Invention

As mentioned above, human TROP-2 (hTROP-2) is a single transmembrane, type 1 membrane protein having a full length of 323 amino acid residues. It has been known that an hTROP-2 gene and a gene product thereof are expressed in various types of cancer cells.

As mentioned above, it has been desired to develop an anti-human hTROP-2 antibody (an anti-human hTROP-2 monoclonal antibody) or the like having high anti-tumor activity in vivo. Under such circumstances, the present inventor performed a screening through an extremely large number of clones, and as a result, the inventor succeeded in obtaining a clone having high anti-tumor activity in vivo. Specifically, the present invention provides a monoclonal antibody, which specifically recognizes the extracellular region of hTROP-2 in vivo, and particularly, a monoclonal antibody exhibiting high affinity at a picomole (pM) order. The antibody of the present invention is extremely useful in that it is an anti-hTROP-2 monoclonal antibody, which exhibits significant tumor growth inhibitory activity at a lower dose than that of the existing anti-hTROP-2 antibody (for example, at a dosage of 1/20) when it is administered singly as a naked antibody, and which also exhibits significant tumor growth inhibitory activity on tumor-bearing mouse treatment models, in which multiple types of human cancer cells are used.

2. Production of Anti-hTROP-2 Antibody (1) Preparation of Antigen

Information regarding the amino acid sequence (SEQ ID NO: 2) of hTROP-2 is disclosed under "Accession number NP_002344" in the website of, for example, NCBI (GenBank). Information regarding a nucleotide sequence (SEQ ID NO: 1) encoding the amino acid sequence of hTROP-2 is disclosed under "Accession number NM_002353" in the same website as described above.

As an antigen, a polypeptide or peptide (which is also simply referred to as a peptide) comprising at least a portion (the entire or a part) of the amino acid sequence of hTROP-2 can be used, and preferably, a peptide comprising at least a portion (the entire or a part) of the amino acid sequence of the extracellular region of hTROP-2 can be used. The extracellular region (including a signal peptide) of hTROP-2 indicates a region comprising the amino acids at positions 1 to 274 from the amino acid sequence shown in SEQ ID NO: 2 (the signal peptide: the amino acids at positions 1 to 26). Herein, with regard to a peptide used as an antigen, the above description "at least a portion of the amino acid sequence" is not particularly limited in terms of length. For example, a region comprising the amino acids at positions 1 to 145 from the amino acid sequence shown in SEQ ID NO: 2, a region comprising the amino acids at positions 146 to 274 from the same amino acid sequence as described above, and the like are preferable.

A peptide used as an antigen may be produced either by chemical synthesis, or by synthesis according to a genetic engineering method using *Escherichia coli* or the like. A method well known to persons skilled in the art may be applied.

When a peptide is produced by chemical synthesis, it can be synthesized by a well known peptide synthesis method. In addition, either a solid-phase synthesis method or a liquid-phase synthesis method can be applied to the peptide synthesis. A commercially available peptide synthesizer (for example, PSSM-8 manufactured by Shimadzu Corporation, etc.) may also be used.

When a peptide is synthesized by a genetic engineering method, first, DNA encoding the peptide is designed and synthesized. The design and synthesis of such DNA can be carried out according to a PCR method, using a vector comprising an entire-length hTROP-2 gene or the like as a template, and also using primers designed to be able to synthesize a desired DNA region. Thereafter, the DNA is ligated to a suitable vector to obtain a recombinant vector used for protein expression, and this recombinant vector is then introduced into a host so that a gene of interest can be expressed therein, thereby obtaining a transformant (Sambrook J. et al., Molecular Cloning, A Laboratory Manual, 3rd edition, Cold Spring Harbor Laboratory Press, 2001).

As a vector, a phage or a plasmid capable of autonomously replicating in a host microorganism is used. Further, an animal virus or an insect virus vector can also be used. To produce a recombinant vector, a purified DNA may be cleaved with suitable restriction enzymes, and the thus cleaved DNA portion may be then inserted into the restriction enzyme site or the like of a suitable vector DNA, so as to ligate it to the vector. The type of a host used in transformation is not particularly limited, as long as it is able to express a gene of interest. Examples of such a host include bacteria (*Escherichia coli, Bacillus subtilis*, etc.), yeasts, animal cells (COS cells, CHO cells, etc.), insect cells, and insects. A mammal such as a goat may also be used as such a host. A method of introducing a recombinant vector into a host is publicly known.

The above-described transformant is cultured, and a peptide used as an antigen is then collected from the culture. The term "culture" is used herein to mean both (a) a culture supernatant, and (b) cultured cells, a cultured cell mass or a disintegrated product thereof.

After completion of the culture, when a peptide of interest is produced in a cell mass or in cells, the peptide is extracted by disintegrating the cell mass or the cells. On the other hand, when a peptide of interest is produced outside a cell mass or outside cells, a culture solution is directly used, or the cell mass or the cells are removed from the culture solution by centrifugation or the like. Thereafter, the peptide of interest can be isolated and purified by a single use of biochemical methods commonly used in the isolation and purification of peptides, such as ammonium sulfate precipitation, gel filtration, ion exchange chromatography and affinity chromatography, or by appropriately combining the aforementioned biochemical methods.

In the present invention, a peptide used as an antigen can also be obtained by in vitro translation using a cell-free synthesis system. In this case, two methods, namely, a method using RNA as a template and a method using DNA as a template (transcription/translation) can be applied. As such a cell-free synthesis system, a commercially available system, such as Expressway™ system (Invitrogen), PURESYSTEM (registered trademark; Post Genome Institute) or TNT system (registered trademark; Promega) can be used.

The thus obtained peptide may bind to a suitable carrier protein such as bovine serum albumin (BSA), keyhole limpet hemocyanin (KLH), human thyroglobulin or chicken γ-globulin.

Moreover, the antigen may be a peptide consisting of an amino acid sequence comprising a deletion, substitution or addition of one or more amino acids with respect to the amino acid sequence of hTROP-2 (SEQ ID NO: 2) or a partial sequence thereof as described above. There can be used, for example, a peptide consisting of an amino acid sequence, in which one or more (preferably one or several (for example, 1 to 10, and more preferably 1 to 5)) amino acids are deleted, or one or more (preferably one or several (for example, 1 to 10, and more preferably 1 to 5)) amino acids are substituted with other amino acids, or one or more (preferably one or several (for example, 1 to 10, and more preferably 1 to 5)) other amino acids are added, with respect to the amino acid sequence of hTROP-2 or a partial sequence thereof.

In the present invention, a gene to be introduced into a cell or the like is a gene encoding an hTROP-2 protein or a partial fragment thereof, or a mutant protein thereof or a fragment thereof. As such a gene, a gene having the nucleotide sequence shown in SEQ ID NO: 1 or a partial sequence thereof can be used, for example.

Furthermore, as a gene to be introduced into a cell or the like, there may also be used a nucleotide sequence hybridizing under stringent conditions with a sequence complementary to the nucleotide sequence shown in SEQ ID NO: 1 and encoding a protein having hTROP-2 activity, or a partial sequence thereof.

The description "stringent conditions" is used herein to mean washing conditions after completion of the hybridization. As such stringent conditions, a salt (sodium) concentration in buffer is 10 to 500 mM and a temperature is 42° C. to 72° C., and preferably, the aforementioned salt condition is 50 to 300 mM and a temperature is 55° C. to 68° C.

Mutation can be introduced into a gene according to a known method such as a Kunkel method or a Gapped duplex method, using, for example, a mutation introduction kit which utilizes site-directed mutagenesis, such as GeneTailor™ Site-Directed Mutagenesis System (manufactured by Invitrogen) or TaKaRa Site-Directed Mutagenesis System (Mutan-K, Mutan-Super Express Km, etc.; manufactured by Takara Bio Inc.).

(2) Production of Polyclonal Antibody

The prepared antigen is administered to a mammal for immunization. The type of such a mammal is not particularly limited. For example, a rat, a mouse and a rabbit can be used, and among them, a mouse is preferable.

The dosage of the antigen per animal can be determined, as appropriate, depending on the presence or absence of an adjuvant. Examples of such an adjuvant include a Freund's complete adjuvant (FCA), a Freund's incomplete adjuvant (FIA) and an aluminum hydroxide adjuvant. Immunization can be carried out mainly by injecting the antigen into the vein, footpad, subcutis or abdominal cavity of an animal. In addition, immunization interval is not particularly limited, and immunization is carried out at intervals of several days to several weeks, preferably at intervals of 1 week, 1 to 10 times, and preferably 2 or 3 times. Three to seven days after the final immunization day, an antibody titer is measured by enzyme immunoassay (ELISA or EIA), radioimmunoassay (RIA) or other methods. On the date at which a desired antibody titer is obtained, blood can be collected to obtain antiserum. In the above-described method of collecting an antibody, if it is necessary to purify the antibody, the antibody can be purified by selecting a suitable method from known methods such as ammonium sulfate precipitation, ion exchange chromatography, gel filtration chromatography and affinity chromatography, or by combining the above-mentioned methods, as appropriate. Thereafter, the reactivity of a polyclonal antibody in the antiserum is measured by the ELISA method or the like.

(3) Production of Monoclonal Antibody (3-1) Collection of Antibody-Producing Cells The anti-hTROP-2 antibody of the present invention is not limited, but it is preferably a monoclonal antibody.

The prepared antigen is administered to a mammal, such as a rat, a mouse or a rabbit, for immunization. The dosage of the antigen per animal can be determined, as appropriate, depending on the presence or absence of an adjuvant. The same adjuvants as described above can be used herein. Also, the same immunization methods as described above can be applied herein. One to sixty days, and preferably, one to fourteen days after the final immunization day, antibody-producing cells are collected. Examples of such antibody-producing cells include splenic cells, lymph node cells and peripheral blood cells. Of these, lymph node cells and splenic cells are preferable.

(3-2) Cell Fusion

In order to obtain hybridomas (an antibody-producing cell line), the cell fusion of antibody-producing cells with myeloma cells is carried out. As myeloma cells to be fused with antibody-producing cells, commonly available established cells from animals such as mice can be used. The cell line used herein is preferably a cell line, which has drug selectivity, cannot survive in an unfused state in a HAT selective medium (containing hypoxanthine, aminopterin and thymidine), and can survive only in a state fused with antibody-producing cells.

Examples of myeloma cells include mouse myeloma cell lines such as P3-X63-Ag8.653, P3-X63-Ag8(X63), P3-X63-Ag8.U1(P3U1), P3/NS I/1-Ag4-1(NS1) and Sp2/0-Ag14 (Sp2/0). Myeloma cells can be selected, while taking into consideration the compatibility with antibody-producing cells, as appropriate.

Subsequently, myeloma cells are fused with antibody-producing cells. For such cell fusion, antibody-producing cells ($1 \times 10^6$ to $1 \times 10^7$ cells/mL) are mixed with myeloma cells ($2 \times 10^5$ to $2 \times 10^6$ cells/mL) in a medium for animal cells, such as DMEM or an RPMI-1640 medium containing no serum. The cell ratio between the antibody-producing cells and the myeloma cells (antibody-producing cells: myeloma cells) is not limited. In general, the cell ratio is preferably 1:1 to 10:1, and more preferably 3:1. Thereafter, a fusion reaction is carried out in the presence of a cell fusion promoter. As such a cell fusion promoter, polyethylene glycol having a mean molecular weight of 1,000 to 6,000 Dalton (D) or the like can be used. In addition, it is also possible to fuse antibody-producing cells with myeloma cells, employing a commercially available cell fusion apparatus which utilizes electrical stimulation (for example, electroporation).

(3-3) Selection and Cloning of Hybridomas

Hybridomas of interest are selected from the cells after the cell fusion treatment. As a method of selecting hybridomas, the cell suspension is appropriately diluted with, for example, a fetal bovine serum-containing RPMI-1640 medium, and the diluted solution is then dispersed on a microtiter plate. Thereafter, a selective medium is added to each well. While the selective medium is appropriately exchanged with a fresh one, culture is carried out. As a result, approximately 14 days after initiation of the culture on the selective medium, cells growing from the selective medium can be obtained as hybridomas.

Subsequently, screening is carried out to examine whether or not an antibody reacting with hTROP-2 is present in a culture supernatant of the growing hybridomas. The screening of hybridomas may be carried out according to an ordinary method, and thus, the screening method is not particularly limited. For example, an aliquot is collected from the culture supernatant of the growing hybridomas contained in the well, and screening is then carried out by ELISA, EIA, RIA or the like.

The cloning of the fused cells can be carried out by a limiting dilution method or the like. An antibody showing high reactivity with hTROP-2 is determined by flow cytometry or the like, and a hybridoma producing this antibody is then selected. The selected hybridoma is established as a clone.

(3-4) Collection of Monoclonal Antibody

As a method of culturing the established hybridoma and then collecting a monoclonal antibody from the obtained culture, a common cell culture method, an ascites formation method or the like can be adopted. The term "culture" is used herein to mean allowing hybridomas to grow in a culture dish or a culture bottle, or allowing hybridomas to grow in the abdominal cavity of an animal, as described below.

In the case of the cell culture method, hybridomas are cultured in a medium for animal cells, such as a 10% fetal bovine serum-containing RPMI-1640 medium, an MEM medium or a serum-free medium, under common culture conditions (for example, 37° C., 5% $CO_2$ concentration) for 7 to 14 days, and thereafter, an antibody can be obtained from the culture supernatant.

In the case of the ascites formation method, approximately $1 \times 10^7$ hybridomas are administered into the abdominal cavity of an animal of the same species as the mammal from which myeloma cells are derived, so that large quantities of hybridomas are allowed to proliferate. Thereafter, 2 to 3 weeks later, ascites is preferably collected.

In the above-described antibody collection methods, if it is necessary to purify the antibody, the antibody can be purified by appropriately selecting a suitable method from known methods such as ammonium sulfate precipitation, ion exchange chromatography, gel filtration and affinity chromatography, or by combining the above-mentioned methods.

(3-5) Selection of Clone Having Anti-Tumor Activity

The anti-hTROP-2 antibody of the present invention is an antibody having anti-tumor activity in vivo.

The term "anti-tumor activity" is used herein to mean activity of killing tumor cells (cancer cells) or activity of inhibiting tumor growth. Preferred examples of such anti-tumor activity include activity of inhibiting the growth of cancer cells and activity of inhibiting tumor angiogenesis. The type of human tumor (tumor cells), on which the antibody of the present invention is able to exhibit anti-tumor activity, includes various types of known human tumors, in which the expression of hTROP-2 has been confirmed. The type of such human tumor is not particularly limited. For example, one or two or more of human pancreatic cancer, human prostate cancer, human colon cancer and human breast cancer are preferable, and human pancreatic cancer is more preferable.

Moreover, the above-described tumor may be a recurrent cancer or a metastatic cancer. The antibody of the present invention is also able to exhibit excellent anti-tumor activity on these types of tumors.

The presence of anti-tumor activity in vivo can be confirmed, for example, by employing a tumor-bearing mouse (a mouse xenograft model), into the subcutis of which desired tumor cells have been transplanted, and then by administering the antibody as obtained above to the mouse. In this case, the antibody may be administered immediately after the transplantation of tumor cells (Prevention models). Alternatively, it may be administered after confirming that the transplanted tumor has reached a predetermined volume (Treatment models). The administration method is not limited. For example, the antibody may be administered once every three days, every one week, every ten days, or every two weeks, or by a single administration (only one time), at a dosage of 5 to 20 mg/kg body weight, via intraperitoneal administration or the like. In the case of prevention models, the presence or absence of anti-tumor activity and the level thereof can be evaluated based on tumor formation frequency and tumor volume. In the case of treatment models, the presence or absence of anti-tumor activity and the level thereof can be evaluated based on tumor volume.

In the present invention, a preferred example of the anti-hTROP-2 antibody having anti-tumor activity in vivo is an antibody in which the amino acid sequences of CDR 1 to 3 of the H chain V region thereof are shown in SEQ ID NOS: 36 to 38, respectively, and/or the amino acid sequences of CDR 1 to 3 of the L chain V region thereof are shown in SEQ ID NOS: 41 to 43, respectively. A preferred example of the H chain V region is an H chain V region consisting of the amino acid sequence shown in SEQ ID NO: 35. A preferred example of the L chain V region is an L chain V region consisting of the amino acid sequence shown in SEQ ID NO: 40.

As another embodiment of the anti-hTROP-2 antibody of the present invention, a preferred example is an antibody in which the amino acid sequences of CDR 1 to 3 of the H chain V region thereof are shown in SEQ ID NOS: 46 to 48, respectively, and/or the amino acid sequences of CDR 1 to 3 of the L chain V region thereof are shown in SEQ ID NOS: 51 to 53, respectively. A preferred example of the H chain V region is an H chain V region consisting of the amino acid sequence shown in SEQ ID NO: 45. A preferred example of the L chain V region is an L chain V region consisting of the amino acid sequence shown in SEQ ID NO: 50.

Likewise, as a further embodiment of the anti-hTROP-2 antibody of the present invention, a preferred example is an antibody in which the amino acid sequences of CDR 1 to 3 of the H chain V region thereof are shown in SEQ ID NOS: 56 to 58, respectively, and/or the amino acid sequences of CDR 1 to 3 of the L chain V region thereof are shown in SEQ ID NOS: 61 to 63, respectively. A preferred example of the H chain V region is an H chain V region consisting of the amino acid sequence shown in SEQ ID NO: 55. A preferred example of the L chain V region is an L chain V region consisting of the amino acid sequence shown in SEQ ID NO: 60.

Likewise, as a further embodiment of the anti-hTROP-2 antibody of the present invention, a preferred example is an antibody in which the amino acid sequences of CDR 1 to 3 of the H chain V region thereof are shown in SEQ ID NOS: 66 to 68, respectively, and/or the amino acid sequences of CDR 1 to 3 of the L chain V region thereof are shown in SEQ ID NOS: 71 to 73, respectively. A preferred example of the H chain V region is an H chain V region consisting of the amino acid sequence shown in SEQ ID NO: 65. A preferred example of the L chain V region is an L chain V region consisting of the amino acid sequence shown in SEQ ID NO: 70.

In the present invention, more specifically, preferred examples of an anti-hTROP-2 antibody having anti-tumor activity in vivo include: an anti-hTROP-2 monoclonal antibody (clone name: K5-70) produced by a hybridoma with Accession number FERM BP-11251; an anti-hTROP-2 monoclonal antibody (clone name: K5-107) produced by a hybridoma with Accession number FERM BP-11252; an anti-hTROP-2 monoclonal antibody (clone name: K5-116-2-1) produced by a hybridoma with Accession number FERM BP-11253; an anti-hTROP-2 monoclonal antibody (clone name: T6-16) produced by a hybridoma with Accession number FERM BP-11346; and an anti-hTROP-2 monoclonal antibody (clone name: T5-86) produced by a hybridoma with Accession number FERM BP-11254.

Herein, the hybridoma with Accession number FERM BP-11251 was named as "Mouse-Mouse Hybridoma K5-70" and was deposited on May 12, 2010; the hybridoma with Accession number FERM BP-11252 was named as "Mouse-Mouse Hybridoma K5-107" and was deposited on May 12, 2010; the hybridoma with Accession number FERM BP-11253 was named as "Mouse-Mouse Hybridoma K5-116-2-1" and was deposited on May 12, 2010; the hybridoma with Accession number FERM BP-11346 was named as "Mouse-Mouse Hybridoma T6-16" and was deposited on Mar. 1, 2011; and the hybridoma with Accession number FERM BP-11254 was named as "Mouse-Mouse Hybridoma T5-86" and was deposited on May 12, 2010. All of these hybridomas were deposited with the International Patent Organism Depositary (IPOD), the National Institute of Advanced Industrial Science and Technology, an Independent Administrative Institution under the Ministry of Economy, Trade and Industry (the AIST, Tsukuba Central 6, Higashi 1-1-1, Tsukuba, Ibaraki, Japan, postal code: 305-8566).

Still further, another preferred example of the anti-hTROP-2 antibody of the present invention is an anti-hTROP-2 antibody that binds to a site (e.g. an epitope), to which a monoclonal antibody produced by the hybridoma having accession No. FERM BP-11251, FERM BP-11252, FERM BP-11253, FERM BP-11346 or FERM BP-11254 binds (recognizes).

Preferred examples of such an epitope will be given in (3-6) below.

(3-6) Epitope of Anti-hTROP-2 Antibody

The type of an epitope (an antigenic determinant) of the anti-hTROP-2 antibody of the present invention is not limited, as long as it is at least a portion of hTROP-2 as an antigen. For example, such an epitope is preferably at least a portion of a region formed by removing a region consisting of amino acids at positions 252 to 260 from the amino acid sequence of hTROP-2 shown in SEQ ID NO: 2, more preferably at least a portion of a region consisting of amino acids at positions 1 to 69 or at least a portion of a region consisting of amino acids at positions 100 to 274 (except for a region consisting of amino acids at position 252 to 260), and further preferably at least a portion of a region consisting of amino acids at positions 27 to 69 or a region consisting of amino acids at positions 109 to 206. Particularly preferred examples of the above-described epitope include a region consisting of amino acids at positions 43 to 65, a region consisting of amino acids at positions 152 to 165, a region consisting of amino acids at positions 171 to 183, a region consisting of amino acids at positions 109 to 120, a region consisting of amino acids at positions 194 to 207, a region consisting of amino acids at positions 43 to 56, and a portion comprising such a region, in the amino acid sequence of hTROP-2 shown in SEQ ID NO: 2. Further particularly preferred examples include a region consisting of amino acids at positions 43 to 65, a region consisting of amino acids at positions 152 to 165, a region consisting of amino acids at positions 171 to 183, a region consisting of amino acids at positions 109 to 120, and a portion comprising such a region. An anti-hTROP-2 antibody, which recognizes the above-described regions (binds to the above-described regions or portions comprising such regions), has high internalization activity into tumor cells, for example, and thus it is extremely useful as an immunoconjugate as described later.

(3-7) Characteristics of Anti-hTROP-2 Antibody

As described above, the anti-hTROP-2 antibody of the present invention is an antibody having high anti-tumor activity in vivo at a low dose. Specifically, it is preferable that the present anti-hTROP-2 antibody exhibits tumor growth inhibitory activity of 50% or more (preferably 80% or more, more preferably 90% or more, further preferably 95% or more, and particularly preferably almost 100% (for example, 98% or more, or 99% or more)) at a dose (as a naked antibody) of 20 mg/kg body weight or less (preferably 10 mg/kg body weight or less, more preferably 5 mg/kg body weight or less, and further preferably 1 mg/kg body weight or less) with respect to a tumor-bearing animal model.

Herein, the tumor growth inhibitory activity (%) can be calculated, for example, by the following formula:

Tumor growth inhibitory activity (%)=100−[(tumor volume or tumor weight of antibody administration group)/(tumor volume or tumor weight of control group)]×100

In addition, the anti-hTROP-2 antibody of the present invention preferably has anti-tumor activity on two or more types of human tumor cell lines. The type of such a human tumor cell line is not limited. For example, such human tumor cell lines are at least two types selected from the group consisting of various types of human pancreatic cancer cell lines, human prostate cancer cell lines, human colon cancer cell lines and human breast cancer cell lines. Specifically, preferred examples of such human tumor cell lines include at least two types selected from the group consisting of a human pancreatic cancer cell line PK-59, a human pancreatic cancer cell line BxPC-3, a human pancreatic cancer cell line KP-3L, a human pancreatic cancer cell line KP-2, a human pancreatic cancer cell line PK-1, a human pancreatic cancer cell line PK-45H, a human pancreatic cancer cell line PK-45P, a human pancreatic cancer cell line TCC-PAN2, a human pancreatic cancer cell line SUIT-2, a human colon cancer cell line CACO-2, a human colon cancer cell line SW480, a human colon cancer cell line DLD-1, a human colon cancer cell line HCT 116, a human breast cancer cell line JIMT-1, a human breast cancer cell line HCC1143, a human breast cancer cell line MCF-7, a human prostate cancer cell line DU145 and a human prostate cancer cell line PC-3. Of these, as the above-described two or more types of human tumor cell lines, the human pancreatic cancer cell line PK-59 and the human pancreatic cancer cell line BxPC-3 are more preferable.

Moreover, the anti-hTROP-2 antibody of the present invention has a dissociation constant (Kd value) of preferably $1.0 \times 10^{-10}$ M or less, more preferably $1.0 \times 10^{-11}$ M or less, and further preferably $1.0 \times 10^{-12}$ M or less. Herein, the binding ability (affinity) of the antibody can be measured in the form of a dissociation constant (Kd value), a dissociation rate constant (Kdiss [1/Sec]) or an association rate constant (Kass [1/M·Sec]), for example, by Scatchard analysis or surface plasmon resonance sensor called Biacore. As such Biacore apparatuses, Biacore 3000, Biacore 2000, Biacore X, Biacore J and Biacore Q (all of which were manufactured by Biacore) may be used, for example. It is preferable that the antibody have a dissociation constant (Kd value) that is as small as possible because it could have high binding ability (affinity). The Kd value is determined based on the two parameters of Kdiss and Kass, and it can be expressed in the formula: Kd[M]=Kdiss/Kass. As a method of calculating the Kd value, the method described in the Examples as described later (specifically, Example 10) can be preferably adopted.

(4) Genetically Recombinant Antibody and Antibody Fragment (4-1) Genetically Recombinant Antibody In a preferred embodiment of the anti-hTROP-2 antibody of the present invention, there is provided a genetically recombinant antibody. The type of such a genetically recombinant antibody is not limited. Examples include a chimeric antibody, a humanized antibody, and a human antibody.

A chimeric antibody (that is, a humanized chimeric antibody) is an antibody formed by ligating (conjugating) the variable region of a mouse-derived antibody to the constant region of a human-derived antibody (please refer to Proc. Natl. Acad. Sci. U.S.A. 81, 6851-6855, (1984), etc.). When such a chimeric antibody is produced, the thus ligated antibody can be easily constructed by a genetic recombination technique.

When a humanized antibody is produced, a complementarity determining region (CDR) is transplanted from the variable region of a mouse antibody into the variable region of a human antibody, so as to produce a reconstructed variable region, in which a framework region (FR) is derived from the human and CDR is derived from the mouse (what is called CDR grafting (CDR transplantation)). Subsequently, the thus humanized, reconstructed human variable region is ligated to a human constant region. Such a method for producing a humanized antibody is well known in the present technical field (please refer to see Nature, 321, 522-525 (1986); J. Mol. Biol., 196, 901-917 (1987); Queen C et al., Proc. Natl. Acad. Sci. USA, 86: 10029-10033 (1989); JP Patent Publication (Kohyo) No. 4-502408 A (1992) (Japanese Patent No. 2828340; Queen et al.), etc.).

In general, in the case of a human antibody (a complete human antibody), its structure comprising a Hyper Variable region that is the antigen-binding site of a V region, other parts of the V region, and a constant region is the same as the structure of the antibody of a human. However, such a Hyper Variable site may also be derived from other animals. A technique of producing a human antibody is publicly known, and a method for producing gene sequences that are common in humans by genetic engineering has been established. A human antibody can be obtained, for example, by a method using a human antibody-producing mouse that has human chromosomal fragments comprising the genes of the H chain and L chain of the human antibody (please refer to Tomizuka, K. et al., Nature Genetics, (1977) 16, 133-143; Kuroiwa, Y. et. al., Nuc. Acids Res., (1998) 26, 3447-3448; Yoshida, H. et. al., Animal Cell Technology: Basic and Applied Aspects, (1999) 10, 69-73 (Kitagawa, Y., Matsuda, T. and Iijima, S. eds.), Kluwer Academic Publishers; Tomizuka, K. et. al., Proc. Natl. Acad. Sci. USA, (2000) 97, 722-727, etc.), or by a method of obtaining a phage display-derived human antibody selected from a human antibody library (please refer to Wormstone, I. M. et. al, Investigative Ophthalmology & Visual Science., (2002) 43 (7), 2301-8; Carmen, S. et. al., Briefings in Functional Genomics and Proteomics, (2002) 1 (2), 189-203; Siriwardena, D. et. al., Opthalmology, (2002) 109 (3), 427-431, etc.).

In the case of the aforementioned chimeric antibody, humanized antibody and human antibody, the N-glycoside-linked sugar chain in the antibody Fc region is preferably a sugar chain, in which fucose does not bind to N-acetylglucosamine at the reducing terminal thereof. A specific example is an antibody consisting of genetically recombinant antibody molecules, which has, in the Fc region of the antibody molecules, a sugar chain in which the position 1 of the fucose does not bind to the position 6 of the N-acetylglucosamine at the reducing terminal of the N-glycoside-linked sugar chain via an a bond. Such an antibody is able to significantly improve ADCC activity. This point (the characteristics of the N-glycoside-linked sugar chain in the antibody Fc region) is preferable also for the aforementioned polyclonal antibody and monoclonal antibody.

(4-2) Antibody Fragment

The anti-hTROP-2 antibody fragment (partial fragment) of the present invention is included in the antibody of the present invention. Herein, the antibody fragment of the present invention has binding activity to hTROP-2 (namely, it is able to bind to hTROP-2) and also has anti-tumor activity in vivo, as in the case of the anti-hTROP-2 antibody of the present invention.

The fragment of the antibody means a region of a portion of an anti-hTROP-2 polyclonal antibody or anti-hTROP-2 monoclonal antibody (namely, an antibody fragment derived from the anti-hTROP-2 antibody of the present invention). Examples of such an antibody fragment include peptides comprising, as at least a portion thereof, Fab, Fab', F(ab')$_2$, Fv (variable fragment of antibody), a single-stranded antibody (an H chain, an L chain, an H chain V region, and an L chain V region, etc.), scFv, diabody (scFv dimer), dsFv (a disulfide-stabilized V region), and a complementarity determining region (CDR).

Fab is an antibody fragment with a molecular weight of approximately 50,000 having antigen-binding activity, which is formed by binding about a half on the N-terminal side of the H chain to the entire L chain via a disulfide bond, among fragments obtained by treating antibody molecules with a protease, papain. In addition, it is also possible to produce such Fab by inserting DNA encoding the Fab of an antibody into a prokaryote expression vector or a eukaryote expression vector, and then introducing the vector into a prokaryote or a eukaryote so as to allow the DNA to express therein.

F(ab')$_2$ is an antibody fragment with a molecular weight of approximately 100,000 having antigen-binding activity, whose size is slightly greater than Fab that binds to Fab via disulfide bond in the hinge region, among fragments obtained by treating antibody molecules with a protease, pepsin. In addition, it is also possible to produce such F(ab')$_2$ by the thioether bond or disulfide bond of Fab, as described later.

Fab' is an antibody fragment with a molecular weight of approximately 50,000 having antigen-binding activity, which is formed by cleaving the disulfide bond in the hinge region of the aforementioned F(ab')$_2$. In addition, it is also possible to produce such Fab' by inserting DNA encoding the Fab' fragment of an antibody into a prokaryote expression vector or a eukaryote expression vector, and then introducing the vector into a prokaryote or a eukaryote so as to allow the DNA to express therein.

scFv is an antibody fragment having antigen-binding activity, which is a VH-P-VL or VL-P-VH polypeptide formed by ligating a single H chain V region (VH) to a single L chain V region (VL) using a suitable peptide linker (P). Such scFv can be produced by obtaining cDNA encoding the VH and VL of an antibody, constructing DNA encoding scFv, inserting the DNA into a prokaryote expression vector or a eukaryote expression vector, and then introducing the vector into a prokaryote or a eukaryote so as to allow the DNA to express therein.

Diabody is an antibody fragment formed by dimerization of scFv, which has divalent antigen-binding activities. Such divalent antigen-binding activities may be identical to each other, or they may also be different from each other. Such diabody can be produced by obtaining cDNA encoding the VH and VL of an antibody, constructing DNA encoding scFv such that the length of the amino acid sequence of P is 8 residues or less, inserting the DNA into a prokaryote expression vector or a eukaryote expression vector, and then introducing the vector into a prokaryote or a eukaryote so as to allow the DNA to express therein.

dsFv is an antibody fragment formed by binding polypeptides, in which one amino acid residue in each of VH and VL has been substituted with a cysteine residue, to each other via a disulfide bond between the cysteine residues. The amino acid residue to be substituted with cysteine residues can be selected based on estimation of the three-dimensional structure of the antibody according to the method of Reiter et al. (Protein Engineering, 7, 697-704, 1994). Such dsFv can be produced by obtaining cDNA encoding the VH and VL of an antibody, constructing DNA encoding dsFv, inserting the DNA into a prokaryote expression vector or a eukaryote expression vector, and then introducing the vector into a prokaryote or a eukaryote so as to allow the DNA to express therein.

A peptide comprising a CDR comprises at least one region of CDRs of VH (CDR 1 to 3) and CDRs of VL (CDR 1 to 3). More preferred examples of such a peptide include a peptide comprising all of the CDRs of VH and a peptide comprising all of the CDRs of VL. A particularly preferred example of the peptide is a peptide comprising all of the CDRs of VH and VL (total 6 regions). Preferred examples of the amino acid sequence of such a CDR include the amino acid sequences shown in SEQ ID NOS: 36 to 38, 41 to 43, 46 to 48, 51 to 53, 56 to 58, 61 to 63, 66 to 68, and 71 to 73, as described above. A peptide comprising multiple CDRs can be bound to one another, directly or via a suitable peptide linker. Such a peptide comprising CDR can be produced by constructing DNA encoding the VH and VL of an antibody, inserting the DNA into a prokaryote expression vector or a eukaryote expression vector, and then introducing the expression vector into a prokaryote or a eukaryote so as to allow the DNA to express therein. Moreover, such a peptide comprising CDR can also be produced by chemical synthesis methods such as a Fmoc method (a fluorenylmethyloxycarbonyl method) and a tBoc method (a t-butyloxycarbonyl method).

The antibody fragment of the present invention, as is, may be an antibody fragment, which comprises a part of or the entire antibody Fc region in which fucose does not bind to N-acetylglucosamine at the reducing terminal of an N-glycoside-linked sugar chain. Otherwise, the antibody fragment of the present invention may also be a fusion protein, in which the aforementioned antibody fragment is fused with a part of or the entire antibody Fc region in which fucose does not bind to N-acetylglucosamine at the reducing terminal of an N-glycoside-linked sugar chain. Such an antibody fragment is able to significantly improve ADCC activity, and thus it is preferable.

Hereinafter, in the descriptions of the present specification, the aforementioned antibody fragments are also included in the anti-hTROP-2 antibody of the present invention.

3. Preparation of Antibody-Drug Conjugate

As an immunoconjugate prepared using the aforementioned anti-hTROP-2 antibody of the present invention, there can be provided an antibody-drug conjugate, which comprises the aforementioned antibody and a substance (a compound, etc.) having anti-tumor activity and/or cell-killing activity. It is to be noted that a conjugate formed by previously preparing each of the aforementioned antibody molecule and the aforementioned substance having anti-tumor activity and/or cell-killing activity, separately, and then combining them, is generally referred to as an immunoconjugate. On the other hand, a conjugate obtained by ligating a protein toxin used as such a substance having anti-tumor activity and/or cell-killing activity to an antibody gene on a gene according to a genetic recombination technique, so as to allow it to express as a single protein (a fusion protein), is generally referred to as an immunotoxin.

Examples of a substance having anti-tumor activity include doxorubicin, calicheamicin, mitomycin C, Auristatin E and radioactive isotope (RI). Examples of a substance having cell-killing activity include saporin, lysine, *pseudomonas* exotoxin, diphtheria toxin and radioactive isotope (RI). Of these, saporin and *pseudomonas* exotoxin are preferably used. The type of RI having anti-tumor activity and/or cell-killing activity is not particularly limited, and examples of such RI include $^{90}Y$, $^{111}In$, $^{125}I$, $^{3}H$, $^{35}S$, $^{14}C$, $^{186}Re$, $^{188}Re$, $^{189}Re$, $^{177}Lu$, $^{67}Cu$, $^{212}Bi$, $^{213}Bi$, $^{211}At$, $^{198}Au$, $^{224}Ac$, $^{126}I$, $^{133}I$, $^{77}Br$, $^{113m}In$, $^{95}Ru$, $^{97}Ru$, $^{103}Ru$, $^{105}Ru$, $^{107}Hg$, $^{203}Hg$, $^{94m}Tc$, $^{121m}Te$, $^{122m}Te$, $^{125m}Te$, $^{165}Tm$, $^{167}Tm$, $^{168}Tm$, $^{111}Ag$, $^{197}Pt$, $^{109}Pd$, $^{32}P$, $^{33}P$, $^{47}Sc$, $^{153}Sm$, $^{177}Lu$, $^{105}Rh$, $^{142}Pr$, $^{143}Pr$, $^{161}Tb$, $^{166}Ho$, $^{199}Au$, $^{57}Co$, $^{58}Co$, $^{51}Cr$, $^{59}Fe$, $^{18}F$, $^{75}Se$, $^{201}Tl$, $^{225}Ac$, $^{76}Br$, $^{86}Y$, $^{169}Yb$, $^{166}Dy$, $^{212}Pb$ and $^{223}Ra$.

A method for producing an antibody-drug conjugate is not limited. For example, a method of coupling an antibody with a drug via a disulfide bond or a hydrazone bond is applied.

The aforementioned anti-hTROP-2 antibody of the present invention is excellent in terms of internalization activity into target tumor cells that express hTROP-2. Thus, by previously combining a substance having anti-tumor activity and cell-killing activity with the anti-hTROP-2 antibody, it becomes possible to allow such a substance to directly and highly selectively act on the tumor cells. The antibody-drug conjugate of the present invention is extremely excellent in terms of ability to deliver the agent to the target tumor cells.

The internalization activity into cells can be evaluated by fluorescently labeling an antibody with rhodamine or the like and then observing the migratory behavior and localization of the antibody using a fluorescence microscope or the like.

Moreover, in the present invention, in addition to the aforementioned antibody-drug conjugate, there can also be provided an antibody fragment-drug conjugate, in which the aforementioned antibody fragment is used instead of an antibody. With regard to the details of such an antibody fragment-drug conjugate, the descriptions of the aforementioned antibody-drug conjugate can be applied, as appropriate.

Hereinafter, in the descriptions of the present specification, such an antibody fragment-drug conjugate is also included in the antibody-drug conjugate of the present invention.

4. Pharmaceutical Composition

The anti-hTROP-2 antibody and antibody-drug conjugate of the present invention are useful as active ingredients contained in a pharmaceutical composition.

The pharmaceutical composition is useful as a pharmaceutical composition for treating and/or diagnosing a tumor. In particular, since the anti-hTROP-2 antibody of the present invention and an antibody-drug conjugate comprising the aforementioned antibody have excellent tumor growth inhibitory activity as such anti-tumor activity, they are preferably used in the treatment of tumor. That is to say, the anti-hTROP-2 antibody and antibody-drug conjugate of the present invention are useful as active ingredients contained in a tumor therapeutic agent and a tumor diagnostic agent. It is to be noted that the above-described treatment of tumor includes inhibition of tumor growth and suppression of tumor growth. Specifically, if it is a tumor therapeutic agent, examples of the tumor therapeutic agent include a tumor growth inhibitor and a tumor growth suppressor.

It is preferable to provide the pharmaceutical composition of the present invention in the form of a pharmaceutical composition comprising the anti-hTROP-2 antibody and/or antibody-drug conjugate of the present invention as active ingredient(s), and further comprising a pharmacologically acceptable carrier. In addition, the pharmaceutical composition of the present invention can be used in combination with known anti-tumor agents. By such a combined use, a higher anti-tumor effect can be obtained.

Target diseases (tumors), to which the pharmaceutical composition of the present invention is applied, include: the aforementioned various types of known human tumors, in which the expression of hTROP-2 has previously been confirmed. Among others, one or two or more types selected from among human pancreatic cancer, human prostate cancer, human colon cancer and human breast cancer are particularly preferable. Such target disease may be a single disease, or two or more diseases may be developed in combination. Moreover, the target tumor may be a recurrent cancer or a metastatic cancer. The pharmaceutical composition of the present invention (further, the anti-hTROP-2 antibody and/or antibody-drug conjugate of the present invention) can be effectively used as a therapeutic agent and a diagnostic agent for a recurrent cancer or a metastatic cancer.

Examples of the "pharmacologically acceptable carrier" include an excipient, a diluent, an extender, a disintegrator, a stabilizer, a preservative, a buffer, an emulsifier, an aromatic, a coloring agent, a sweetener, a thickener, a corrigent, a solubilizer and other additives. Using one or more types of such carriers, a pharmaceutical composition can be prepared in the form of an injection, a liquid agent, a capsule, a suspension, an emulsion, a syrup, etc. These pharmaceutical compositions can be administered orally or parenterally. Another form for parenteral administration is, for example, an injection comprising one or more active ingredients, which is prepared by an ordinary method. Such an injection can be produced by dissolving or suspending the present antibody in a pharmacologically acceptable carrier such as a normal saline solution or a commercially available distilled water used for injection.

In particular, when an antibody fragment derived from the anti-hTROP-2 antibody of the present invention (particularly, an antibody fragment with a low molecular weight) is administered into a living body, a colloidal dispersion system can be used in addition to the aforementioned components. Such a colloidal dispersion system is anticipated to have an effect of enhancing the stability of a compound (an antibody fragment) in a living body or an effect of efficiently transporting such a compound to a specific organ, tissue, or cell. The type of such a colloidal dispersion system is not limited, as long as it is commonly used. Examples of such a colloidal dispersion system include dispersion systems comprising, as bases, polyethylene glycol, a macromolecular conjugate, a macromolecular aggregate, a nanocapsule, microsphere, beads, and lipids including an oil in water emulsifier, micelle, mixed micelle and liposome. Preferred examples of such a colloidal dispersion system include multiple liposomes and the vesicles of artificial membrane, which have an effect of efficiently transporting such a compound to a specific organ, tissue, or cell (Mannino et al., Biotechniques, 1988, 6, 682; Blume and Cevc, Biochem. et Biophys. Acta, 1990, 1029, 91; Lappalainen et al., Antiviral Res., 1994, 23, 119; Chonn and Cullis, Current Op. Biotech., 1995, 6, 698).

The dosage of the pharmaceutical composition of the present invention differs depending on the age, sex, body weight and symptoms of a patient, therapeutic effects, an administration method, a treatment time, the types of the anti-hTROP-2 antibody and antibody-drug conjugate of the present invention contained in the pharmaceutical composition, etc. In general, the present pharmaceutical composition may be administered within the range between 600 μg and 6,000 mg per adult per administration. However, the dose is not limited to the aforementioned range.

In a case in which the pharmaceutical composition is administered in the form of an injection, for example, it may be administered at a dosage of 100 μg to 100 mg, per administration, per body weight of a human patient, once or divided over several administrations, as an average daily dose. Preferably, the pharmaceutical composition may be administered once every three days, once a week, once every ten days, or once every two weeks, or by a single administration (wherein the total number of administrations is 1). Examples of the dosage form include intravenous injection, subcutaneous injection, intradermal injection, intramuscular injection and intraperitoneal injection. Of these, intravenous injection is preferable. In addition, such an injection may be prepared in the form of a nonaqueous diluent (e.g. polyethylene glycol, vegetable oil such as olive oil, alcohols such as ethanol, etc.), a suspension, or an emulsion. Such an injection can be sterilized by mechanical sterilization using a filter, the mixing of a microbicide, etc. The injection can be produced in the form of an injection to be prepared before using. That is, a sterilized solid composition is prepared by a freeze-drying method or the like, and the composition is then dissolved in sterilized distilled water used for injection or other solvents before it is used, so that it can be then used.

The present invention provides a use of the aforementioned anti-hTROP-2 antibody and/or antibody-drug conjugate of the present invention in the production of a pharmaceutical agent (a drug) for treating and/or diagnosing a tumor. In addition, the present invention provides the aforementioned anti-hTROP-2 antibody and/or antibody-drug conjugate of the present invention, which are used for treating and/or diagnosing a tumor.

Moreover, the present invention provides a method for treating and/or diagnosing a tumor, which is characterized in that it comprises using (namely, administering to patients) the aforementioned anti-hTROP-2 antibody and/or antibody-drug conjugate of the present invention. Furthermore, the present invention also provides the use of the aforementioned anti-hTROP-2 antibody and/or antibody-drug conjugate of the present invention in the treatment and/or diagnosis of tumor.

5. Method for Detecting Tumor

The method for detecting a tumor of the present invention is characterized in that it comprises allowing the aforementioned anti-hTROP-2 antibody of the present invention to react with a sample collected from a living body (hereinafter referred to as a biological sample), and detecting a signal(s) of the reacted antibody.

As described above, hTROP-2 has been confirmed to be specifically expressed in various types of tumor cells. Thus, hTROP-2, and particularly, free hTROP-2 (an extracellular region portion of hTROP-2) can be used as a marker for various types of tumors. In particular, such hTROP-2 can be preferably used as a marker for human pancreatic cancer, human prostate cancer, human colon cancer and human breast cancer.

Hence, the anti-hTROP-2 antibody of the present invention is allowed to react with a biological sample, and a signal of the reacted antibody is then detected, so as to detect a tumor. The obtained antibody signal can be used as an indicator of the amount of an antigen in the biological sample (that is, an hTROP-2 amount or a free hTROP-2 amount). In detection of a tumor using the antibody of the present invention, first, a biological sample collected as an analyte from a subject, such as a tissue section or blood used as a test target, is allowed to bind to the antibody of the present invention by an antigen-antibody reaction. Subsequently, based on the measurement results of the amount of the bound antibody, the amount of an antigen of interest contained in the biological sample is measured. This measurement may be carried out in accordance with known immunoassay methods. For example, an immunoprecipitation method, an immunoagglutination method, radioimmunoassay, immunonephelometry, a Western blot method, flow cytometry and the like can be used. In radioimmunoassay, a labeled antibody is used, and thus an antibody signal is expressed as the amount of the labeled antibody that is directly detected. Otherwise, an antibody whose concentration or antibody titer has been known may be used as a standard solution, and thus a signal of the target antibody may be expressed as a relative value. That is, both the standard solution and the analyte may be measured using a measurement device, and an antibody signal in a biological sample may be expressed as a value relative to the value of the standard solution used as a criterion. Examples of such radioimmunoassay include the ELISA method, the EI method, the RIA method, fluorescence immunoassay (FIA), and luminescence immunoassay. Of these, the ELISA method is particularly preferable in that it is simple and highly sensitive.

In the present invention, the state of a tumor can be evaluated or diagnosed, using the detection result obtained by the aforementioned detection method as an indicator. For example, when the detection result exceeds a predetermined standard value, the state of a tumor is defined as tumor positive, and when the detection result is less than the predetermined standard value, it is defined as tumor negative. In the case of tumor positive, it is determined that a certain type of tumor could have been developed, and thus the tumor state can be evaluated. The term "the state of a tumor" is used herein to mean the presence or absence of the development of a tumor, or the progression degree thereof. Thus, specific examples of the state of a tumor include the presence or absence of the development of a tumor, the progression degree thereof, the degree of malignancy, the presence or absence of metastasis, and the presence or absence of recurrence.

In the aforementioned evaluation, as a state of a tumor to be evaluated, only one state may be selected from the aforementioned examples, or multiple examples may be combined and selected. The presence or absence of a tumor can be evaluated by determining whether or not the tumor has been developed, with reference to the predetermined standard value used as a boundary, based on the obtained detection result. The degree of malignancy is used as an indicator that indicates the progression degree of a cancer. Based on the detection result, the target tumor can be classified into a certain disease stage and it can be evaluated. Otherwise, an early cancer and an advanced cancer can be distinguished from each other, and then they can be evaluated. For example, it is also possible to determine the target tumor as an early cancer or an advanced cancer, using the detection result as an indicator. The metastasis of tumor can be evaluated by determining whether or not neoplasm has appeared at a site apart from the position of the initial lesion, using the detection result as an indicator. The recurrence can be evaluated by determining whether or not the detection result has exceeded the predetermined standard value again after interval stage or remission.

6. Kit for Detecting or Diagnosing Tumor

The anti-hTROP-2 antibody of the present invention can be provided in the form of a kit for detecting or diagnosing a tumor. The kit of the present invention comprises a labeling substance, a solid-phase reagent on which the antibody or the labeled antibody has been immobilized, etc., as well as the aforementioned antibody. A labeling substance that labels the antibody means a substance labeled with an enzyme, a radioisotope, a fluorescent compound, a chemiluminescent compound, etc. The kit of the present invention may also comprise other reagents used for carrying out the detection of the present invention, in addition to the aforementioned constitutional elements. For example, when such a labeling substance is an enzyme labeling substance, the kit of the present invention may comprise an enzyme substrate (a chromogenic substrate, etc.), an enzyme substrate-solving solution, an enzyme reaction stop solution, a diluent used for analytes, etc. Moreover, the present kit may further comprise various types of buffers, sterilized water, various types of cell culture vessels, various types of reactors (an Eppendorf tube, etc.), a blocking agent (a serum component such as bovine serum albumin (BSA), skim milk, or goat serum), a washing agent, a surfactant, various types of plates, an antiseptic such as sodium azide, an experimental operation manual (instruction), etc.

The kit of the present invention can be effectively used to carry out the aforementioned detection method of the present invention, and thus it is extremely useful.

Hereinafter, the present invention will be more specifically described in the following examples. However, these examples are not intended to limit the scope of the present invention.

Example 1

Cloning of hTROP-2 Gene

A full-length hTROP-2 gene was isolated from human fetal liver (10-week-old embryo) according to an RT-PCR method. First, the following PCR primers were designed based on the sequence of an hTROP-2 gene (Genbank accession No. NM_002353).

```
Forward primer:
                                        (SEQ ID NO: 3)
5'-ttcctccgccccaccatggc-3'

Reverse primer:
                                        (SEQ ID NO: 4)
5'-ctcgagcaagctcggttcctttctc-3'
```

When these primers were designed, a XhoI restriction enzyme-digested sequence except for a stop codon was added to the reverse primer. cDNA was synthesized from total RNA (TAKARA) prepared from human fetal liver (10-week-old embryo). Using this cDNA as a template, a PCR reaction was carried out with the aforementioned primers. Thereafter, development by agarose gel electrophoresis and extraction of a band of interest were carried out, and it was then cloned into a pCRII vector (Invitrogen) (pCRII-hTROP-2). The cloned hTROP-2 cDNA was confirmed by sequencing.

An expression vector was constructed by cleaving a EcoRI/XhoI fragment comprising an hTROP-2 gene from pCRII-hTROP-2, and then inserting the fragment into the EcoRI/XhoI site of a pcDNA4/myc-His© A vector (Invitrogen) (pcDNA4-hTROP-2-myc/His). Moreover, a HindIIIPmeI fragment comprising an hTROP-2 gene was cut out of pcDNA4-hTROP-2-myc/His (wherein the HindIII cleavage portion was blunt-ended), and the fragment was then inserted into a PmeI site of a pcDNA3.1(+) vector (Invitrogen), so as to construct an expression vector comprising a neomycin resistance gene (pcDNA3.1-hTROP-2-myc/His).

Example 2

Construction of Cell Line Capable of Stably Expressing hTROP-2 Gene

The expression vector (pcDNA3.1-hTROP-2-myc/His) encoding the full-length cDNA of hTROP-2, which had been produced by the above-described method, was introduced into HEK293 cells (RIKEN), HuH-7 cells (HSRRB), 7E2-C cells (described in WO 2005/052156) and CHO-K1 cells (HSRRB), using a lipofectamine 2000 reagent (Invitrogen), and selection was then carried out using an antibiotic G418 (geneticin; GIBCO BRL). Thereafter, a cell line, which stably expressed hTROP-2, was established and obtained.

Example 3

Production of Recombinant Protein of hTROP-2 Extracellular Region

A gene fragment encoding a portion of the extracellular region of hTROP-2 (specifically, a region consisting of amino acids at positions 1 to 263 from the amino acid sequence shown in SEQ ID NO: 2) was amplified by a PCR method. The following primers were used in the amplification.

```
Forward primer:
                                        (SEQ ID NO: 3)
5'-ttcctccgccccaccatggc-3'

Reverse primer:
                                        (SEQ ID NO: 5)
5'-ctcgagctcgtccaggtaatagatgagcg-3'
```

In this operation, a XhoI restriction enzyme-digested sequence was added to the reverse primer. The DNA fragment amplified by the PCR method was developed by agarose gel electrophoresis, and it was then purified using QIAquick (registered trademark) Gel Extraction Kit (QIAGEN). The purified DNA fragment was subcloned into a pCR Blunt vector (Invitrogen) (pCRB-hTROP-2 EC), and the gene sequence was confirmed. Subsequently, a EcoRI/XhoI fragment comprising the gene fragment encoding the extracellular region of hTROP-2 was cut out of the pCRB-hTROP-2 EC, and it was then inserted into the EcoRI/XhoI site of a pcDNA4/myc-His© A vector (Invitrogen) (pcDNA4mH-hTROP-2 EC).

Further, in order to produce a NruI restriction enzyme cleavage site, the following oligonucleotides were associated and inserted into the BamHI/EcoRI site of the pcDNA4mH-hTROP-2 EC.

```
Oligonucleotide 1:
                             (SEQ ID NO: 6)
5'-gatccactagtcgcgagtggtgg-3'

Oligonucleotide 2:
                             (SEQ ID NO: 7)
5'-aattccaccactcgcgactagtgg-3'
```

Likewise, a pBgl II linker (TAKARA) was inserted into the PmeI site of the pcDNA4mH-hTROP-2 EC (pcDNA4mH-NB-hTROP-2 EC). In order to produce a recombinant protein using baculovirus, a NruI/BglII fragment comprising the gene fragment encoding the extracellular region of hTROP-2 was cut out of the pcDNA4mH-NB-hTROP-2 EC, and it was then inserted into the NruI/BglII site of a pPSC8 vector (Nosan Corporation) (pPSC8-hTROP-2 EC). The production of the recombinant protein of the extracellular region of hTROP-2 using baculovirus was delegated to Nosan Corporation.

The recombinant protein of the extracellular region of hTROP-2 was purified as follows. Ni Sepharose 6 Fast Flow (GE Healthcare Biosciences) was added to a culture supernatant comprising the recombinant protein, so that they were allowed to bind to each other at 4° C. for 2 hours. Thereafter, the resultant was washed with a phosphate buffer containing 20 mM imidazole, employing EconoColumn (BIO RAD), and it was then eluted with a phosphate buffer containing 300 mM imidazole, so that it was purified.

Example 4

Isolation of Human EpCAM cDNA and Construction of Expression Vector

A full-length human EpCAM gene was isolated from human fetal liver (10-week-old embryo) according to an RT-PCR method. First, the following PCR primers were designed based on the sequence of a human EpCAM gene (Genbank accession No. NM_002354).

```
Forward primer:
                             (SEQ ID NO: 8)
5'-tcctcgtgtcccactcccgg-3'

Reverse primer:
                             (SEQ ID NO: 9)
5'-ctcgagtgcattgagttccctatgc-3'
```

When these primers were designed, a XhoI restriction enzyme-digested sequence except for a stop codon was added to the reverse primer. cDNA was synthesized from total RNA (TAKARA) from human fetal liver (10-week-old embryo). Using this cDNA as a template, a PCR reaction was carried out with the aforementioned primers. Thereafter, development by agarose gel electrophoresis and extraction of a band of interest were carried out, and it was then cloned into a pCRII vector (Invitrogen) (pCRII-hEpCAM). The cloned human EpCAM cDNA was confirmed by sequencing.

An expression vector was constructed by cleaving a EcoRI/XhoI fragment comprising a human EpCAM gene from pCRII-hEpCAM, and then inserting the fragment into the EcoRI/XhoI site of a pcDNA4/myc-His© A vector (Invitrogen) (pcDNA4-hEpCAM-myc/His). Moreover, a HindIII/PmeI fragment comprising a human EpCAM gene was cut out of pcDNA4-hEpCAM-myc/His (wherein the HindIII cleavage portion was blunt-ended), and the fragment was then inserted into the PmeI site of a pcDNA3.1(+) vector (Invitrogen), so as to construct an expression vector comprising a neomycin resistance gene (pcDNA3.1-hEpCAM-myc/His).

Example 5

Production of Anti-hTROP-2 Monoclonal Antibody

As immunogens, there were used cell lines capable of stably expressing hTROP-2 (HEK293-hTROP-2 cells, CHO-K1-hTROP-2 cells and 7E2-C-hTROP-2 cells); human pancreatic cancer cell line endogenously expressing an hTROP-2 protein on the cell surface (PK-59, RCB1901; purchased from RIKEN cell bank); and the recombinant protein of the extracellular region of hTROP-2 produced by the above-described method.

In the case of the cell lines capable of stably expressing hTROP-2, $1\times10^7$ cells were used, and in the case of the recombinant hTROP-2 protein, 20 µg of the protein was used. The cell lines or the recombinant protein was mixed with an adjuvant TiterMax Gold (Funakoshi Corporation) at a mixing ratio of 1:1, so as to prepare an emulsion. The emulsion was then injected into the two footpads or abdominal cavity of a mouse (C57/BL6, Balb/c) (initial immunization). When immunization was carried out by injection into the two footpads for a short period of time, booster was carried out three to ten days after the initial immunization. On the day following the final immunization, lymph nodes were collected from both knees, and lymphocytes were then prepared. When immunization was carried out by injection into the abdominal cavity for a long period of time, boosters were carried out at intervals of once a week after the initial immunization (wherein boosters were carried out for 1 to 2 months). Thereafter, B cells were isolated from the spleen according to an ordinary method. In the case of immunization using cells as immunogens, a cell suspension which was PBS containing $5\times10^6$ cells was used for boosters. In the case of using a protein as an immunogen, 5 µg of a PBS solution was used.

The prepared lymphocytes were mixed with a mouse myeloma cell line (P3-X63-Ag8.653) at a mixing ratio of 3:1, and cell fusion was then carried out according to a polyethylene glycol method. Thereafter, the fused cells were cultured for 7 to 28 days in a methyl cellulose medium (trade name: ClonaCell-HY Cloning Medium D; Stem Cell), which contained HAT (hypoxanthine, aminopterin and thymidine). Single colonies of growing hybridomas were each picked up and placed on a 96-well flat-bottom plate, and using a liquid selective medium containing HAT, the hybridomas were cultured in a 5% $CO_2$ incubator. A culture supernatant of growing hybridomas from single colonies was subjected to a primary screening via Cell ELISA (described later) and then to a secondary screening via FACS analysis using HuH-7-hTROP-2 cells, PK-59, thereby establishing 300 types of hybridomas, which produce anti-hTROP-2 monoclonal antibodies recognizing hTROP-2 proteins expressed on the cell surface of living cells.

Example 6

Primary Screening Using Cell ELISA

CHO-K1 cells (hTROP-2 negative control; purchased from Japan Health Sciences Foundation) and CHO-K1-hTROP-2 cells (or HUH-7 cells (hTROP-2 negative control;

purchased from Japan Health Sciences Foundation) and HuH-7-hTROP-2 cells) were alternately inoculated on a 96-well culture plate (BD Falcon) at a cell density of 3×10$^4$ cells/well, and the cells were then cultured in a 5% $CO^2$ atmosphere at 37° C. for 1 to 2 days. The cell culture medium was removed by decantation. Thereafter, the cells were washed with ice-cold PBS, and were then treated with 4% paraformaldehyde-PBS for 5 minutes, so that the cells were immobilized. The cells were washed with PBS which had been cooled on ice, and an ELISA plate was then prepared. Thereafter, ELISA was carried out according to an ordinary method. Specific procedures will be described below.

First, blocking with a 2% skim milk-PBS solution was carried out at room temperature for 30 minutes to 1 hour. Subsequently, the hybridoma culture supernatant was added thereto, and they were then reacted at room temperature for 1 hour. Thereafter, the resultant was washed with a 0.1% Tween20-PBS solution three times. As a secondary antibody, Horseradish peroxidase (HRP)-labeled anti-mouse IgG (GE Healthcare Biosciences), which had been 1000 times diluted with a blocking solution, was added to the resultant, and they were then reacted at room temperature for 1 hour. Thereafter, the resultant was washed with a 0.1% Tween20-PBS solution three times. A TMB (3,3',5,5'-tetramethylbenzidine: SIGMA) substrate solution was added to the reaction solution to carry out a color reaction, and the reaction was then terminated by adding 1 M sulfuric acid. Thereafter, absorbance (405 nm) was measured using Microplate reader Model 550 (BIO RAD). Hybridomas corresponding to a hybridoma culture supernatant exhibiting a high absorbance value to the negative control were subjected to a large-scale culture on a 24-well flat-bottom plate, and were then subjected to a secondary screening using FACS analysis.

Example 7

Secondary Screening Using FACS Analysis

Hybridomas, which were found positive in the above-described primary screening using Cell ELISA, were subjected to a secondary screening using FACS analysis. In the evaluation of Hybridoma cells, HuH-7 cells, which were human liver cancer cells which did not express hTROP-2, were used as negative control cells and the reactivity with HuH-7-hTROP-2 cells, which were stably expressing hTROP-2, was used as an indicator. Then, the evaluation was carried out based on the reactivity with PK-59 cells (RCB1901; purchased from RIKEN cell bank), which were human pancreatic cancer cells endogenously expressing an hTROP-2 protein on the cell surface.

The cells were removed from the culture dish by a trypsin treatment, and a cell suspension was then prepared (cell density: 2×10$^6$ cells/mL). The hybridoma culture supernatant, which exhibited positive in the primary screening using Cell ELISA, was reacted with 100 μL of the cell suspension at 4° C. for 20 minutes. The reaction mixture was washed with PBS, and it was then reacted with PE-labeled mouse IgG (BD Pharmingen) (0.1 μg) 4° C., 30 minutes). Thereafter, the reaction mixture was analyzed using FACSCalibur (Becton, Dickinson and Company).

Eventually, approximately 300 types of hybridomas, which produce an anti-hTROP-2 monoclonal antibody recognizing an hTROP-2 protein expressed on the cell surface of living cells, were established.

Example 8

Identification of Isotype

The isotype of the produced anti-hTROP-2 monoclonal antibody was identified using MOUSE MONOCLONAL ANTIBODY ISOTYPING TEST KIT (Serotec) in accordance with a method included with the above-mentioned kit.

Example 9

Ascites Formation and Purification of TROP-2 Antibody

The hybridoma clones produced by the above-described method were administered at a density of 3×10$^6$ clones into the abdominal cavity of a BALB/c nude mouse, to which 2,6,10,14-tetramethylpentadecane (pristane) had previously (seven days before) been administered. Two weeks later, ascites was collected. Moreover, this ascites was subjected to caprylic acid precipitation, and then to affinity purification using a protein G column (HiTrap protein G; GE Healthcare Biosciences) or a protein A column (HiTrap protein A; GE Healthcare Biosciences), so as to obtain anti-hTROP-2 monoclonal antibodies from individual hybridoma clones.

Example 10

Measurement of Antigen Binding Affinity (Measurement of Kd Value)

The antigen binding affinity (Kd value) of the generated anti-hTROP-2 monoclonal antibody was calculated by a method using ELISA (Djavadi-Ohaniance L. et al (1996), In Antibody Engineering, Chapter 4, pp. 77-97. IRL Press, Oxford).

Specifically, the purified recombinant hTROP-2 protein (0.1 μg/mL) was added to a 96-well culture plate (Corning) so that the antigen was solid-phased (at room temperature for 1 hour, or at 4° C. overnight). Subsequently, the resultant was washed with PBS three times, and 2% skim milk (PBS solution) was then added thereto to block it (at room temperature for 1 hour). The resultant was washed with PBS twice. Thereafter, an antigen-antibody complex which had previously been formed by mixing an antigen solution (a purified hTROP-2 protein; 50, 25, 12.5, 6.25, or 3.125 nM) with each clone (0.5 nM) of the anti-hTROP-2 monoclonal antibody and then equilibrating the mixture, was added to the above-described ELISA plate, and they were reacted (at room temperature for 1 hour). The reaction product was washed with PBS three times, and it was then reacted with HRP-labeled anti-mouse IgG (final concentration: 1 μg/mL) (GE Healthcare Biosciences) diluted with a blocking solution (at room temperature for 1 hour). Subsequently, the reaction product was washed with a 0.1% Tween20-PBS solution three times, and a TMB (3,3',5,5'-tetramethylbenzidine: SIGMA) substrate solution was then added to the resultant to carry out a color reaction. Then, 1 M sulfuric acid was added to the reaction product to terminate the reaction. Using Microplate reader Model 550 (BIO RAD), absorbance was measured.

The following calculation expressions were used to measure dissociation constant (Kd).

In accordance with the law of mass action, an antigen-antibody reaction is represented by the following expressions.

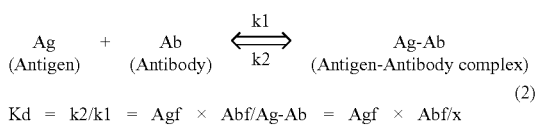

$$Ag + Ab \underset{k2}{\overset{k1}{\longleftrightarrow}} Ag\text{-}Ab \quad (1)$$
(Antigen) (Antibody) (Antigen-Antibody complex)

$$Kd = k2/k1 = Agf \times Abf/Ag\text{-}Ab = Agf \times Abf/x \quad (2)$$

In the expression (2), Agf represents the concentration of a free antigen, Abf represents the concentration of a free antibody, and Ag–Ab represents the concentration of an antigen-antibody complex. If Ag-Ab=x, the free antibody concentration is represented by the following expression.

$$Abf = Abt - x \quad (3)$$

The above expression (2) therefore can be $$Kd = Agf \times (Abt-x)/x \quad (4)$$

If both terms of the expression (4) are multiplied by x/Kd×Abt, $$x/Abt = Agf \times (1-x/Abt) \times 1/Kd$$

$$x/Abt \times 1/Agf = (1-x/Abt) \times 1/Kd \quad (5)$$

If X=x/Abt and Y=x/Abt×Agf in the expression (5), $$Y = (1-X) \times 1/Kd \quad (6)$$

Based on the expression (6), the Kd value was calculated.

The Kd values of the generated 300 anti-hTROP-2 monoclonal antibody clones were measured by the above-described method. As a result, there were 133 clones exhibiting a Kd value of $1\times10^{-10}$ (M) or less, 59 clones exhibiting a Kd value of $1\times10^{-11}$ (M) or less, and 2 clones exhibiting a Kd value of $1\times10^{-12}$ (M) or less.

Among the anti-hTROP-2 monoclonal antibodies, which exhibited tumor growth inhibitory activity in vivo, the Kd values of 5-70 (mouse IgG2a), T6-16 (mouse IgG2a), K5-107 (mouse IgG1), K5-116-2-1 (mouse IgG1) and T5-86 (mouse IgG1) were found to be $6.8\times10^{-12}$ (M), $4.3\times10^{-12}$ (M), $4.7\times10^{-12}$ (M), $2.69\times10^{-11}$ (M) and $8.49\times10^{-11}$ (M), respectively (FIG. 1 and Table 1).

TABLE 1

Kd values of anti-hTROP-2 monoclonal antibodies

| Clone No. | K5-70 | T6-16 | K5-107 | K5-116-2-1 | T5-86 |
|---|---|---|---|---|---|
| Kd ($\times 10^{-12}$ M) | 6.8 | 4.3 | 4.7 | 26.9 | 84.9 |

Example 11

Reactivity of Anti-hTROP-2 Monoclonal Antibodies with Human Cancer Cell Lines

The human cancer cell lines (human tumor cell lines) used in this studies were acquired from Health Science Research Resources Bank (HSRRB), RIKEN cell bank (RIKEN), ATCC (American Type Culture Collection), ECACC (European Collection of Cell Cultures) and DSMZ (German Collection of Microorganisms and Cell Cultures). Specifically, the following cancer cell lines were used.

huH-1 (HSRRB), HUH-6 (HSRRB), HuH-7 (HSRRB), JHH-5 (HSRRB), JHH-6 (HSRRB), JHH-7(HSRRB), HLE (HSRRB), HLF (HSRRB), HepG2 (HSRRB), Alexander (HSRRB), KP-1N (HSRRB), KP-1NL (HSRRB), KP-2 (HSRRB), KP-3 (HSRRB), KP-3L (HSRRB), PK-1 (RIKEN), PANC-1 (RIKEN), MIA PaCa-2 (HSRRB), PK-59 (RIKEN), PK-45H (RIKEN), PK-45P (RIKEN), BxPC-3 (ATCC), SUIT-2 (HSRRB), TCC-PAN2 (HSRRB), SW480 (ATCC), DLD-1 (HSRRB), LoVo (HSRRB), COLO-320 (RIKEN), CACO-2 (RIKEN), CW-2 (RIKEN), HCT 116 (ATCC), HCC-56 (HSRRB), MCF-7 (HSRRB), JIMT-1 (DSMZ), HCC1143 (ATCC), A549 (HSRRB), DU145 (RIKEN) and PC-3 (HSRRB).

Cancer cells were removed from a culture dish by a trypsin treatment, and a cell suspension was then prepared (cell density: $2\times10^6$ cells/mL). An anti-hTROP-2 monoclonal antibody (0.1 µg) was added to 100 µL, of the cell suspension, and they were then reacted at 4° C. for 20 minutes. The reaction solution was washed with PBS, and it was then reacted with PE-labeled anti-mouse IgG (BD Biosciences Pharmingen) (0.1 µg) (at 4° C. for 30 minutes). Thereafter, the resultant was analyzed by FACSCalibur (Becton, Dickinson and Company).

Figure 2:
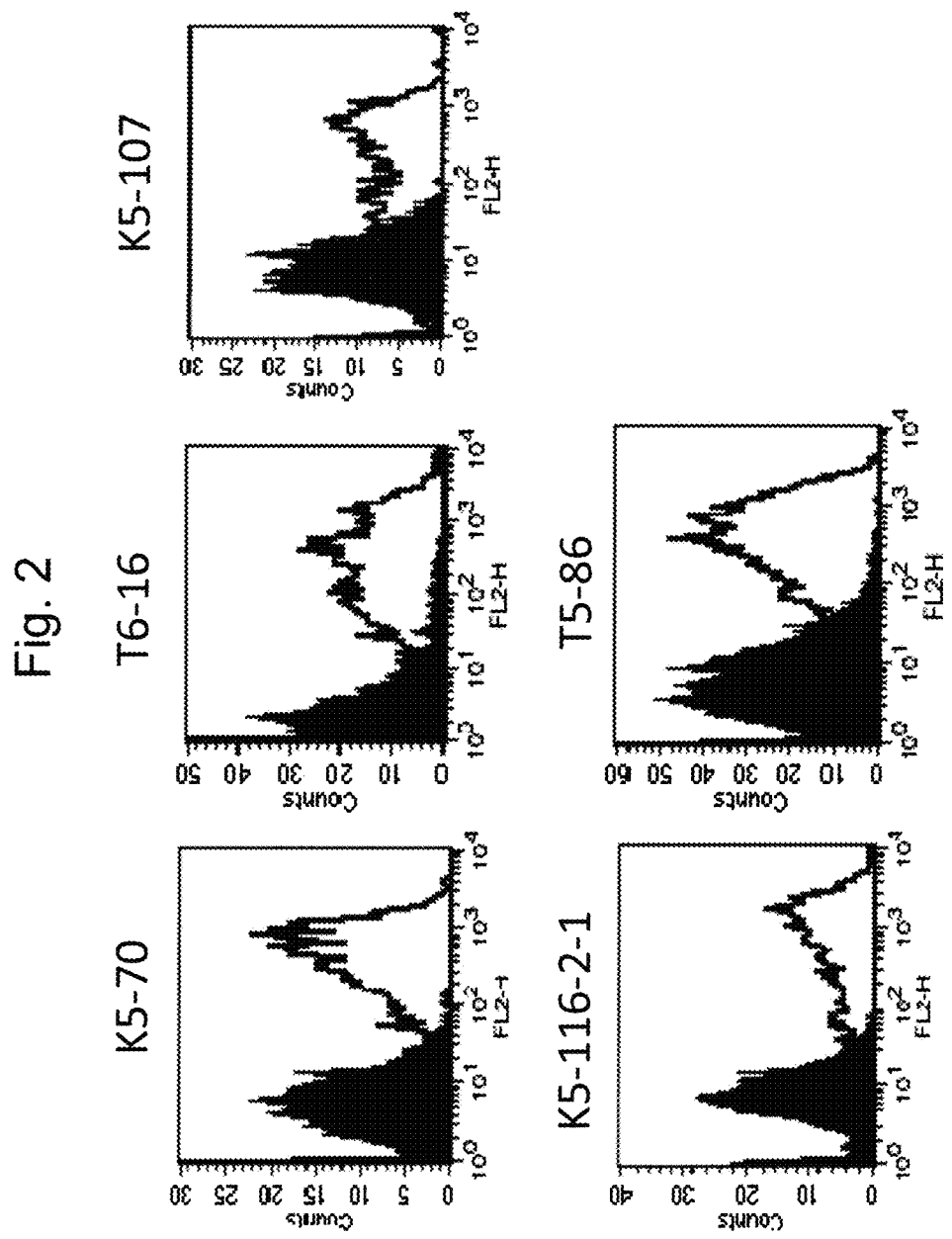
FIG. 2 shows the reactivity of a culture supernatant of hybridoma producing an anti-hTROP-2 monoclonal antibody, with HuH-7 cells (TROP-2-negative) and HuH-7-hTROP-2 cells. The filled histogram indicates HuH-7 cells, and the open histogram indicates HuH-7-hTROP-2 cells.
Figure 3:
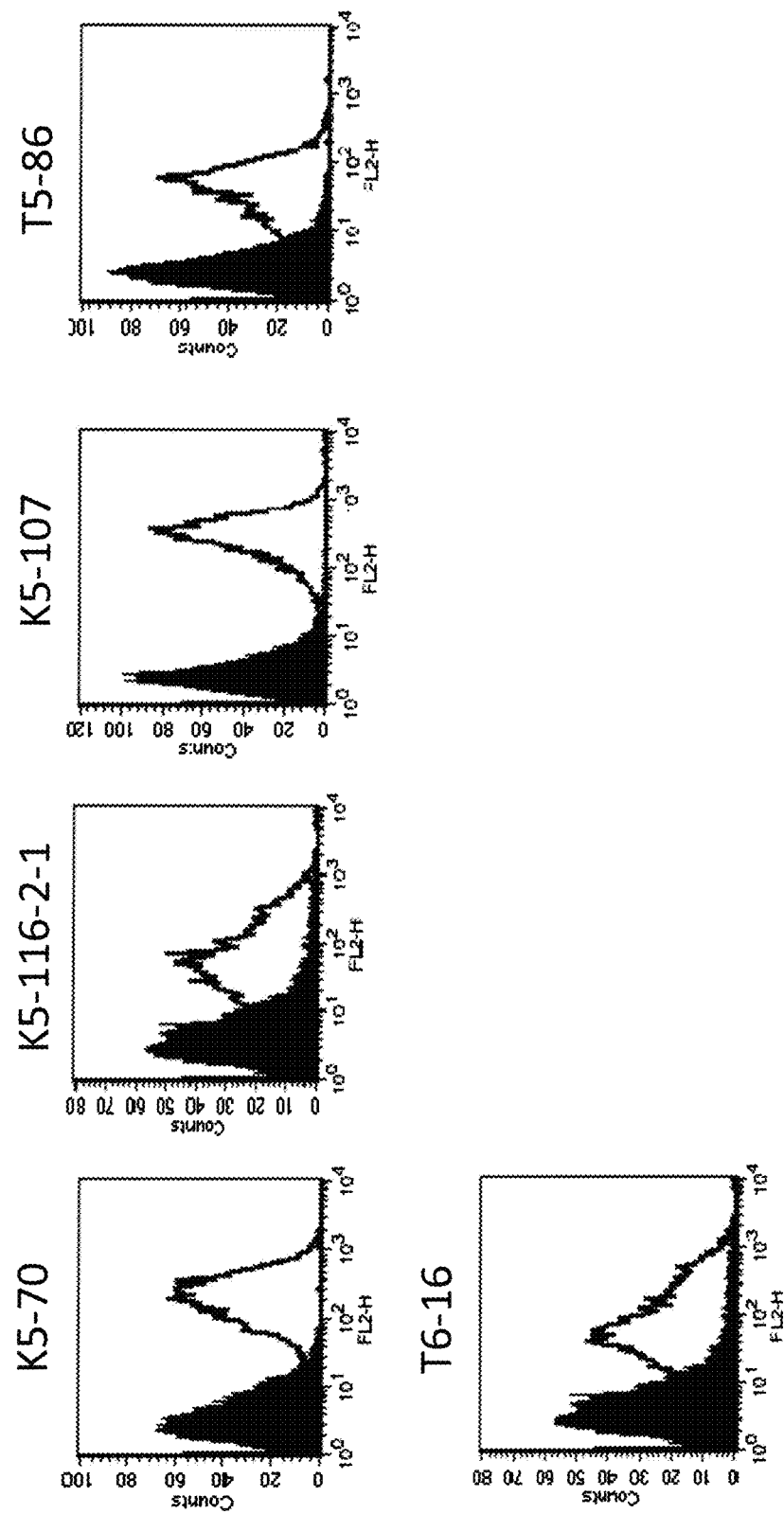
FIG. 3 shows the reactivity of an anti-hTROP-2 monoclonal antibody with a human pancreatic cancer cell line (PK-59 cells), which endogenously expresses hTROP-2 on the cell surface. The filled histogram indicates the reaction of the cell line only with a secondary antibody (PE-labeled anti-mouse IgG), and the open histogram indicates the reaction of the cell line with each anti-hTROP-2 monoclonal antibody.
Figure 4:
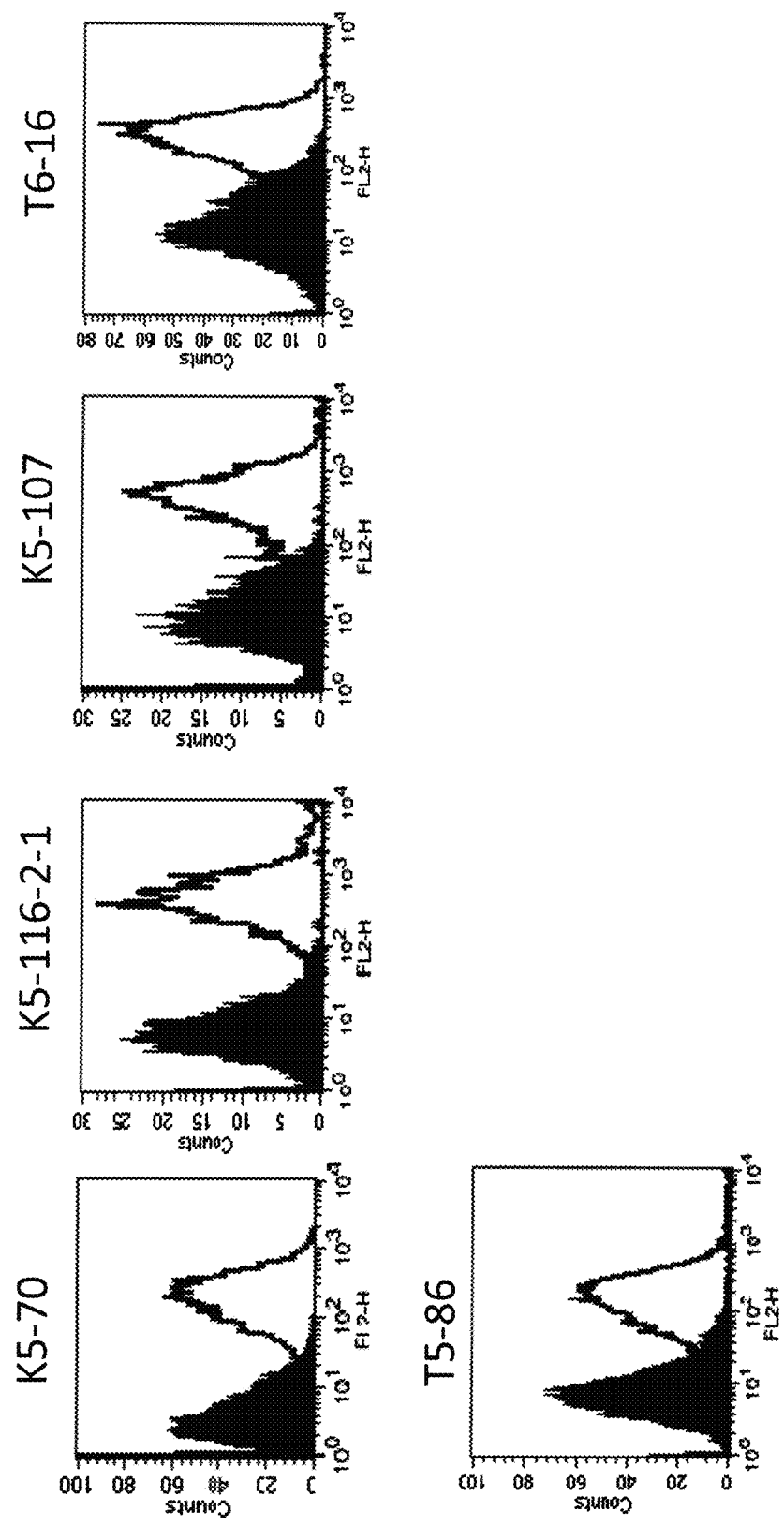
FIG. 4 shows the reactivity of an anti-hTROP-2 monoclonal antibody with a human pancreatic cancer cell line (BxPC-3 cells), which endogenously expresses hTROP-2 on the cell surface. The filled histogram indicates the reaction of the cell line only with a secondary antibody (PE-labeled anti-mouse IgG), and the open histogram indicates the reaction of the cell line with each anti-hTROP-2 monoclonal antibody.

All of the generated anti-hTROP-2 antibodies did not bind to a human liver cancer cell line HuH-7, which did not endogenously express hTROP-2. On the other hand, the anti-hTROP-2 antibodies bound to HuH-7-hTROP-2 cells, in which an hTROP-2 gene was stably expressed (FIG. 2). Subsequently, the reactivity of the generated anti-hTROP-2 monoclonal antibodies with human cancer cell lines (in which an hTROP-2 protein was endogenously expressed on the cell surface) was examined by FACS analysis. As a result, the generated 300 types of anti-hTROP-2 monoclonal antibodies all bound to human pancreatic cancer cell lines (PK-59 and BxPC-3). In particular, K5-70, T6-16, K5-107, K5-116-2-1 and T5-86 antibodies, which exhibited tumor growth inhibitory activity in vivo, all bound to human cancer cell lines at high levels. For example, when compared with a case in which cancer cell lines were reacted with only PE-labeled anti-mouse IgG (BD Biosciences Pharmingen), the aforementioned antibodies exhibited the following binding ability to PK-59 cells and to BxPC-3 cells at mean fluorescence intensity: K5-70 (44 times), T6-16 (59 times), K5-107 (89 times), K5-116-2-1 (122 times) and T5-86 (15 times) (to PK-59 cells; FIG. 3); and K5-70 (45 times), T6-16 (25 times), K5-107 (90 times), K5-116-2-1 (121 times) and T5-86 (10 times) (to BxPC-3 cells; FIG. 4).

Figure 5:
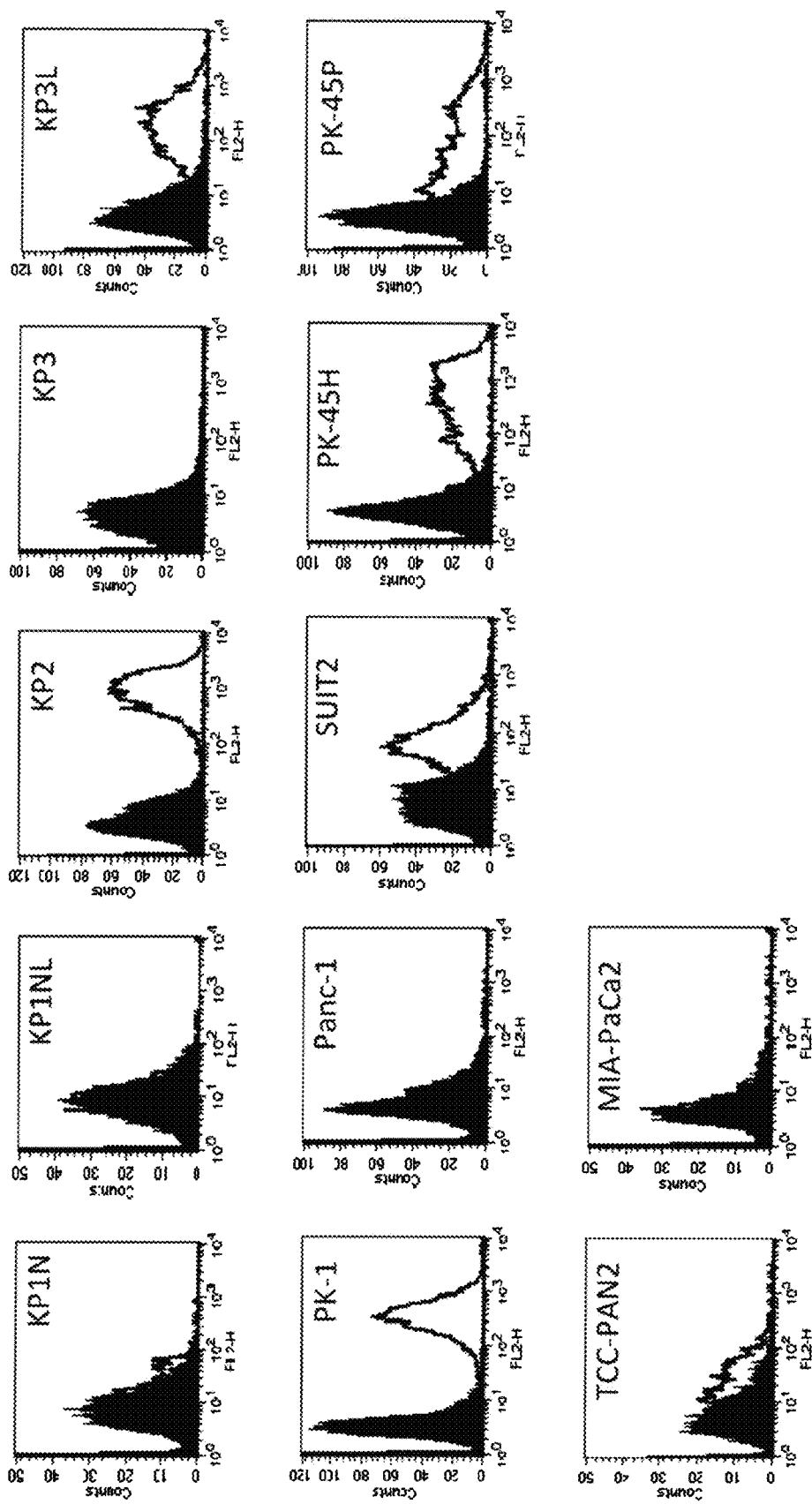
FIG. 5 shows the reactivity of an anti-hTROP-2 monoclonal antibody (K5-70) with human pancreatic cancer cell lines. The filled histogram indicates the reaction of the cell line only with a secondary antibody (PE-labeled anti-mouse IgG), and the open histogram indicates the reaction of the cell line with each anti-hTROP-2 monoclonal antibody.
Figure 6:
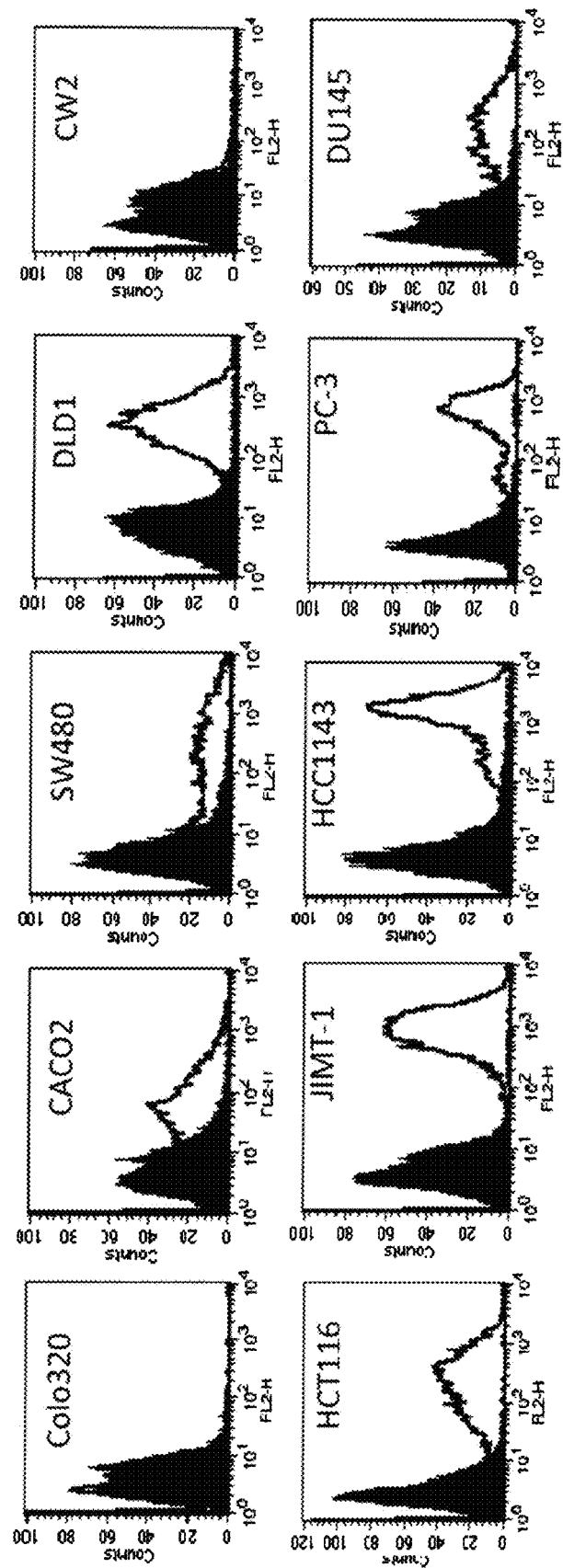
FIG. 6 shows the reactivity of an anti-hTROP-2 monoclonal antibody (K5-70) with human colon cancer cell lines (Colo320, CACO2, SW480, DLD1, CW2 and HCT 116), human breast cancer cell lines (JIMT-1 and HCC1143), and human prostate cancer cell lines (PC-3 and DU145). The filled histogram indicates the reaction of the cell line only with a secondary antibody (PE-labeled anti-mouse IgG), and the open histogram indicates the reaction of the cell line with the anti-hTROP-2 monoclonal antibody.

With regard to human cancer cell lines other than PK-59 and BxPC-3, among 12 types of pancreatic cancer cell lines, the anti-hTROP-2 monoclonal antibodies bound to KP-2, KP-3L, PK-1, PK-45H, SUIT-2 and TCC-PAN2, and did not bind to KP-1N, KP-1NL, KP-3, PANC-1 and MIA-PaCa2 (FIG. 5). Among human colon cancer cell lines, the anti-hTROP-2 monoclonal antibodies bound to CACO-2, SW480, DLD-1 and HCT 116, and did not bind to COLO-320 and CW-2 (FIG. 6). Furthermore, the anti-hTROP-2 monoclonal antibodies bound to JIMT-1 and HCC1143 (which were both human breast cancer cell lines) and to PC-3 and DU145 (which were both human prostate cancer cell lines). Thus, they recognized hTROP-2 proteins endogenously expressing on the cell surface of many types of human cancer cell lines (FIG. 6).

Example 12

Cross-Reactivity with Mouse TROP-2 Protein and Human TROP-1/EpCAM Protein

For the purpose of examining the specificity of the generated anti-hTROP-2 monoclonal antibodies, the reactivity of the antibodies with a mouse TROP-2 protein showing homology of 80% at the amino acid sequence level with the hTROP-2 protein, and with a human TROP-1/EpCAM protein showing homology of 50% at the amino acid sequence level with the hTROP-2 protein, was examined by FACS analysis.

Specifically, each of an expression vector (mouse TROP-2-pcDNA3.1(+), furnished by the Institute of Molecular and Cellular Biosciences, the University of Tokyo) comprising the full-length cDNA of a mouse TROP-2 gene (GenBank accession No. NM_020047, Y08830), and an expression vector (pcDNA3.1-hEpCAM-myc/His) comprising the full-length cDNA of a human TROP-1/EpCAM gene (GenBank accession No. NM_002354), was transiently introduced into CHO-K1 cells, using Lipofectamine2000 reagent (Invitrogen). Thereafter, 24 to 48 hours later, the cells were removed from a culture dish by treating them with trypsin, and a cell suspension was then prepared. The thus prepared cell suspension was successively reacted with the produced anti-hTROP-2 monoclonal antibody (0.1 µg) and with PE-labeled anti-mouse IgG, and it was then analyzed by FACSCalibur.

Figure 7:
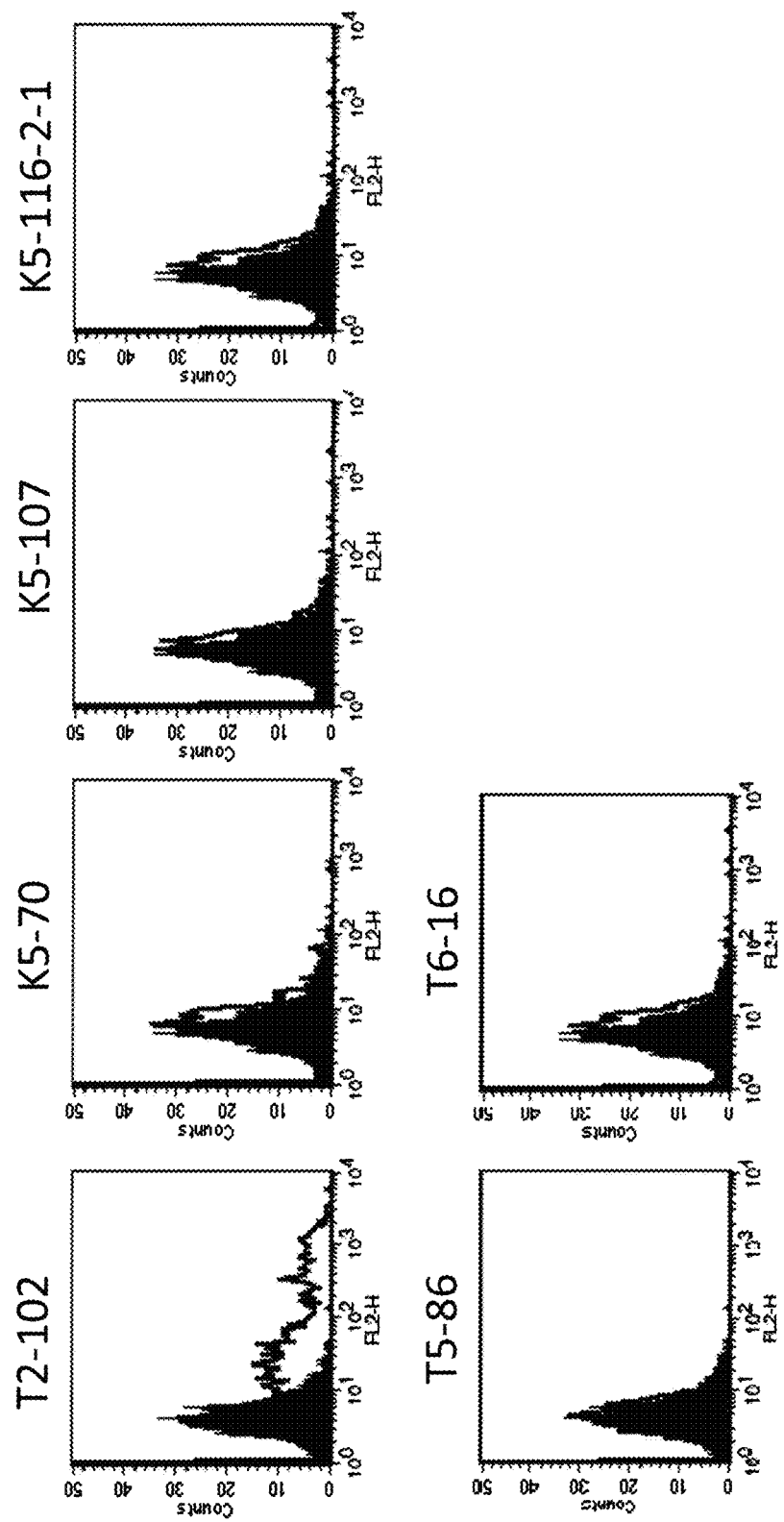
FIG. 7 shows the cross-reactivity of anti-hTROP-2 monoclonal antibodies with mouse TROP-2. Cells prepared by allowing a mouse TROP-2 gene to be transiently expressed in CHO-K1 cells were used, and a T2-102 antibody (mouse IgG1) exhibiting cross-reactivity with mouse TROP-2 was used as a positive control antibody. The filled histogram indicates the reaction of the cells only with a secondary antibody (PE-labeled anti-mouse IgG), and the open histogram indicates the reaction of the cells with each anti-hTROP-2 monoclonal antibody.

A T2-102 antibody (mouse IgG1) used as a positive control, which showed cross-reactivity with mouse TROP-2, exhibited high binding ability to the CHO-K1 cells in which the mouse TROP-2 gene was transiently expressed. On the other hand, K5-70, T6-16, K5-107, K5-116-2-1 and T5-86 antibodies did not show such cross-reactivity with mouse TROP-2 (FIG. 7).

Figure 8:
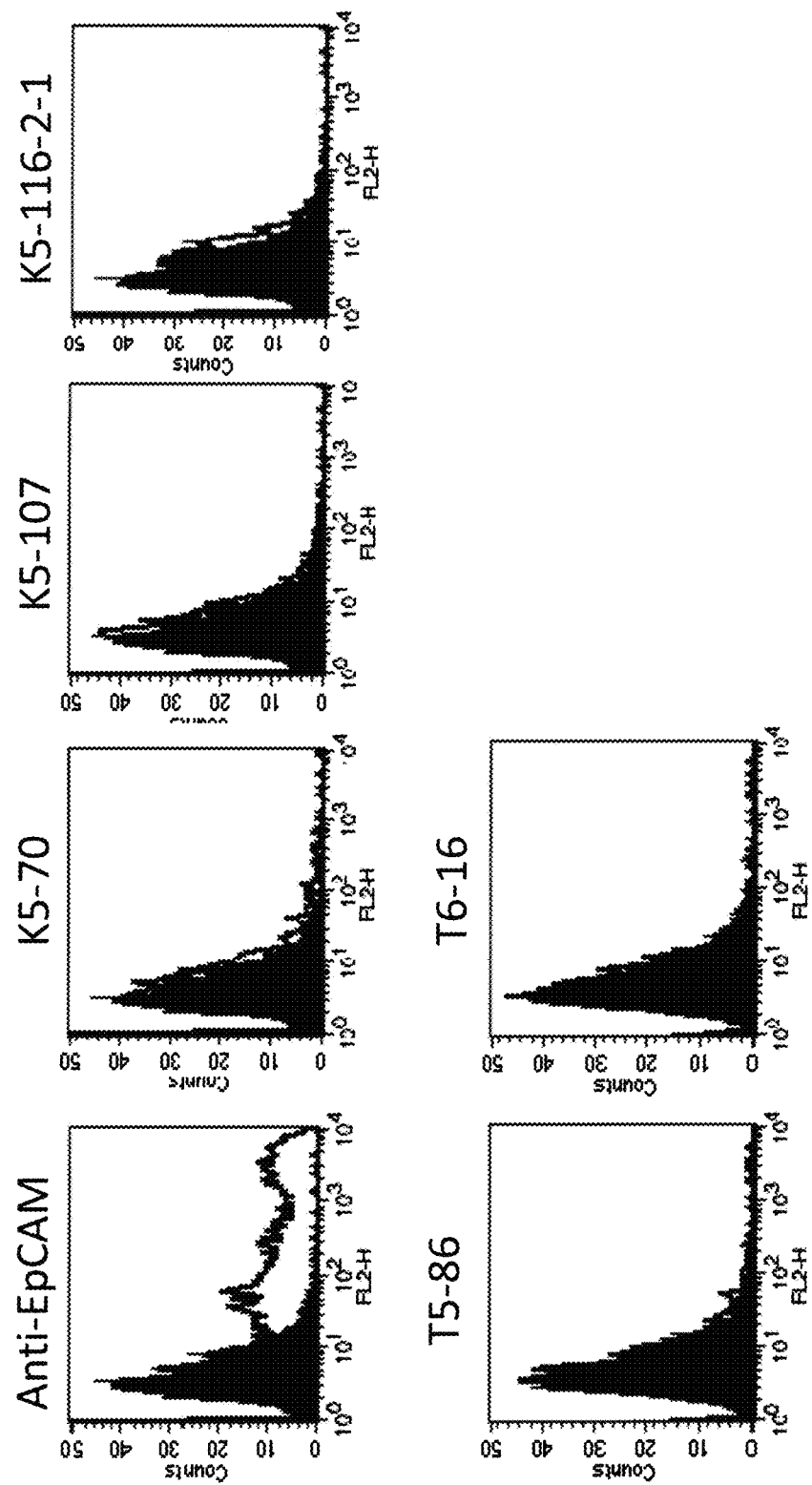
FIG. 8 shows the cross-reactivity of anti-hTROP-2 monoclonal antibodies with human EpCAM/TROP-1. Cells prepared by allowing a human EpCAM/TROP-1 gene to be transiently expressed in CHO-K1 cells were used, and a PE-labeled anti-human EpCAM monoclonal antibody (Becton, Dickinson and Company) was used as a positive control antibody. The filled histogram indicates the reaction of the cells only with a secondary antibody (PE-labeled anti-mouse IgG), and the open histogram indicates the reaction of the cells with each anti-hTROP-2 monoclonal antibody.

Similarly, an anti-human EpCAM monoclonal antibody (BD Biosciences Pharmingen) used as a positive control exhibited high binding ability to the CHO-K1 cells in which the human EpCAM/TROP-1 was transiently expressed. On the other hand, K5-70, T6-16, K5-107, K5-116-2-1 and T5-86 antibodies did not show such cross-reactivity with human EpCAM/TROP-1 (FIG. 8).

The aforementioned results demonstrated that the generated anti-hTROP-2 monoclonal antibodies, and in particular, K5-70, T6-16, K5-107, K5-116-2-1 and T5-86 antibodies, which exhibited anti-tumor activity in vivo, specifically bound to hTROP-2.

Example 13

Measurement of Cell Growth Inhibitory Activity

As a method of examining the activity of the anti-hTROP-2 monoclonal antibody to inhibit the function of hTROP-2, the influence of the antibody on the cell growth of human cancer cells, which endogenously express hTROP-2 on the cell surface, was evaluated by measuring the number of living cells using TetraColor ONE (Seikagaku Corporation). Specifically, PK-59 cells were suspended in an RPMI1640 medium containing 0.5% fetal bovine serum (manufactured by Bio-West) at a cell concentration of $2\times10^5$ cells/mL, and 100 µL of the prepared cell suspension was then added to each well of a 96-well culture plate. Subsequently, mouse IgG (negative control) and anti-hTROP-2 monoclonal antibodies (final concentrations: 0.1 and 1 µg/mL) were added to the wells, and the mixtures were then cultured at 37° C. in a 5% $CO_2$ incubator for 72 hours. As a control, a commercially available anti-hTROP-2 monoclonal antibody (clone YY01, Santa Cruz) was used. TetraColor ONE (Seikagaku Corporation) was added to the wells, and they were then reacted in a 5% $CO_2$ incubator for 1 to 2 hours. After completion of the reaction, the 96-well culture plate was directly subjected to the measurement of absorbance at a wavelength of 490 nm (control wavelength: 655 nm), using Microplate Reader. The experiment was carried out using 3 wells for each group. A significant difference test was carried out according to Student's t-test, and P<0.05 was determined to be statistically significant.

Figure 9:
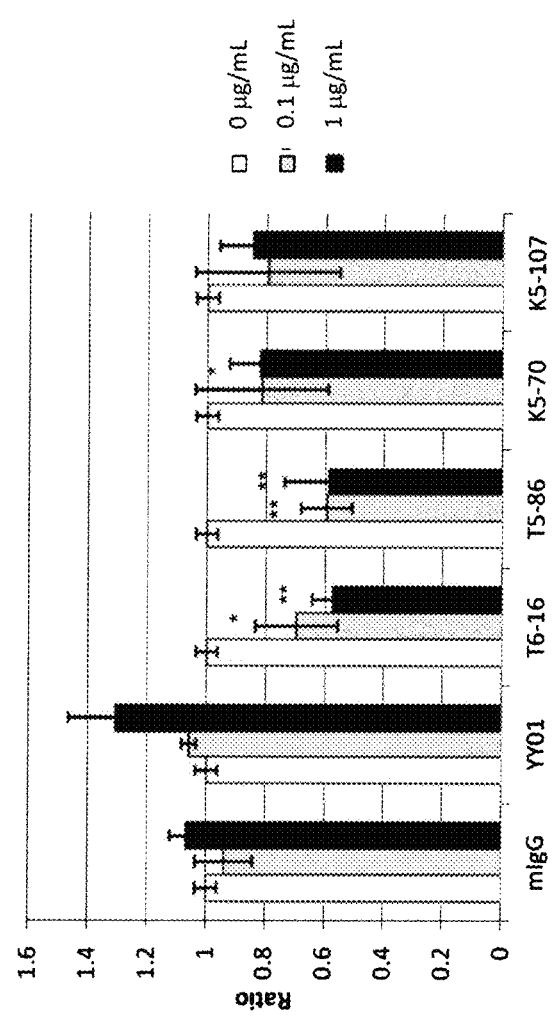
FIG. 9 shows the cell growth inhibitory activity of anti-hTROP-2 antibodies (T6-16, T5-86, K5-70 and K5-107) on a human pancreatic cancer cell line (PK-59 cells). mIgG indicates a control antibody (mouse IgG), and YY01 indicates a commercially available anti-hTROP-2 antibody (Santa Cruz). White column: 0 µg/mL; gray column: 0.1 µg/mL; black column: 1 µg/mL. The activity level was expressed as a ratio to the value in the case of not adding antibody (0 µg/mL). The error bar indicates a standard deviation. *P<0.05, **P<0.01 (by Student's t-test).

Among anti-hTROP-2 monoclonal antibodies, which had been generated by our own company so far, approximately 160 clones were examined by the above-described method, in terms of their effect on the cell growth of PK-59 cells. As a result, T6-16, T5-86, K5-70 and K5-107, which had exhibited tumor growth inhibitory activity in vivo, were confirmed to have cell growth inhibitory activity of 20% to 40%, when compared with mouse IgG (negative control). It became clear that these anti-hTROP-2 antibodies have activity to bind to hTROP-2 proteins, which were expressed on the surface of human cancer cells, to neutralize the hTROP-2 proteins, and to inhibit the growth of the cancer cells (FIG. 9).

Example 14

Scratch Assay

The effect of an anti-hTROP-2 monoclonal antibody on the migratory ability of human cancer cells was evaluated by a scratch assay. PK-59 cells were suspended in an RPMI1640 medium containing 10% fetal bovine serum at a cell concentration of $3\times10^5$ cells/mL, and 100 µL of the prepared cell suspension was then added to each well of a 96-well culture plate. When the cells became confluent, a portion of the monolayer-cultured cells was peeled, such that the plate was scratched in a longitudinal direction with the end of a tip. An anti-hTROP-2 monoclonal antibody and mouse IgG used as a negative control were added to the medium to final concentrations of 0.1 and 1 µg/mL, respectively, and culture was then carried out for 24 hours. Before addition of the antibody (Day 0) and 24 hours after the culture (Day 1), the cell peeled region was photographed, and the distance between the cells was then measured. Moreover, the area of such a peeled region was quantified using Scion Image software. The experiment was carried out using 8 wells for each group. A significant difference test was carried out according to Student's t-test, and P<0.05 was determined to be statistically significant.

The effect of an hTROP-2 antibody on the migratory ability of the cells invading the scratch region was examined. As with the cell growth inhibition assay, antibodies having beneficial effects were evaluated. As an evaluation method, the cells were photographed on Day 0 (when the antibody was added) and on Day 1 (24 hours after the addition of the antibody), and the migratory distance (µm) and the area of a scratch region were determined by image analysis. As a result, as shown in FIG. 10, clear differences were observed in terms of the migratory ability of the cells. The antibodies T6-16 and K5-70, which were used in the present test, had significant cell growth inhibitory activity, when compared with the control. Even in a reproducibility test, the same tendency was observed. Particularly, T6-16 had a result of P<0.01 (by Student's t-test), and there was found correlation with the in vivo test.

Example 15

Evaluation of Beneficial Effects of Anti-hTROP-2 Monoclonal Antibody on Tumor-Bearing Mice Prevention Model Pancreatic cancer cell lines (PK-59 and BxPC-3), which expressed hTROP-2, were removed by treating the cells with trypsin, and PBS was added to them to prepare a cell suspension having a concentration of $1\times10^8$ cells/mL. The thus prepared cell suspension was mixed with an equal amount of Matrigel (BD Biosciences Pharmingen) on ice. Using a 26 G syringe, 100 μL of the obtained mixture (5×10⁶ cells) was injected into the subcutis of the right flank of each of 6-week-old female nude mouse (Balb/c, nu/nu). On the day of the transplantation of the cancer cells (Day 1), the mice were divided into groups, and administration of the antibody (1, 5 or 10 mg/kg body weight, intraperitoneal administration) was initiated. Thereafter, administration of the antibody was continued at intervals of once every three days. Anti-tumor activity was evaluated based on tumor formation frequency and tumor volume. The tumor volume was calculated by the following formula.

$$\text{Tumor volume (mm}^3\text{)} = (\text{minor axis})^2 \times (\text{major axis}) \times \pi/6$$

Treatment Model

Pancreatic cancer cell lines (PK-59 and BxPC-3), which expressed hTROP-2, were removed by treating the cells with trypsin, and PBS was added to them to prepare a cell suspension having a concentration of $1 \times 10^8$ cells/mL. The thus prepared cell suspension was mixed with an equal amount of Matrigel (BD Biosciences Pharmingen) on ice. Using a 26 G syringe, 100 μL of the obtained mixture ($5 \times 10^6$ cells) was injected into the subcutis of the right flank of each of 6-week-old female nude mouse (Balb/c, nu/nu). Five to six days after the transplantation of the cancer cells, mice whose tumor volume had increased to 50 to 150 mm³ (mean value: approximately 100 mm³) were divided into groups. The day on which the mice were divided into groups was defined as a first day (Day 1), and administration of the antibody was initiated. The antibody was intraperitoneally administered at intervals of once every three days (10 mg/kg body weight). Anti-tumor activity was evaluated by measuring tumor volume. A significant difference test was carried out according to Student's t-test, and P<0.05 was determined to be statistically significant.

Example 16

Analysis of In Vivo Anti-Tumor Activity of Anti-hTROP-2 Monoclonal Antibody on Human Pancreatic Cancer Cell Xenograft Model It is essential for an antibody used for the treatment of cancer, which targets hTROP-2, to have the activity of specifically killing tumor tissues expressing hTROP-2 or inhibiting the growth of tumor.

Figure 11:
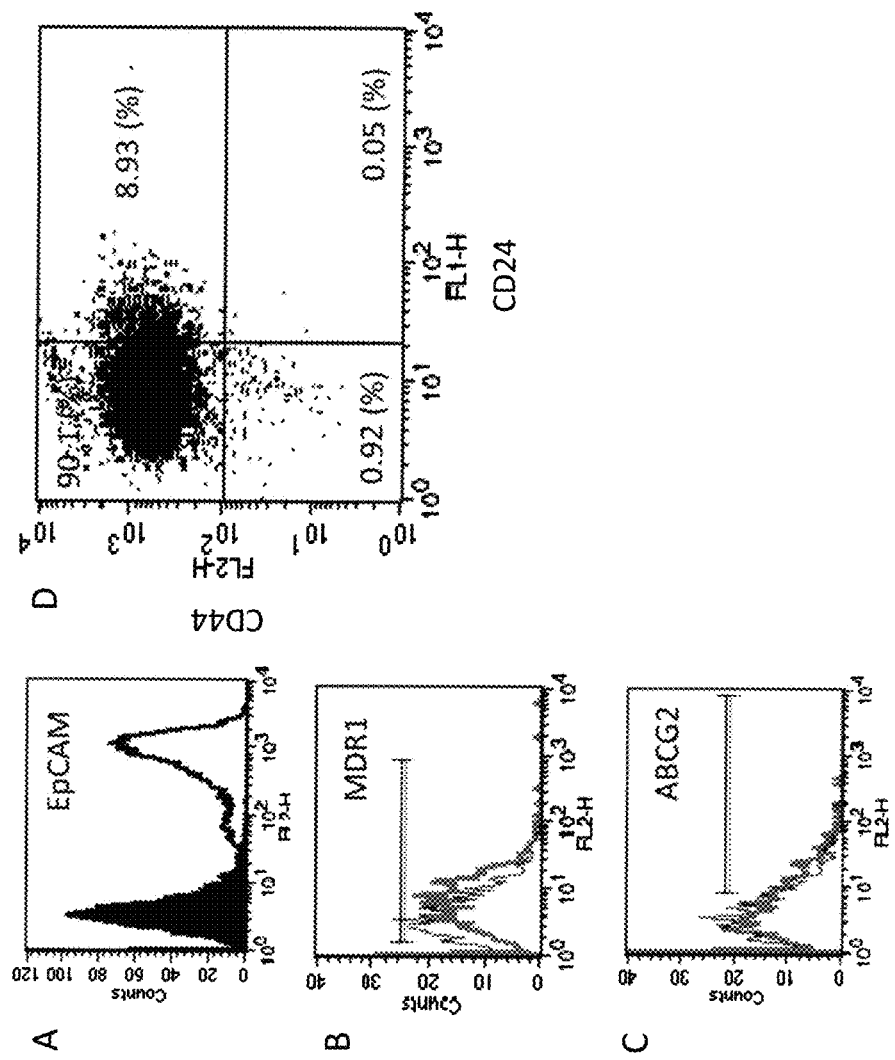
FIG. 11 shows FACS analysis using a stem cell marker, which has been performed on a human pancreatic cancer cell line PK-59.

Anti-hTROP-2 monoclonal antibodies (approximately 160 clones), which were newly produced in the present invention, were evaluated using the xenograft treatment models of a pancreatic cancer cell line PK-59. The PK-59 cells express, on the surface thereof, EpCAM (FIG. 11A) acting as a pancreatic cancer stem cell marker (Chenwei Li, et al. Cancer Res 2007; 67: (3). 1030-1037), and also express P-glycoprotein/MDR1 (FIG. 11B) and ABCG2/CDw338 (FIG. 11C) (Chen, C. J. et al. Cell 47 (3), 381-389 (1986), Allikmets, R., et al. Hum. Mol. Genet. 5 (10), 1649-1655 (1996)), which are ABC transporters associated with drug resistance. In addition, the PK-59 cells contain a cell fraction (8.93%) (FIG. 11D) positive for both CD24 and CD44, which is characteristic for pancreatic cancer stem cells, and they are assumed to be a highly malignant human pancreatic cancer cell line (Chenwei Li, et al. Cancer Res 2007; 67: (3). 1030-1037, Jane E. Visvader and Geoffrey J. Lindeman. Nat Rev Cancer. Vol. 8(10): 755-68, 2008).

Most of the newly generated approximately 160 clones did not exhibit beneficial effects on the xenograft treatment models of PK-59 cells. Among such clones, clones exhibiting significant tumor growth inhibitory activity, namely clones K5-70, T6-16, K5-107, T5-86 and K5-116-2-1 could be obtained.

Figure 12:
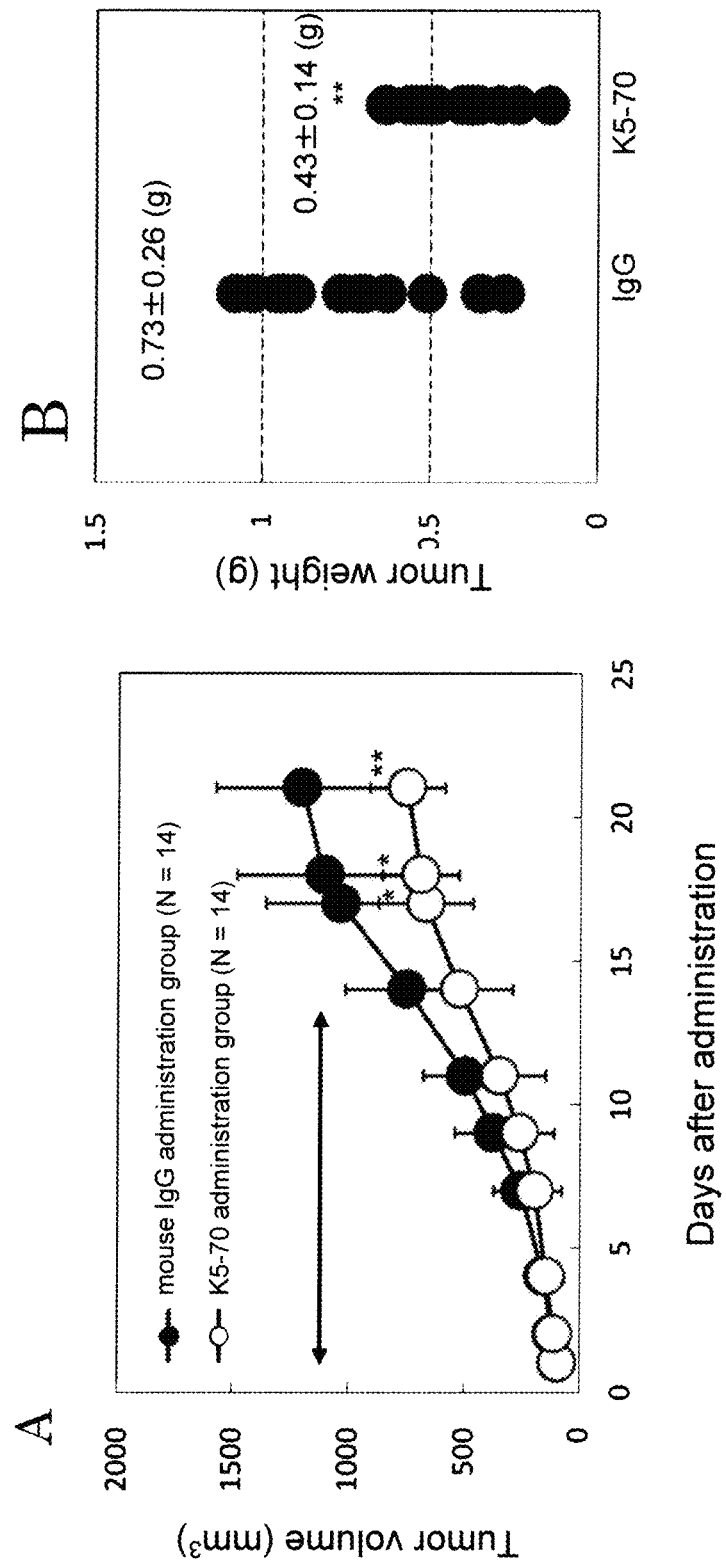
FIG. 12 shows the evaluation of the anti-tumor activity of a novel anti-hTROP-2 monoclonal antibody clone K5-70 (mouse IgG2a) on xenograft treatment models using PK-59 cells.

In a clone K5-70 (mouse IgG2a) administration group, tumor growth rate is statistically significantly inhibited. On the 21$^{st}$ day after initiation of the administration (day 21), the tumor volume of a control group (N=14) was 1200.8±377.3 mm³, whereas the tumor volume of the clone K5-70 administration group was 748.7±162.9 mm³ (P<0.01 by Student's t-test) (FIG. 12A). When the tumor volume at the time of initiation of the administration of the antibody was defined as 1.0, the tumor volume on the 21$^{st}$ day (Day 21) was 7.8 in the clone K5-70 administration group, whereas the tumor volume of the control group was 12.5 (FIG. 12A). The weight of the tumor excised was 0.43±0.14 g (P<0.01 by Student's t-test) in the clone K5-70 administration group, whereas that of the control group was 0.73±0.26 g. Thus, the clone K5-70 exhibited inhibitory activity of approximately 60% (FIG. 12B).

Figure 13:
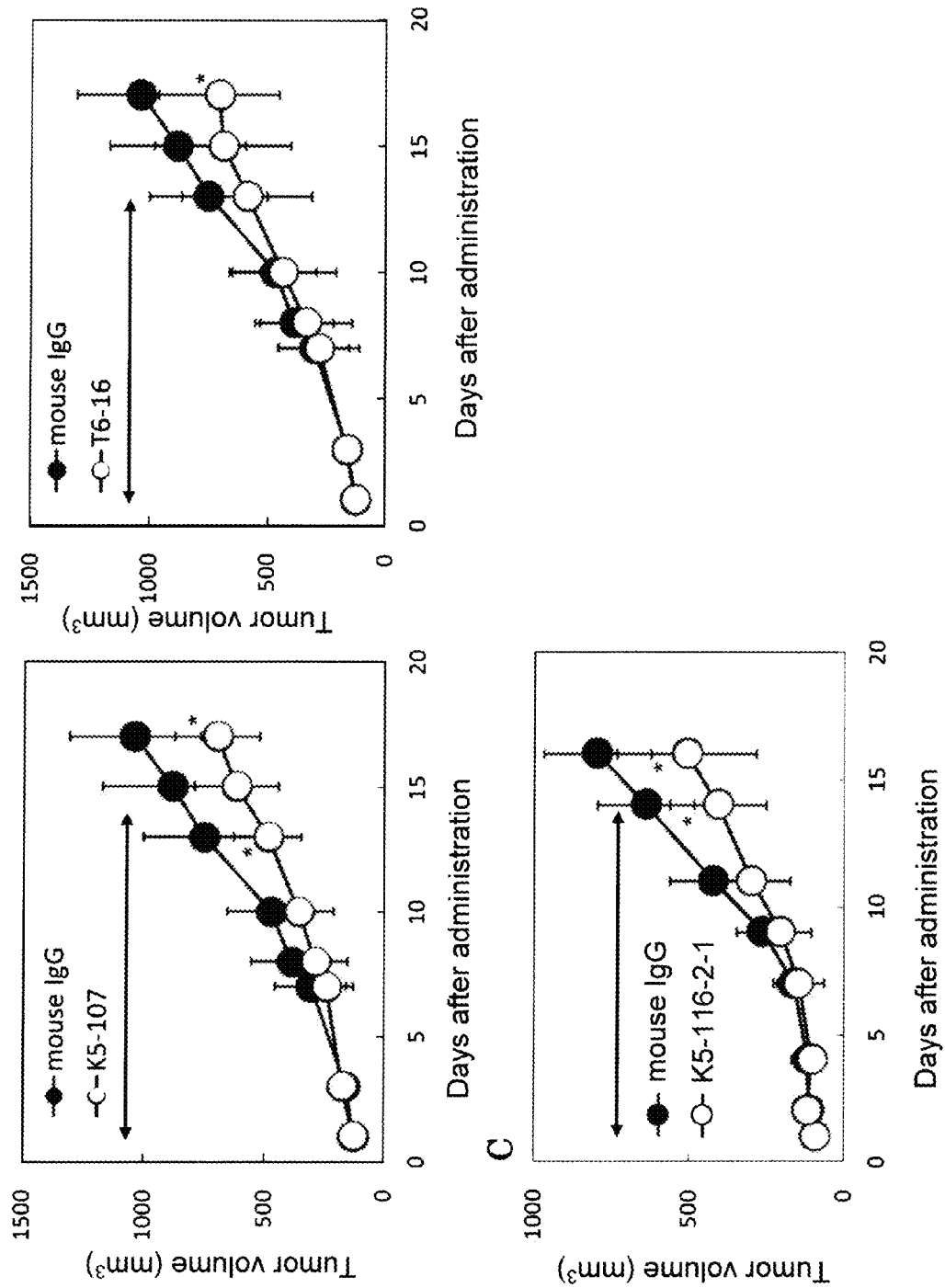
FIG. 13 shows the evaluation of the anti-tumor activity of a clone K5-107 (A), a clone T6-16 (B) and a clone K5-116-2-1 (C) on xenograft treatment models using PK-59 cells. The symbol "●" indicates a control group (mouse IgG), and the symbol "○" indicates an anti-hTROP-2 antibody administration group. The arrow in the graph indicates an antibody administration period, and the numerical value on each plot indicates a mean value±standard deviation. * P<0.05 (by Student's t-test).

Similarly, tumor growth rate was statistically significantly inhibited even in a clone K5-107 (mouse IgG1) administration group (N=8), a clone T6-16 (mouse IgG2a) administration group (N=8), a clone T5-86 (mouse IgG1) administration group and a clone K5-116-2-1 (mouse IgG2a) administration group (N=8). On the 17$^{th}$ day after initiation of the administration (Day 17), the tumor volumes of the clone K5-107 administration group (N=8) and the clone T6-16 administration group (N=8) were 698.2±175.9 mm³ (P<0.05 by Student's t-test) and 707.2±254.5 mm³ (P<0.05 by Student's t-test), respectively, whereas the tumor volume of the control group was 1039.3±271.6 mm³. Likewise, on the 16$^{th}$ day after initiation of the administration (Day 16), the tumor volume of the clone K5-116-2-1 administration group (N=8) was 508.5±225.2 mm³ (P<0.05 by Student's t-test), whereas the tumor volume of the control group (N=8) was 797.0±172.9 mm³ (FIG. 13).

On the other hand, in the case of the clone T5-86, on the 15$^{th}$ day after initiation of the administration (Day 15), the tumor of the clone T5-86 administration group (N=8) was 744.1±289.1 mm³, whereas the tumor volume of the control group (N=8) was 1033.2±319.4 mm³. Thus, there was found no significant difference in terms of tumor volume. However, in the comparison of tumor weight, which was performed on the same day, the tumor weight of the clone T5-86 administration group was 0.44±0.13 g (P<0.05 by Student's t-test), whereas the tumor weight of the control group was 0.62±0.14 g. Thus, the clone T5-86 exhibited significant inhibitory activity.

Moreover, in terms of both tumor volume and tumor weight, the ratio (T/C) of each clone antibody administration group to the control group on the final day of experiment is shown in Table 2 below. As shown in Table 2, each clone antibody exhibited significant inhibitory activity (T/C=62% to 72%) on each clone antibody administration group.

TABLE 2

| Group | N (number of mice) | Tumor volume T/C (%) | Tumor weight T/C (%) |
|---|---|---|---|
| K5-70 | 14 | 62.3** | 58.8** |
| K5-107 | 8 | 67.2* | 65.0* |
| T6-16 | 8 | 68.0* | 64.7* |
| T5-86 | 8 | 72.0 | 70.5* |
| K5-116-2-1 | 8 | 63.8* | 60.5* |

*P < 0.05,
**P < 0.01 (by Student's t-test)

Furthermore, the anti-tumor activity of each of the clones K5-70, T6-16 and K5-116-2-1 on the xenograft prevention models of the pancreatic cancer cell line PK-59 was analyzed. After completion of the administration of each antibody clone, tumor growth was inhibited in all individuals (N=8). On the 18$^{th}$ day after initiation of the administration (Day 18), the tumor volume of the clone K5-70 administration group (10 mg/kg body weight) was 62.4±80.4 mm$^3$ (P<0.01 by Student's t-test), whereas the tumor volume of the control group (N=8) was 880.8±206.4 mm$^3$. Thus, the clone K5-70 exhibited tumor growth inhibitory activity of 92.9%. On the 28$^{th}$ day after initiation of the administration (Day 28), the tumor volume of the clone T6-16 administration group (10 mg/kg body weight) was 152.4±122.3 mm$^3$ (P<0.01 by Student's t-test), whereas the tumor volume of the control group (N=8) was 992.3±250.8 mm$^3$. Thus, the clone T6-16 exhibited tumor growth inhibitory activity of 84.6%. On the 20$^{th}$ day after initiation of the administration (Day 20), the tumor volume of the clone K5-116-2-1 administration group (10 mg/kg body weight) was 207.7±319 2 mm$^3$ (P<0.01 by Student's t-test), whereas the tumor volume of the control group (N=8) was 1159.4±413.3 mm$^3$. Thus, the clone K5-116-2-1 exhibited tumor growth inhibitory activity of 82.1% (FIG. 14 and Table 3). Moreover, in all of the experiments, there was no significant difference between the control group and each anti-hTROP-2 antibody administration group in terms of a change in mean body weight throughout the test period.

In terms of both tumor volume and tumor weight, the ratio (T/C) of each clone antibody administration group to the control group on the final day of experiment is shown in Table 3 below. As shown in Table 3, significant tumor growth inhibition was observed in each clone antibody administration group, and in particular, a significant effect such as T/C=10% or less was confirmed in the clone K5-70 administration group.

TABLE 3

| Group | N (number of mice) | Tumor volume T/C (%) | Tumor weight T/C (%) |
|---|---|---|---|
| K5-70 | 8 | 7.1** | 5.8** |
| T6-16 | 8 | 15.3** | 10.5** |
| K5-116-2-1 | 8 | 23.2** | 21.5** |

**P < 0.01 (by Student's t-test)

The known anti-TROP-2 antibody AR47A6.4.2 (U.S. Pat. No. 7,420,041) has exhibited the effect of inhibiting tumor growth, at a dosage of 20 mg/kg, on xenograft prevention models using various human cancer cell lines. This anti-TROP-2 antibody AR47A6.4.2 has inhibited the tumor growth of a human pancreatic cancer cell line PL45 at a percentage of almost 100%. However, this antibody has had the effect of inhibiting tumor on a pancreatic cancer cell line BxPC-3 at a percentage of approximately 50%, on a prostate cancer cell line PC-3 at a percentage of approximately 40%, on a breast cancer cell line MCF-7 at a percentage of approximately 60%, and on a colon cancer cell line Colo205 at a percentage of approximately 40%. In contrast, the anti-hTROP-2 antibody of the invention of the present application has exhibited a higher tumor growth inhibitory effect at a dosage of half the aforementioned dose (10 mg/kg).

Example 17

Analysis of Anti-Tumor Activity on Xenograft Models (Prevention Models and Treatment Models) of Human Pancreatic Cancer Cell Line BxPC-3

As in the case of using the above-described xenograft treatment models of the human pancreatic cancer cell line PK-59, the anti-tumor activity of the clone K5-70 on xenograft prevention models and xenograft treatment models of a human pancreatic cancer cell line BxPC-3 was analyzed.

Figure 15:
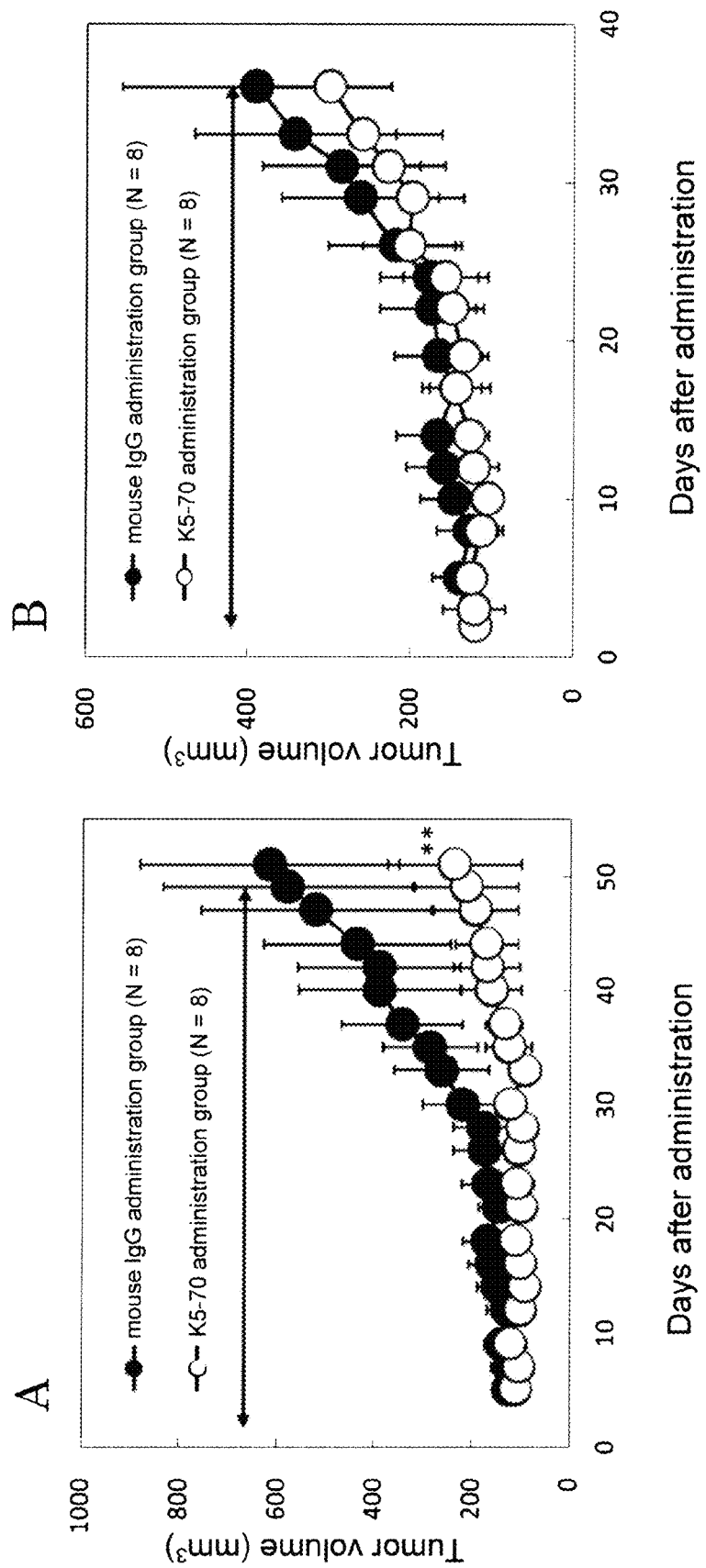
FIG. 15 shows the evaluation of the anti-tumor activity of a clone K5-70 on xenograft prevention and treatment models using BxPC-3 cells.

When compared with a control group (N=8), the tumor growth of the clone K-70 administration group was significantly inhibited. On the 52" day (Day 52), the tumor volume of the clone K5-70 administration group (N=8) was 236.0±136.4 mm$^3$, whereas the tumor volume of the control group (N=8) was 616.3±266.8 mm$^3$. Thus, the clone K-70 exhibited a tumor growth inhibitory effect of 61.7% (P<0.01 by Student's t-test) (FIG. 15).

From the aforementioned results, it became clear that the anti-hTROP-2 monoclonal antibody exhibits significant tumor growth inhibitory activity in vivo on at least two cancer cell species.

Example 18

Dose-Dependent Anti-Tumor Activity of Anti-hTROP-2 Antibody (Clone K5-70) on Xenograft Prevention Models of hTROP-2-Expressing Pancreatic Cancer Cell Line (PK-59 Cells)

Figure 16:
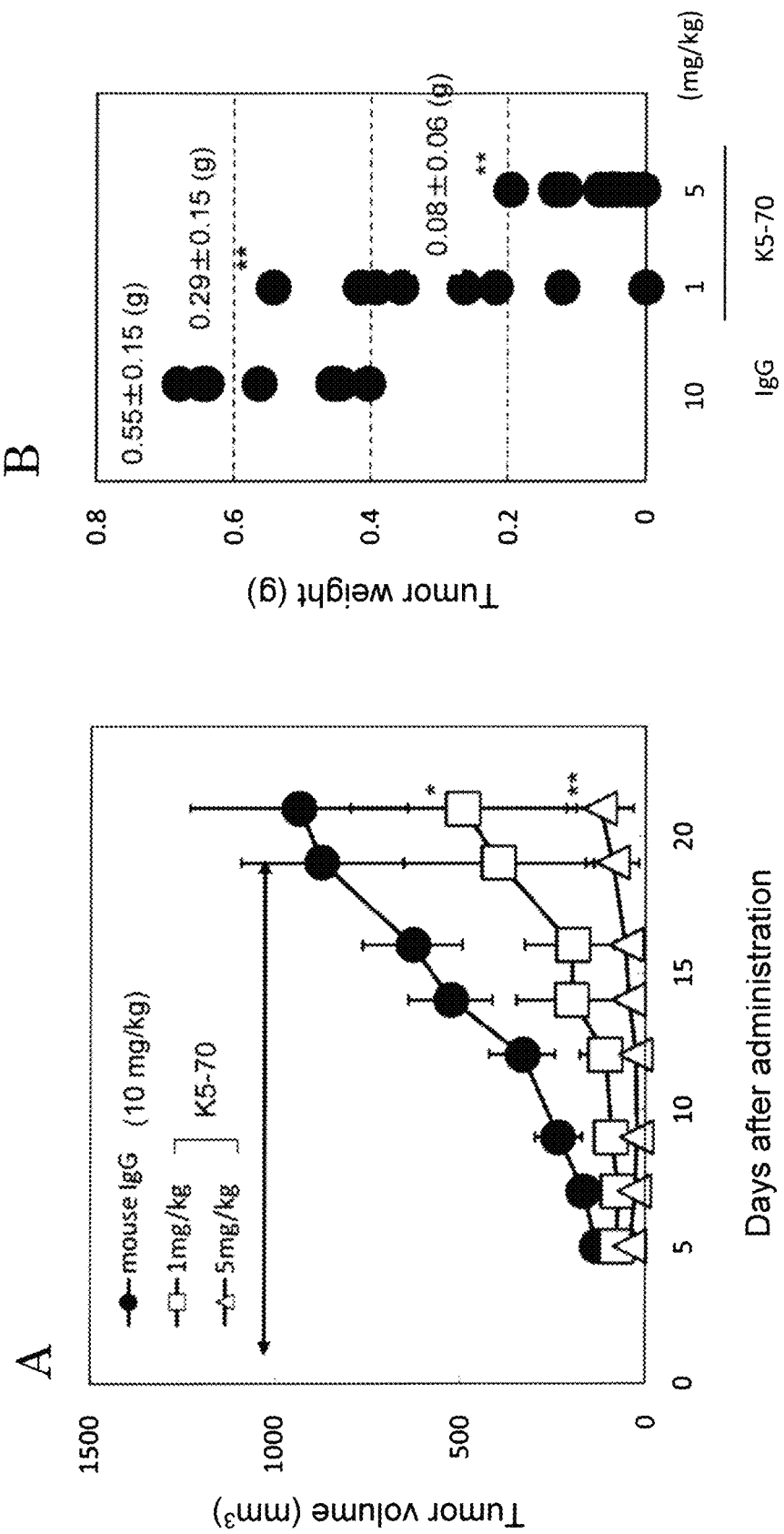
FIG. 16 shows the dose-dependent anti-tumor activity of a clone K5-70 on xenograft prevention models using PK-59 cells. The volume of a tumor is expressed as a mean value±standard deviation.

For the purpose of analyzing more in detail the tumor growth inhibitory activity in vivo of the anti-hTROP-2 antibody, a dose-dependent test was carried out. As shown in FIG. 16, the tumor growth of PK-59 cells was dose-dependently inhibited by administration of K5-70. On the 21$^{st}$ day after administration of the antibody (Day 21), the tumor volume of the control group (N=7) was 937.8±295.3 mm$^3$. On the other hand, the tumor volume of the K5-70 (1 mg/kg) administration group (N=8) was 493.5±305.1 mm$^3$, showing an inhibitory rate of 50%, and the tumor volume of the K5-70 (5 mg/kg) administration group (N=8) was 124.7±89.0 mm$^3$, showing an inhibitory rate of 90%. Thus, it became clear that, when compared with the known anti-TROP-2 antibody AR47A6.4.2 (U.S. Pat. No. 7,420,041), the anti-hTROP-2 antibody of the present invention exhibits in vivo a tumor growth inhibitory effect equivalent to that of the anti-TROP-2 antibody AR47A6.4.2 at a dosage of one-twentieth the anti-TROP-2 antibody AR47A6.4.2, and that it exhibits a higher inhibitory effect of 90% at a dosage of one-fourth thereof.

Example 19

Epitope Assay

Preparation of Human/Mouse Chimeric TROP-2 Protein

A human/mouse TROP-2 gene was prepared according to a PCR method. PCR primers as shown below were designed based on a human TROP-2 gene sequence and a mouse TROP-2 gene sequence (Genbank accession No. NM_020047).

```
Human/mouse TROP-2-C primers
Y606 (forward side):
                              (SEQ ID NO: 10)
5'-cctgagcctacgctgcgacgaagtggtgcg-3'

Y607 (reverse side):
                              (SEQ ID NO: 11)
5'-cgcaccacttcgtcgcagcgtaggctcagg-3'

Human/mouse TROP-2-A primers
Y612 (forward side):
                              (SEQ ID NO: 12)
5'-gactgctccacgctgacttccaagtgcctg-3'
```

-continued

Y613 (reverse side):
(SEQ ID NO: 13)
5'-caggcacttggaagtcagcgtggagcagtc-3'

Human/mouse TROP-2-B primers
Y614 (forward side):
(SEQ ID NO: 14)
5'-ctcgtggacaacgatggcctctacgacccg-3'

Y615 (reverse side):
(SEQ ID NO: 15)
5'-cgggtcgtagaggccatcgttgtccacgag-3'

Mouse/human TROP-2-D primers
Y608 (forward side):
(SEQ ID NO: 16)
5'-ccaaagcctgcgctgcgatgagctggtgcgc-3'

Y609 (reverse side):
(SEQ ID NO: 17)
5'-gcgcaccagctcatcgcagcgcaggctttgg-3'

Mouse/human TROP-2-E primers
Y616 (forward side):
(SEQ ID NO: 18)
5'-agcttcctatccgcggtgcactacgagcag-3'

Y617 (reverse side):
(SEQ ID NO: 19)
5'-ctgctcgtagtgcaccgcggataggaagct-3'

Mouse/human TROP-2-F primers
Y618 (forward side):
(SEQ ID NO: 20)
5'-gacattaaaggcgagtctctattccagggc-3'

Y619 (reverse side):
(SEQ ID NO: 21)
5'-gccctggaatagagactcgcctttaatgtc-3'

Mouse TROP-2 primers
Forward primer:
(SEQ ID NO: 22)
5-ctactccaccccaccctggcg-3'

Reverse primer:
(SEQ ID NO: 23)
5'-ctcgagcaagctaggttcgcttctc-3'

Figure 17:
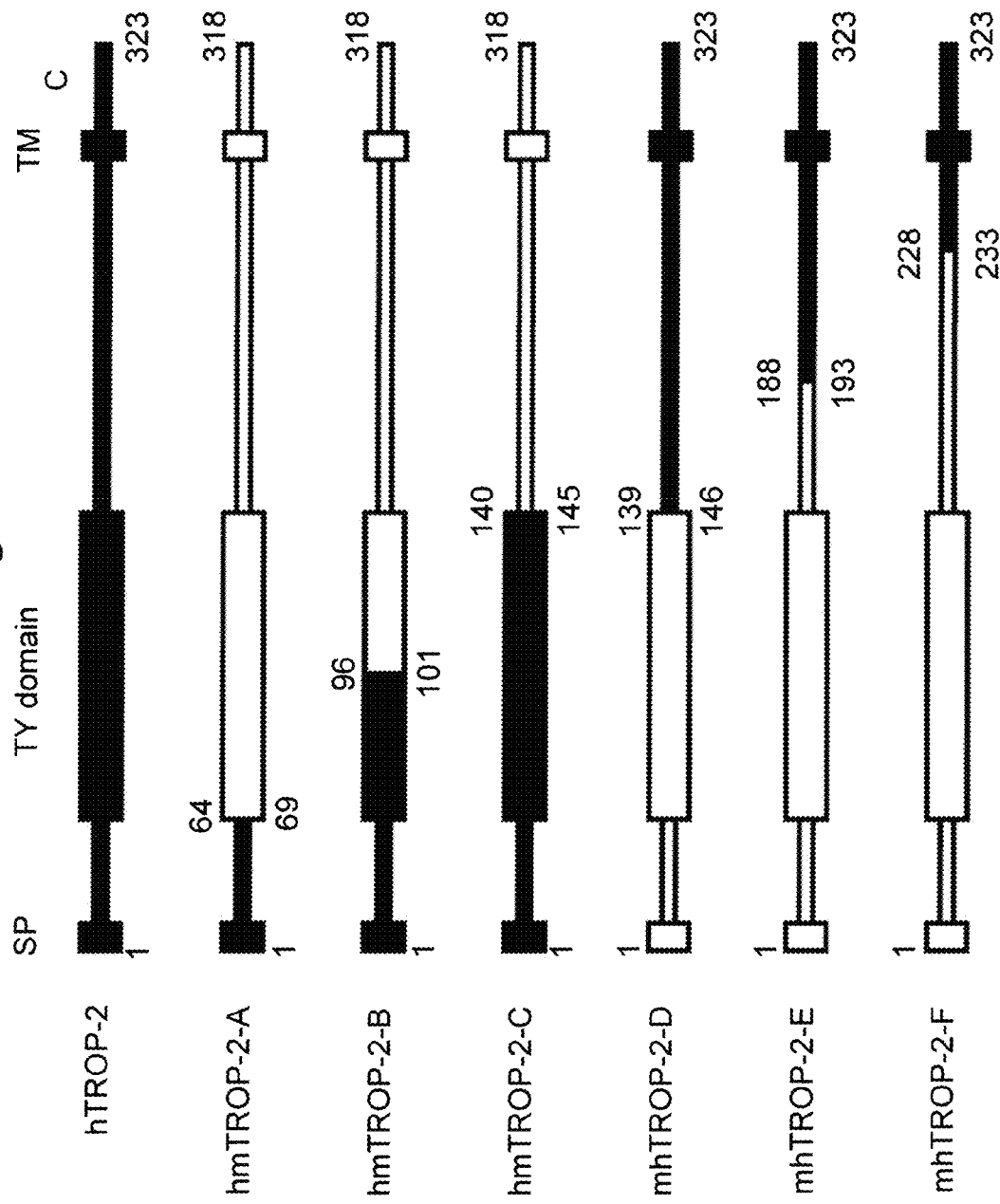
FIG. 17 is a schematic view of a human/mouse chimeric TROP-2 protein used in the experiment. SP: signal sequence; TY domain: thyroglobulin type 1 region; TM: transmembrane region; C: intracellular region, wherein the filled region is a polypeptide derived from hTROP-2, whereas the open region is a polypeptide derived from mouse TROP-2. The number in the upper position of the schematic view of the chimeric protein indicates the amino acid number of a mouse TROP-2 protein, and the number in the lower position thereof indicates the amino acid number of an hTROP-2 protein.

To the mouse TROP-2 reverse primer, a XhoI restriction enzyme-digested sequence except for a stop codon was added. A schematic view of the prepared human/mouse chimeric TROP-2 proteins is shown in FIG. 17.

The hmTROP-2-A chimeric protein is a chimeric protein, which consists of a polypeptide ranging from the N-terminus to the amino acid at position 69 of the hTROP-2 protein and a polypeptide ranging from the amino acid at position 64 to the C-terminus of the mouse TROP-2 protein. The hmTROP-2-B chimeric protein is a chimeric protein, which consists of a polypeptide ranging from the N-terminus to the amino acid at position 101 of the hTROP-2 protein and a polypeptide ranging from the amino acid at position 96 to the C-terminus of the mouse TROP-2 protein. The hmTROP-2-C chimeric protein is a chimeric protein, which consists of a polypeptide ranging from the N-terminus to the amino acid at position 145 of the hTROP-2 protein and a polypeptide ranging from the amino acid at position 140 to the C-terminus of the mouse TROP-2 protein. The mhTROP-2-D chimeric protein is a chimeric protein, which consists of a polypeptide ranging from the N-terminus to the amino acid at position 139 of the mouse TROP-2 protein and a polypeptide ranging from the amino acid at position 146 to the C-terminus of the hTROP-2 protein. The mhTROP-2-E chimeric protein is a chimeric protein, which consists of a polypeptide ranging from the N-terminus to the amino acid at position 187 of the mouse TROP-2 protein and a polypeptide ranging from the amino acid at position 194 to the C-terminus of the hTROP-2 protein. The mhTROP-2-F chimeric protein is a chimeric protein, which consists of a polypeptide ranging from the N-terminus to the amino acid at position 227 of the mouse TROP-2 protein and a polypeptide ranging from the amino acid at position 234 to the C-terminus of the hTROP-2 protein.

Expression vectors used in the preparation of the above-described chimeric proteins were specifically constructed by the following methods. In order to prepare an hmTROP-2-A chimeric gene, the hTROP-2 gene was used as a template, and PCR was carried out using the hTROP-2 forward primer and the human/mouse TROP-2-A primer Y613. Likewise, the mouse TROP-2 gene was used as a template, and PCR was carried out using the human/mouse TROP-2-A primer Y612 and the mouse TROP-2 reverse primer. A DNA fragment amplified by the PCR was developed using acrylamide gel, and a band of interest was then recovered by extraction. Subsequently, the extracted two types of DNA fragments were mixed to prepare a template, and PCR was then carried out using the hTROP-2 forward primer and the mouse TROP-2 reverse primer. A PCR product was developed by agarose gel electrophoresis, and a DNA fragment of interest was then extracted. The extracted DNA fragment was cloned into a pCR (registered trademark)-Blunt vector (Invitrogen) (pCRB-hmTROP-2-A), and a gene sequence was then confirmed. An expression vector for animal cells was produced by removing the hTROP-2 gene from pcDNA3.1-hTROP-2-myc/His by EcoRI/XhoI digestion, and then inserting therein an EcoRI/XhoI fragment containing an hmTROP-2-A chimeric gene prepared from pCRB-hmTROP-2-A (pcDNA3.1-hmTROP-2-A-myc/His). Additionally, the following chimeric genes were prepared by the same method as described above, and expression vectors were constructed: hmTROP-2-B (using a human TROP-2 forward primer, a human/mouse TROP-2-B primer Y615, a human/mouse TROP-2-B primer Y614 and a mouse TROP-2 reverse primer), hmTROP-2-C (using a human TROP-2 forward primer, a human/mouse TROP-2-C primer Y607, a human/mouse TROP-2-C primer Y606 and a mouse TROP-2 reverse primer), mhTROP-2-D (using a mouse TROP-2 forward primer, a mouse/human TROP-2-D primer Y609, a mouse/human TROP-2-D primer Y608 and a human TROP-2 reverse primer), mhTROP-2-E (using a mouse TROP-2 forward primer, a mouse/human TROP-2-E primer Y617, a mouse/human TROP-2-E primer Y616 and a human TROP-2 reverse primer), mhTROP-2-F (using a mouse TROP-2 forward primer, a mouse/human TROP-2-F primer Y619, a mouse/human TROP-2-F primer Y618 and a human TROP-2 reverse primer) (pcDNA3.1-hmTROP-2-B-myc/His, pcDNA3.1-hmTROP-2-C-myc/His, pcDNA3.1-mhTROP-2-D-myc/His, pcDNA3.1-mhTROP-2-E-myc/His, and pcDNA3.1-mhTROP-2-F-myc/His).

Establishment of HEK293 Cell Lines, which Constitutively Express hTROP-2, Human/Mouse TROP-2-C and Mouse/Human TROP-2-D Chimeric Proteins The above-described expression vectors pcDNA3.1-hTROP-2-myc/His, pcDNA3.1-hmTROP-2-C-myc/His and pcDNA3.1-mhTROP-2-D-myc/His were each introduced into HEK293 cells. Selection was carried out using an antibiotic G418 (Calbiochem), and HEK293 cell lines constitutively expressing the hTROP-2 protein, the hmTROP-2-C chimeric protein and the mhTROP-2-D chimeric protein were established.

Figure 18:
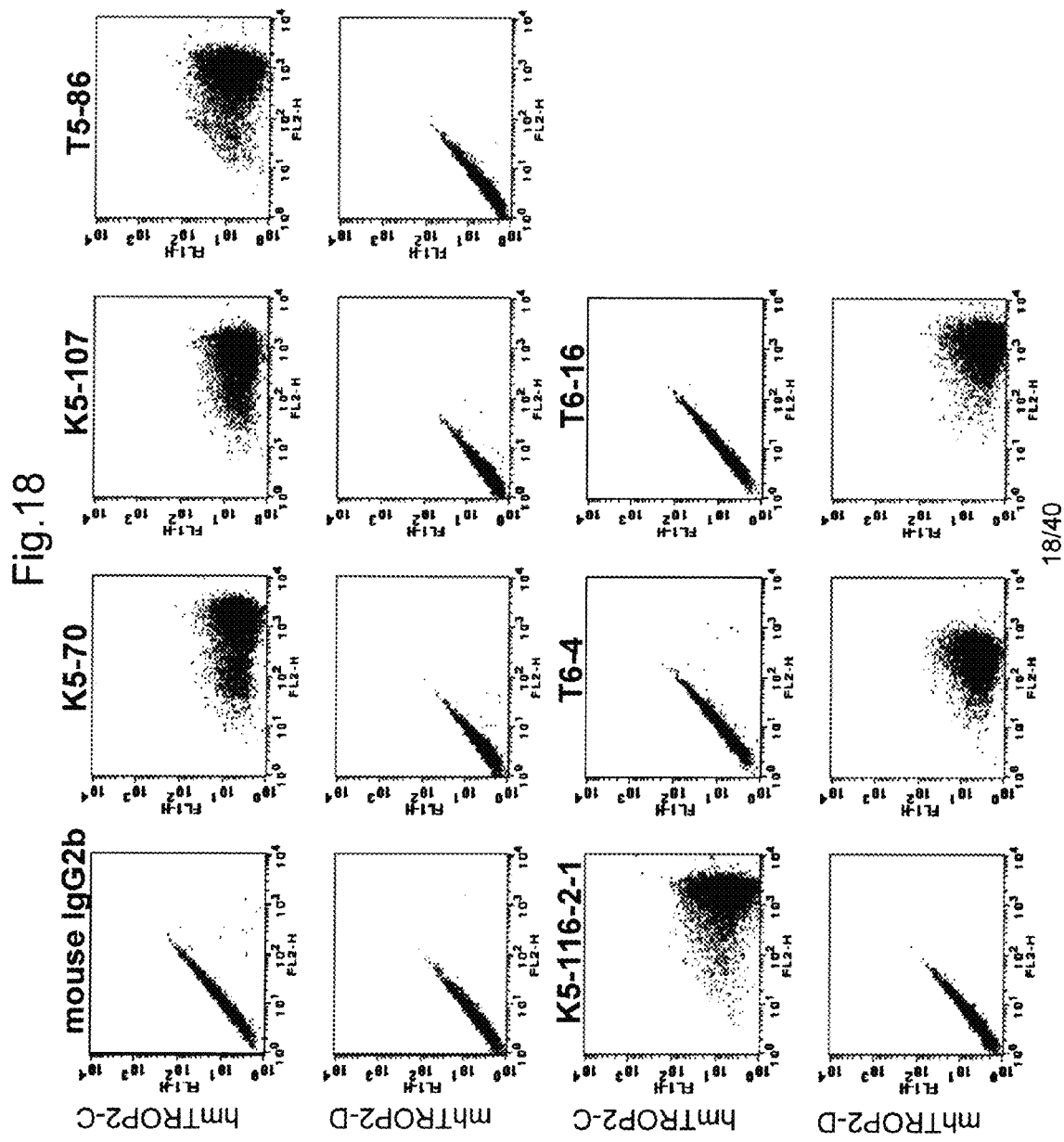
FIG. 18 shows the results obtained by identifying an anti-hTROP-2 monoclonal antibody-binding region, using human/mouse chimeric TROP-2. Using HEK293 cells, which constantly express either human/mouse chimeric TROP-2-C (hmTROP-2-C) or mouse/human chimeric TROP-2-D (mhTROP-2-D) proteins, the reactivity with the anti-hTROP-2 monoclonal antibodies shown in the figure was studied. As a negative control, mouse IgG2b was used.

The binding regions of the anti-hTROP-2 monoclonal antibodies K5-70, T5-86, K5-107, T6-4, T6-16 and K5-116-2-1, which had exhibited beneficial effects on the xenograft treatment models of the pancreatic cancer cell line PK-59, were identified. First, the reactivity of the anti-hTROP-2 monoclonal antibodies exhibiting beneficial effects with HEK293 cells, which constantly express the chimeric proteins hmTROP-2-C and mhTROP-2-D, was examined by FACS analysis (FIG. 18). As a result, it was found that K5-70, K5-107, T5-86 and K5-116-2-1 reacted with hmTROP-2-C, but that these antibodies did not react with mhTROP-2-D. On the other hand, T6-4 and T6-16 reacted with mhTROP-2-D, but they did not react with hmTROP-2-C. From these results, the binding region of each of K5-70, K5-107, T5-84 and K5-116-2-1 was limited to a region ranging from the N-terminus to the amino acid at position 145 of hTROP-2, and the binding region of each of T6-4 and T6-16 was limited to a region ranging from the amino acid at position 146 to the amino acid at position 274 of hTROP-2 (FIG. 18).

Figure 19:
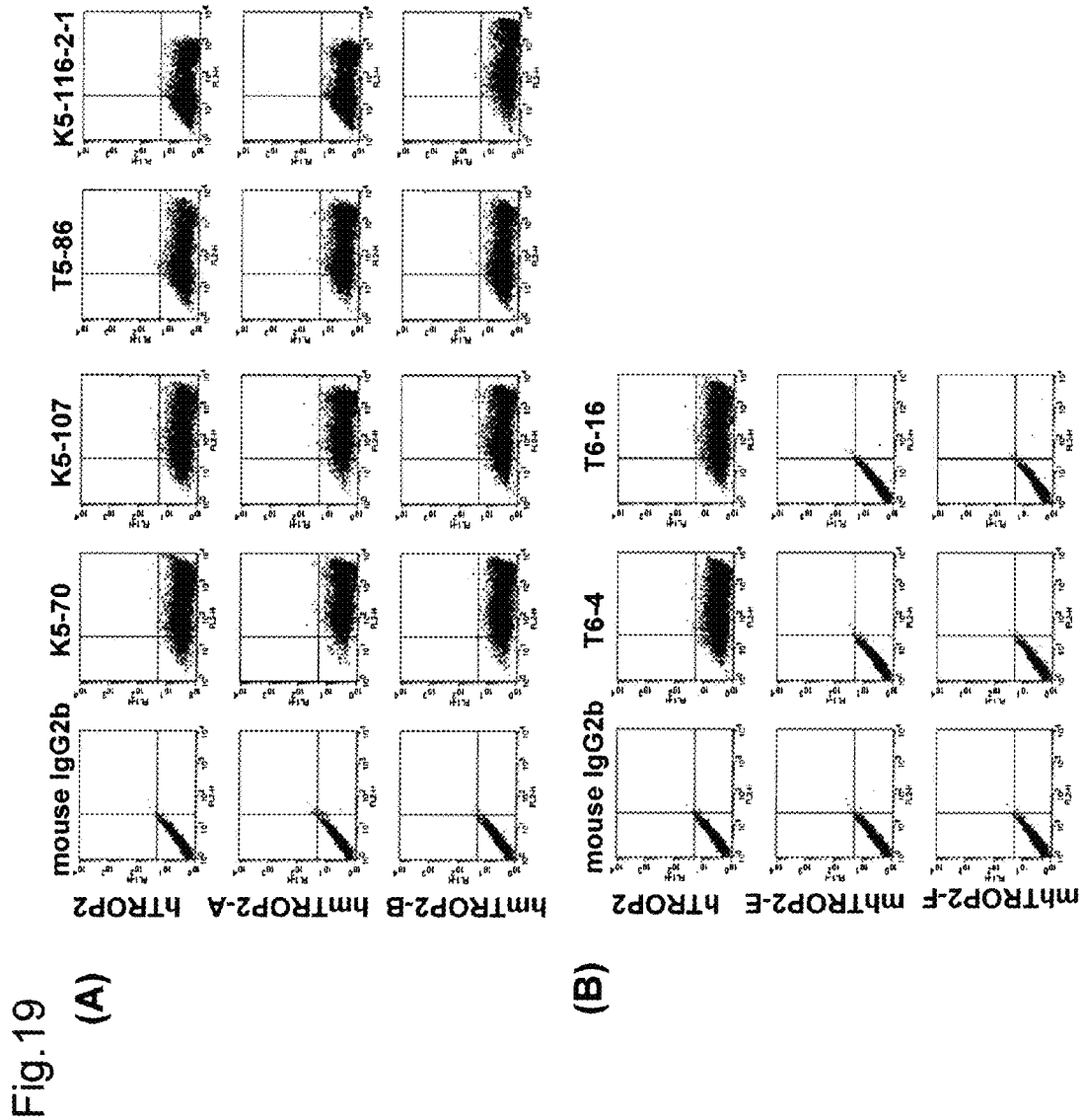
FIG. 19 shows the results obtained by identifying the antibody-binding region of an anti-hTROP-2 monoclonal antibody.

In order to analyze the binding regions more in detail, vectors used in the expression of hmTROP-2-A, hmTROP-2-B, mhTROP-2-E and mhTROP-2-F chimeric proteins were prepared, and the reactivity of the chimeric proteins with the anti-hTROP-2 monoclonal antibodies exhibiting beneficial effects was analyzed (FIG. 19). The newly prepared expression vectors, which were to be used in the expression of the chimeric proteins, were each introduced into HEK293 cells, and FACS analysis was then carried out, using the cells which transiently expressed the chimeric proteins. K5-70, K5-107, T5-86 and K5-116-2-1 reacted with hmTROP-2-A, but did not react with mhTROP-2-B. The examined 6 types of monoclonal antibodies all reacted with hTROP-2. These results clearly showed that the binding region of K5-70, K5-107, T5-86 and K5-116-2-1 is present in a region ranging from the N-terminus to the amino acid at position 69 of hTROP-2. Moreover, T6-4 and T6-16 reacted with neither mhTROP-2-E nor mhTROP-2-F. This suggested that these antibodies recognize a region ranging from the amino acid at position 146 to the amino acid at position 193 of hTROP-2.

Example 20

Immunohistochemistry

<Materials/Method>
The following normal and cancer tissue arrays were used in immunohistostaining.
Human Normal Tissue Arrays:
  Human, normal organs in duplicates (Catalog No.: AB1, Super Bio Chips)
  Normal tissues more than single spots (Catalog No.: A103 (VI), ISU ABXIS)
Lung Cancer Tissue Arrays:
  Human lung cancer-metastasis-normal (Catalog No.: CCA3, Super Bio Chips)
  Human lung carcinoma tissue with margin tissue, 2 location cores (Catalog No.: OD-CT-RsLug03-002, Shanghai Outdo Biotech)
Pancreatic Cancer Tissue Array:
  Human pancreas carcinoma tissue with mono-pathological type from 60 cases, 2 location cores (Catalog No.: OD-CT-DgPan03-001, Shanghai Outdo Biotech)
Liver Cancer Tissue Arrays:
  Hepatocellular carcinoma, grades I to III with normal tissue controls, 63 cases tissue arrays (Catalog No.: CS03-01-002U, Cybrdi)
  Human liver carcinoma tissue with mono-pathological type from 30 cases, 2 location cores (Catalog No.: OD-CT-DgLiv02-002, Shanghai Outdo Biotech)
Colon Cancer Tissue Arrays:
  Human, colorectal cancer (Catalog No.: CD3, Super Bio Chips)
  Human colon carcinoma with margin tissue, 2 location cores (Catalog No.: OD-CT-DgCo103-002, Shanghai Outdo Biotech)
Colon Cancer Lymph Node Metastasis and Liver Metastasis Tissue Arrays:
  Colorectal (colon and rectum) cancer with matched lymph node metastasis tissue array, 44 cases/99 cores, trial slide (Catalog No.: CO991t, Biomax us)
  Colorectal (colon and rectum) cancer with matched lymph node metastasis and normal adjacent tissue array, 43 cases/99 cores (Catalog No.: CO992, Biomax us)
  Colon cancer tissues liver metastasis (Catalog No.: A203 (IV), ISU ABXIS)
Breast Cancer Tissue Arrays:
  Human, breast cancer-metastasis-normal (Catalog No.: CBA3, Super Bio Chips)
  Human breast carcinoma with margin tissue, 2 location cores (Catalog No.: OD-CT-RpBre03-002, Shanghai Outdo Biotech)
Stomach Cancer Tissue Arrays:
  Human, stomach cancer (Catalog No.: CQ1, Super Bio Chips) Human gastric carcinoma with margin tissue, 2 location cores (Catalog No.: OD-CT-DgStm03-002, Shanghai Outdo Biotech)
Esophagus Cancer Tissue Array:
  Human, esophagus cancer (Catalog No.: CR1, Super Bio Chips)
  Human esophagus carcinoma with margin tissue, 2 location cores (Catalog No.: OD-CT-DgEso03-002, Shanghai Outdo Biotech)
Ovary Cancer Tissue Array:
  Human, ovary cancer (Catalog No.: CJ1, Super Bio Chips)
Prostate Cancer Tissue Array:
  Human, prostate cancer-normal (Catalog No.: CA3, Super Bio Chips) Bladder cancer tissue array:
  Bladder carcinoma/transitional cell carcinoma, grades I to III with normal tissue arrays (Catalog No.: CC12-01-001U, Cybrdi)

Patient information and clinical information regarding the above-described tissue arrays were obtained from data sheets attached herewith and the homepages of individual companies.

Immunohistostaining Method

After completion of a deparaffinization treatment, the tissue array slides of human normal tissues and cancer tissues were subjected to a protease treatment with pepsin at 37° C. for 5 minutes. Thereafter, the sections were used in immunostaining using an anti-hTROP-2 monoclonal antibody. A color reaction was carried out using DAB (3,3'-diaminobenzidine) as a substrate, and as a counter staining, nuclear staining was then carried out using hematoxylin.

Figure 20:
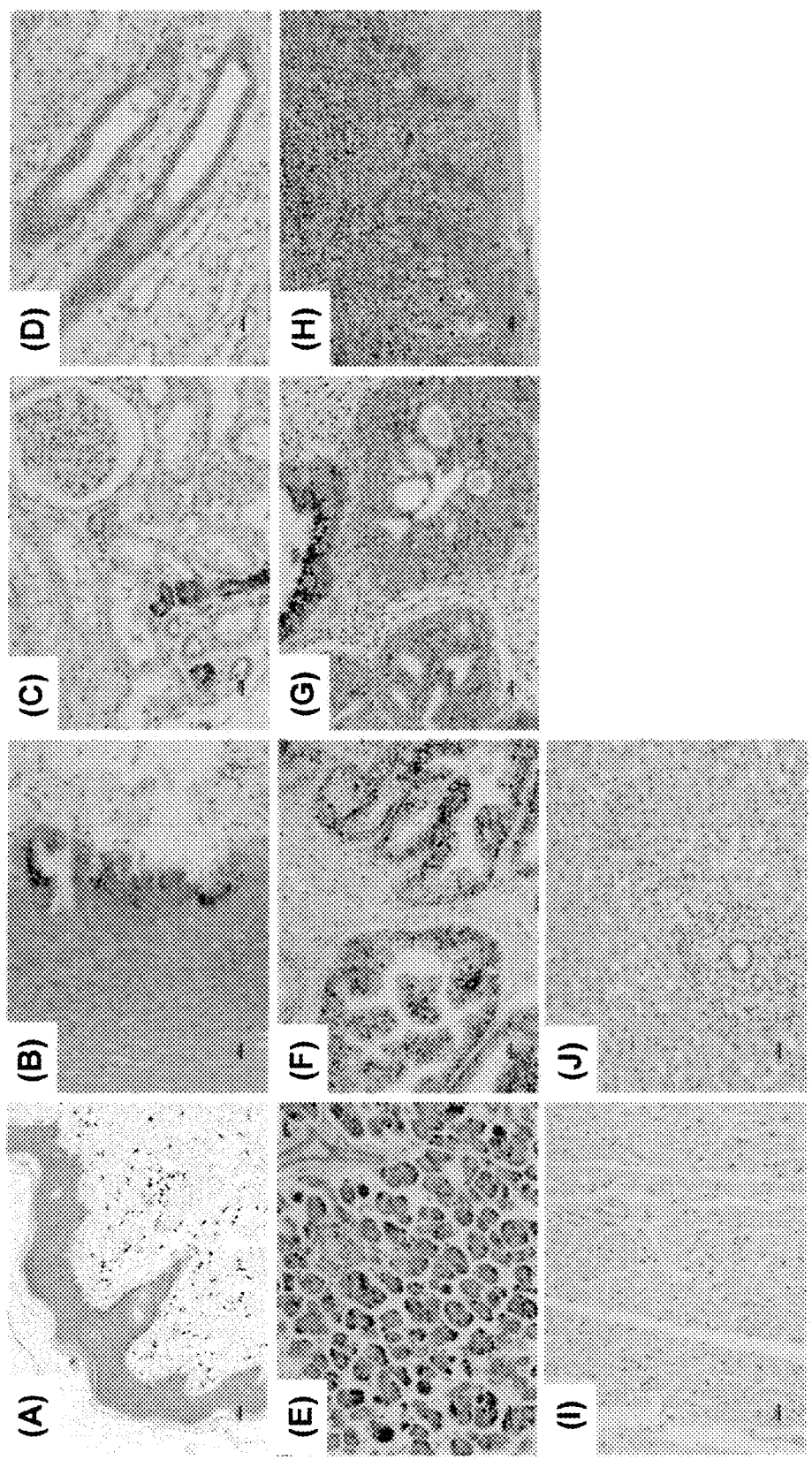
FIG. 20 shows the expression of hTROP-2 in human normal tissues. Human normal tissue arrays were immunostained with an anti-hTROP-2 monoclonal antibody clone K5-63-17. (A) skin, (B) esophagus, (C) kidney (cortex), (D) kidney (medulla), (E) pancreas, (F) prostate, (G) bladder, (H) tonsil, (I) heart, (J) liver (magnification: ×200)

More specifically, these operations were carried out as follows. A paraffin-embedded section was subjected to a deparaffinization treatment, and was then subjected to a protease treatment with pepsin (DAKO) at 37° C. for 5 minutes. After activation of the antigen, the section was treated at room temperature for 20 minutes using a solution prepared by adding a hydrogen peroxide solution to methanol to a final concentration of 0.3%, so that endogenous peroxidase activity was eliminated. The resultant was washed with PBS at room temperature for 5 minutes twice, and it was then blocked at room temperature for 30 minutes using a PBS solution containing 1.5% normal horse serum (DAKO), so as to carry out an operation to block non-specific binding in the tissues. Subsequently, the resultant was reacted with antihTROP-2 monoclonal antibody clone K5-63-17 (final concentration: 10 μg/ml), which had been diluted with a PBS solution containing 1.5% normal horse serum, at room temperature for 1 hour, and was then washed with PBS at room temperature for 5 minutes three times. Thereafter, a biotinylated anti-mouse IgG antibody (Vector), which had been 200 times diluted with a PBS solution containing 1.5% normal horse serum, was reacted at room temperature for 30 minutes. The reaction product was washed with PBS at room temperature for 5 minutes three times, and a reagent of Vectastain ABC kit (Vector) was mixed in accordance with the instruction manual included therewith, so as to prepare an ABC complex. This ABC complex was reacted at room temperature for 30 minutes. The reaction product was washed with PBS at room temperature for 5 minutes three times, and color development was then carried out using Histofine Peroxidase Substrate Simple Stain DAB solution (Nichirei Biosciences). After completion of the color development, the reaction product was washed with deionized water for 5 minutes, and the nucleus was stained with Mayer's hematoxylin solution (Wako Pure Chemical Industries, Ltd.). Thereafter, dehydration was carried out with alcohol, followed by penetration with xylene and mounting in Entellan New (Merck Japan).
<Results>
Expression of hTROP-2 in Human Normal Tissues The expression pattern of hTROP-2 in human normal tissues was analyzed using the anti-hTROP-2 monoclonal antibody clone K5-63-17. A human normal tissue array (Catalog No.: AB1, Super Bio Chips) was deparaffinized, and was then subjected to a hydrophilic treatment. Thereafter, the antigen was activated with a protease, pepsin, and immunostaining was then carried out using the anti-hTROP-2 monoclonal antibody clone K5-63-17 (FIG. 20). As a result, staining was observed in the skin, esophagus, kidney (cortex and medulla), pancreas, prostate, bladder and tonsil. A majority of stained images localized in the cell membrane (FIGS. 20A, B, C, D, F, G and H), but hTROP-2 expression was partially observed even in the cytoplasm (FIGS. 20E and H). On the other hand, such staining was not observed in the heart, liver, stomach, small intestine, large intestine, skeletal muscle, lung, spleen, *thymus* gland and the like (FIGS. 20I and J).

Expression of hTROP-2 in Human Cancer Tissues

In order to examine the expression of hTROP-2 (hTROP-2-positive rate) in human cancer tissues, the cancer tissue arrays of various human cancer species were immunostained using the anti-hTROP-2 monoclonal antibody clone K5-63-17. A tissue section, in which 10% or more of cancer cells were stained, was defined as hTROP-2-positive. The staining results are shown in Table 4.

TABLE 4

| Cancer tissues | number of TROP-2-positive cases/total number of cases | TROP-2-positive rate (%) |
|---|---|---|
| Breast cancer | 32/80 | 40 |
| Lung cancer | 53/81 | 65.4 |
| Esophagus cancer | 69/90 | 76.7 |
| Stomach cancer | 25/90 | 27.8 |
| Colon cancer | 29/178 | 16.3 |
| Pancreatic cancer | 26/62 | 41.9 |
| Liver cancer | 7/92 | 7.61 |
| Bladder cancer | 42/59 | 71.2 |
| Prostate cancer | 35/38 | 92.1 |
| Ovary cancer | 14/58 | 24.1 |

Figure 21:
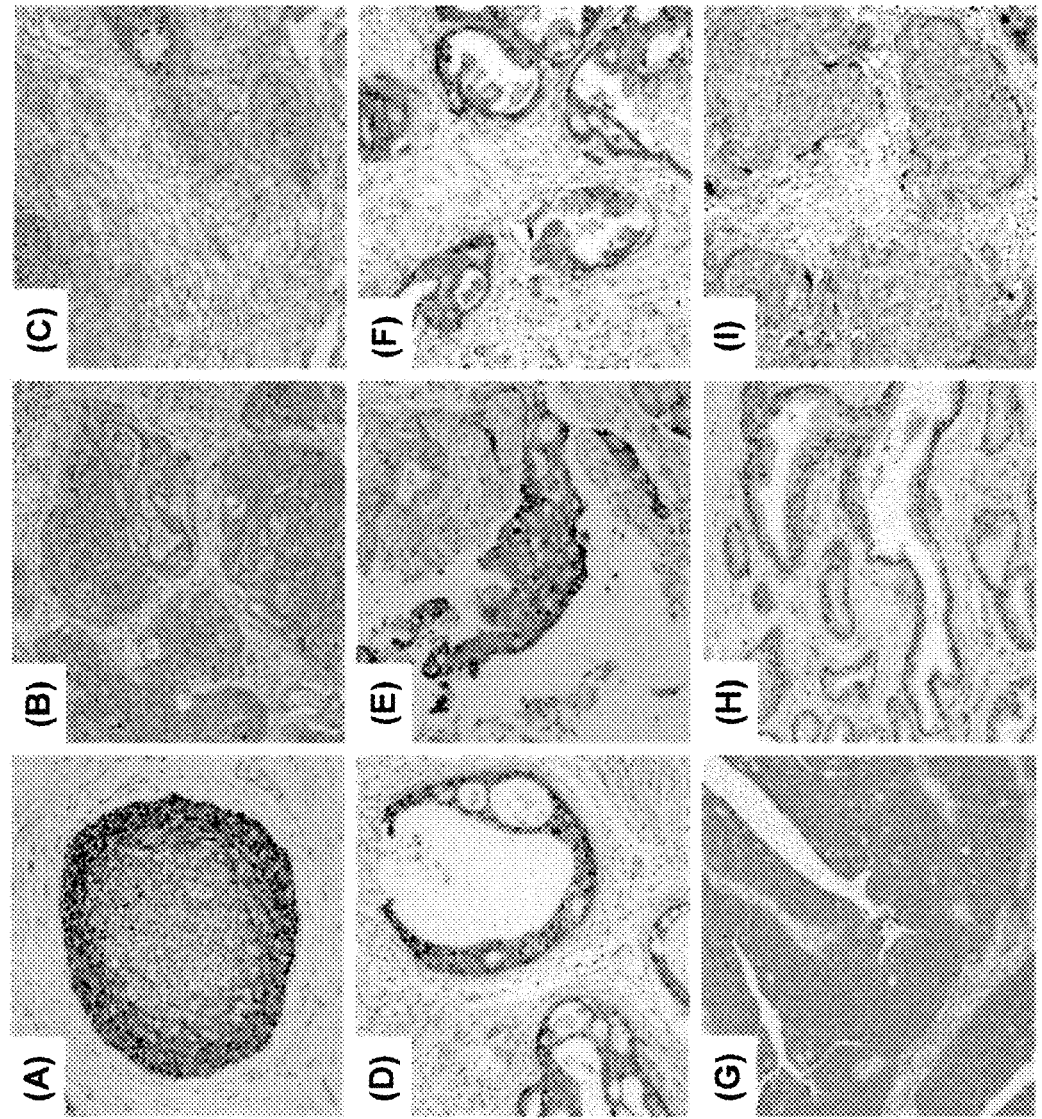
FIG. 21 shows the expression of hTROP-2 in cancer tissues. Human cancer tissue arrays were immunostained with an anti-hTROP-2 monoclonal antibody clone K5-63-17. (A) breast cancer, (B) lung cancer, (C) esophagus cancer, (D) stomach cancer, (E) pancreatic cancer, (F) colon cancer, (G) bladder cancer, (H) prostate cancer, (I) ovary cancer (magnification: ×100)

Representative stained images are shown in FIG. 21. Among cancer species, regarding which the expression of hTROP-2 had been analyzed, prostate cancer had the highest positive rate (92.1%), and also, lung cancer (65.4%), esophagus cancer (76.7%), bladder cancer (71.2%) and the like had high positive rates. Liver cancer had the lowest positive rate (7.61%). It was observed from stained images that, as with in normal cells, hTROP-2 was highly localized in the cell membrane even in the case of cancer cells (FIGS. 21 A to F, H and I). In addition, hTROP-2 was also localized in the cytoplasm in some cases (FIGS. 21A, B, E and G).

The hTROP-2-positive rate in pancreatic cancer was 41.9%. The relationship between this hTROP-2-positive rate and the grade (degree of differentiation) of pancreatic cancer was analyzed. As a result, hTROP-2 was expressed at high frequency in pancreatic cancer with a high grade, namely, with a low degree of differentiation (Table 5).

TABLE 5

| Pancreatic cancer hTROP-2-positive spots 26/62 (41.94%) | | | |
|---|---|---|---|
| Grade | − | + | Positive rate |
| I | 8 | 0 | 0% |
| I-II | 5 | 0 | 0% |
| II | 19 | 21 | 52.5% |
| II-III | 4 | 5 | 55.6% |
| total | 36 | 26 | |

$p < 0.01$

Example 21

Anti-Tumor Activity of K5-70 Antibody by Single Administration on Xenograft Prevention Models of Human Pancreatic Cancer Cell Line PK-59

Figure 22:
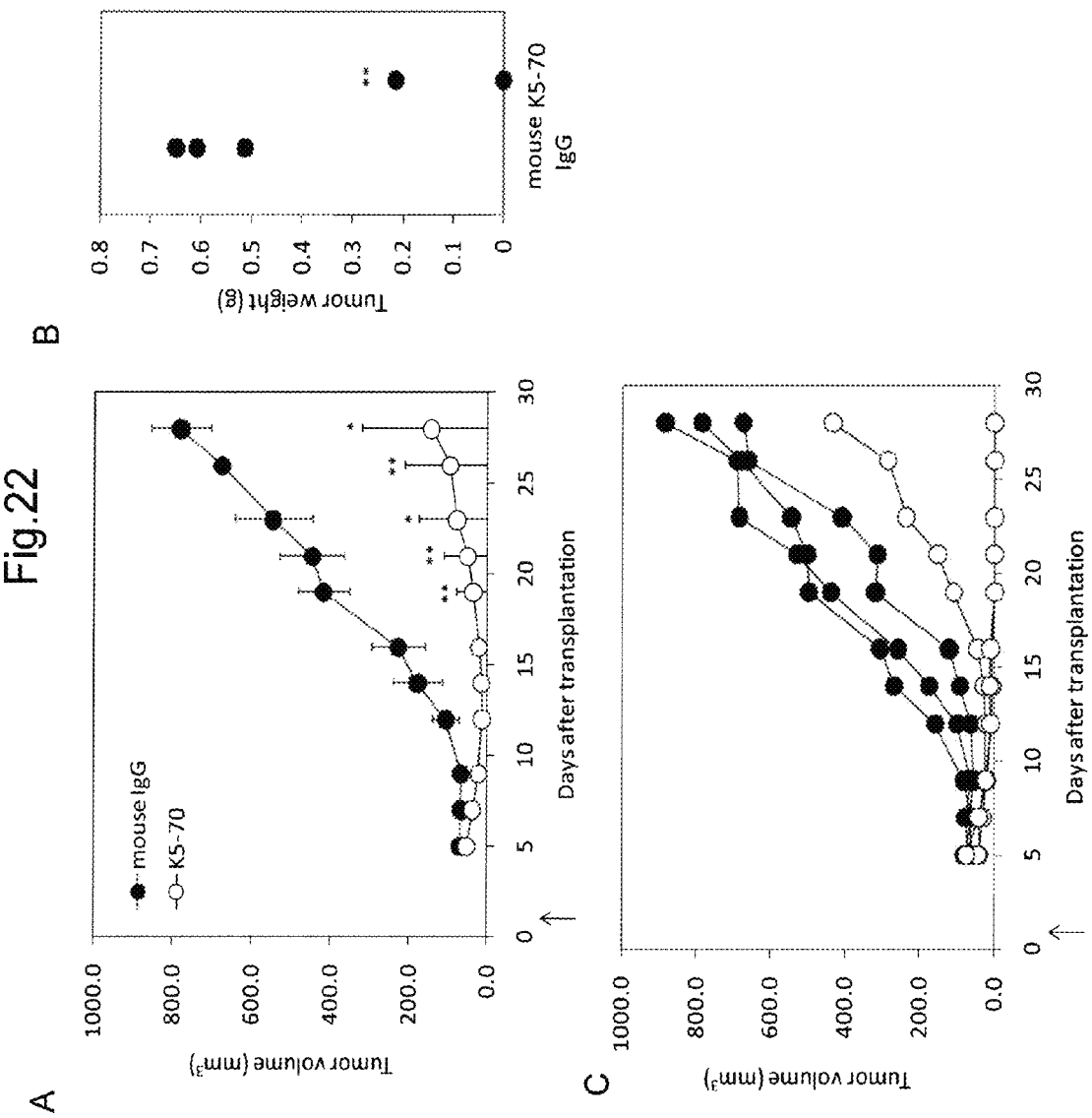
FIG. 22 shows the anti-tumor activity of a clone K5-70 by a single administration on xenograft prevention models using PK-59 cells.

Strong anti-tumor activity in vivo of a clone K5-70 (mouse IgG2a) was exhibited even by a single administration of K5-70 at a dosage of 10 mg/kg body weight to xenograft prevention models using a human pancreatic cancer cell line PK-59. In a control group (mouse IgG, 10 mg/kg body weight, N=3), tumor formation was observed in all of the individuals, and the tumor volume on the $28^{th}$ day after cell transplantation (Day 28) was 781.7±74.5 mm³. On the other hand, in a group in which K5-70 was administered only once on the day of transplantation of the cancer cells (Day 1) (10 mg/kg body weight, N=3), the tumor volume on Day 28 was 144.4±176.9 mm³ (P<0.05 by Student's t-test), showing tumor growth inhibitory activity of 81.5% (FIG. 22A). With regard to tumor weight, the tumor weight of the control group on Day 28 was 0.59±0.06 g. In contrast, the tumor weight of the clone K5-70 administration group was 0.07±0.10 g (P<0.01 by Student's t-test), showing an inhibitory activity of 88% (FIG. 22B). With regard to both tumor volume and tumor weight, tumor formation was completely inhibited in 2 out of 3 individuals in the K5-70 administration group at a dosage of 10 mg/kg body weight per administration (FIG. 22C).

Example 22

Anti-Tumor Activity of Anti-Human TROP-2 Monoclonal Antibody on Xenograft Treatment Models of Human Colon Cancer Cell Line SW480

Figure 23:
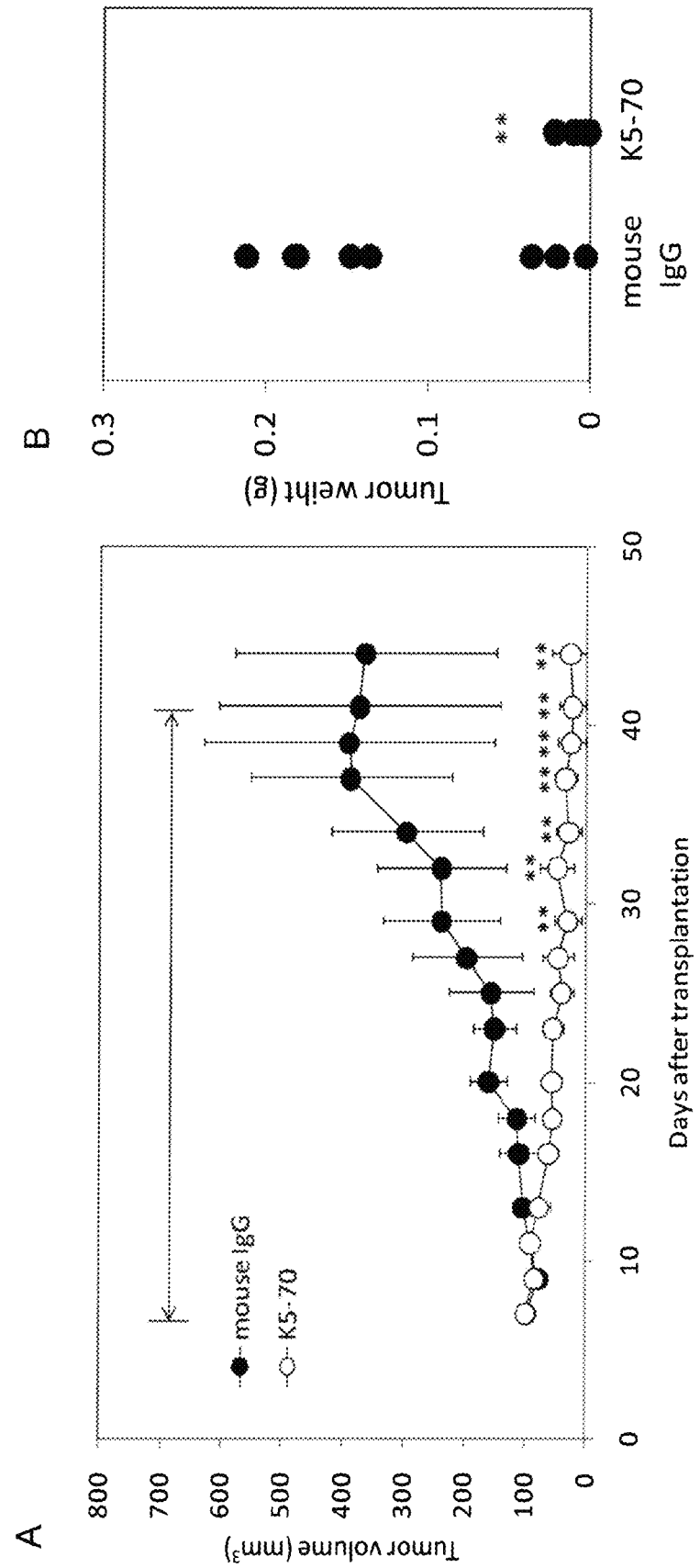
FIG. 23 shows the anti-tumor activity of a clone K5-70 on xenograft treatment models using human colon cancer SW480 cells.

The anti-tumor activity of each of anti-human TROP-2 monoclonal antibodies (clones K5-70, K5-116-2-1, and T6-16) was examined with xenograft treatment models using a human colon cancer cell line SW480. SW480 cells (5×10⁶ cells) were subcutaneously transplanted into the right flank of each of 6-week-old female NOD-scid mouse (Day 1). When the mean tumor volume reached 100 mm$^3$, grouping was carried out (Day 7 or Day 10). From Day 7 or Day 10, intraperitoneal administration of the antibody was carried out at administration intervals of once every three days. The anti-tumor activity of clone K5-70 and the anti-tumor activities of clones K5-116-2-1 and T6-16 were evaluated by independent studies, separately. In the study of evaluating the anti-tumor activity of K5-70, the tumor volume of a control group (mouse IgG (10 mg/kg body weight), N=8) on the 44$^{th}$ day after cancer cell transplantation (Day 44) was 365.4±214.6 mm$^3$. On the other hand, the tumor volume of a K5-70 (10 mg/kg body weight) administration group was 27.4±29.4 mm$^3$ (P<0.01 by Student's t-test), and thus, tumor formation was significantly inhibited in the K5-70 administration group (inhibitory rate: 92.5%) (FIG. 23A). With regard to tumor weight, the tumor weight of the control group was 0.11±0.07 g, whereas the tumor weight of the K5-70 administration group was 0.005±0.007 (g) (P<0.01 by Student's t-test), showing an inhibitory rate of 95.5% (FIG. 23B). In particular, in two out of the eight individual mice in the K5-70 administration group, tumor formation was completely inhibited, and the presence of tumor could not be confirmed.

Figure 24:
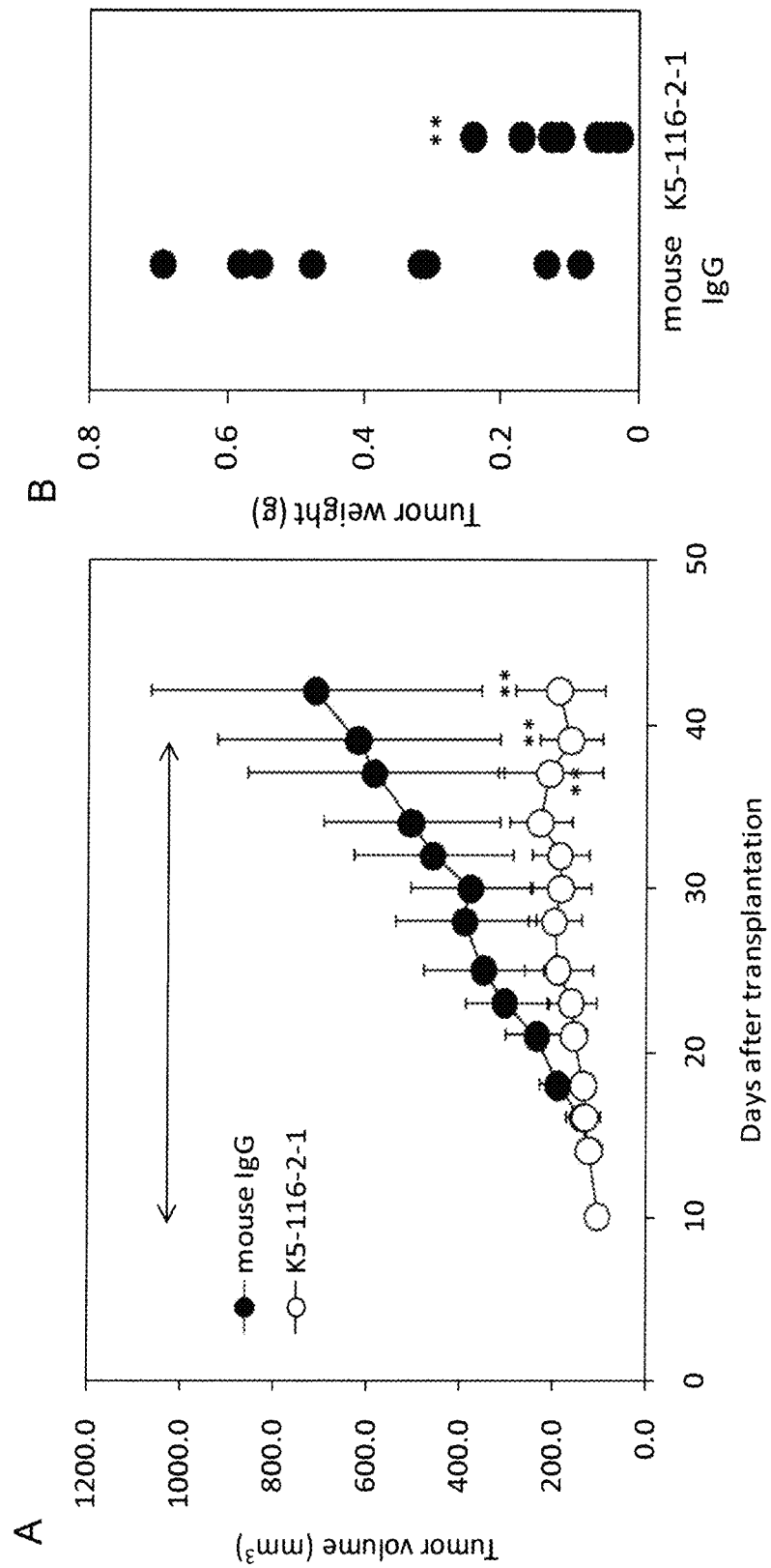
FIG. 24 shows the anti-tumor activity of a clone K5-116-2-1 on xenograft treatment models using SW480 cells.
Figure 25:
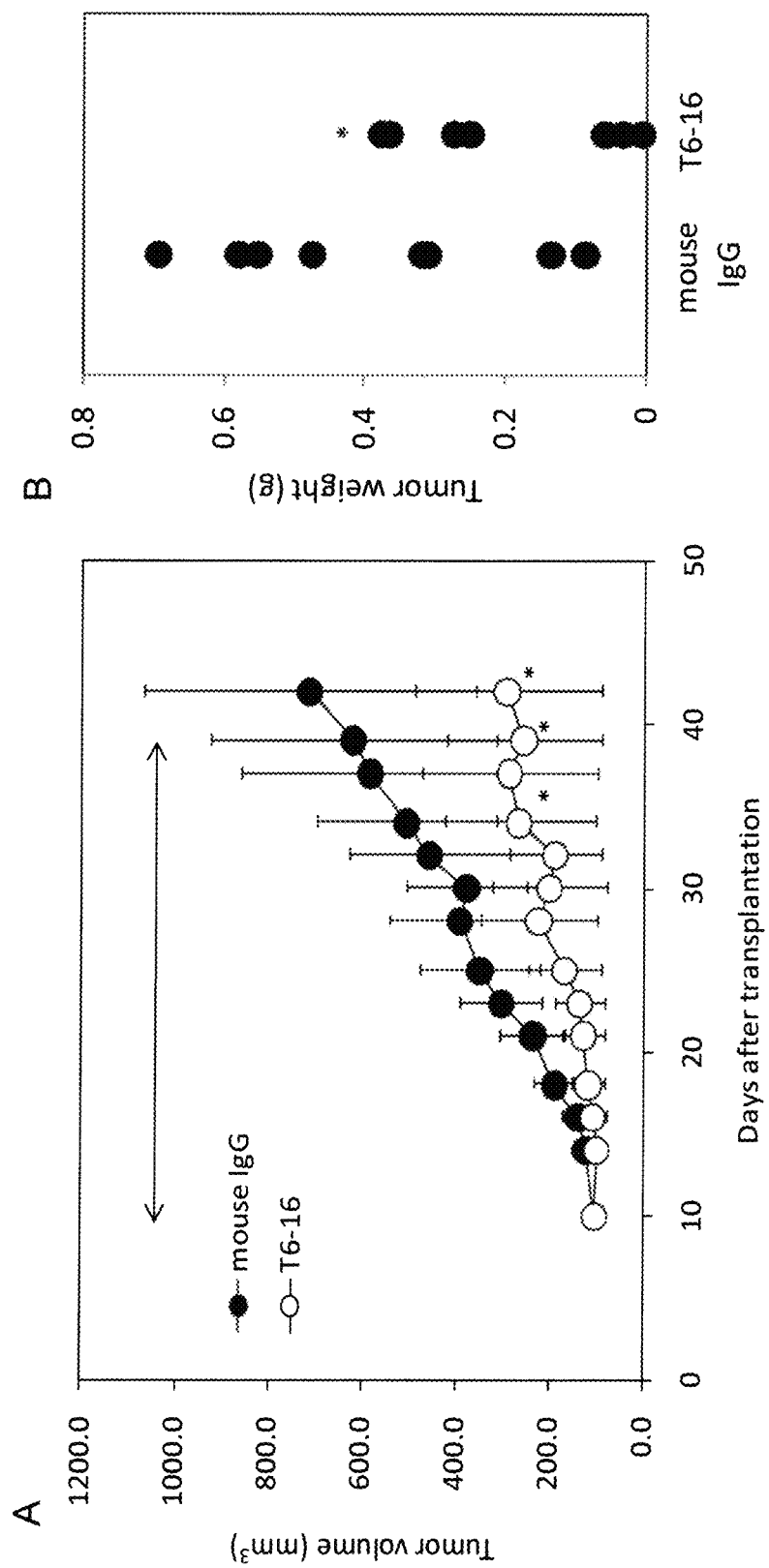
FIG. 25 shows the anti-tumor activity of a clone T6-16 on xenograft treatment models using SW480 cells.

In the study of evaluating the anti-tumor activities of K5-116-2-1 and T6-16, which was carried out separately, the tumor volume of the control group on Day 42 was 713.8±354.5 mm$^3$ (N=8). In contrast, the tumor volume of the K5-116-2-1 administration group (10 mg/kg body weight) was 188.9±97.4 mm$^3$ (N=8, P<0.01 by Student's t-test) (FIG. 24A), and the tumor volume of the T6-16 administration group (10 mg/kg body weight) was 292.8±199.7 mm$^3$ (N=8, P<0.05 by Student's t-test) (FIG. 25A). Thus, the two above administration groups showed inhibitory rates of 73.5% and 59.0%, respectively. With regard to tumor weight as well, the tumor weight of the control group was 0.39±0.19 g. In contrast, the tumor weight of the K5-116-2-1 administration group was 0.10±0.07 g (P<0.01 by Student's t-test), and the tumor weight of the T6-16 administration group was 0.17±0.14 g (P<0.05 by Student's t-test). Thus, the two above administration groups showed inhibitory rates of 72.2% and 56.4%, respectively (FIG. 24B and FIG. 25B).

Example 23

Dose-Dependent Anti-Tumor Activity of Clone K5-70 on Xenograft Treatment Models Using Human Colon Cancer Cell Line SW480

Figure 26:
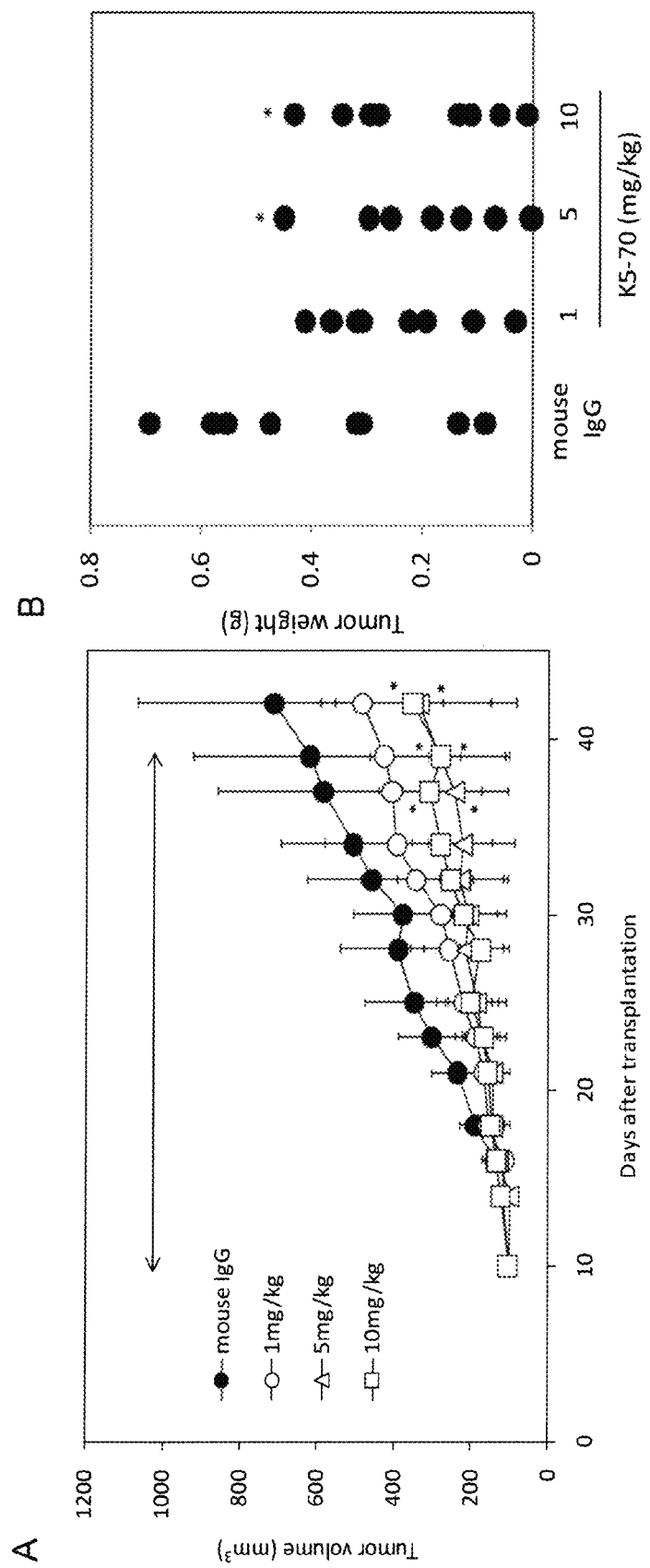
FIG. 26 shows the dose-dependent anti-tumor activity of a clone K5-70 on xenograft treatment models using SW480 cells.

Subsequently, the dose-dependent anti-tumor activity of clone K5-70 (mouse IgG2a) was examined with xenograft treatment models using a human colon cancer cell line SW480. SW480 cells (5×10$^6$ cells) were subcutaneously transplanted into the right flank of each of 6-week-old female NOD-scid mouse. Ten days after the transplantation (Day 10) at which the mean tumor volume reached 100 mm$^3$, the mice were divided into a control group (mouse IgG, 10 mg/kg body weight administration group, N=8, 104.4±17 6 mm$^3$), a K5-70 (1 mg/kg body weight) administration group (N=8, 104.3±16.1 mm$^3$), a K5-70 (5 mg/kg body weight) administration group (N=8, 104.6±15 9 mm$^3$), and a K5-70 (10 mg/kg body weight) administration group (N=8, 104.8±14.9 mm$^3$). Then, intraperitoneal administration was carried out at administration intervals of once every three days. On Day 42, the tumor volume of the control group was 713.8±354.5 mm$^3$. On the other hand, in the K5-70 administration groups, dose-dependent tumor formation inhibitory activity was observed. That is, the tumor volume of the 1 mg/kg body weight administration group was 485.0±207.3 mm$^3$ (inhibitory rate: 32.1%), the tumor volume of the 5 mg/kg body weight administration group was 339.5±253.2 mm$^3$ (inhibitory rate: 52.4%), and the tumor volume of the 10 mg/kg body weight administration group was 355.4±202.8 mm$^3$ (inhibitory rate: 50.2%, P<0.05 by Student's t-test) (FIG. 26A). Likewise, with regard to tumor weight on Day 42, the tumor weight of the control group was 0.39±0.19 g. On the other hand, the tumor weight of the K5-70 (1 mg/kg body weight) administration group was 0.24±0.11 g (inhibitory rate: 37.8%), the tumor weight of the 5 mg/kg body weight administration group was 0.17±0.14 g (inhibitory rate: 55.8%, P<0.05 by Student's t-test), and the tumor weight of the 10 mg/kg body weight administration group was 0.20±0.13 g (inhibitory rate: 47.1%). Thus, dose-dependent anti-tumor activity was confirmed (FIG. 26B).

Example 24

Analysis of Administration Intervals of Clone K5-70 to Xenograft Treatment Models Using Human Colon Cancer Cell Line SW480

Figure 27:
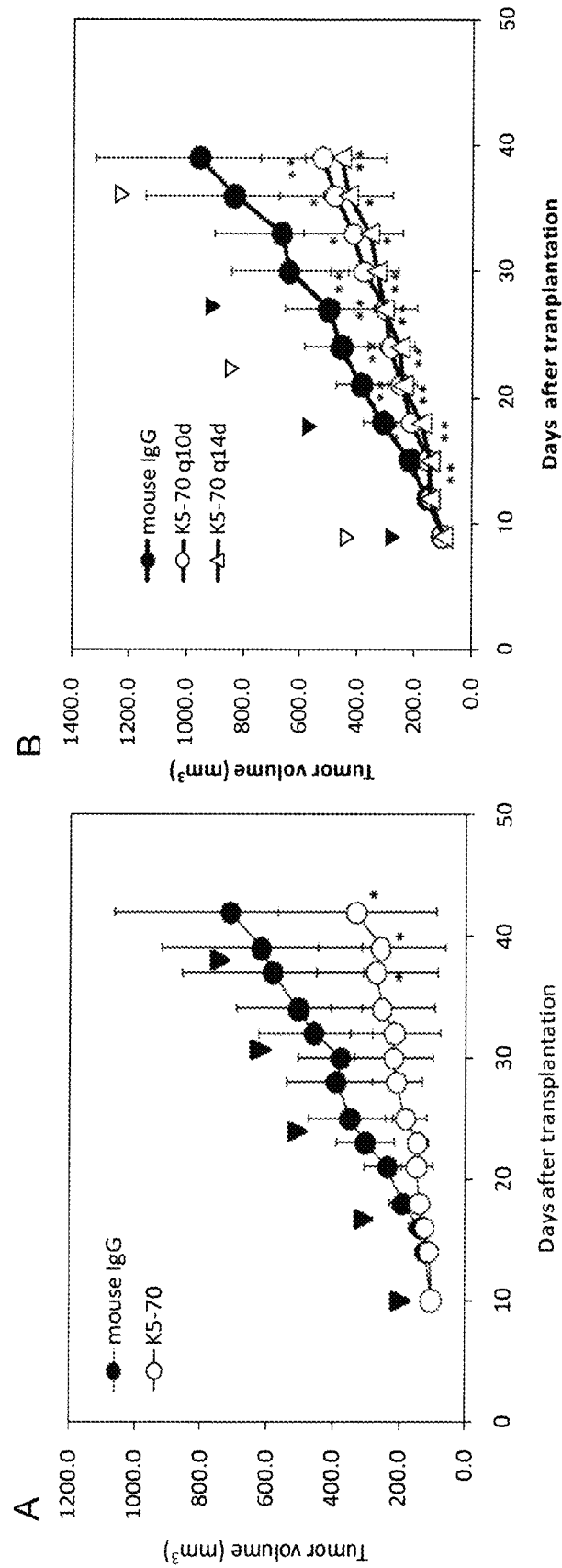
FIG. 27 shows the anti-tumor activity of a clone K5-70 on xenograft treatment models using SW480 cells.

Subsequently, in order to analyze optimal administration intervals of clone K5-70 (mouse IgG2a), the anti-tumor activity of the clone K5-70 when it was administered once a week (once every 7 days) was examined with xenograft treatment models using a human colon cancer cell line SW480. SW480 cells (5×10$^6$ cells) were subcutaneously transplanted into the right flank of each of 6-week-old female NOD-scid mouse. Ten days after the transplantation (Day 10) at which the mean tumor volume reached 100 mm$^3$, the mice were divided into a control group (mouse IgG, 10 mg/kg body weight administration group, N=8, 104.4±17.6 mm$^3$) and a K5-70 (10 mg/kg body weight, once a week) administration group (N=8, 104.3±16.1 mm$^3$). Then, intraperitoneal administration was carried out once every 7 days. On Day 42, the tumor volume of the control group was 713.8±354.5 mm$^3$, whereas the tumor volume of the K5-70 administration group (once a week) was 323.3±239.9 mm$^3$ (inhibitory rate: 55%, P<0.05 by Student's t-test) (FIG. 27A). Moreover, when the administration interval was increased to once every 10 days and to once every two weeks, the tumor volume of the control group on Day 39 was 956.9±367.8 mm$^3$. On the other hand, the tumor volume of the K5-70 administration group (administered once every 10 days) on Day 39 was 525.4±180.6 mm$^3$ (inhibitory rate: 45.1%, P<0.01 by Student's t-test), and the tumor volume of the K5-70 administration group (administered once every 14 days) was 459.4±217.6 mm$^3$ (inhibitory rate: 52.0%, P<0.01 by Student's t-test) (FIG. 27B). In the prior arts (U.S. Pat. No. 7,420,040 and U.S. Pat. No. 7,420,041), when antibodies were administered to xenograft treatment models using a pancreatic cancer cell line (BxPC-3) at a dosage of 20 mg/kg body weight, three times a week (at administration intervals of 2 days), the antibodies exhibited anti-tumor activity at an inhibitory rate of 50% to 60%. In contrast, the K-70 antibody exhibited anti-tumor activity equivalent to those of the prior arts, at a dosage of half of the prior arts (10 mg/kg body weight), once every 2 weeks (at administration intervals of 12 days). If taking into consideration a single dosage and administration intervals, it became clear that the K5-70 antibody exhibited significant anti-tumor activity at a total dosage of at least one twelfth of those of the prior-arts.

Example 25

Dose-Dependent Anti-Tumor Activity of Clone T6-16 on Xenograft Treatment Models Using Human Colon Cancer Cell Line SW480

Subsequently, the dose-dependent anti-tumor activity of clone T6-16 (mouse IgG2a) was examined with xenograft treatment models using a human colon cancer cell line SW480. SW480 cells ($5 \times 10^6$ cells) were subcutaneously transplanted into the right flank of each of 6-week-old female NOD-scid mice. Ten days after the transplantation (Day 10) at which the mean tumor volume reached 100 mm$^3$, the mice were divided into a control group (mouse IgG, 10 mg/kg body weight administration group, N=8, 105.8±9.9 mm$^3$), a T6-16 (1 mg/kg body weight) administration group (N=8, 104.4±13.3 mm$^3$), a T6-16 (5 mg/kg body weight) administration group (N=8, 104.7±13 0 mm$^3$), and a T6-16 (10 mg/kg body weight) administration group (N=8, 104.8±12.4 mm$^3$). Then, intraperitoneal administration was carried out at administration intervals of once every three days. On Day 43, the tumor volume of the control group was 473.5±137.0 mm$^3$. On the other hand, in the T6-16 administration groups, dose-dependent tumor formation inhibitory activity was observed. That is, the tumor volume of the 1 mg/kg body weight administration group was 397.9±97.5 mm$^3$ (inhibitory rate: 16.0%), the tumor volume of the 5 mg/kg body weight administration group was 195.9±89.7 mm$^3$ (inhibitory rate: 58.7%, P<0.01 by Student's t-test), and the tumor volume of the 10 mg/kg body weight administration group was 190.2±56.5 mm$^3$ (inhibitory rate: 59.8%, P<0.01 by Student's t-test) (FIG. 28A). Likewise, with regard to tumor weight on Day 43, the tumor weight of the control group was 0.19±0.07 g. On the other hand, the tumor weight of the T6-16 (1 mg/kg body weight) administration group was 0.20±0.08 g, the tumor weight of the 5 mg/kg body weight administration group was 0.08±0.04 g (inhibitory rate: 57.9%, P<0.01 by Student's t-test), and the tumor weight of the 10 mg/kg body weight administration group was 0.09±0.04 g (inhibitory rate: 52.6%, P<0.01 by Student's t-test). Thus, dose-dependent anti-tumor activity was confirmed (FIG. 28B).

Example 26

Analysis of Administration Intervals of Clone T6-16 to Xenograft Treatment Models Using Human Colon Cancer Cell Line SW480

Figure 29:
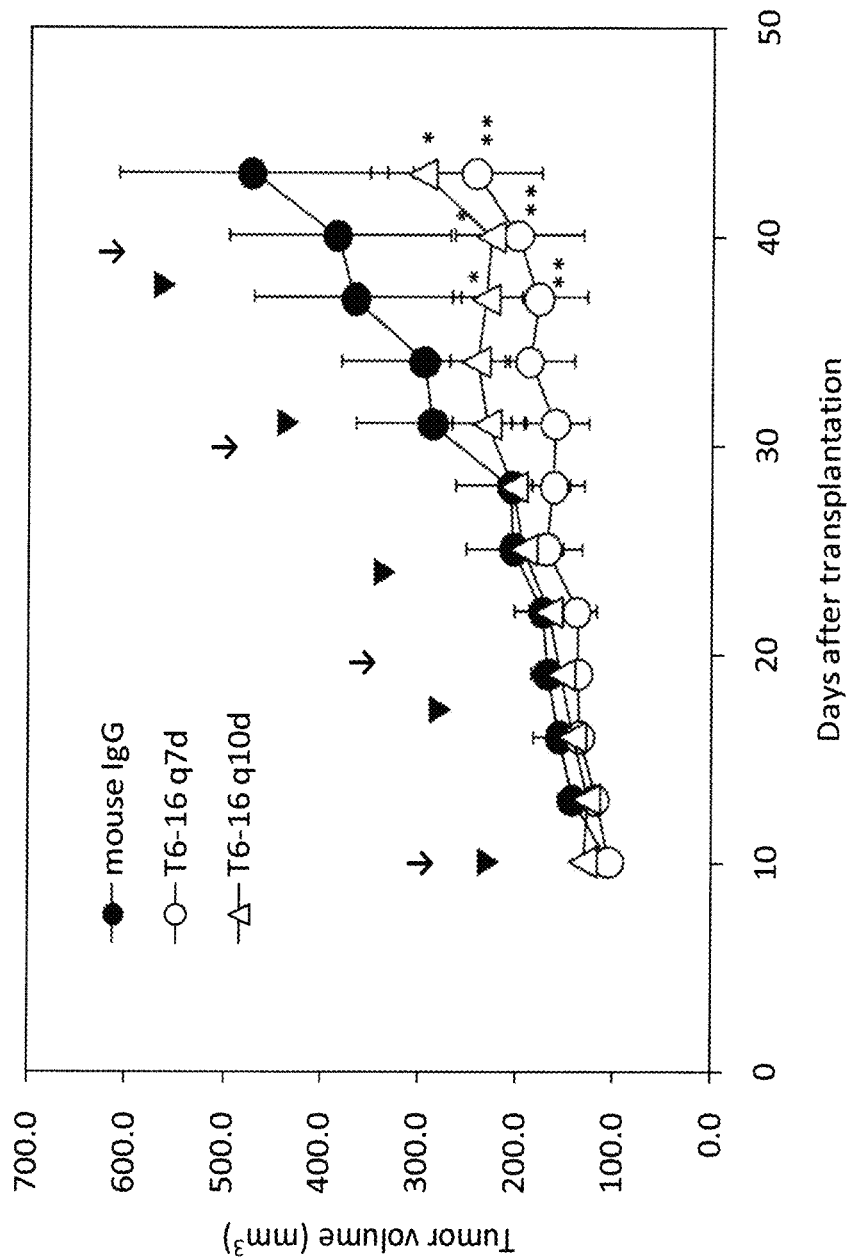
FIG. 29 shows the anti-tumor activity of a clone T6-16 on xenograft treatment models using SW480 cells. Time course of tumor formation in a control group (●: mouse IgG, 10 mg/kg) and in a T6-16 (10 mg/kg) administration group (○: q7d, Δ: q10d) is shown (a mean value±standard deviation). The arrowheads (Days 10, 17, 24, 31, and 38) and the arrows (Days 10, 20, 30, and 40) indicate administration of a T6-16 antibody. Administration was carried out once every three days to the control group. * P<0.05, ** P<0.01 by Student's t-test.

Subsequently, in order to analyze optimal administration intervals of clone T6-16 (mouse IgG2a), the anti-tumor activity of the clone T6-16 when it was administered at administration intervals of once a week (once every 7 days) and once every 10 days was examined with xenograft treatment models using a human colon cancer cell line SW480. SW480 cells ($5 \times 10^6$ cells) were subcutenously transplanted into the right flank of each of 6-week-old female NOD-scid mouse. Ten days after the transplantation (Day 10) at which the mean tumor volume reached 100 mm$^3$, the mice were divided into a control group (mouse IgG, 10 mg/kg body weight administration group, N=8, 105.8±9.9 mm$^3$), a T6-16 (10 mg/kg body weight, once a week) administration group (N=8, 105.0±11.6 mm$^3$), a T6-16 (10 mg/kg body weight, once every 10 days) administration group (N=5, 130.8±2.4 mm$^3$). Then, administration was initiated. On Day 43, the tumor volume of the control group was 473.5±137.0 mm$^3$. On the other hand, the tumor volume of the T6-16 (once a week) administration group was 243.7±65.3 mm$^3$ (inhibitory rate: 48.5%, P<0.01 by Student's t-test), and the tumor volume of the T6-16 (once every 10 days) administration group was 297.8±54.4 mm$^3$ (inhibitory rate: 37.1%, P<0.05 by Student's t-test) (FIG. 29). In the prior arts (U.S. Pat. No. 7,420,040 and U.S. Pat. No. 7,420,041), when antibodies were administered to xenograft treatment models using a pancreatic cancer cell line (BxPC-3) at a dosage of 20 mg/kg body weight, three times a week (at administration intervals of 2 days), the antibodies exhibited anti-tumor activity at an inhibitory rate of 50% to 60%. In contrast, the T6-16 antibody was found to exhibit significant anti-tumor activity, when it was administered at a dosage of half of the prior arts once every 10 day (at administration intervals of 8 days). If taking into consideration a single dosage and administration intervals, it became clear that the T6-16 antibody exhibited significant anti-tumor activity at a total dosage of at least one eighth of those of the prior-arts.

Example 27

Analysis of Anti-Tumor Activity of Clone K5-70 on Xenograft Prevention Models Using Human Prostate Cancer Cell Line DU-145

Figure 30:
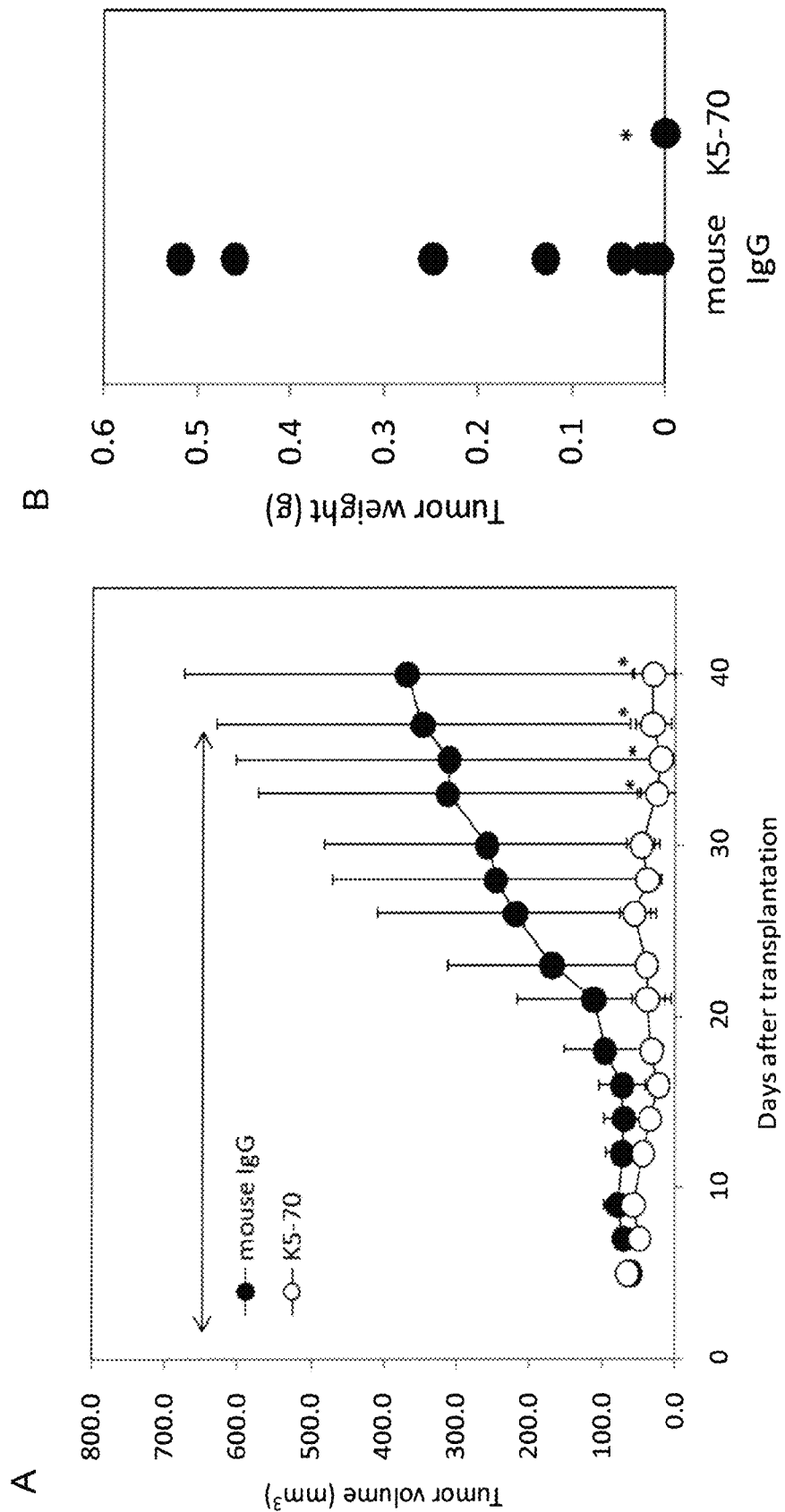
FIG. 30 shows the anti-tumor activity of a clone K5-70 on xenograft prevention models using human prostate DU-145 cells.

The anti-tumor activity of clone K5-70 on human prostate cancer was evaluated with xenograft prevention models using DU-145 cells (RIKEN Cell Bank, RCB2143). DU-145 cells ($5 \times 10^6$ cells) were subcutaneously transplanted into each of 6-week-old female nude mouse (Balb/c, nu/nu). The day on which the transplantation was carried out was defined as Day 1. The mice were divided into a control group (N=8) and a K5-70 administration group (N=8). From Day 1, K-70 was intraperitoneally administered to the mice at a frequency of once every 3 days at a dosage of 10 mg/kg body weight. On Day 40, the tumor volume of the control group was 368.2±307.8 mm$^3$. On the other hand, the tumor volume of the K5-70 administration group was 30.6±29.6 mm$^3$ (P<0.05 by Student's t-test), showing a tumor formation inhibitory activity of approximately 90% (FIG. 30A). With regard to tumor weight, further significant anti-tumor activity was observed. The tumor weight of the control group on Day 40 was 0.18±0.18 g. In contrast, in the K5-70 administration group, tumors disappeared from all of the 8 individual mice, and thus, tumor formation was completely inhibited (FIG. 30B). From the above-mentioned results, it became clear that the anti-human TROP-2 monoclonal antibody clone K5-70 shows strong anti-tumor activity even on human prostate cancer.

Example 28

Metastasis-Inhibitory Activity of Clone K5-70 on Liver Metastasis Models Using Human Pancreatic Cancer Cell Line PK-59

Cancer metastasis is an important factor that influences clinical prognosis in the treatment of gastrointestinal cancer. The control of metastasis is therapeutically significantly important. If not only tumor formation but also the metastasis of cancer to other organs could be suppressed by administering an antibody for use in cancer therapy that targets to TROP-2, high clinical usefulness would be anticipated. Thus, this is a desired property as a cancer therapeutic antibody.

The expression of TROP-2 was confirmed in many types of carcinomas. It was reported that TROP-2 was expressed at a high level particularly in metastatic foci (Br. J. Cancer (2008); 99: 1290-1295, Clin. Cancer Res. (2006); 12: 3057-3063, Mod. Pathol. (2008); 21: 186-191). Moreover, it was also reported that, when Trop-2-gene-introduced cancer cells were transplanted into nude mice via transsplenic or transpancreastic administration, the incidence of liver metastasis increased (WO 2010/089782, Molecular Cancer (2010); 9: 253), and thus, the report suggested the importance of TROP-2 in the cancer metastasis process. However, to date, there have been no reports specifically describing that an antibody that targets TROP-2 has metastasis-inhibitory action in vivo.

The anti-hTROP-2 mouse monoclonal antibody K5-70, which was discovered by the present invention, exhibits high therapeutic effects on xenograft models, into the subcutis of which pancreatic cancer cells had been transplanted. It was demonstrated by a scratch assay performed in vitro that the antibody K5-70 is able to suppress the migration ability of pancreatic cancer cells PK-59, in addition to the effect of suppressing the growth of cancer cells. Thus, it was considered that the antibody K5-70 could inhibit cancer metastasis in vivo. Hence, the metastasis-inhibitory effect of an anti-hTROP-2 mouse monoclonal antibody was examined, using models in which pancreatic cancer cells PK-59 were injected into the spleen of nude mice so that liver metastasis was developed.

A pancreatic cancer cell line (PK-59) endogenously expressing hTROP-2 was harvest by treatment with trypsin, and a $2\times10^7$ cells/mL cell suspension was then prepared with PBS. The cell suspension was preserved on ice until transplantation. Each of 6- or 7-week-old female nude mouse (Balb/c, nu/nu) was anesthetized by intraperitoneal administration of pentobarbital, and 10 to 15 mm of the left flank thereof was excised under anesthesia. The spleen was taken out of the abdominal cavity, and 50 μL, of the cell suspension ($1\times10^6$ cells) was then injected into the spleen using a 26G syringe. Four minutes after injection of the cells, the hilum of spleen was ligated with 5-0 silk sutures, and the spleen was then excised. The cut peritoneum was closed with 5-0 silk sutures, and the surgical site was then closed with Wound Clips (AUTOCLIP 9 mm, Becton Dickinson). On the day before cancer cell transplantation, the mice were divided into groups. An anti-hTROP-2 monoclonal antibody (K5-70) or a control antibody (purified mouse IgG) was intraperitoneally administered to mice at a dosage of 10 mg/kg body weight. In addition, seven days after cancer cell transplantation, such an antibody was administered in the same manner as described above. Four to six weeks after the cancer cell transplantation, the mice were subjected to euthanasia by cervical dislocation. Then, the liver was excised from each mouse, and the presence or absence of metastatic foci was confirmed.

In the control group in which the mouse IgG was administered to the mice, in 4 out of the 6 mice into which PK-59 cells had been transplanted, apparent metastatic foci (2 to 7 foci) were observed around the liver lobe four to six weeks after the transplantation (FIG. 31A, incidence of metastasis: 67%, Table 6). In contrast, in four mice in the K5-70 administration group, into which the PK-59 cells had also been transplanted, such metastatic foci were not observed in the liver of all of the mice, and thus, an incidence of metastasis was 0% (FIG. 31B, Table 6).

TABLE 6

Metastasis-suppressing effect of clone K5-70 on liver metastasis models produced by transsplenic transplantation of PK-59 cells into nude mice

| Administration group | Weeks after transplantation | Individual No. | Number of metastatic foci | Determination of metastasis | |
|---|---|---|---|---|---|
| Control group | 4W | C-1 | 0 | – | |
| | 4W | C-2 | 5 | ++ | |
| | 6W | C-3 | 7 | ++ | |
| | 6W | C-4 | 7 | ++ | |
| | 6W | C-5 | 2 | + | |
| | 6W | C-6 | 0 | – | |
| | | Average number of metastatic foci | 3.5 | Incidence of metastasis | 67% |
| K5-70 administration group | 4W | K-1 | 0 | – | |
| | 6W | K-2 | 0 | – | |
| | 6W | K-3 | 0 | – | |
| | 6W | K-4 | 0 | – | |
| | | Average number of metastatic foci | 0 | Incidence of metastasis | 0% |

From these results, it became clear that the anti-hTROP-2 antibody K5-70 has extremely strong inhibitory action on the liver metastasis of the pancreatic cancer cells PK-59.

Example 29

Anti-Tumor Activity of K5-70 Antibody on Xenograft Models Using Colon Cancer Cell Line SW480, which are Recurrent Cancer Models after Administration of Irinotecan Hydrochloride In recent years, many chemotherapeutical drugs for suppressing the growth of cancer cells have been developed as cancer therapeutic drugs. These drugs have achieved certain treatment results. However, these chemotherapeutical drugs have been problematic in terms of side effects associated with the growth suppressive action thereof on normal cells other than cancer cells and the recurrence of cancer after suspension of the treatment. Accordingly, if tumor recurrence after completion of the treatment with chemotherapeutical drugs could be suppressed by administration of a cancer therapeutic antibody targeting to TROP-2, high clinical usefulness would be anticipated. Thus, this is a desired property as a cancer therapeutic antibody.

Figure 32:
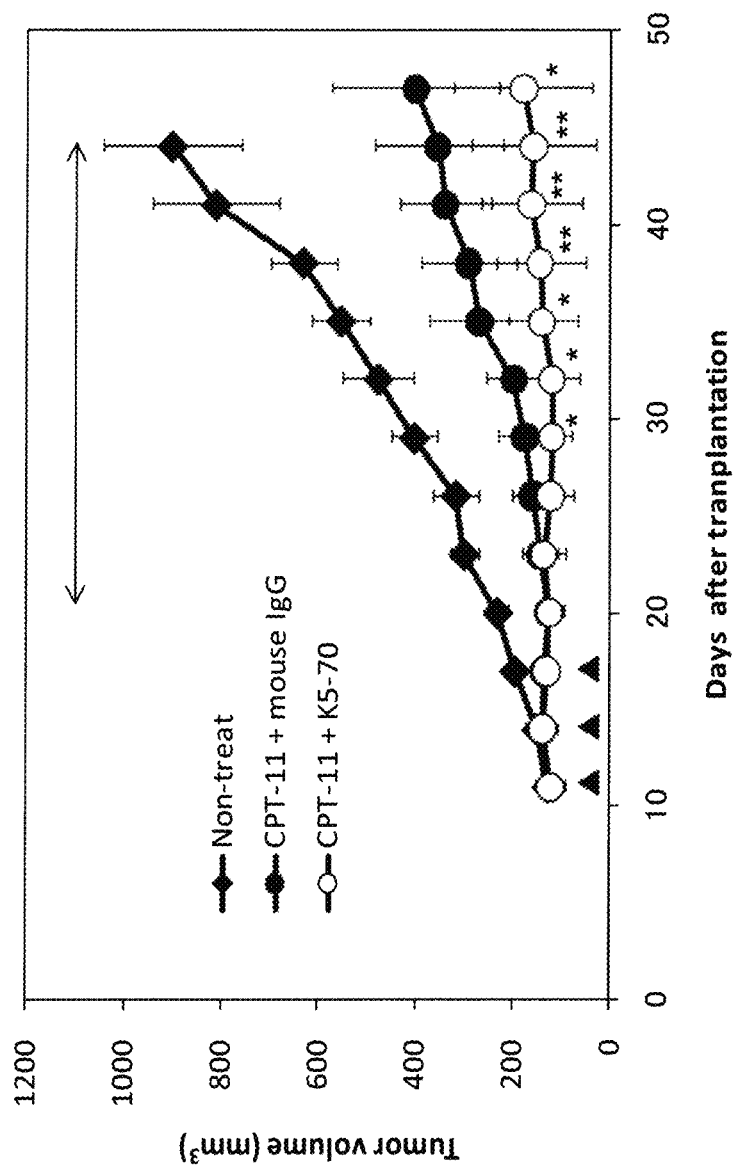
FIG. 32 shows the anti-tumor activity of K5-70 on xenograft models using SW480 cells, which are recurrent cancer models after administration of irinotecan hydrochloride. This figure shows time course of tumor formation in a non-treat group (▲), in an irinotecan hydrochloride (40 mg/kg)+K5-70 (○: 10 mg/kg) administration group, and in an irinotecan hydrochloride (40 mg/kg)+mouse IgG (●: 10 mg/kg) administration group (a mean value±standard deviation). The arrowheads (Days 11, 14, and 17) indicate administration of irinotecan hydrochloride. The K-70 antibody or the mouse IgG was administered once every three days from Day 20. The arrow indicates an antibody administration period. *P<0.05, **P<0.01 by Student's t-test.

As therapeutic agents for colon cancer, in addition to 5-FU and platinum-containing drugs, irinotecan hydrochloride (Topotecin, Daiichi Sankyo Co., Ltd.) having a topoisomerase inhibitory effect has been recently applied to clinical sites. With regard to animal models as well, the anti-tumor effect of irinotecan hydrochloride on mouse models, into which various types of human tumor cells including colon cancer as a typical example had been transplanted, has been reported (Cancer Chemother Pharmacol. (1991); 28(3):192-8). Thus, the recurrence-preventing effect of the anti-hTROP-2 antibody clone K5-70 (mouse IgG2a) on recurrent tumor after administration of irinotecan hydrochloride has been examined with xenograft models using a human colon cancer cell line SW480. SW480 cells (5×10⁶ cells) were subcutaneously transplanted into the right flank of 8-week-old female NOD-scid mice. Eleven days after the transplantation (Day 11) at which the mean tumor volume reached 100 mm³, the mice were divided into a non-treat group (normal saline administration group, N=8, 130.7±16 2 mm³) and an irinotecan hydrochloride (CPT-11, Topotecin, Daiichi Sankyo Co., Ltd.) administration group (N=16, 123.0±21.4 mm³) Thereafter, irinotecan hydrochloride was intraperitoneally administered to the mice at a dosage of 40 mg/kg body weight, once every 3 days, total 3 times (Days 11, 14, and 17). On the third day after the final administration of irinotecan hydrochloride (Day 20), the tumor volume of the non-treat group reached 232.1±21.1 mm³. On the other hand, the tumor volume of the irinotecan hydrochloride administration group was 126.6±26.6 mm³ ($P<0.01$ by Student's t-test), and thus, an apparent tumor-suppressing effect was observed. At this stage, the irinotecan hydrochloride administration group was divided into two groups based on tumor size. One group was defined as a K5-70 (10 mg/kg body weight) administration group (N=8, tumor volume on Day 20: 126.0±28.0 mm³), and the other group was defined as a mouse IgG (10 mg/kg body weight) administration group (N=8, tumor size on Day 20: 127.2±27.0 mm³). Intraperitoneal administration and the measurement of tumor volume were carried out on each group once every 3 days, so that the recurrence of tumor was evaluated (FIG. 32). In the mouse IgG administration group, from the 18$^{th}$ day after the final administration of irinotecan hydrochloride (Day 35), several mice having an apparent recurrent tumor with a tumor volume of greater than 300 mm³ were observed. On the 30$^{th}$ day after the final administration of irinotecan hydrochloride (Day 47), a tumor with a tumor volume of greater than 300 mm³ was observed in 5 out of the 8 mice (mean tumor volume: 401.7±172.7 mm³) In contrast, in the K5-70 administration group, tumor recurrence was significantly suppressed, and the mean tumor volume was 180.5±142.1 mm³ ($P<0.05$ by Student's t-test) (FIG. 32). In particular, in the K5-70 administration group, the tumor volume on Day 47 became smaller than the tumor volume when the mice were divided into groups (126.0±28.0 mm³). The tumor volume became less than 100 mm³ in 4 out of the 8 mice. From these results, it became clear that the anti-hTROP-2 antibody K5-70 has extremely strong suppressive action even on recurrent tumor after administration of irinotecan hydrochloride.

Example 30

Epitope Mapping Using CLIPS Technology

<Materials and Methods>
Peptide Synthesis 15-mer and 30-mer of linear peptides derived from TROP-2 extracellular domains, which were used in the present experiment, were obtained by solid-phase synthesis according to a Fmoc (9-Fluorenylmethoxycarbonyl) method. In addition, for discontinuous epitope analysis, a 17-mer peptides derived from a TROP-2 extracellular domain, to both ends of which cysteine residues had been added, was synthesized, and a conformation having one or two loop structures was reconstructed by CLIPS technology (Chemically Linked Peptides on Scaffolds technology). When another cysteine residue was present close to the added cysteine residue, it was substituted with alanine.

Epitope Screening ELISA 5034 types of the synthesized peptides were covalently bound to PEPSCAN cards (455 peptides/card), and the binding of the synthesized peptides to antibodies was then analyzed by the ELISA method. The PEPSCAN cards were allowed to react with anti-human TROP-2 monoclonal antibodies (K5-70, K5-107, K5-116-2-1, T5-86, and T6-16) that had been diluted to a concentration of 1 μg/mL with a blocking buffer (a phosphate buffer containing 4% horse serum, 5% ovalbumin, and 1% Tween). After washing, the resultant was allowed to react with a 1000-fold diluted peroxidase-secondary antibody complex at 25° C. for 1 hour. After washing, a substrate solution (a solution containing 2,2'-azino-di-3-ethylbenzthiazoline sulfonate (ABTS) and 2 A of 3% hydrogen peroxide solution) was added to the reaction solution, followed by a chromogenic reaction for 1 hour. The binding activity of the antibodies was quantified by photographing with a CCD camera and then performing an image analysis.

<Results>

The anti-human TROP-2 monoclonal antibodies K5-70, K5-107, K5-116-2-1, T5-86 and T6-16, which exhibited beneficial effects, were subjected to epitope analysis using CLIPS (Chemically Linked Peptides on Scaffolds) technology. It is to be noted that the term "amino acid number of SEQ ID NO: 2" is used in the present examples to mean the amino acid residue numbers in the amino acid sequence shown in SEQ ID NO: 2 (hTROP-2 protein (323 amino acid residues)).

The result of analysis for the K5-70 antibody is shown in Table 7 below. As a result, it was found that 33 peptides exhibit strong binding activity to the K5-70 antibody. In these 33 peptides, a sequence comprising VCSPDGPGGRCQCRALGSGMAVD (amino acid numbers 43-65 of SEQ ID NO: 2) (peptide Nos. 1-7 and 9 in Table 7), a sequence comprising HHILIDLRHRPTAG (amino acid numbers 152-165 of SEQ ID NO: 2) (peptide Nos. 14, 22-24, and 28 in Table 7), a sequence comprising VHYEQPTIQIELRQ (amino acid numbers—194-207 of SEQ ID NO: 2) (peptide Nos. 10, 12, 13, 18, 20, 21, 23, 26-28, 30 and 32 in Table 7), and a sequence comprising DLDAELRRLFRER (amino acid numbers 171-183 of SEQ ID NO: 2) (peptide Nos. 11, 16, 18, 19, 21, 22, 29, 31 and 33 in Table 7) appeared repeatedly. The K5-70 antibody particularly strongly bound to the sequence comprising VCSPDGPGGRCQCRALGSGMAVD (amino acid numbers 43-65 of SEQ ID NO: 2). From these results, it was suggested that, in the hTROP-2 protein, the aforementioned 4 types of peptide sequence regions are likely to be epitopes of the K5-70 antibody.

TABLE 7

Binding of K5-70 antibody to CLIPS peptides derived from human TROP-2 extracellular domains

| number | peptide | binding of K5-70 | SEQ ID NO: |
|---|---|---|---|
| 1 | NKMTVCSPDGPGGRCQCRALGSGMAVDCST | 2742 | 74 |
| 2 | TVCSPDGPGGRCQCRALGSGMAVDCSTLTS | 2604 | 75 |
| 3 | TNKMTVCSPDGPGGRCQCRALGSGMAVDCS | 2562 | 76 |
| 4 | MTVCSPDGPGGRCQCRALGSGMAVDCSTLT | 2402 | 77 |
| 5 | KMTVCSPDGPGGRCQCRALGSGMAVDCSTL | 1770 | 78 |
| 6 | PTNNKMTVCSPDGPGGRCQCRALGSGMAVDC | 1391 | 79 |
| 7 | VCSPDGPGGRCQCRALGSGMAVDCSTLTSK | 932 | 80 |
| 8 | CAAVHYEQPTIQIELRCAAVHYEQPTIQIELRC | 876 | 81 |
| 9 | CPTNKMTVCSPDGPGGRCQCRALGSGMAVD | 839 | 82 |
| 10 | CVHYEQPTIQIELRQNCVHYEQPTIQIELRQNC | 825 | 83 |
| 11 | HSDLDAELRRLFRERCHSDLDAELRRLFRERC | 725 | 84 |
| 12 | RLFRERYRLHPKFVAAVHYEQPTIQIELRQ | 687 | 85 |
| 13 | AVHYEQPTIQIELRQ | 642 | 86 |
| 14 | CAGAFNHSDLDAELRRCHHILIDLRHRPTAGAC | 624 | 87 |
| 15 | CPKFVAAVHYEQPTIQCGLDLRVRGEPLQVERC | 579 | 88 |
| 16 | CHSDLDAELRRLFRERCGLDLRV | 538 | 89 |
| 17 | FQGRGGLDLRVRGEP | 538 | 90 |
| 18 | CVHYEQPTIQIELRQNCDLDAELRRLFRERYRC | 524 | 91 |
| 19 | CHSDLDAELRRLFRERCRGEPLQ | 519 | 92 |
| 20 | CTIQIELRQNTSQKAACVHYEQPTIQIELRQNC | 513 | 93 |
| 21 | CVHYEQPTIQIELRQNCHSDLDAELRRLFRERC | 511 | 94 |
| 22 | CHHILIDLRHRPTAGACHSDLDAELRRLFRERC | 489 | 95 |
| 23 | CHHILIDLRHRPTAGACVHYEQPTIQIELRQNC | 489 | 96 |
| 24 | CHHILIDLRHRPTAGACGLDLRVRGEPLQVERC | 488 | 97 |
| 25 | CDAELRRLFRERYRLHCDELVRTHHILIDLRHC | 483 | 98 |
| 26 | CVHYEQPTIQIELRQNC | 483 | 99 |
| 27 | CAFNHSDLDAELRRLFCVHYEQPTIQIELRQNC | 478 | 100 |
| 28 | CVHYEQPTIQIELRQNCHHILIDLRHRPTAGAC | 473 | 101 |
| 29 | CDAELRRLFRERYRLHCDELVRTHHILIDLRHC | 472 | 102 |
| 30 | VHYEQPTIQIELRQNCGLDLRVRGEPLQVERC | 470 | 103 |
| 31 | CDELVRTHHILIDLRHCDLDAELRRLFRERC | 469 | 104 |
| 32 | AVHYEQPTIQIELRQCAVHYEQPTIQIELRQC | 468 | 105 |
| 33 | CHSDLDAELRRLFRERCDELVRTHHILIDLRHC | 466 | 106 |

The result of analysis for the K5-107 antibody is shown in Table 8 below. As a result, it was found that a sequence comprising VCSPDGPGGRCQCRALGSGMAVD (amino acid numbers 43-65 of SEQ ID NO: 2) was comprised in 9 out of the 20 peptides (peptide Nos. 1-6, 8, 9 and 17 in Table 8) (Table 8).

Accordingly, it was suggested that, in the hTROP-2 protein, the aforementioned peptide sequence region consisting of VCSPDGPGGRCQCRALGSGMAVD (amino acid numbers 43-65 of SEQ ID NO: 2) may be an epitope of the K5-107 antibody.

The result of analysis for the K5-116-2-1 antibody is shown in Table 9 below. In this analysis, three types of peptide sequences, namely, a sequence comprising VCSPDGPG-GRCQCRALGSGMAVD (amino acid numbers 43-65 of SEQ ID NO: 2) (peptide Nos. 1-7, and 15 in Table 9), a sequence comprising HHILIDLRHRPTAG (amino acid numbers 152-165 of SEQ ID NO: 2) (peptide Nos. 8-11, 16, 20, 22, 24, and 27-28 in Table 9), and a sequence comprising DLDAELRRLFRER (amino acid numbers 171-183 of SEQ ID NO: 2) (peptide Nos. 11-13, 17, 19, 21, and 29 in Table 9) appeared several times (Table 9). Accordingly, it was sug-

TABLE 8

Binding of K5-107 antibody to CLIPS peptides derived from human TROP-2 extracellular domains

| number | peptide | binding of K5-107 | SEQ ID NO: |
|---|---|---|---|
| 1 | TNKMTVCSPDGPGGRCQCRALGSGMAVDCS | 2763 | 107 |
| 2 | NKMTVCSPDGPGGRCQCRALGSGMAVDCST | 2761 | 108 |
| 3 | KMTVCSPDGPGGRCQCRALGSGMAVDCSTL | 2752 | 109 |
| 4 | MTVCSPDGPGGRCQCRALGSGMAVDCSTLT | 2726 | 110 |
| 5 | CPTNKMTVCSPDGPGGRCQCRALGSGMAVD | 2723 | 111 |
| 6 | TVCSPDGPGGRCQCRALGSGMAVDCSTLTS | 2720 | 112 |
| 7 | TCPTNKMTVCSPDGPGGRCQCRALGSGMAV | 2716 | 113 |
| 8 | VCSPDGPGGRCQCRALGSGMAVDCSTLTSK | 2689 | 114 |
| 9 | CSPDGPGGRCQCRALGSGMAVDCSTLTSKC | 2655 | 115 |
| 10 | CTCPTNKMTVCSPDGPGGRCQCRALGSGMA | 2655 | 116 |
| 11 | NCTCPTNKMTVCSPDGPGGRCQCRALGSGM | 2207 | 117 |
| 12 | DNCTCPTNKMTVCSPDGPGGRCQCRALGSG | 1816 | 118 |
| 13 | TNKMTVCSPDGPGGRCQCRALGSGMAVDCS | 1525 | 119 |
| 14 | CTVCSPDGPGGRCQCRALGSGMAVDASTLTSKC | 1118 | 120 |
| 15 | QDNCTCPTNKMTVCSPDGPGGRCQCRALGS | 874 | 121 |
| 16 | SPDGPGGRCQCRALGSGMAVDCSTLTSKCL | 561 | 122 |
| 17 | CTNKMTVCSPDGPGGRCQCRALGSGMAVDASTC | 380 | 123 |
| 18 | TVCSPDGPGGRCQCR | 312 | 124 |
| 19 | CAPKNARTLVRPSEHACARTLVRPSEHALVDNC | 284 | 125 |
| 20 | HSDLDAELRRLFRERCHSDLDAELRRLFRERC | 272 | 126 | gested that, in the hTROP-2 protein, these three types of peptide sequence regions may be epitopes of the K5-116-2-1 antibody.

tioned peptide sequence was comprised in 17 out of the 26 peptides binding to the T5-86 antibody (peptide Nos. 1-4, 6-8, 10, 12-13, 16-18, 22, and 24-26 in Table 10), and it was

TABLE 9

Binding of K5-116-2-1 antibody to CLIPS peptides
derived from human TROP-2 extracellular domains

| number | peptide | binding of K5-116-2-1 | SEQ ID NO: |
|---|---|---|---|
| 1 | TVCSPDGPGGRCQCRALGSGMAVDCSTLTS | 2672 | 127 |
| 2 | NKMTVCSPDGPGGRCQCRALGSGMAVDCST | 2613 | 128 |
| 3 | TNKMTVCSPDGPGGRCQCRALGSGMAVDCS | 2482 | 129 |
| 4 | MTVCSPDGPGGRCQCRALGSGMAVDCSTLT | 2440 | 130 |
| 5 | KMTVCSPDGPGGRCQCRALGSGMAVDCSTL | 2423 | 131 |
| 6 | CPTNKMTVCSPDGPGGRCQCRALGSGMAVD | 2136 | 132 |
| 7 | PTNKMTVCSPDGPGGRCQCRALGSGMAVDC | 1723 | 133 |
| 8 | CAGAFNHSDLDAELRRCHHILIDLRHRPTAGAC | 1643 | 134 |
| 9 | CTHHILIDLRHRPTAGC | 1586 | 135 |
| 10 | CVHYEQPTIQIELRQNCHHILIDLRHRPTAGAC | 1504 | 136 |
| 11 | CHHILIDLRHRPTAGCHSDLDAELRRLFRERC | 1475 | 137 |
| 12 | HSDLDAELRRLFRERCHSDLDAELRRLFRERC | 1467 | 138 |
| 13 | CDAELRRLFRERYRLHCHSDLDAELRRLFRERC | 1462 | 139 |
| 14 | CDAELRRLFRERYRLHCPK | 1442 | 140 |
| 15 | VCSPDGPGGRCQCRALGSGMAVDCSTLTSK | 1432 | 141 |
| 16 | DLSLRCDELVRTHHILIDLRHRPTAGAFNH | 1421 | 142 |
| 17 | CDELVRTHHILIDLRHCDLDAELRRLFRERYRC | 1392 | 143 |
| 18 | CFQGRGGLDLRVRGEPC | 1376 | 144 |
| 19 | CDAELRRLFRERYRLHCDELVRTHHILIDLRHC | 1366 | 145 |
| 20 | CGLDLRVRGEPLQVERCHHILIDLRHRPTAGAC | 1342 | 146 |
| 21 | CHSDLDAELRRLFRERCHSDLDAELRRLFRERC | 1331 | 147 |
| 22 | CDELVRTHHILIDLRHCHHILIDLRHRPTAGAC | 1323 | 148 |
| 23 | CDAELRRLFRERYRLHCDELVRTHHILIDLRHC | 1266 | 149 |
| 24 | CHHILIDLRHRPTAGACRGEPLQVERTLIYYLC | 1229 | 150 |
| 25 | CSPDGPGGRCQCRAL | 1227 | 151 |
| 26 | CTVASPDGPGGRAQARACVHYEQPTIQIELRQNC | 1223 | 152 |
| 27 | CHHILIDLRHRPTAGACVNYEQPTIQIELRQNC | 1222 | 153 |
| 28 | LSLRCDELVRTHHILIDLRHRPTAGAFNHS | 1220 | 154 |
| 29 | CDELVRTHHILIDLRHCHSDIDAELRRLFRERC | 1205 | 155 |

The results of analysis for the T5-86 and T6-16 antibodies are shown in Table 10 and Table 11 below, respectively. In these analyses, the antibodies strongly bound to a peptide comprising a sequence consisting of DPEGRFKARQ (amino acid numbers 109-118 of SEQ ID NO: 2). The above-mentioned peptide sequence was comprised in 4 out of the 26 peptides binding to the T6-16 antibody (peptde Nos. 1, 2, 9 and 13 in Table 11) (Table 10 and Table 11). Moreover, in the analysis regarding the T5-86 antibody, other than the sequence comprising DPEGR-FKARQ (amino acid numbers 109-118 of SEQ ID NO: 2), a sequence comprising CSPDGPGGRCQCR (amino acid numbers 44-56 of SEQ ID NO: 2) (peptide Nos. 4, and 14 in Table 10) appeared twice. Furthermore, in the analysis regarding the T6-16 antibody as well, another sequence comprising HHILIDLRHRPTAG (amino acid numbers 152-165 of SEQ ID NO: 2) (peptide Nos. 7-8, 10-12, 19, 23, and 25 in Table 11) was found several times. Accordingly, it was suggested that, in the hTROP-2 protein, two types of peptide sequence regions, namely, DPEGRFKARQ (amino acid numbers 109-118 of SEQ ID NO: 2) and CSPDGPGGRC-QCR (amino acid numbers 44-56 of SEQ ID NO: 2), may be epitopes of the K5-86 antibody. It was also suggested that, in the hTROP-2 protein, two types of peptide sequence regions, namely, DPEGRFKARQ (amino acid numbers 109-118 of SEQ ID NO: 2) and HHILIDLRHRPTAG (amino acid numbers 152-165 of SEQ ID NO: 2), may be epitopes of the T6-16 antibody.

TABLE 10

Binding of T5-86 antibody to CLIPS peptides derived from human TROP-2 extracellular domains

| number | peptide | binding of T5-86 | SEQ ID NO: |
|---|---|---|---|
| 1 | CYDPDADPEGRFKARQCADPEGRFKARQANQTC | 2306 | 156 |
| 2 | PDCDPEGRFKARQCN | 2292 | 157 |
| 3 | CADPEGRFKARQANCPDADPEGRFKARQANC | 2287 | 158 |
| 4 | VCSPDGPGGRCQCRA | 2263 | 159 |
| 5 | CYDPDADPEGRFKARQCPDADPEGRFKARQANC | 2260 | 160 |
| 6 | CADPEGRFKARQANQTCTDPDADPEGRFKARQC | 2240 | 161 |
| 7 | CADPEGRFKARQANQTCYDPDADPEGRFKARQC | 2208 | 162 |
| 8 | DCDPEGRFKARQCNQ | 2150 | 163 |
| 9 | CTVASPDGPGGRAQARCHSDLDAELRRLFRERC | 2086 | 164 |
| 10 | CDADPEGRFKARQANQCDADPEGRFKARQANQC | 2035 | 165 |
| 11 | DGRFKARQANQTSVAWCARTLVRPSEHALVDNC | 2019 | 166 |
| 12 | DADPEGRFKARQANQTCPDADPEGRFKARQANC | 1980 | 167 |
| 13 | CPDADPEGRFKARQANCPDADPEGRFKARQANC | 1950 | 168 |
| 14 | CSPDGPGGRCQCRAL | 1946 | 169 |
| 15 | CEGRFKARQANQTSVACEGRFKARQANQTSVAC | 1895 | 170 |
| 16 | CTVASPDGPGGRAQARCPDADPEGRFKARQANC | 1890 | 171 |
| 17 | CGLYDPDADPEGRFKACPDADPEGRFKARQANC | 1857 | 172 |
| 18 | DPDCDPEGRFKARQCNCQTSVCWCVNSVGVR | 1850 | 173 |
| 19 | CPEGRFKARQANQTSVCDELVRHHILIDLRHC | 1841 | 174 |
| 20 | CPDGPGGRAQARALGSCHSDLDAELRRLFRERC | 1830 | 175 |
| 21 | CTLVRPSEHALVDNDGCGRFKARQANQTSVAWC | 1820 | 176 |
| 22 | CPDADPEGRFKARQANCYDPDADPEGRFKARQC | 1795 | 177 |
| 23 | CGLYDPDADPEGRFKACPEGRFKARQANQTSVC | 1793 | 178 |
| 24 | YDPDCDPEGRFKARQ | 1775 | 179 |
| 25 | CPDADPEGRFKARQANCADPEGRFKARQANQTC | 1773 | 180 |
| 26 | CDPEGRFKARQCNQT | 1772 | 181 |

TABLE 11

Binding of T6-16 antibody to CLIPS peptides derived from human TROP-2 extracellular domains

| number | peptide | binding of T6-16 | SEQ ID NO: |
|---|---|---|---|
| 1 | CVNSVGVRRTDKGDLSCPDCYDPDADPEGRFKARQC | 1072 | 182 |
| 2 | CSVGVRRTDKGDLSLRCYDPDADPEGRFKARQC | 786 | 183 |
| 3 | HSDLDAELRRLFRERCHSDLDAELRRLFRERC | 714 | 184 |
| 4 | CDELVRTHHILIDLRHCDLDAELRRLFRERYRC | 713 | 185 |
| 5 | CVNSVGVRRTDKGDLSLRCDELVRTHHILI | 688 | 186 |
| 6 | VRRTDKGDLSLRCDELVRTHHILIDLRHRP | 670 | 187 |
| 7 | CVERTLIYYLDEIPPKCHHILIDLRHRPTAGAC | 626 | 188 |
| 8 | CHHILIDLRHRPTAGACHSDLDAELRRLFRERC | 620 | 189 |
| 9 | CVNSVGVRRTDKGDLSCPDADPEGRFKARQANC | 611 | 190 |
| 10 | CVHYEQPTIQIELRQNCHHILIDLRHRPTAGAC | 602 | 191 |
| 11 | VGVRRTDKGDLSLRCDELVRTHHILIDLRH | 601 | 192 |
| 12 | CAGAFNHSDLDAELRRCHHILIDLRHRPTAGAC | 592 | 193 |
| 13 | CSVGVRRTDKGDLSLRCPDADPEGRFKARQANC | 585 | 194 |
| 14 | CVRPSEHALVDNDGLYCSVGVRRTDKGDLSLRC | 573 | 195 |
| 15 | CDAELRRLFRERYRLHCHSDLDAELRRLFRERC | 566 | 196 |
| 16 | CSVGVRRTDKGDISLRCNDGLYDPDADPEGRFC | 559 | 197 |
| 17 | CVNSVGVRRTDKGDLSCGLYDPDADPEGRFKAC | 553 | 198 |
| 18 | CDLDAELRRLFRERYRCHSDLDAELRRLFRERC | 534 | 199 |
| 19 | CDELVRTHHILIDLRHCHHILIDLRHRPTAGAC | 534 | 200 |
| 20 | CAGAFNHSDLDAELRRCDLDAELRRLFRERYRC | 529 | 201 |
| 21 | CDAELRRLFRERYRLHCDELVRTHHILIDLRHC | 527 | 202 |
| 22 | CVHYEQPTIQIELRQNCDLDAELRRLFRERYRC | 526 | 203 |
| 23 | CHHILIDLRHRPTAGACVHYEQPTIQIELRQNC | 524 | 204 |
| 24 | CGVRRTDKGDLSLRADCGVRRTDKGOLSLRADC | 524 | 205 |
| 25 | CGLDLRVRGEPLQVERCHHILIDLRHRPTAGAC | 521 | 206 |
| 26 | CDLDAELRRLFRERYRCDELVRTHHILIDLRHC | 516 | 207 |

Example 31

Sequencing of Variable Regions of Antibody Genes of Mouse Anti-Human TROP-2 Antibodies (Clones K5-70, K5-107, K5-116-2-1, and T6-16)

Total RNA was extracted from $3 \times 10^6$ mouse anti-TROP-2 monoclonal antibody-producing hybridomas, using TRIzol reagent (Invitrogen). With regard to the clone K5-70, clone K5-107, and clone K5-116-2-1, cDNA was synthesized employing SMARTer™ RACE cDNA Amplification kit (Clontech) according to the method included with the kit, using a mouse IgG H chain-specific primer (5'-TCCAK-AGTT-3' (SEQ ID NO: 24)) and a mouse IgG L chain-specific primer (5'-GCTGTCCTGATC-3' (SEQ ID NO: 25)). With regard to the clone T6-16, cDNA was synthesized employing GeneRacer kit (Invitrogen) according to the method included with the kit, using an oligo dT primer. Genes encoding the variable regions (VH, VL) of the H and L chains of clone K5-70 (mouse IgG2a), clone K5-107 (mouse IgG1) and clone K5-116-2-1 (mouse IgG2a) were each cloned by a PCR method using the above-synthesized cDNA as a template. In this operation, 10× Universal Primer A Mix (UPM) included with SMARTer™ RACE cDNA Amplification kit was used as a 5'-primer. On the other hand, as a 3'-primer for VH amplification, a primer having a sequence specific to the mouse IgG H chain was used, and as a 3'-primer for VL amplification, a primer having a sequence specific to the mouse IgG L chain was used.

```
Long (0.4 µM)
                                                      (SEQ ID NO: 26)
5'-CTAATACGACTCACTATAGGGCAAGCAGTGGTATCAACGCAGAGT-3'

Short (2 µM)
                                                      (SEQ ID NO: 27)
5'-CTAATACGACTCACTATAGGGC-3'

VH:
                                                      (SEQ ID NO: 28)
5'-GGGAARTARCCCTTGACCAGGCA-3'

(SEQ ID NO: 29)
5'-GGGAARTAGCCTTTGACAAGGCA-3'

VL:
                                                      (SEQ ID NO: 30)
5'-CACTGCCATCAATVTTCCACTTGACA-3'
```

Using each of the above-described primers, PCR was carried out under the following composition of reaction solution and reaction conditions. In addition, a R primer for amplification of VH cDNA was prepared by mixing the two above sequences with each other at an equimolar ratio and was then used.

<Composition of Reaction Solution>

| Template cDNA: | 2.5 µL |
|---|---|
| 5 × PrimeSTAR buffer (Mg$^{2+}$ plus): | 10 µL |
| 2.5 mM dNTP: | 4 µL |
| PrimeSTAR HS DNA polymerase (2.5 U/µL): | 0.5 µL |
| 10 × Universal Primer A Mix (UPM): | 5 µL |
| R primer (10 µM): | 1 µL |
| Sterilized water: | 27 µL |
| Total: | 50 µL |

<Reaction Conditions>

A reaction was carried out at 94° C. (10 sec), and thereafter, a cycle consisting of "heat denaturation/dissociation at 98° C. (10 sec) annealing at 60° C. (5 sec) synthesis/elongation at 72° C. (60 sec)" was carried out 30 times in total. Finally, a reaction was carried out at 72° C. (3 min).

The synthesized VH and VL cDNAs were subcloned into a pMD20-T vector (Takara Bio Inc.), and the nucleotide sequences thereof were determined. The nucleotide sequences of a plurality of VH clones and VL clones were decoded, and nucleotide sequences specific to the variable regions of mouse H chain and L chain were identified. FIG. 33 and FIG. 34 show the consensus cDNA nucleotide sequences of the VH and VL of K5-70, and putative amino acid sequences. FIG. 35 and FIG. 36 show the consensus cDNA nucleotide sequences of the VH and VL of K5-107, and putative amino acid sequences. FIG. 37 and FIG. 38 show the consensus cDNA nucleotide sequences of the VH and VL of K5-116-2-1, and putative amino acid sequences.

Genes encoding the variable regions (VH, VL) of the H and L chains of clone T6-16 were cloned by a PCR method using the above-synthesized cDNA as a template. In this operation, a primer included with GeneRacer kit was used as a 5'-primer. On the other hand, as a 3'-primer for VH amplification, a primer having a sequence specific to the mouse IgG H chain was used, and as a 3'-primer for VL amplification, a primer having a sequence specific to the mouse IgG L chain was used.

```
                                                      (SEQ ID NO: 31)
5'-CGACTGGAGCACGAGGACACTGA-3'

(SEQ ID NO: 32)
VH:        5'- GCCAGTGGATAGACAGATGG-3'

(SEQ ID NO: 33)
VL:        5'- GATGGATACAGTTGGTGCAGC-3'
```

Using each of the above-described primers, PCR was carried out under the following composition of reaction solution and reaction conditions.

| Template cDNA: | 1.0 µL |
|---|---|
| 5 × PrimeSTAR buffer (Mg$^{2+}$ plus): | 10 µL |
| 2.5 mM dNTP: | 4 µL |
| PrimeSTAR HS DNA polymerase (2.5 U/µL): | 0.5 µL |
| F primer (10 µM): | 3 µL |
| R primer (10 µM): | 1.0 µL |
| Sterilized water: | 30.5 µL |
| Total: | 50 µL |

<Reaction Conditions>

A cycle consisting of "heat denaturation/dissociation at 98° C. (10 sec)→annealing at 57° C. (10 sec)→synthesis/elongation at 72° C. (60 sec)" was carried out 35 times in total.

The synthesized VH and VL cDNAs were subcloned into a pCR4Blunt-TOPO vector (Invitrogen), and the nucleotide sequences thereof were determined. The nucleotide sequences of a plurality of VH clones and VL clones were decoded, and nucleotide sequences specific to the variable regions of mouse H chain and L chain were identified. FIG. 39 and FIG. 40 show the consensus cDNA nucleotide sequences of the VH and VL of T6-16, and putative amino acid sequences.

INDUSTRIAL APPLICABILITY

The present invention is able to provide an antibody, which specifically reacts with hTROP-2 and has high anti-tumor activity in vivo, and particularly, a monoclonal antibody having high anti-tumor activity in vivo at a low dose. In addition, the present invention is able to provide a hybridoma, which produces the antibody, a fragment of the antibody, a complex of the antibody or the like and various types of drugs, a pharmaceutical composition for diagnosing or treating a tumor, a method for detecting a tumor, and a kit for detecting or diagnosing a tumor.

[Sequence Listing Free Text]
SEQ ID NO: 3 Synthetic DNA
SEQ ID NO: 4 Synthetic DNA
SEQ ID NO: 5 Synthetic DNA
SEQ ID NO: 6 Synthetic DNA
SEQ ID NO: 7 Synthetic DNA
SEQ ID NO: 8 Synthetic DNA
SEQ ID NO: 9 Synthetic DNA
SEQ ID NO: 10 Synthetic DNA
SEQ ID NO: 11 Synthetic DNA
SEQ ID NO: 12 Synthetic DNA
SEQ ID NO: 13 Synthetic DNA
SEQ ID NO: 14 Synthetic DNA
SEQ ID NO: 15 Synthetic DNA
SEQ ID NO: 16 Synthetic DNA
SEQ ID NO: 17 Synthetic DNA
SEQ ID NO: 18 Synthetic DNA
SEQ ID NO: 19 Synthetic DNA SEQ ID NO: 20 Synthetic DNA
SEQ ID NO: 21 Synthetic DNA
SEQ ID NO: 22 Synthetic DNA
SEQ ID NO: 23 Synthetic DNA
SEQ ID NO: 24 Synthetic DNA
SEQ ID NO: 25 Synthetic DNA
SEQ ID NO: 26 Synthetic DNA SEQ ID NO: 27 Synthetic DNA
SEQ ID NO: 28 Synthetic DNA
SEQ ID NO: 29 Synthetic DNA
SEQ ID NO: 30 Synthetic DNA
SEQ ID NO: 31 Synthetic DNA
SEQ ID NO: 32 Synthetic DNA
SEQ ID NO: 33 Synthetic DNA

The invention claimed is:

1. An antibody against human TROP-2, which has anti-tumor activity in vivo, wherein the amino acid sequences of CDR 1 to 3 of the H chain V region of the antibody are shown in SEQ ID NOS: 66 to 68, respectively, and/or the amino acid sequences of CDR 1 to 3 of the L chain V region of the antibody are shown in SEQ ID NOS: 71 to 73, respectively.

2. The antibody according to claim 1, which exhibits 50% or more of tumor growth inhibitory activity at a dosage of 5 to 20 mg/kg body weight.

3. The antibody according to claim 2, wherein the frequency of administration for exhibiting the tumor growth inhibitory activity is at most once a week.

4. The antibody according to claim 1, which exhibits 50% or more of the tumor growth inhibitory activity by a single administration of the antibody at a dosage of 10 mg/kg body weight.

5. The antibody according to claim 1, which has anti-tumor activity on two or more types of human tumor cell lines.

6. The antibody according to claim 5, wherein the tumor cell lines are at least two types selected from the group consisting of a human pancreatic cancer cell line PK-59, a human pancreatic cancer cell line BxPC-3, a human pancreatic cancer cell line KP-3L, a human pancreatic cancer cell line KP-2, a human pancreatic cancer cell line PK-1, a human pancreatic cancer cell line PK-45H, a human pancreatic cancer cell line PK-45P, a human pancreatic cancer cell line TCC-PAN2, a human pancreatic cancer cell line SUIT-2, a human colon cancer cell line CACO-2, a human colon cancer cell line SW480, a human colon cancer cell line DLD-1, a human colon cancer cell line HCT 116, a human breast cancer cell line JIMT-1, a human breast cancer cell line HCC1143, a human breast cancer cell line MCF-7, a human prostate cancer cell line DU145 and a human prostate cancer cell line PC-3.

7. The antibody according to claim 5, wherein the tumor cell lines are the human pancreatic cancer cell line PK-59 and the human pancreatic cancer cell line BxPC-3.

8. The antibody according to claim 1, wherein the dissociation constant (Kd value) is $1.0 \times 10^{-10}$ M or less.

9. The antibody according to claim 1, which is a monoclonal antibody.

10. The antibody according to claim 1, wherein the tumor is at least one type selected from the group consisting of human pancreatic cancer, human prostate cancer, human colon cancer and human breast cancer.

11. The antibody according to claim 1, wherein the tumor is human pancreatic cancer.

12. The antibody according to claim 1, wherein the tumor is a recurrent cancer or a metastatic cancer.

13. The antibody according to claim 1, wherein the antibody is a recombinant antibody.

14. The antibody according to claim 13, wherein the recombinant antibody is a chimeric antibody, a humanized antibody, or a human antibody.

15. An antigen binding fragment derived from the antibody according to claim 1.

16. An antibody-drug conjugate, which comprises the antibody according to claim 1 and a substance having anti-tumor activity and/or cell-killing activity.

17. The conjugate according to claim 16, wherein the tumor is at least one type selected from the group consisting of human pancreatic cancer, human prostate cancer, human colon cancer and human breast cancer.

18. The conjugate according to claim 16, wherein the tumor is human pancreatic cancer.

19. The conjugate according to claim 16, wherein the tumor is a recurrent cancer of a metastatic cancer.

20. An antigen binding fragment-drug conjugate, which comprises the antigen binding fragment according to claim 15 and a substance having anti-tumor activity and/or cell-killing activity.

21. An antigen binding fragment derived from an antibody against human TROP-2, which has anti-tumor activity in vivo, wherein the fragment comprises the amino acid sequences shown in SEQ ID NOS: 66 to 68 and/or the amino acid sequences shown in SEQ ID NOS: 71 to 73.

22. The antigen binding fragment according to claim 21, which comprises the amino acid sequence shown in SEQ ID NO: 65 and/or the amino acid sequence shown in SEQ ID NO: 70.

23. A recombinant antibody against human TROP-2, which is a chimeric antibody, a humanized antibody, or a human antibody, and has anti-tumor activity in vivo, wherein the H chain V region of the chimeric antibody consists of the amino acid sequence shown in SEQ ID NO: 65, and/or the L chain V region thereof consists of the amino acid sequence shown in SEQ ID NO: 70.

24. A monoclonal antibody against human TROP-2, which is produced by a hybridoma having accession No. FERM BP-11346.

25. A hybridoma producing a monoclonal antibody against human TROP-2, which has accession No. FERM BP-11346.

26. An antibody against human TROP-2, which has anti-tumor activity in vivo, which binds to the same epitope, to which the monoclonal antibody produced by the hybridoma having accession No. FERM BP-11346 binds.

27. The antibody according to claim 26, which exhibits 50% or more of tumor growth inhibitory activity at a dosage of 5 to 20 mg/kg body weight.

28. The antibody according to claim 27, wherein the frequency of administration for exhibiting the tumor growth inhibitory activity is at most once a week.

29. The antibody according to claim 26, which exhibits 50% or more of the tumor growth inhibitory activity by a single administration of the antibody at a dosage of 10 mg/kg body weight.

30. The antibody according to claim 26, which has anti-tumor activity on two or more types of human tumor cell lines.

31. The antibody according to claim 30, wherein the tumor cell lines are at least two types selected from the group consisting of a human pancreatic cancer cell line PK-59, a human pancreatic cancer cell line BxPC-3, a human pancreatic cancer cell line KP-3L, a human pancreatic cancer cell line KP-2, a human pancreatic cancer cell line PK-1, a human pancreatic cancer cell line PK-45H, a human pancreatic cancer cell line PK-45P, a human pancreatic cancer cell line TCC-PAN2, a human pancreatic cancer cell line SUIT-2, a human colon cancer cell line CACO-2, a human colon cancer cell line SW480, a human colon cancer cell line DLD-1, a human colon cancer cell line HCT 116, a human breast cancer cell line JIMT-1, a human breast cancer cell line HCC1143, a human breast cancer cell line MCF-7, a human prostate cancer cell line DU145 and a human prostate cancer cell line PC-3.

32. The antibody according to claim 30, wherein the tumor cell lines are the human pancreatic cancer cell line PK-59 and the human pancreatic cancer cell line BxPC-3.

33. The antibody according to claim 26, wherein the dissociation constant (Kd value) is $1.0 \times 10^{-10}$ M or less.

34. The antibody according to claim 26, which is a monoclonal antibody.

35. The antibody according to claim 26, wherein the tumor is at least one type selected from the group consisting of human pancreatic cancer, human prostate cancer, human colon cancer and human breast cancer.

36. The antibody according to claim 26, wherein the tumor is human pancreatic cancer.

37. The antibody according to claim 26, wherein the tumor is a recurrent cancer or a metastatic cancer.

38. The antibody according to claim 26, wherein the antibody is a recombinant antibody.

39. The antibody according to claim 38, wherein the recombinant antibody is a chimeric antibody, a humanized antibody, or a human antibody.

40. An antigen binding fragment derived from the antibody according to claim 26.

41. The antigen binding fragment according to claim 40, which comprises the amino acid sequences shown in SEQ ID NOS: 66 to 68 and/or the amino acid sequences shown in SEQ ID NOS: 71 to 73.

42. An antibody-drug conjugate, which comprises the antibody according to claim 26 and a substance having anti-tumor activity and/or cell-killing activity.

43. The conjugate according to claim 42, wherein the tumor is at least one type selected from the group consisting of human pancreatic cancer, human prostate cancer, human colon cancer and human breast cancer.

44. The conjugate according to claim 42, wherein the tumor is a recurrent cancer of a metastatic cancer.

45. An antigen binding fragment-drug conjugate, which comprises the antigen binding fragment according to claim 40 and a substance having anti-tumor activity and/or cell-killing activity.

* * * * *

SEQUENCE LISTING

```
<160> NUMBER OF SEQ ID NOS: 207

<210> SEQ ID NO 1
<211> LENGTH: 2080
<212> TYPE: DNA
<213> ORGANISM: Homo sapiens
<220> FEATURE:
<221> NAME/KEY: CDS
<222> LOCATION: (339)..(1307)

<400> SEQUENCE: 1
gcgggtcccc agaagcctac aggtgagtat cggttctccc cttcccggct ttcggtccgg      60
aggaggcggg agcagcttcc ctgttctgat cctatcgcgg gcggcgcagg gccggcttgg     120
ccttccgtgg gacggggagg ggggcgggat gtgtcaccca ataccagtg gggacggtcg      180 gtggtggaac cagccgggca gtcgggtag agtataagag ccggagggag cggccgggcg      240
gcagacgcct gcagaccatc ccagacgccg gagcccgagc cccgacgagt ccccgcgcct     300
catccgcccg cgtccggtcc gcgttcctcc gccccacc atg gct cgg ggc ccc ggc    356
                                            Met Ala Arg Gly Pro Gly
                                             1               5 ctc gcg ccg cca ccg ctg cgg ctg ccg ctg ctg ctg ctg gtg ctg gcg      404
Leu Ala Pro Pro Pro Leu Arg Leu Pro Leu Leu Leu Leu Val Leu Ala
            10                  15                  20 gcg gtg acc ggc cac acg gcc gcg cag gac aac tgc acg tgt ccc acc      452
Ala Val Thr Gly His Thr Ala Ala Gln Asp Asn Cys Thr Cys Pro Thr
        25                  30                  35 aac aag atg acc gtg tgc agc ccc gac ggc ccc ggc ggc cgc tgc cag      500
Asn Lys Met Thr Val Cys Ser Pro Asp Gly Pro Gly Gly Arg Cys Gln
    40                  45                  50 tgc cgc gcg ctg ggc tcg ggc atg gcg gtc gac tgc tcc acg ctg acc      548
Cys Arg Ala Leu Gly Ser Gly Met Ala Val Asp Cys Ser Thr Leu Thr
55                  60                  65                  70 tcc aag tgt ctg ctg ctc aag gcg cgc atg agc gcc ccc aag aac gcc      596
Ser Lys Cys Leu Leu Leu Lys Ala Arg Met Ser Ala Pro Lys Asn Ala
                75                  80                  85 cgc acg ctg gtg cgg ccg agt gag cac gcg ctc gtg gac aac gat ggc      644
Arg Thr Leu Val Arg Pro Ser Glu His Ala Leu Val Asp Asn Asp Gly
            90                  95                 100 ctc tac gac ccc gac tgc gac ccc gag ggc cgc ttc aag gcg cgc cag      692
Leu Tyr Asp Pro Asp Cys Asp Pro Glu Gly Arg Phe Lys Ala Arg Gln
        105                 110                 115 tgc aac cag acg tcg gtg tgc tgg tgc gtg aac tcg gtg ggc gtg cgc      740
Cys Asn Gln Thr Ser Val Cys Trp Cys Val Asn Ser Val Gly Val Arg
    120                 125                 130 cgc acg gac aag ggc gac ctg agc cta cgc tgc gat gag ctg gtg cgc      788
Arg Thr Asp Lys Gly Asp Leu Ser Leu Arg Cys Asp Glu Leu Val Arg
135                 140                 145                 150 acc cac cac atc ctc att gac ctg cgc cac cgc ccc acc gcc ggc gcc      836
Thr His His Ile Leu Ile Asp Leu Arg His Arg Pro Thr Ala Gly Ala
                155                 160                 165 ttc aac cac tca gac ctg gac gcc gag ctg agg cgg ctc ttc cgc gag      884
Phe Asn His Ser Asp Leu Asp Ala Glu Leu Arg Arg Leu Phe Arg Glu
```

```
            170                 175                 180
cgc tat cgg ctg cac ccc aag ttc gtg gcg gcc gtg cac tac gag cag      932
Arg Tyr Arg Leu His Pro Lys Phe Val Ala Ala Val His Tyr Glu Gln
            185                 190                 195 ccc acc atc cag atc gag ctg cgg cag aac acg tct cag aag gcc gcc      980
Pro Thr Ile Gln Ile Glu Leu Arg Gln Asn Thr Ser Gln Lys Ala Ala
        200                 205                 210 ggt gac gtg gat atc ggc gat gcc gcc tac tac ttc gag agg gac atc     1028
Gly Asp Val Asp Ile Gly Asp Ala Ala Tyr Tyr Phe Glu Arg Asp Ile
215                 220                 225                 230 aag ggc gag tct cta ttc cag ggc cgc ggc ggc ctg gac ttg cgc gtg     1076
Lys Gly Glu Ser Leu Phe Gln Gly Arg Gly Gly Leu Asp Leu Arg Val
                235                 240                 245 cgc gga gaa ccc ctg cag gtg gag cgc acg ctc atc tat tac ctg gac     1124
Arg Gly Glu Pro Leu Gln Val Glu Arg Thr Leu Ile Tyr Tyr Leu Asp
            250                 255                 260 gag att ccc ccg aag ttc tcc atg aag cgc ctc acc gcc ggc ctc atc     1172
Glu Ile Pro Pro Lys Phe Ser Met Lys Arg Leu Thr Ala Gly Leu Ile
        265                 270                 275 gcc gtc atc gtg gtg gtc gtg gtg gcc ctc gtc gcc ggc atg gcc gtc     1220
Ala Val Ile Val Val Val Val Val Ala Leu Val Ala Gly Met Ala Val
280                 285                 290 ctg gtg atc acc aac cgg aga aag tcg ggg aag tac aag aag gtg gag     1268
Leu Val Ile Thr Asn Arg Arg Lys Ser Gly Lys Tyr Lys Lys Val Glu
295                 300                 305                 310 atc aag gaa ctg ggg gag ttg aga aag gaa ccg agc ttg taggtacccg      1317
Ile Lys Glu Leu Gly Glu Leu Arg Lys Glu Pro Ser Leu
                315                 320 gcggggcagg ggatggggtg gggtaccgga tttcggtatc gtcccagacc caagtgagtc   1377
acgcttcctg attcctcggc gcaaaggaga cgtttatcct ttcaaattcc tgccttcccc   1437
ctcccttttg cgcacacacc aggtttaata gatcctggcc tcagggtctc ctttctttct   1497
cacttctgtc ttgaaggaag catttctaaa atgtatcccc tttcggtcca acaacaggaa   1557
acctgactgg ggcagtgaag gaagggatgg catagcgtta tgtgtaaaaa acaagtatct   1617
gtatgacaac ccgggatcgt ttgcaagtaa ctgaatccat tgcgacattg tgaaggctta   1677
aatgagttta gatgggaaat agcgttgtta tcgccttggg tttaaattat ttgatgagtt   1737
ccacttgtat catggcctac ccgaggagaa gaggagtttg ttaactgggc ctatgtagta   1797
gcctcattta ccatcgtttg tattactgac cacatatgct tgtcactggg aagaagcct    1857
gtttcagctg cctgaacgca gtttggatgt ctttgaggac agacattgcc cggaaactca   1917
gtctatttat tcttcagctt gcccttactg ccactgatat tggtaatgtt ctttttttgta  1977
aaatgtttgt acatatgttg tctttgataa tgttgctgta attttttaaa ataaaacacg   2037
aatttaataa aatatgggaa aggcacaaac cagaaaaaaa aaa                     2080

<210> SEQ ID NO 2
<211> LENGTH: 323
<212> TYPE: PRT
<213> ORGANISM: Homo sapiens

<400> SEQUENCE: 2

Met Ala Arg Gly Pro Gly Leu Ala Pro Pro Leu Arg Leu Pro Leu
1               5                   10                  15

Leu Leu Leu Val Leu Ala Ala Val Thr Gly His Thr Ala Ala Gln Asp
            20                  25                  30

Asn Cys Thr Cys Pro Thr Asn Lys Met Thr Val Cys Ser Pro Asp Gly
```

```
                35                  40                  45
Pro Gly Gly Arg Cys Gln Cys Arg Ala Leu Gly Ser Gly Met Ala Val
 50                  55                  60

Asp Cys Ser Thr Leu Thr Ser Lys Cys Leu Leu Leu Lys Ala Arg Met
 65                  70                  75                  80

Ser Ala Pro Lys Asn Ala Arg Thr Leu Val Arg Pro Ser Glu His Ala
                 85                  90                  95

Leu Val Asp Asn Asp Gly Leu Tyr Asp Pro Cys Asp Pro Glu Gly
                100                 105                 110

Arg Phe Lys Ala Arg Gln Cys Asn Gln Thr Ser Val Cys Trp Cys Val
                115                 120                 125

Asn Ser Val Gly Val Arg Arg Thr Asp Lys Gly Asp Leu Ser Leu Arg
130                 135                 140

Cys Asp Glu Leu Val Arg Thr His His Ile Leu Ile Asp Leu Arg His
145                 150                 155                 160

Arg Pro Thr Ala Gly Ala Phe Asn His Ser Asp Leu Asp Ala Glu Leu
                165                 170                 175

Arg Arg Leu Phe Arg Glu Arg Tyr Arg Leu His Pro Lys Phe Val Ala
                180                 185                 190

Ala Val His Tyr Glu Gln Pro Thr Ile Gln Ile Glu Leu Arg Gln Asn
                195                 200                 205

Thr Ser Gln Lys Ala Ala Gly Asp Val Asp Ile Gly Asp Ala Ala Tyr
210                 215                 220

Tyr Phe Glu Arg Asp Ile Lys Gly Glu Ser Leu Phe Gln Gly Arg Gly
225                 230                 235                 240

Gly Leu Asp Leu Arg Val Arg Gly Glu Pro Leu Gln Val Glu Arg Thr
                245                 250                 255

Leu Ile Tyr Tyr Leu Asp Glu Ile Pro Pro Lys Phe Ser Met Lys Arg
                260                 265                 270

Leu Thr Ala Gly Leu Ile Ala Val Ile Val Val Val Val Ala Leu
                275                 280                 285

Val Ala Gly Met Ala Val Leu Val Ile Thr Asn Arg Arg Lys Ser Gly
290                 295                 300

Lys Tyr Lys Lys Val Glu Ile Lys Glu Leu Gly Glu Leu Arg Lys Glu
305                 310                 315                 320

Pro Ser Leu

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ttcctccgcc ccaccatggc                                              20

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
```
ctcgagcaag ctcggttcct ttctc                                              25

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctcgagctcg tccaggtaat agatgagcg                                          29

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gatccactag tcgcgagtgg tgg                                                23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aattccacca ctcgcgacta gtg                                                23

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tcctcgtgtc ccactcccgg                                                    20

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctcgagtgca ttgagttccc tatgc                                              25

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cctgagccta cgctgcgacg aagtggtgcg                                         30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cgcaccactt cgtcgcagcg taggctcagg                                       30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gactgctcca cgctgacttc caagtgcctg                                       30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
caggcacttg gaagtcagcg tggagcagtc                                       30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctcgtggaca acgatggcct ctacgacccg                                       30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cgggtcgtag aggccatcgt tgtccacgag                                       30

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ccaaagcctg cgctgcgatg agctggtgcg c                                     31

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gcgcaccagc tcatcgcagc gcaggctttg g                                 31

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agcttcctat ccgcggtgca ctacgagcag                                   30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ctgctcgtag tgcaccgcgg ataggaagct                                   30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gacattaaag gcgagtctct attccagggc                                   30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gccctggaat agagactcgc ctttaatgtc                                   30

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ctactccacc ccaccctggc g                                            21

```
<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ctcgagcaag ctaggttcgc ttctc                                           25

<210> SEQ ID NO 24
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24 tccakagtt                                                              9

<210> SEQ ID NO 25
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gctgtcctga tc                                                         12

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ctaatacgac tcactatagg gcaagcagtg gtatcaacgc agagt                     45

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ctaatacgac tcactatagg gc                                              22

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gggaartarc ccttgaccag gca                                             23

<210> SEQ ID NO 29
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gggaartagc ctttgacaag gca                                              23

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cactgccatc aatvttccac ttgaca                                           26

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cgactggagc acgaggacac tga                                              23

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gccagtggat agacagatgg                                                  20

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gatggataca gttggtgcag c                                                21

<210> SEQ ID NO 34
<211> LENGTH: 402
<212> TYPE: DNA
<213> ORGANISM: Homo sapiens
<220> FEATURE:
<221> NAME/KEY: CDS
<222> LOCATION: (1)..(402)

<400> SEQUENCE: 34 atg gga tgg agc tgt atc atc ctc ttc ttg gta gca aca gct aca ggt        48
Met Gly Trp Ser Cys Ile Ile Leu Phe Leu Val Ala Thr Ala Thr Gly
1               5                   10                  15 gtc cac tcc cag gtc caa ctg cag cag cct ggg gct gag ctg gtg agg        96
```

```
                Val His Ser Gln Val Gln Leu Gln Gln Pro Gly Ala Glu Leu Val Arg
                            20                  25                  30 cct ggg gct tca gtg aag ctg tcc tgc aag gct tct ggc tac acc ttc        144
Pro Gly Ala Ser Val Lys Leu Ser Cys Lys Ala Ser Gly Tyr Thr Phe
            35                  40                  45 acc atc tac tgg ata aac tgg gtg aaa cag agg cct gga caa ggc ctt        192
Thr Ile Tyr Trp Ile Asn Trp Val Lys Gln Arg Pro Gly Gln Gly Leu
        50                  55                  60 gag tgg atc gga aat att tat cct tct gat agt tat act aac tac aat        240
Glu Trp Ile Gly Asn Ile Tyr Pro Ser Asp Ser Tyr Thr Asn Tyr Asn
65                  70                  75                  80 caa aag ttc aag gac aag gcc aca ttg act gta gac aaa tcc tcc agc        288
Gln Lys Phe Lys Asp Lys Ala Thr Leu Thr Val Asp Lys Ser Ser Ser
                85                  90                  95 aca gcc tac atg cag ctc agc agc ccg aca tct gag gac tct gcg gtc        336
Thr Ala Tyr Met Gln Leu Ser Ser Pro Thr Ser Glu Asp Ser Ala Val
            100                 105                 110 tat tac tgt aca aga acg tct atg gcg gac tac tgg ggc caa ggc acc        384
Tyr Tyr Cys Thr Arg Thr Ser Met Ala Asp Tyr Trp Gly Gln Gly Thr
        115                 120                 125 act ctc aca gtc tcc tca                                                402
Thr Leu Thr Val Ser Ser
    130

<210> SEQ ID NO 35
<211> LENGTH: 134
<212> TYPE: PRT
<213> ORGANISM: Homo sapiens

<400> SEQUENCE: 35

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ile Tyr Trp Ile Asn Trp Val Lys Gln Arg Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Thr Arg Thr Ser Met Ala Asp Tyr Trp Gly Gln Gly Thr
        115                 120                 125

Thr Leu Thr Val Ser Ser
    130

<210> SEQ ID NO 36
<211> LENGTH: 5
<212> TYPE: PRT
<213> ORGANISM: Homo sapiens

<400> SEQUENCE: 36

Ile Tyr Trp Ile Asn
1               5

<210> SEQ ID NO 37
```

<211> LENGTH: 17
<212> TYPE: PRT
<213> ORGANISM: Homo sapiens

<400> SEQUENCE: 37

Asn Ile Tyr Pro Ser Asp Ser Tyr Thr Asn Tyr Asn Gln Lys Phe Lys
1               5                   10                  15

Asp

<210> SEQ ID NO 38
<211> LENGTH: 6
<212> TYPE: PRT
<213> ORGANISM: Homo sapiens

<400> SEQUENCE: 38

Thr Ser Met Ala Asp Tyr
1               5

<210> SEQ ID NO 39
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 39 atg gta tcc aca cct cag ttc ctt gta ttt ttg ctt ttc tgg att cca      48
Met Val Ser Thr Pro Gln Phe Leu Val Phe Leu Leu Phe Trp Ile Pro
1               5                   10                  15 gcc tcc aga ggt gac atc ttg ctg act cag tct cca gcc atc ctg tct      96
Ala Ser Arg Gly Asp Ile Leu Leu Thr Gln Ser Pro Ala Ile Leu Ser
                20                  25                  30 gtg agt cca gga gaa aga gtc agt ttc tcc tgc agg gcc agt cag agc     144
Val Ser Pro Gly Glu Arg Val Ser Phe Ser Cys Arg Ala Ser Gln Ser
            35                  40                  45 att ggc aca agc ata cac tgg tat cag caa aga aca aat ggt tct cca     192
Ile Gly Thr Ser Ile His Trp Tyr Gln Gln Arg Thr Asn Gly Ser Pro
        50                  55                  60 agg ctt ctc ata aag tat gct tct gag tct atc tct ggg atc cct tcc     240
Arg Leu Leu Ile Lys Tyr Ala Ser Glu Ser Ile Ser Gly Ile Pro Ser
65                  70                  75                  80 agg ttt agt ggc agt gga tca ggg aca gat ttt act ctt agc atc aac     288
Arg Phe Ser Gly Ser Gly Ser Gly Thr Asp Phe Thr Leu Ser Ile Asn
                85                  90                  95 agt gtg gag tct gaa gat att gca gat tat tac tgt caa caa agt aat     336
Ser Val Glu Ser Glu Asp Ile Ala Asp Tyr Tyr Cys Gln Gln Ser Asn
                100                 105                 110 agc tgg cca ttc acg ttc ggc tcg ggg aca aag ttg gaa ata aaa         381
Ser Trp Pro Phe Thr Phe Gly Ser Gly Thr Lys Leu Glu Ile Lys
            115                 120                 125

<210> SEQ ID NO 40
<211> LENGTH: 127
<212> TYPE: PRT
<213> ORGANISM: Homo sapiens

<400> SEQUENCE: 40

Met Val Ser Thr Pro Gln Phe Leu Val Phe Leu Leu Phe Trp Ile Pro
1               5                   10                  15

Ala Ser Arg Gly Asp Ile Leu Leu Thr Gln Ser Pro Ala Ile Leu Ser
                20                  25                  30

-continued

```
Val Ser Pro Gly Glu Arg Val Ser Phe Ser Cys Arg Ala Ser Gln Ser
            35                  40                  45

Ile Gly Thr Ser Ile His Trp Tyr Gln Gln Arg Thr Asn Gly Ser Pro
 50                  55                  60

Arg Leu Leu Ile Lys Tyr Ala Ser Glu Ser Ile Ser Gly Ile Pro Ser
 65                  70                  75                  80

Arg Phe Ser Gly Ser Gly Ser Gly Thr Asp Phe Thr Leu Ser Ile Asn
                85                  90                  95

Ser Val Glu Ser Glu Asp Ile Ala Asp Tyr Tyr Cys Gln Gln Ser Asn
            100                 105                 110

Ser Trp Pro Phe Thr Phe Gly Ser Gly Thr Lys Leu Glu Ile Lys
        115                 120                 125
```

<210> SEQ ID NO 41
<211> LENGTH: 11
<212> TYPE: PRT
<213> ORGANISM: Homo sapiens

<400> SEQUENCE: 41

```
Arg Ala Ser Gln Ser Ile Gly Thr Ser Ile His
1               5                   10
```

<210> SEQ ID NO 42
<211> LENGTH: 7
<212> TYPE: PRT
<213> ORGANISM: Homo sapiens

<400> SEQUENCE: 42

```
Tyr Ala Ser Glu Ser Ile Ser
1               5
```

<210> SEQ ID NO 43
<211> LENGTH: 9
<212> TYPE: PRT
<213> ORGANISM: Homo sapiens

<400> SEQUENCE: 43

```
Gln Gln Ser Asn Ser Trp Pro Phe Thr
1               5
```

<210> SEQ ID NO 44
<211> LENGTH: 402
<212> TYPE: DNA
<213> ORGANISM: Homo sapiens
<220> FEATURE:
<221> NAME/KEY: CDS
<222> LOCATION: (1)..(402)

<400> SEQUENCE: 44

```
atg gga tgg agc tgt atc atc ctc ttc ttg gta gca aca gct aca ggt     48
Met Gly Trp Ser Cys Ile Ile Leu Phe Leu Val Ala Thr Ala Thr Gly
1               5                   10                  15 gtc cac tcc cag gtc caa ctg cag caa cct ggg tct gag ctg gtg agg     96
Val His Ser Gln Val Gln Leu Gln Gln Pro Gly Ser Glu Leu Val Arg
            20                  25                  30 cct gga gct tca gtg aag ctg tcc tgc aag gct tct ggc tac aca ttc    144
Pro Gly Ala Ser Val Lys Leu Ser Cys Lys Ala Ser Gly Tyr Thr Phe
        35                  40                  45 acc agc tac tgg atg cac tgg gtg aag cag agg cat gga caa ggc ctt    192
Thr Ser Tyr Trp Met His Trp Val Lys Gln Arg His Gly Gln Gly Leu
    50                  55                  60 gag tgg att gga aat att tat cct ggt ggt ggt tat act aac tac gat    240
```

```
Glu Trp Ile Gly Asn Ile Tyr Pro Gly Gly Gly Tyr Thr Asn Tyr Asp
 65                  70                  75                  80 gag aag ttc aag agc aag ggc aca ctg act gta gac aca tcc tcc agc      288
Glu Lys Phe Lys Ser Lys Gly Thr Leu Thr Val Asp Thr Ser Ser Ser
                 85                  90                  95 aca gcc tac atg cac ctc agc agc ctg aca tct gag gac tct gcg gtc      336
Thr Ala Tyr Met His Leu Ser Ser Leu Thr Ser Glu Asp Ser Ala Val
                100                 105                 110 tat tac tgt aca aga tca tcc gtt ttt gac tac tgg ggc caa ggc acc      384
Tyr Tyr Cys Thr Arg Ser Ser Val Phe Asp Tyr Trp Gly Gln Gly Thr
                115                 120                 125 act ctc aca gtc tcc tca                                              402
Thr Leu Thr Val Ser Ser
    130
```

<210> SEQ ID NO 45
<211> LENGTH: 134
<212> TYPE: PRT
<213> ORGANISM: Homo sapiens

<400> SEQUENCE: 45

```
Met Gly Trp Ser Cys Ile Ile Leu Phe Leu Val Ala Thr Ala Thr Gly
 1               5                  10                  15

Val His Ser Gln Val Gln Leu Gln Gln Pro Gly Ser Glu Leu Val Arg
                 20                  25                  30

Pro Gly Ala Ser Val Lys Leu Ser Cys Lys Ala Ser Gly Tyr Thr Phe
             35                  40                  45

Thr Ser Tyr Trp Met His Trp Val Lys Gln Arg His Gly Gln Gly Leu
         50                  55                  60

Glu Trp Ile Gly Asn Ile Tyr Pro Gly Gly Gly Tyr Thr Asn Tyr Asp
 65                  70                  75                  80

Glu Lys Phe Lys Ser Lys Gly Thr Leu Thr Val Asp Thr Ser Ser Ser
                 85                  90                  95

Thr Ala Tyr Met His Leu Ser Ser Leu Thr Ser Glu Asp Ser Ala Val
                100                 105                 110

Tyr Tyr Cys Thr Arg Ser Ser Val Phe Asp Tyr Trp Gly Gln Gly Thr
                115                 120                 125

Thr Leu Thr Val Ser Ser
    130
```

<210> SEQ ID NO 46
<211> LENGTH: 5
<212> TYPE: PRT
<213> ORGANISM: Homo sapiens

<400> SEQUENCE: 46

```
Ser Tyr Trp Met His
 1               5
```

<210> SEQ ID NO 47
<211> LENGTH: 17
<212> TYPE: PRT
<213> ORGANISM: Homo sapiens

<400> SEQUENCE: 47

```
Asn Ile Tyr Pro Gly Gly Gly Tyr Thr Asn Tyr Asp Glu Lys Phe Lys
 1               5                  10                  15

Ser
```

-continued

<210> SEQ ID NO 48
<211> LENGTH: 6
<212> TYPE: PRT
<213> ORGANISM: Homo sapiens

<400> SEQUENCE: 48

Ser Ser Val Phe Asp Tyr
1               5

<210> SEQ ID NO 49
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 49

```
atg gta tcc aca cct cag ttc ctt gta ttt ttg ctt ttc tgg att cca      48
Met Val Ser Thr Pro Gln Phe Leu Val Phe Leu Leu Phe Trp Ile Pro
1               5                   10                  15 gcc tcc aga ggt gac atc ttg ctg act cag tct cca gcc atc ctg tct      96
Ala Ser Arg Gly Asp Ile Leu Leu Thr Gln Ser Pro Ala Ile Leu Ser
            20                  25                  30 gtg agt cca gga gaa aga gtc agt ttc tcc tgc agg gcc agt cag aac     144
Val Ser Pro Gly Glu Arg Val Ser Phe Ser Cys Arg Ala Ser Gln Asn
        35                  40                  45 att ggc aca agc ata cac tgg ttt cag caa aga aca aat ggt tct cca     192
Ile Gly Thr Ser Ile His Trp Phe Gln Gln Arg Thr Asn Gly Ser Pro
    50                  55                  60 agg ctt ctc ata aag tat gct tct gag tct atc tct ggg atc cct tcc     240
Arg Leu Leu Ile Lys Tyr Ala Ser Glu Ser Ile Ser Gly Ile Pro Ser
65                  70                  75                  80 agg ttt agt ggc agt gga tca ggg aca gat ttt act ctt agc atc aac     288
Arg Phe Ser Gly Ser Gly Ser Gly Thr Asp Phe Thr Leu Ser Ile Asn
                85                  90                  95 agt gtg gag tct gaa gat att gca gat tat tac tgt caa caa agt aat     336
Ser Val Glu Ser Glu Asp Ile Ala Asp Tyr Tyr Cys Gln Gln Ser Asn
            100                 105                 110 agc tgg cca ttc acg ttc ggc tcg ggg aca aag ttg gaa ata aaa         381
Ser Trp Pro Phe Thr Phe Gly Ser Gly Thr Lys Leu Glu Ile Lys
        115                 120                 125
```

<210> SEQ ID NO 50
<211> LENGTH: 127
<212> TYPE: PRT
<213> ORGANISM: Homo sapiens

<400> SEQUENCE: 50

Met Val Ser Thr Pro Gln Phe Leu Val Phe Leu Leu Phe Trp Ile Pro
1               5                   10                  15

Ala Ser Arg Gly Asp Ile Leu Leu Thr Gln Ser Pro Ala Ile Leu Ser
            20                  25                  30

Val Ser Pro Gly Glu Arg Val Ser Phe Ser Cys Arg Ala Ser Gln Asn
        35                  40                  45

Ile Gly Thr Ser Ile His Trp Phe Gln Gln Arg Thr Asn Gly Ser Pro
    50                  55                  60

Arg Leu Leu Ile Lys Tyr Ala Ser Glu Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

```
Ser Val Glu Ser Glu Asp Ile Ala Asp Tyr Tyr Cys Gln Gln Ser Asn
            100                 105                 110

Ser Trp Pro Phe Thr Phe Gly Ser Gly Thr Lys Leu Glu Ile Lys
        115                 120                 125
```

<210> SEQ ID NO 51
<211> LENGTH: 11
<212> TYPE: PRT
<213> ORGANISM: Homo sapiens

<400> SEQUENCE: 51

```
Arg Ala Ser Gln Asn Ile Gly Thr Ser Ile His
1               5                   10
```

<210> SEQ ID NO 52
<211> LENGTH: 7
<212> TYPE: PRT
<213> ORGANISM: Homo sapiens

<400> SEQUENCE: 52

```
Tyr Ala Ser Glu Ser Ile Ser
1               5
```

<210> SEQ ID NO 53
<211> LENGTH: 9
<212> TYPE: PRT
<213> ORGANISM: Homo sapiens

<400> SEQUENCE: 53

```
Gln Gln Ser Asn Ser Trp Pro Phe Thr
1               5
```

<210> SEQ ID NO 54
<211> LENGTH: 396
<212> TYPE: DNA
<213> ORGANISM: Homo sapiens
<220> FEATURE:
<221> NAME/KEY: CDS
<222> LOCATION: (1)..(396)

<400> SEQUENCE: 54

```
atg gga tgg agc tgt atc atc ctc ttc ttg gta gca aca gct aca ggt        48
Met Gly Trp Ser Cys Ile Ile Leu Phe Leu Val Ala Thr Ala Thr Gly
1               5                   10                  15 gtc cac tcc cag gtc caa ctg cag cag cct ggg gct gag ctg gtg agg        96
Val His Ser Gln Val Gln Leu Gln Gln Pro Gly Ala Glu Leu Val Arg
                20                  25                  30 cct ggg gct tca gtg aag ctg tcc tgc aag gct tct ggc tac acc ttc       144
Pro Gly Ala Ser Val Lys Leu Ser Cys Lys Ala Ser Gly Tyr Thr Phe
            35                  40                  45 acc agc tac tgg ata acc tgg gtg aag cag agg cct gga caa ggc ctt       192
Thr Ser Tyr Trp Ile Thr Trp Val Lys Gln Arg Pro Gly Gln Gly Leu
        50                  55                  60 gag tgg atc gga aat att tat cct tct gat agt tat act aac tac aat       240
Glu Trp Ile Gly Asn Ile Tyr Pro Ser Asp Ser Tyr Thr Asn Tyr Asn
65                  70                  75                  80 caa aag ttc agg gac aag gcc aca ttg act gta gac aaa tcc tcc agt       288
Gln Lys Phe Arg Asp Lys Ala Thr Leu Thr Val Asp Lys Ser Ser Ser
                85                  90                  95 aca gcc tac atg cag ctc agc agc ccg aca tct gag gac tct gcg gtc       336
Thr Ala Tyr Met Gln Leu Ser Ser Pro Thr Ser Glu Asp Ser Ala Val
            100                 105                 110 tat tac tgt tca gcc ctc ttt gac tac tgg ggc caa ggc acc act ctc       384
```

```
Tyr Tyr Cys Ser Ala Leu Phe Asp Tyr Trp Gly Gln Gly Thr Thr Leu
        115                 120                 125 aca gtc tcc tca                                                      396
Thr Val Ser Ser
    130
```

<210> SEQ ID NO 55
<211> LENGTH: 132
<212> TYPE: PRT
<213> ORGANISM: Homo sapiens

<400> SEQUENCE: 55

```
Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Ile Thr Trp Val Lys Gln Arg Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Lys Phe Arg Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Ser Ala Leu Phe Asp Tyr Trp Gly Gln Gly Thr Thr Leu
        115                 120                 125

Thr Val Ser Ser
    130
```

<210> SEQ ID NO 56
<211> LENGTH: 5
<212> TYPE: PRT
<213> ORGANISM: Homo sapiens

<400> SEQUENCE: 56

```
Ser Tyr Trp Ile Thr
1               5
```

<210> SEQ ID NO 57
<211> LENGTH: 17
<212> TYPE: PRT
<213> ORGANISM: Homo sapiens

<400> SEQUENCE: 57

```
Asn Ile Tyr Pro Ser Asp Ser Tyr Thr Asn Tyr Asn Gln Lys Phe Arg
1               5                   10                  15

Asp
```

<210> SEQ ID NO 58
<211> LENGTH: 4
<212> TYPE: PRT
<213> ORGANISM: Homo sapiens

<400> SEQUENCE: 58

```
Leu Phe Asp Tyr
1
```

<210> SEQ ID NO 59

```
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 59 atg gta tcc aca cct cag ttc ctt gta ttt ttg ctt ttc tgg att cca     48
Met Val Ser Thr Pro Gln Phe Leu Val Phe Leu Leu Phe Trp Ile Pro
1               5                   10                  15 gcc tcc aga ggt gac atc ttg ctg act cag tct cca gcc atc ctg tct     96
Ala Ser Arg Gly Asp Ile Leu Leu Thr Gln Ser Pro Ala Ile Leu Ser
            20                  25                  30 gtg agt cca gga gaa aga gtc agt ttc tcc tgc agg gcc agt cag agc    144
Val Ser Pro Gly Glu Arg Val Ser Phe Ser Cys Arg Ala Ser Gln Ser
        35                  40                  45 att ggc aca agc ata cac tgg tat cag caa aga aca aat ggt tct cca    192
Ile Gly Thr Ser Ile His Trp Tyr Gln Gln Arg Thr Asn Gly Ser Pro
    50                  55                  60 agg ctt ctc ata aag tat gct tct gag tct atc tct ggg atc cct tcc    240
Arg Leu Leu Ile Lys Tyr Ala Ser Glu Ser Ile Ser Gly Ile Pro Ser
65                  70                  75                  80 agg ttt agt ggc agt gga tca ggg aca gat ttt att ctt agc atc aac    288
Arg Phe Ser Gly Ser Gly Ser Gly Thr Asp Phe Ile Leu Ser Ile Asn
                85                  90                  95 agt gtg gag tct gaa gat att gca gat tat tac tgt caa caa agt aat    336
Ser Val Glu Ser Glu Asp Ile Ala Asp Tyr Tyr Cys Gln Gln Ser Asn
            100                 105                 110 agc tgg cca ttc acg ttc ggc tcg ggg aca aag ttg gaa ata aaa        381
Ser Trp Pro Phe Thr Phe Gly Ser Gly Thr Lys Leu Glu Ile Lys
        115                 120                 125

<210> SEQ ID NO 60
<211> LENGTH: 127
<212> TYPE: PRT
<213> ORGANISM: Homo sapiens

<400> SEQUENCE: 60

Met Val Ser Thr Pro Gln Phe Leu Val Phe Leu Leu Phe Trp Ile Pro
1               5                   10                  15

Ala Ser Arg Gly Asp Ile Leu Leu Thr Gln Ser Pro Ala Ile Leu Ser
            20                  25                  30

Val Ser Pro Gly Glu Arg Val Ser Phe Ser Cys Arg Ala Ser Gln Ser
        35                  40                  45

Ile Gly Thr Ser Ile His Trp Tyr Gln Gln Arg Thr Asn Gly Ser Pro
    50                  55                  60

Arg Leu Leu Ile Lys Tyr Ala Ser Glu Ser Ile Ser Gly Ile Pro Ser
65                  70                  75                  80

Arg Phe Ser Gly Ser Gly Ser Gly Thr Asp Phe Ile Leu Ser Ile Asn
                85                  90                  95

Ser Val Glu Ser Glu Asp Ile Ala Asp Tyr Tyr Cys Gln Gln Ser Asn
            100                 105                 110

Ser Trp Pro Phe Thr Phe Gly Ser Gly Thr Lys Leu Glu Ile Lys
        115                 120                 125

<210> SEQ ID NO 61
<211> LENGTH: 11
<212> TYPE: PRT
<213> ORGANISM: Homo sapiens
```

<400> SEQUENCE: 61

Arg Ala Ser Gln Ser Ile Gly Thr Ser Ile His
1               5                   10

<210> SEQ ID NO 62
<211> LENGTH: 7
<212> TYPE: PRT
<213> ORGANISM: Homo sapiens

<400> SEQUENCE: 62

Tyr Ala Ser Glu Ser Ile Ser
1               5

<210> SEQ ID NO 63
<211> LENGTH: 9
<212> TYPE: PRT
<213> ORGANISM: Homo sapiens

<400> SEQUENCE: 63

Gln Gln Ser Asn Ser Trp Pro Phe Thr
1               5

<210> SEQ ID NO 64
<211> LENGTH: 423
<212> TYPE: DNA
<213> ORGANISM: Homo sapiens
<220> FEATURE:
<221> NAME/KEY: CDS
<222> LOCATION: (1)..(423)

<400> SEQUENCE: 64

| | | | | | | | | | | | | | | | | |
|---|---|---|---|---|---|---|---|---|---|---|---|---|---|---|---|---|
| atg | gga | tgg | agc | tgg | atc | ttt | ctc | ttc | ctc | ctg | tca | gga | act | gca | ggc | 48 |
| Met | Gly | Trp | Ser | Trp | Ile | Phe | Leu | Phe | Leu | Leu | Ser | Gly | Thr | Ala | Gly | |
| 1 | | | 5 | | | | | 10 | | | | | 15 | | | |
| gtc | cac | tct | gag | gtc | cag | ctt | cag | cag | tca | gga | cct | gag | ctg | gtg | aaa | 96 |
| Val | His | Ser | Glu | Val | Gln | Leu | Gln | Gln | Ser | Gly | Pro | Glu | Leu | Val | Lys | |
| | | | 20 | | | | | 25 | | | | | 30 | | | |
| cct | ggg | gcc | tca | gtg | aag | att | tcc | tgc | aag | gct | tct | gga | tac | aca | ttc | 144 |
| Pro | Gly | Ala | Ser | Val | Lys | Ile | Ser | Cys | Lys | Ala | Ser | Gly | Tyr | Thr | Phe | |
| | | 35 | | | | | 40 | | | | | 45 | | | | |
| act | gac | tac | aat | atg | cac | tgg | gtg | aag | cag | agc | cat | gga | aag | aac | ctt | 192 |
| Thr | Asp | Tyr | Asn | Met | His | Trp | Val | Lys | Gln | Ser | His | Gly | Lys | Asn | Leu | |
| | 50 | | | | | 55 | | | | | 60 | | | | | |
| gaa | tgg | att | gga | tat | att | tat | cct | tac | aat | ggt | ggt | act | ggc | tac | aac | 240 |
| Glu | Trp | Ile | Gly | Tyr | Ile | Tyr | Pro | Tyr | Asn | Gly | Gly | Thr | Gly | Tyr | Asn | |
| 65 | | | | 70 | | | | | 75 | | | | | 80 | | |
| cag | agg | ttc | aag | agc | agg | gcc | aca | atg | act | gta | gac | aaa | tcc | tcc | agc | 288 |
| Gln | Arg | Phe | Lys | Ser | Arg | Ala | Thr | Met | Thr | Val | Asp | Lys | Ser | Ser | Ser | |
| | | | 85 | | | | | 90 | | | | | 95 | | | |
| aca | gcc | tac | atg | gag | ctc | cgc | agc | ctg | aca | tct | gat | gac | tct | gca | gtc | 336 |
| Thr | Ala | Tyr | Met | Glu | Leu | Arg | Ser | Leu | Thr | Ser | Asp | Asp | Ser | Ala | Val | |
| | | | 100 | | | | | 105 | | | | | 110 | | | |
| tat | tac | tgt | gca | aga | gaa | gac | tac | ggt | agt | agc | ccc | tct | tat | gct | atg | 384 |
| Tyr | Tyr | Cys | Ala | Arg | Glu | Asp | Tyr | Gly | Ser | Ser | Pro | Ser | Tyr | Ala | Met | |
| | | 115 | | | | | 120 | | | | | 125 | | | | |
| gac | tat | tgg | ggt | caa | gga | acc | tca | gtc | atc | gtc | tcc | tca | | | | 423 |
| Asp | Tyr | Trp | Gly | Gln | Gly | Thr | Ser | Val | Ile | Val | Ser | Ser | | | | |
| | 130 | | | | | 135 | | | | | 140 | | | | | |

<210> SEQ ID NO 65
<211> LENGTH: 141
<212> TYPE: PRT
<213> ORGANISM: Homo sapiens

<400> SEQUENCE: 65

Met Gly Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met His Trp Val Lys Gln Ser His Gly Lys Asn Leu
    50                  55                  60

Glu Trp Ile Gly Tyr Ile Tyr Pro Tyr Asn Gly Gly Thr Gly Tyr Asn
65                  70                  75                  80

Gln Arg Phe Lys Ser Arg Ala Thr Met Thr Val Asp Lys Ser Ser Ser
                85                  90                  95

Thr Ala Tyr Met Glu Leu Arg Ser Leu Thr Ser Asp Asp Ser Ala Val
            100                 105                 110

Tyr Tyr Cys Ala Arg Glu Asp Tyr Gly Ser Ser Pro Ser Tyr Ala Met
        115                 120                 125

Asp Tyr Trp Gly Gln Gly Thr Ser Val Ile Val Ser Ser
    130                 135                 140

<210> SEQ ID NO 66
<211> LENGTH: 5
<212> TYPE: PRT
<213> ORGANISM: Homo sapiens

<400> SEQUENCE: 66

Asp Tyr Asn Met His
1               5

<210> SEQ ID NO 67
<211> LENGTH: 17
<212> TYPE: PRT
<213> ORGANISM: Homo sapiens

<400> SEQUENCE: 67

Tyr Ile Tyr Pro Tyr Asn Gly Gly Thr Gly Tyr Asn Gln Arg Phe Lys
1               5                   10                  15

Ser

<210> SEQ ID NO 68
<211> LENGTH: 13
<212> TYPE: PRT
<213> ORGANISM: Homo sapiens

<400> SEQUENCE: 68

Glu Asp Tyr Gly Ser Ser Pro Ser Tyr Ala Met Asp Tyr
1               5                   10

<210> SEQ ID NO 69
<211> LENGTH: 390
<212> TYPE: DNA
<213> ORGANISM: Homo sapiens
<220> FEATURE:
<221> NAME/KEY: CDS
<222> LOCATION: (1)..(390)

<400> SEQUENCE: 69 atg aag ttg cct gtt agg ctg ttg gtg ctg atg ttc tgg att cct gct    48
Met Lys Leu Pro Val Arg Leu Leu Val Leu Met Phe Trp Ile Pro Ala
1               5                   10                  15

```
tcc agc agt gat gtt gtg atg acc caa act cca ctc tcc ctg cct gtc    96
Ser Ser Ser Asp Val Val Met Thr Gln Thr Pro Leu Ser Leu Pro Val
            20                  25                  30 agt ctt gga gat cag gcc tcc atc tct tgc aga tct agt cag agc ctt   144
Ser Leu Gly Asp Gln Ala Ser Ile Ser Cys Arg Ser Ser Gln Ser Leu
        35                  40                  45 gta cac ggt aat gga aac acc tat tta cat tgg tac ctg cag aag cca   192
Val His Gly Asn Gly Asn Thr Tyr Leu His Trp Tyr Leu Gln Lys Pro
 50                  55                  60 ggc cag tct cca aag ctc ctg atc tac aaa gtt tcc aac cga ttt tct   240
Gly Gln Ser Pro Lys Leu Leu Ile Tyr Lys Val Ser Asn Arg Phe Ser
65                  70                  75                  80 ggg gtc cca gac agg ttc agt ggc agt gga tca ggg acg gat ttc aca   288
Gly Val Pro Asp Arg Phe Ser Gly Ser Gly Ser Gly Thr Asp Phe Thr
                85                  90                  95 ctc aag atc agc aga gtg gag gct gag gat ctg gga gtt tat ttc tgc   336
Leu Lys Ile Ser Arg Val Glu Ala Glu Asp Leu Gly Val Tyr Phe Cys
            100                 105                 110 tct caa act aca cat gtt ccc acg ttc ggc tcg ggg aca aag ttg gaa   384
Ser Gln Thr Thr His Val Pro Thr Phe Gly Ser Gly Thr Lys Leu Glu
        115                 120                 125 ata aaa                                                           390
Ile Lys
    130

<210> SEQ ID NO 70
<211> LENGTH: 130
<212> TYPE: PRT
<213> ORGANISM: Homo sapiens

<400> SEQUENCE: 70

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Gly Asn Gly Asn Thr Tyr Leu His Trp Tyr Leu Gln Lys Pro
 50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Thr Thr His Val Pro Thr Phe Gly Ser Gly Thr Lys Leu Glu
        115                 120                 125

Ile Lys
    130

<210> SEQ ID NO 71
<211> LENGTH: 16
<212> TYPE: PRT
<213> ORGANISM: Homo sapiens

<400> SEQUENCE: 71

Arg Ser Ser Gln Ser Leu Val His Gly Asn Gly Asn Thr Tyr Leu His
1               5                   10                  15
```

<210> SEQ ID NO 72
<211> LENGTH: 7
<212> TYPE: PRT
<213> ORGANISM: Homo sapiens

<400> SEQUENCE: 72

Lys Val Ser Asn Arg Phe Ser
1               5

<210> SEQ ID NO 73
<211> LENGTH: 8
<212> TYPE: PRT
<213> ORGANISM: Homo sapiens

<400> SEQUENCE: 73

Ser Gln Thr Thr His Val Pro Thr
1               5

<210> SEQ ID NO 74
<211> LENGTH: 30
<212> TYPE: PRT
<213> ORGANISM: Homo sapiens

<400> SEQUENCE: 74

Asn Lys Met Thr Val Cys Ser Pro Asp Gly Pro Gly Gly Arg Cys Gln
1               5                   10                  15

Cys Arg Ala Leu Gly Ser Gly Met Ala Val Asp Cys Ser Thr
            20                  25                  30

<210> SEQ ID NO 75
<211> LENGTH: 30
<212> TYPE: PRT
<213> ORGANISM: Homo sapiens

<400> SEQUENCE: 75

Thr Val Cys Ser Pro Asp Gly Pro Gly Gly Arg Cys Gln Cys Arg Ala
1               5                   10                  15

Leu Gly Ser Gly Met Ala Val Asp Cys Ser Thr Leu Thr Ser
            20                  25                  30

<210> SEQ ID NO 76
<211> LENGTH: 30
<212> TYPE: PRT
<213> ORGANISM: Homo sapiens

<400> SEQUENCE: 76

Thr Asn Lys Met Thr Val Cys Ser Pro Asp Gly Pro Gly Gly Arg Cys
1               5                   10                  15

Gln Cys Arg Ala Leu Gly Ser Gly Met Ala Val Asp Cys Ser
            20                  25                  30

<210> SEQ ID NO 77
<211> LENGTH: 30
<212> TYPE: PRT
<213> ORGANISM: Homo sapiens

<400> SEQUENCE: 77

Met Thr Val Cys Ser Pro Asp Gly Pro Gly Gly Arg Cys Gln Cys Arg
1               5                   10                  15

Ala Leu Gly Ser Gly Met Ala Val Asp Cys Ser Thr Leu Thr
            20                  25                  30

```
<210> SEQ ID NO 78
<211> LENGTH: 30
<212> TYPE: PRT
<213> ORGANISM: Homo sapiens

<400> SEQUENCE: 78

Lys Met Thr Val Cys Ser Pro Asp Gly Pro Gly Gly Arg Cys Gln Cys
1               5                   10                  15

Arg Ala Leu Gly Ser Gly Met Ala Val Asp Cys Ser Thr Leu
            20                  25                  30

<210> SEQ ID NO 79
<211> LENGTH: 30
<212> TYPE: PRT
<213> ORGANISM: Homo sapiens

<400> SEQUENCE: 79

Pro Thr Asn Lys Met Thr Val Cys Ser Pro Asp Gly Pro Gly Gly Arg
1               5                   10                  15

Cys Gln Cys Arg Ala Leu Gly Ser Gly Met Ala Val Asp Cys
            20                  25                  30

<210> SEQ ID NO 80
<211> LENGTH: 30
<212> TYPE: PRT
<213> ORGANISM: Homo sapiens

<400> SEQUENCE: 80

Val Cys Ser Pro Asp Gly Pro Gly Gly Arg Cys Gln Cys Arg Ala Leu
1               5                   10                  15

Gly Ser Gly Met Ala Val Asp Cys Ser Thr Leu Thr Ser Lys
            20                  25                  30

<210> SEQ ID NO 81
<211> LENGTH: 33
<212> TYPE: PRT
<213> ORGANISM: Homo sapiens

<400> SEQUENCE: 81

Cys Ala Ala Val His Tyr Glu Gln Pro Thr Ile Gln Ile Glu Leu Arg
1               5                   10                  15

Cys Ala Ala Val His Tyr Glu Gln Pro Thr Ile Gln Ile Glu Leu Arg
            20                  25                  30

Cys

<210> SEQ ID NO 82
<211> LENGTH: 30
<212> TYPE: PRT
<213> ORGANISM: Homo sapiens

<400> SEQUENCE: 82

Cys Pro Thr Asn Lys Met Thr Val Cys Ser Pro Asp Gly Pro Gly Gly
1               5                   10                  15

Arg Cys Gln Cys Arg Ala Leu Gly Ser Gly Met Ala Val Asp
            20                  25                  30

<210> SEQ ID NO 83
<211> LENGTH: 33
<212> TYPE: PRT
<213> ORGANISM: Homo sapiens

<400> SEQUENCE: 83
```

```
Cys Val His Tyr Glu Gln Pro Thr Ile Gln Ile Glu Leu Arg Gln Asn
1               5                   10                  15

Cys Val His Tyr Glu Gln Pro Thr Ile Gln Ile Glu Leu Arg Gln Asn
            20                  25                  30

Cys
```

<210> SEQ ID NO 84
<211> LENGTH: 32
<212> TYPE: PRT
<213> ORGANISM: Homo sapiens

<400> SEQUENCE: 84

```
His Ser Asp Leu Asp Ala Glu Leu Arg Arg Leu Phe Arg Glu Arg Cys
1               5                   10                  15

His Ser Asp Leu Asp Ala Glu Leu Arg Arg Leu Phe Arg Glu Arg Cys
            20                  25                  30
```

<210> SEQ ID NO 85
<211> LENGTH: 30
<212> TYPE: PRT
<213> ORGANISM: Homo sapiens

<400> SEQUENCE: 85

```
Arg Leu Phe Arg Glu Arg Tyr Arg Leu His Pro Lys Phe Val Ala Ala
1               5                   10                  15

Val His Tyr Glu Gln Pro Thr Ile Gln Ile Glu Leu Arg Gln
            20                  25                  30
```

<210> SEQ ID NO 86
<211> LENGTH: 15
<212> TYPE: PRT
<213> ORGANISM: Homo sapiens

<400> SEQUENCE: 86

```
Ala Val His Tyr Glu Gln Pro Thr Ile Gln Ile Glu Leu Arg Gln
1               5                   10                  15
```

<210> SEQ ID NO 87
<211> LENGTH: 33
<212> TYPE: PRT
<213> ORGANISM: Homo sapiens

<400> SEQUENCE: 87

```
Cys Ala Gly Ala Phe Asn His Ser Asp Leu Asp Ala Glu Leu Arg Arg
1               5                   10                  15

Cys His His Ile Leu Ile Asp Leu Arg His Arg Pro Thr Ala Gly Ala
            20                  25                  30

Cys
```

<210> SEQ ID NO 88
<211> LENGTH: 33
<212> TYPE: PRT
<213> ORGANISM: Homo sapiens

<400> SEQUENCE: 88

```
Cys Pro Lys Phe Val Ala Val His Tyr Glu Gln Pro Thr Ile Gln
1               5                   10                  15

Cys Gly Leu Asp Leu Arg Val Arg Gly Glu Pro Leu Gln Val Glu Arg
            20                  25                  30

Cys
```

```
<210> SEQ ID NO 89
<211> LENGTH: 23
<212> TYPE: PRT
<213> ORGANISM: Homo sapiens

<400> SEQUENCE: 89

Cys His Ser Asp Leu Asp Ala Glu Leu Arg Arg Leu Phe Arg Glu Arg
1               5                   10                  15

Cys Gly Leu Asp Leu Arg Val
            20

<210> SEQ ID NO 90
<211> LENGTH: 15
<212> TYPE: PRT
<213> ORGANISM: Homo sapiens

<400> SEQUENCE: 90

Phe Gln Gly Arg Gly Gly Leu Asp Leu Arg Val Arg Gly Glu Pro
1               5                   10                  15

<210> SEQ ID NO 91
<211> LENGTH: 33
<212> TYPE: PRT
<213> ORGANISM: Homo sapiens

<400> SEQUENCE: 91

Cys Val His Tyr Glu Gln Pro Thr Ile Gln Ile Glu Leu Arg Gln Asn
1               5                   10                  15

Cys Asp Leu Asp Ala Glu Leu Arg Arg Leu Phe Arg Glu Arg Tyr Arg
            20                  25                  30

Cys

<210> SEQ ID NO 92
<211> LENGTH: 23
<212> TYPE: PRT
<213> ORGANISM: Homo sapiens

<400> SEQUENCE: 92

Cys His Ser Asp Leu Asp Ala Glu Leu Arg Arg Leu Phe Arg Glu Arg
1               5                   10                  15

Cys Arg Gly Glu Pro Leu Gln
            20

<210> SEQ ID NO 93
<211> LENGTH: 33
<212> TYPE: PRT
<213> ORGANISM: Homo sapiens

<400> SEQUENCE: 93

Cys Thr Ile Gln Ile Glu Leu Arg Gln Asn Thr Ser Gln Lys Ala Ala
1               5                   10                  15

Cys Val His Tyr Glu Gln Pro Thr Ile Gln Ile Glu Leu Arg Gln Asn
            20                  25                  30

Cys

<210> SEQ ID NO 94
<211> LENGTH: 33
<212> TYPE: PRT
<213> ORGANISM: Homo sapiens

<400> SEQUENCE: 94
```

```
Cys Val His Tyr Glu Gln Pro Thr Ile Gln Ile Glu Leu Arg Gln Asn
1               5                   10                  15
Cys His Ser Asp Leu Asp Ala Glu Leu Arg Arg Leu Phe Arg Glu Arg
            20                  25                  30
Cys
```

<210> SEQ ID NO 95
<211> LENGTH: 33
<212> TYPE: PRT
<213> ORGANISM: Homo sapiens

<400> SEQUENCE: 95

```
Cys His His Ile Leu Ile Asp Leu Arg His Arg Pro Thr Ala Gly Ala
1               5                   10                  15
Cys His Ser Asp Leu Asp Ala Glu Leu Arg Arg Leu Phe Arg Glu Arg
            20                  25                  30
Cys
```

<210> SEQ ID NO 96
<211> LENGTH: 33
<212> TYPE: PRT
<213> ORGANISM: Homo sapiens

<400> SEQUENCE: 96

```
Cys His His Ile Leu Ile Asp Leu Arg His Arg Pro Thr Ala Gly Ala
1               5                   10                  15
Cys Val His Tyr Glu Gln Pro Thr Ile Gln Ile Glu Leu Arg Gln Asn
            20                  25                  30
Cys
```

<210> SEQ ID NO 97
<211> LENGTH: 33
<212> TYPE: PRT
<213> ORGANISM: Homo sapiens

<400> SEQUENCE: 97

```
Cys His His Ile Leu Ile Asp Leu Arg His Arg Pro Thr Ala Gly Ala
1               5                   10                  15
Cys Gly Leu Asp Leu Arg Val Arg Gly Glu Pro Leu Gln Val Glu Arg
            20                  25                  30
Cys
```

<210> SEQ ID NO 98
<211> LENGTH: 33
<212> TYPE: PRT
<213> ORGANISM: Homo sapiens

<400> SEQUENCE: 98

```
Cys Asp Ala Glu Leu Arg Arg Leu Phe Arg Glu Arg Tyr Arg Leu His
1               5                   10                  15
Cys Asp Glu Leu Val Arg Thr His His Ile Leu Ile Asp Leu Arg His
            20                  25                  30
Cys
```

<210> SEQ ID NO 99
<211> LENGTH: 17
<212> TYPE: PRT
<213> ORGANISM: Homo sapiens

<400> SEQUENCE: 99

```
Cys Val His Tyr Glu Gln Pro Thr Ile Gln Ile Glu Leu Arg Gln Asn
1               5                   10                  15

Cys
```

<210> SEQ ID NO 100
<211> LENGTH: 33
<212> TYPE: PRT
<213> ORGANISM: Homo sapiens

<400> SEQUENCE: 100

```
Cys Ala Phe Asn His Ser Asp Leu Asp Ala Glu Leu Arg Arg Leu Phe
1               5                   10                  15

Cys Val His Tyr Glu Gln Pro Thr Ile Gln Ile Glu Leu Arg Gln Asn
                20                  25                  30

Cys
```

<210> SEQ ID NO 101
<211> LENGTH: 33
<212> TYPE: PRT
<213> ORGANISM: Homo sapiens

<400> SEQUENCE: 101

```
Cys Val His Tyr Glu Gln Pro Thr Ile Gln Ile Glu Leu Arg Gln Asn
1               5                   10                  15

Cys His His Ile Leu Ile Asp Leu Arg His Arg Pro Thr Ala Gly Ala
                20                  25                  30

Cys
```

<210> SEQ ID NO 102
<211> LENGTH: 33
<212> TYPE: PRT
<213> ORGANISM: Homo sapiens

<400> SEQUENCE: 102

```
Cys Asp Leu Asp Ala Glu Leu Arg Arg Leu Phe Arg Glu Arg Tyr Arg
1               5                   10                  15

Cys Asp Glu Leu Val Arg Thr His Ile Leu Ile Asp Leu Arg His
                20                  25                  30

Cys
```

<210> SEQ ID NO 103
<211> LENGTH: 32
<212> TYPE: PRT
<213> ORGANISM: Homo sapiens

<400> SEQUENCE: 103

```
Val His Tyr Glu Gln Pro Thr Ile Gln Ile Glu Leu Arg Gln Asn Cys
1               5                   10                  15

Gly Leu Asp Leu Arg Val Arg Gly Glu Pro Leu Gln Val Glu Arg Cys
                20                  25                  30
```

<210> SEQ ID NO 104
<211> LENGTH: 33
<212> TYPE: PRT
<213> ORGANISM: Homo sapiens

<400> SEQUENCE: 104

```
Cys Asp Glu Leu Val Arg Thr His Ile Leu Ile Asp Leu Arg His
1               5                   10                  15
```

```
Cys Asp Leu Asp Ala Glu Leu Arg Arg Leu Phe Arg Glu Arg Tyr Arg
            20                  25                  30

Cys

<210> SEQ ID NO 105
<211> LENGTH: 32
<212> TYPE: PRT
<213> ORGANISM: Homo sapiens

<400> SEQUENCE: 105

Ala Val His Tyr Glu Gln Pro Thr Ile Gln Ile Glu Leu Arg Gln Cys
1               5                   10                  15

Ala Val His Tyr Glu Gln Pro Thr Ile Gln Ile Glu Leu Arg Gln Cys
            20                  25                  30

<210> SEQ ID NO 106
<211> LENGTH: 33
<212> TYPE: PRT
<213> ORGANISM: Homo sapiens

<400> SEQUENCE: 106

Cys His Ser Asp Leu Asp Ala Glu Leu Arg Arg Leu Phe Arg Glu Arg
1               5                   10                  15

Cys Asp Glu Leu Val Arg Thr His Ile Leu Ile Asp Leu Arg His
            20                  25                  30

Cys

<210> SEQ ID NO 107
<211> LENGTH: 30
<212> TYPE: PRT
<213> ORGANISM: Homo sapiens

<400> SEQUENCE: 107

Thr Asn Lys Met Thr Val Cys Ser Pro Asp Gly Pro Gly Arg Cys
1               5                   10                  15

Gln Cys Arg Ala Leu Gly Ser Gly Met Ala Val Asp Cys Ser
            20                  25                  30

<210> SEQ ID NO 108
<211> LENGTH: 30
<212> TYPE: PRT
<213> ORGANISM: Homo sapiens

<400> SEQUENCE: 108

Asn Lys Met Thr Val Cys Ser Pro Asp Gly Pro Gly Arg Cys Gln
1               5                   10                  15

Cys Arg Ala Leu Gly Ser Gly Met Ala Val Asp Cys Ser Thr
            20                  25                  30

<210> SEQ ID NO 109
<211> LENGTH: 30
<212> TYPE: PRT
<213> ORGANISM: Homo sapiens

<400> SEQUENCE: 109

Lys Met Thr Val Cys Ser Pro Asp Gly Pro Gly Arg Cys Gln Cys
1               5                   10                  15

Arg Ala Leu Gly Ser Gly Met Ala Val Asp Cys Ser Thr Leu
            20                  25                  30

<210> SEQ ID NO 110
```

```
<211> LENGTH: 30
<212> TYPE: PRT
<213> ORGANISM: Homo sapiens

<400> SEQUENCE: 110

Met Thr Val Cys Ser Pro Asp Gly Pro Gly Gly Arg Cys Gln Cys Arg
1               5                   10                  15

Ala Leu Gly Ser Gly Met Ala Val Asp Cys Ser Thr Leu Thr
            20                  25                  30

<210> SEQ ID NO 111
<211> LENGTH: 30
<212> TYPE: PRT
<213> ORGANISM: Homo sapiens

<400> SEQUENCE: 111

Cys Pro Thr Asn Lys Met Thr Val Cys Ser Pro Asp Gly Pro Gly Gly
1               5                   10                  15

Arg Cys Gln Cys Arg Ala Leu Gly Ser Gly Met Ala Val Asp
            20                  25                  30

<210> SEQ ID NO 112
<211> LENGTH: 30
<212> TYPE: PRT
<213> ORGANISM: Homo sapiens

<400> SEQUENCE: 112

Thr Val Cys Ser Pro Asp Gly Pro Gly Gly Arg Cys Gln Cys Arg Ala
1               5                   10                  15

Leu Gly Ser Gly Met Ala Val Asp Cys Ser Thr Leu Thr Ser
            20                  25                  30

<210> SEQ ID NO 113
<211> LENGTH: 30
<212> TYPE: PRT
<213> ORGANISM: Homo sapiens

<400> SEQUENCE: 113

Thr Cys Pro Thr Asn Lys Met Thr Val Cys Ser Pro Asp Gly Pro Gly
1               5                   10                  15

Gly Arg Cys Gln Cys Arg Ala Leu Gly Ser Gly Met Ala Val
            20                  25                  30

<210> SEQ ID NO 114
<211> LENGTH: 30
<212> TYPE: PRT
<213> ORGANISM: Homo sapiens

<400> SEQUENCE: 114

Pro Thr Asn Lys Met Thr Val Cys Ser Pro Asp Gly Pro Gly Gly Arg
1               5                   10                  15

Cys Gln Cys Arg Ala Leu Gly Ser Gly Met Ala Val Asp Cys
            20                  25                  30

<210> SEQ ID NO 115
<211> LENGTH: 30
<212> TYPE: PRT
<213> ORGANISM: Homo sapiens

<400> SEQUENCE: 115

Val Cys Ser Pro Asp Gly Pro Gly Gly Arg Cys Gln Cys Arg Ala Leu
1               5                   10                  15
```

```
Gly Ser Gly Met Ala Val Asp Cys Ser Thr Leu Thr Ser Lys
            20                  25                  30

<210> SEQ ID NO 116
<211> LENGTH: 30
<212> TYPE: PRT
<213> ORGANISM: Homo sapiens

<400> SEQUENCE: 116

Cys Ser Pro Asp Gly Pro Gly Gly Arg Cys Gln Cys Arg Ala Leu Gly
1               5                   10                  15

Ser Gly Met Ala Val Asp Cys Ser Thr Leu Thr Ser Lys Cys
            20                  25                  30

<210> SEQ ID NO 117
<211> LENGTH: 30
<212> TYPE: PRT
<213> ORGANISM: Homo sapiens

<400> SEQUENCE: 117

Cys Thr Cys Pro Thr Asn Lys Met Thr Val Cys Ser Pro Asp Gly Pro
1               5                   10                  15

Gly Gly Arg Cys Gln Cys Arg Ala Leu Gly Ser Gly Met Ala
            20                  25                  30

<210> SEQ ID NO 118
<211> LENGTH: 30
<212> TYPE: PRT
<213> ORGANISM: Homo sapiens

<400> SEQUENCE: 118

Asn Cys Thr Cys Pro Thr Asn Lys Met Thr Val Cys Ser Pro Asp Gly
1               5                   10                  15

Pro Gly Gly Arg Cys Gln Cys Arg Ala Leu Gly Ser Gly Met
            20                  25                  30

<210> SEQ ID NO 119
<211> LENGTH: 30
<212> TYPE: PRT
<213> ORGANISM: Homo sapiens

<400> SEQUENCE: 119

Asp Asn Cys Thr Cys Pro Thr Asn Lys Met Thr Val Cys Ser Pro Asp
1               5                   10                  15

Gly Pro Gly Gly Arg Cys Gln Cys Arg Ala Leu Gly Ser Gly
            20                  25                  30

<210> SEQ ID NO 120
<211> LENGTH: 33
<212> TYPE: PRT
<213> ORGANISM: Homo sapiens

<400> SEQUENCE: 120

Cys Thr Val Ala Ser Pro Asp Gly Pro Gly Gly Arg Ala Gln Ala Arg
1               5                   10                  15

Cys Leu Gly Ser Gly Met Ala Val Asp Ala Ser Thr Leu Thr Ser Lys
            20                  25                  30

Cys

<210> SEQ ID NO 121
<211> LENGTH: 30
<212> TYPE: PRT
```

<213> ORGANISM: Homo sapiens

<400> SEQUENCE: 121

Gln Asp Asn Cys Thr Cys Pro Thr Asn Lys Met Thr Val Cys Ser Pro
1               5                   10                  15

Asp Gly Pro Gly Gly Arg Cys Gln Cys Arg Ala Leu Gly Ser
            20                  25                  30

<210> SEQ ID NO 122
<211> LENGTH: 30
<212> TYPE: PRT
<213> ORGANISM: Homo sapiens

<400> SEQUENCE: 122

Ser Pro Asp Gly Pro Gly Gly Arg Cys Gln Cys Arg Ala Leu Gly Ser
1               5                   10                  15

Gly Met Ala Val Asp Cys Ser Thr Leu Thr Ser Lys Cys Leu
            20                  25                  30

<210> SEQ ID NO 123
<211> LENGTH: 33
<212> TYPE: PRT
<213> ORGANISM: Homo sapiens

<400> SEQUENCE: 123

Cys Thr Asn Lys Met Thr Val Cys Ser Pro Asp Gly Pro Gly Gly Arg
1               5                   10                  15

Cys Gln Cys Arg Ala Leu Gly Ser Gly Met Ala Val Asp Ala Ser Thr
            20                  25                  30

Cys

<210> SEQ ID NO 124
<211> LENGTH: 15
<212> TYPE: PRT
<213> ORGANISM: Homo sapiens

<400> SEQUENCE: 124

Thr Val Cys Ser Pro Asp Gly Pro Gly Gly Arg Cys Gln Cys Arg
1               5                   10                  15

<210> SEQ ID NO 125
<211> LENGTH: 33
<212> TYPE: PRT
<213> ORGANISM: Homo sapiens

<400> SEQUENCE: 125

Cys Ala Pro Lys Asn Ala Arg Thr Leu Val Arg Pro Ser Glu His Ala
1               5                   10                  15

Cys Ala Arg Thr Leu Val Arg Pro Ser Glu His Ala Leu Val Asp Asn
            20                  25                  30

Cys

<210> SEQ ID NO 126
<211> LENGTH: 32
<212> TYPE: PRT
<213> ORGANISM: Homo sapiens

<400> SEQUENCE: 126

His Ser Asp Leu Asp Ala Glu Leu Arg Arg Leu Phe Arg Glu Arg Cys
1               5                   10                  15

His Ser Asp Leu Asp Ala Glu Leu Arg Arg Leu Phe Arg Glu Arg Cys

<210> SEQ ID NO 127
<211> LENGTH: 30
<212> TYPE: PRT
<213> ORGANISM: Homo sapiens

<400> SEQUENCE: 127

Thr Val Cys Ser Pro Asp Gly Pro Gly Gly Arg Cys Gln Cys Arg Ala
1               5                   10                  15

Leu Gly Ser Gly Met Ala Val Asp Cys Ser Thr Leu Thr Ser
            20                  25                  30

<210> SEQ ID NO 128
<211> LENGTH: 30
<212> TYPE: PRT
<213> ORGANISM: Homo sapiens

<400> SEQUENCE: 128

Asn Lys Met Thr Val Cys Ser Pro Asp Gly Pro Gly Gly Arg Cys Gln
1               5                   10                  15

Cys Arg Ala Leu Gly Ser Gly Met Ala Val Asp Cys Ser Thr
            20                  25                  30

<210> SEQ ID NO 129
<211> LENGTH: 30
<212> TYPE: PRT
<213> ORGANISM: Homo sapiens

<400> SEQUENCE: 129

Thr Asn Lys Met Thr Val Cys Ser Pro Asp Gly Pro Gly Gly Arg Cys
1               5                   10                  15

Gln Cys Arg Ala Leu Gly Ser Gly Met Ala Val Asp Cys Ser
            20                  25                  30

<210> SEQ ID NO 130
<211> LENGTH: 30
<212> TYPE: PRT
<213> ORGANISM: Homo sapiens

<400> SEQUENCE: 130

Met Thr Val Cys Ser Pro Asp Gly Pro Gly Gly Arg Cys Gln Cys Arg
1               5                   10                  15

Ala Leu Gly Ser Gly Met Ala Val Asp Cys Ser Thr Leu Thr
            20                  25                  30

<210> SEQ ID NO 131
<211> LENGTH: 30
<212> TYPE: PRT
<213> ORGANISM: Homo sapiens

<400> SEQUENCE: 131

Lys Met Thr Val Cys Ser Pro Asp Gly Pro Gly Gly Arg Cys Gln Cys
1               5                   10                  15

Arg Ala Leu Gly Ser Gly Met Ala Val Asp Cys Ser Thr Leu
            20                  25                  30

<210> SEQ ID NO 132
<211> LENGTH: 30
<212> TYPE: PRT
<213> ORGANISM: Homo sapiens

<400> SEQUENCE: 132

```
Cys Pro Thr Asn Lys Met Thr Val Cys Ser Pro Asp Gly Pro Gly Gly
1               5                   10                  15

Arg Cys Gln Cys Arg Ala Leu Gly Ser Gly Met Ala Val Asp
            20                  25                  30
```

<210> SEQ ID NO 133
<211> LENGTH: 30
<212> TYPE: PRT
<213> ORGANISM: Homo sapiens

<400> SEQUENCE: 133

```
Pro Thr Asn Lys Met Thr Val Cys Ser Pro Asp Gly Pro Gly Gly Arg
1               5                   10                  15

Cys Gln Cys Arg Ala Leu Gly Ser Gly Met Ala Val Asp Cys
            20                  25                  30
```

<210> SEQ ID NO 134
<211> LENGTH: 33
<212> TYPE: PRT
<213> ORGANISM: Homo sapiens

<400> SEQUENCE: 134

```
Cys Ala Gly Ala Phe Asn His Ser Asp Leu Asp Ala Glu Leu Arg Arg
1               5                   10                  15

Cys His His Ile Leu Ile Asp Leu Arg His Arg Pro Thr Ala Gly Ala
            20                  25                  30

Cys
```

<210> SEQ ID NO 135
<211> LENGTH: 17
<212> TYPE: PRT
<213> ORGANISM: Homo sapiens

<400> SEQUENCE: 135

```
Cys Thr His His Ile Leu Ile Asp Leu Arg His Arg Pro Thr Ala Gly
1               5                   10                  15

Cys
```

<210> SEQ ID NO 136
<211> LENGTH: 33
<212> TYPE: PRT
<213> ORGANISM: Homo sapiens

<400> SEQUENCE: 136

```
Cys Val His Tyr Glu Gln Pro Thr Ile Gln Ile Glu Leu Arg Gln Asn
1               5                   10                  15

Cys His His Ile Leu Ile Asp Leu Arg His Arg Pro Thr Ala Gly Ala
            20                  25                  30

Cys
```

<210> SEQ ID NO 137
<211> LENGTH: 33
<212> TYPE: PRT
<213> ORGANISM: Homo sapiens

<400> SEQUENCE: 137

```
Cys His His Ile Leu Ile Asp Leu Arg His Arg Pro Thr Ala Gly Ala
1               5                   10                  15

Cys His Ser Asp Leu Asp Ala Glu Leu Arg Arg Leu Phe Arg Glu Arg
            20                  25                  30
```

Cys

<210> SEQ ID NO 138
<211> LENGTH: 32
<212> TYPE: PRT
<213> ORGANISM: Homo sapiens

<400> SEQUENCE: 138

His Ser Asp Leu Asp Ala Glu Leu Arg Arg Leu Phe Arg Glu Arg Cys
1               5                   10                  15

His Ser Asp Leu Asp Ala Glu Leu Arg Arg Leu Phe Arg Glu Arg Cys
            20                  25                  30

<210> SEQ ID NO 139
<211> LENGTH: 33
<212> TYPE: PRT
<213> ORGANISM: Homo sapiens

<400> SEQUENCE: 139

Cys Asp Ala Glu Leu Arg Arg Leu Phe Arg Glu Arg Tyr Arg Leu His
1               5                   10                  15

Cys His Ser Asp Leu Asp Ala Glu Leu Arg Arg Leu Phe Arg Glu Arg
            20                  25                  30

Cys

<210> SEQ ID NO 140
<211> LENGTH: 19
<212> TYPE: PRT
<213> ORGANISM: Homo sapiens

<400> SEQUENCE: 140

Cys Asp Ala Glu Leu Arg Arg Leu Phe Arg Glu Arg Tyr Arg Leu His
1               5                   10                  15

Cys Pro Lys

<210> SEQ ID NO 141
<211> LENGTH: 30
<212> TYPE: PRT
<213> ORGANISM: Homo sapiens

<400> SEQUENCE: 141

Val Cys Ser Pro Asp Gly Pro Gly Gly Arg Cys Gln Cys Arg Ala Leu
1               5                   10                  15

Gly Ser Gly Met Ala Val Asp Cys Ser Thr Leu Thr Ser Lys
            20                  25                  30

<210> SEQ ID NO 142
<211> LENGTH: 30
<212> TYPE: PRT
<213> ORGANISM: Homo sapiens

<400> SEQUENCE: 142

Asp Leu Ser Leu Arg Cys Asp Glu Leu Val Arg Thr His His Ile Leu
1               5                   10                  15

Ile Asp Leu Arg His Arg Pro Thr Ala Gly Ala Phe Asn His
            20                  25                  30

<210> SEQ ID NO 143
<211> LENGTH: 33
<212> TYPE: PRT
<213> ORGANISM: Homo sapiens

<400> SEQUENCE: 143

Cys Asp Glu Leu Val Arg Thr His His Ile Leu Ile Asp Leu Arg His
1               5                   10                  15

Cys Asp Leu Asp Ala Glu Leu Arg Arg Leu Phe Arg Glu Arg Tyr Arg
                20                  25                  30

Cys

<210> SEQ ID NO 144
<211> LENGTH: 17
<212> TYPE: PRT
<213> ORGANISM: Homo sapiens

<400> SEQUENCE: 144

Cys Phe Gln Gly Arg Gly Gly Leu Asp Leu Arg Val Arg Gly Glu Pro
1               5                   10                  15

Cys

<210> SEQ ID NO 145
<211> LENGTH: 33
<212> TYPE: PRT
<213> ORGANISM: Homo sapiens

<400> SEQUENCE: 145

Cys Asp Ala Glu Leu Arg Arg Leu Phe Arg Glu Arg Tyr Arg Leu His
1               5                   10                  15

Cys Asp Glu Leu Val Arg Thr His His Ile Leu Ile Asp Leu Arg His
                20                  25                  30

Cys

<210> SEQ ID NO 146
<211> LENGTH: 33
<212> TYPE: PRT
<213> ORGANISM: Homo sapiens

<400> SEQUENCE: 146

Cys Gly Leu Asp Leu Arg Val Arg Gly Glu Pro Leu Gln Val Glu Arg
1               5                   10                  15

Cys His His Ile Leu Ile Asp Leu Arg His Arg Pro Thr Ala Gly Ala
                20                  25                  30

Cys

<210> SEQ ID NO 147
<211> LENGTH: 33
<212> TYPE: PRT
<213> ORGANISM: Homo sapiens

<400> SEQUENCE: 147

Cys His Ser Asp Leu Asp Ala Glu Leu Arg Arg Leu Phe Arg Glu Arg
1               5                   10                  15

Cys His Ser Asp Leu Asp Ala Glu Leu Arg Arg Leu Phe Arg Glu Arg
                20                  25                  30

Cys

<210> SEQ ID NO 148
<211> LENGTH: 33
<212> TYPE: PRT
<213> ORGANISM: Homo sapiens

<400> SEQUENCE: 148

```
Cys Asp Glu Leu Val Arg Thr His His Ile Leu Ile Asp Leu Arg His
1               5                   10                  15

Cys His His Ile Leu Ile Asp Leu Arg His Arg Pro Thr Ala Gly Ala
            20                  25                  30

Cys
```

<210> SEQ ID NO 149
<211> LENGTH: 33
<212> TYPE: PRT
<213> ORGANISM: Homo sapiens

<400> SEQUENCE: 149

```
Cys Asp Ala Glu Leu Arg Arg Leu Phe Arg Glu Arg Tyr Arg Leu His
1               5                   10                  15

Cys Asp Glu Leu Val Arg Thr His His Ile Leu Ile Asp Leu Arg His
            20                  25                  30

Cys
```

<210> SEQ ID NO 150
<211> LENGTH: 33
<212> TYPE: PRT
<213> ORGANISM: Homo sapiens

<400> SEQUENCE: 150

```
Cys His His Ile Leu Ile Asp Leu Arg His Arg Pro Thr Ala Gly Ala
1               5                   10                  15

Cys Arg Gly Glu Pro Leu Gln Val Glu Arg Thr Leu Ile Tyr Tyr Leu
            20                  25                  30

Cys
```

<210> SEQ ID NO 151
<211> LENGTH: 15
<212> TYPE: PRT
<213> ORGANISM: Homo sapiens

<400> SEQUENCE: 151

```
Cys Ser Pro Asp Gly Pro Gly Gly Arg Cys Gln Cys Arg Ala Leu
1               5                   10                  15
```

<210> SEQ ID NO 152
<211> LENGTH: 33
<212> TYPE: PRT
<213> ORGANISM: Homo sapiens

<400> SEQUENCE: 152

```
Cys Thr Val Ala Ser Pro Asp Gly Pro Gly Gly Arg Ala Gln Ala Arg
1               5                   10                  15

Cys Val His Tyr Glu Gln Pro Thr Ile Gln Ile Glu Leu Arg Gln Asn
            20                  25                  30

Cys
```

<210> SEQ ID NO 153
<211> LENGTH: 33
<212> TYPE: PRT
<213> ORGANISM: Homo sapiens

<400> SEQUENCE: 153

```
Cys His His Ile Leu Ile Asp Leu Arg His Arg Pro Thr Ala Gly Ala
1               5                   10                  15
```

-continued

Cys Val His Tyr Glu Gln Pro Thr Ile Gln Ile Glu Leu Arg Gln Asn
            20                  25                  30

Cys

<210> SEQ ID NO 154
<211> LENGTH: 30
<212> TYPE: PRT
<213> ORGANISM: Homo sapiens

<400> SEQUENCE: 154

Leu Ser Leu Arg Cys Asp Glu Leu Val Arg Thr His His Ile Leu Ile
1               5                   10                  15

Asp Leu Arg His Arg Pro Thr Ala Gly Ala Phe Asn His Ser
            20                  25                  30

<210> SEQ ID NO 155
<211> LENGTH: 33
<212> TYPE: PRT
<213> ORGANISM: Homo sapiens

<400> SEQUENCE: 155

Cys Asp Glu Leu Val Arg Thr His His Ile Leu Ile Asp Leu Arg His
1               5                   10                  15

Cys His Ser Asp Leu Asp Ala Glu Leu Arg Arg Leu Phe Arg Glu Arg
            20                  25                  30

Cys

<210> SEQ ID NO 156
<211> LENGTH: 33
<212> TYPE: PRT
<213> ORGANISM: Homo sapiens

<400> SEQUENCE: 156

Cys Tyr Asp Pro Asp Ala Asp Pro Glu Gly Arg Phe Lys Ala Arg Gln
1               5                   10                  15

Cys Ala Asp Pro Glu Gly Arg Phe Lys Ala Arg Gln Ala Asn Gln Thr
            20                  25                  30

Cys

<210> SEQ ID NO 157
<211> LENGTH: 15
<212> TYPE: PRT
<213> ORGANISM: Homo sapiens

<400> SEQUENCE: 157

Pro Asp Cys Asp Pro Glu Gly Arg Phe Lys Ala Arg Gln Cys Asn
1               5                   10                  15

<210> SEQ ID NO 158
<211> LENGTH: 31
<212> TYPE: PRT
<213> ORGANISM: Homo sapiens

<400> SEQUENCE: 158

Cys Ala Asp Pro Glu Gly Arg Phe Lys Ala Arg Gln Ala Asn Cys Pro
1               5                   10                  15

Asp Ala Asp Pro Glu Gly Arg Phe Lys Ala Arg Gln Ala Asn Cys
            20                  25                  30

<210> SEQ ID NO 159
<211> LENGTH: 33

```
<212> TYPE: PRT
<213> ORGANISM: Homo sapiens

<400> SEQUENCE: 159

Cys Pro Asp Ala Asp Pro Glu Gly Arg Phe Lys Ala Arg Gln Ala Asn
1               5                   10                  15

Cys Pro Asp Ala Asp Pro Glu Gly Arg Phe Lys Ala Arg Gln Ala Asn
            20                  25                  30

Cys

<210> SEQ ID NO 160
<211> LENGTH: 15
<212> TYPE: PRT
<213> ORGANISM: Homo sapiens

<400> SEQUENCE: 160

Val Cys Ser Pro Asp Gly Pro Gly Gly Arg Cys Gln Cys Arg Ala
1               5                   10                  15

<210> SEQ ID NO 161
<211> LENGTH: 33
<212> TYPE: PRT
<213> ORGANISM: Homo sapiens

<400> SEQUENCE: 161

Cys Tyr Asp Pro Asp Ala Asp Pro Glu Gly Arg Phe Lys Ala Arg Gln
1               5                   10                  15

Cys Pro Asp Ala Asp Pro Glu Gly Arg Phe Lys Ala Arg Gln Ala Asn
            20                  25                  30

Cys

<210> SEQ ID NO 162
<211> LENGTH: 33
<212> TYPE: PRT
<213> ORGANISM: Homo sapiens

<400> SEQUENCE: 162

Cys Ala Asp Pro Glu Gly Arg Phe Lys Ala Arg Gln Ala Asn Gln Thr
1               5                   10                  15

Cys Tyr Asp Pro Asp Ala Asp Pro Glu Gly Arg Phe Lys Ala Arg Gln
            20                  25                  30

Cys

<210> SEQ ID NO 163
<211> LENGTH: 15
<212> TYPE: PRT
<213> ORGANISM: Homo sapiens

<400> SEQUENCE: 163

Asp Cys Asp Pro Glu Gly Arg Phe Lys Ala Arg Gln Cys Asn Gln
1               5                   10                  15

<210> SEQ ID NO 164
<211> LENGTH: 33
<212> TYPE: PRT
<213> ORGANISM: Homo sapiens

<400> SEQUENCE: 164

Cys Thr Val Ala Ser Pro Asp Gly Pro Gly Gly Arg Ala Gln Ala Arg
1               5                   10                  15

Cys His Ser Asp Leu Asp Ala Glu Leu Arg Arg Leu Phe Arg Glu Arg
```

```
            20                  25                  30

Cys

<210> SEQ ID NO 165
<211> LENGTH: 33
<212> TYPE: PRT
<213> ORGANISM: Homo sapiens

<400> SEQUENCE: 165

Cys Asp Ala Asp Pro Glu Gly Arg Phe Lys Ala Arg Gln Ala Asn Gln
1               5                  10                  15

Cys Asp Ala Asp Pro Glu Gly Arg Phe Lys Ala Arg Gln Ala Asn Gln
            20                  25                  30

Cys

<210> SEQ ID NO 166
<211> LENGTH: 33
<212> TYPE: PRT
<213> ORGANISM: Homo sapiens

<400> SEQUENCE: 166

Cys Gly Arg Phe Lys Ala Arg Gln Ala Asn Gln Thr Ser Val Ala Trp
1               5                  10                  15

Cys Ala Arg Thr Leu Val Arg Pro Ser Glu His Ala Leu Val Asp Asn
            20                  25                  30

Cys

<210> SEQ ID NO 167
<211> LENGTH: 33
<212> TYPE: PRT
<213> ORGANISM: Homo sapiens

<400> SEQUENCE: 167

Cys Ala Asp Pro Glu Gly Arg Phe Lys Ala Arg Gln Ala Asn Gln Thr
1               5                  10                  15

Cys Pro Asp Ala Asp Pro Glu Gly Arg Phe Lys Ala Arg Gln Ala Asn
            20                  25                  30

Cys

<210> SEQ ID NO 168
<211> LENGTH: 33
<212> TYPE: PRT
<213> ORGANISM: Homo sapiens

<400> SEQUENCE: 168

Cys Pro Asp Ala Asp Pro Glu Gly Arg Phe Lys Ala Arg Gln Ala Asn
1               5                  10                  15

Cys Pro Asp Ala Asp Pro Glu Gly Arg Phe Lys Ala Arg Gln Ala Asn
            20                  25                  30

Cys

<210> SEQ ID NO 169
<211> LENGTH: 15
<212> TYPE: PRT
<213> ORGANISM: Homo sapiens

<400> SEQUENCE: 169

Cys Ser Pro Asp Gly Pro Gly Gly Arg Cys Gln Cys Arg Ala Leu
1               5                  10                  15
```

<210> SEQ ID NO 170
<211> LENGTH: 33
<212> TYPE: PRT
<213> ORGANISM: Homo sapiens

<400> SEQUENCE: 170

Cys Glu Gly Arg Phe Lys Ala Arg Gln Ala Asn Gln Thr Ser Val Ala
1               5                   10                  15

Cys Glu Gly Arg Phe Lys Ala Arg Gln Ala Asn Gln Thr Ser Val Ala
            20                  25                  30

Cys

<210> SEQ ID NO 171
<211> LENGTH: 33
<212> TYPE: PRT
<213> ORGANISM: Homo sapiens

<400> SEQUENCE: 171

Cys Thr Val Ala Ser Pro Asp Gly Pro Gly Arg Ala Gln Ala Arg
1               5                   10                  15

Cys Pro Asp Ala Asp Pro Glu Gly Arg Phe Lys Ala Arg Gln Ala Asn
            20                  25                  30

Cys

<210> SEQ ID NO 172
<211> LENGTH: 33
<212> TYPE: PRT
<213> ORGANISM: Homo sapiens

<400> SEQUENCE: 172

Cys Gly Leu Tyr Asp Pro Asp Ala Asp Pro Glu Gly Arg Phe Lys Ala
1               5                   10                  15

Cys Pro Asp Ala Asp Pro Glu Gly Arg Phe Lys Ala Arg Gln Ala Asn
            20                  25                  30

Cys

<210> SEQ ID NO 173
<211> LENGTH: 31
<212> TYPE: PRT
<213> ORGANISM: Homo sapiens

<400> SEQUENCE: 173

Asp Pro Asp Cys Asp Pro Glu Gly Arg Phe Lys Ala Arg Gln Cys Asn
1               5                   10                  15

Cys Gln Thr Ser Val Cys Trp Cys Val Asn Ser Val Gly Val Arg
            20                  25                  30

<210> SEQ ID NO 174
<211> LENGTH: 32
<212> TYPE: PRT
<213> ORGANISM: Homo sapiens

<400> SEQUENCE: 174

Cys Pro Glu Gly Arg Phe Lys Ala Arg Gln Ala Asn Gln Thr Ser Val
1               5                   10                  15

Cys Asp Glu Leu Val Arg His His Ile Leu Ile Asp Leu Arg His Cys
            20                  25                  30

<210> SEQ ID NO 175
<211> LENGTH: 33

<212> TYPE: PRT
<213> ORGANISM: Homo sapiens

<400> SEQUENCE: 175

Cys Pro Asp Gly Pro Gly Gly Arg Ala Gln Ala Arg Ala Leu Gly Ser
1               5                   10                  15

Cys His Ser Asp Leu Asp Ala Glu Leu Arg Arg Leu Phe Arg Glu Arg
                20                  25                  30

Cys

<210> SEQ ID NO 176
<211> LENGTH: 33
<212> TYPE: PRT
<213> ORGANISM: Homo sapiens

<400> SEQUENCE: 176

Cys Thr Leu Val Arg Pro Ser Glu His Ala Leu Val Asp Asn Asp Gly
1               5                   10                  15

Cys Gly Arg Phe Lys Ala Arg Gln Ala Asn Gln Thr Ser Val Ala Trp
                20                  25                  30

Cys

<210> SEQ ID NO 177
<211> LENGTH: 33
<212> TYPE: PRT
<213> ORGANISM: Homo sapiens

<400> SEQUENCE: 177

Cys Pro Asp Ala Asp Pro Glu Gly Arg Phe Lys Ala Arg Gln Ala Asn
1               5                   10                  15

Cys Tyr Asp Pro Asp Ala Asp Pro Glu Gly Arg Phe Lys Ala Arg Gln
                20                  25                  30

Cys

<210> SEQ ID NO 178
<211> LENGTH: 33
<212> TYPE: PRT
<213> ORGANISM: Homo sapiens

<400> SEQUENCE: 178

Cys Gly Leu Tyr Asp Pro Asp Ala Asp Pro Glu Gly Arg Phe Lys Ala
1               5                   10                  15

Cys Pro Glu Gly Arg Phe Lys Ala Arg Gln Ala Asn Gln Thr Ser Val
                20                  25                  30

Cys

<210> SEQ ID NO 179
<211> LENGTH: 15
<212> TYPE: PRT
<213> ORGANISM: Homo sapiens

<400> SEQUENCE: 179

Tyr Asp Pro Asp Cys Asp Pro Glu Gly Arg Phe Lys Ala Arg Gln
1               5                   10                  15

<210> SEQ ID NO 180
<211> LENGTH: 33
<212> TYPE: PRT
<213> ORGANISM: Homo sapiens

<400> SEQUENCE: 180

```
Cys Pro Asp Ala Asp Pro Glu Gly Arg Phe Lys Ala Arg Gln Ala Asn
1               5                   10                  15

Cys Ala Asp Pro Glu Gly Arg Phe Lys Ala Arg Gln Ala Asn Gln Thr
                20                  25                  30

Cys
```

<210> SEQ ID NO 181
<211> LENGTH: 15
<212> TYPE: PRT
<213> ORGANISM: Homo sapiens

<400> SEQUENCE: 181

```
Cys Asp Pro Glu Gly Arg Phe Lys Ala Arg Gln Cys Asn Gln Thr
1               5                   10                  15
```

<210> SEQ ID NO 182
<211> LENGTH: 33
<212> TYPE: PRT
<213> ORGANISM: Homo sapiens

<400> SEQUENCE: 182

```
Cys Val Asn Ser Val Gly Val Arg Arg Thr Asp Lys Gly Asp Leu Ser
1               5                   10                  15

Cys Tyr Asp Pro Asp Ala Asp Pro Glu Gly Arg Phe Lys Ala Arg Gln
                20                  25                  30

Cys
```

<210> SEQ ID NO 183
<211> LENGTH: 33
<212> TYPE: PRT
<213> ORGANISM: Homo sapiens

<400> SEQUENCE: 183

```
Cys Ser Val Gly Val Arg Arg Thr Asp Lys Gly Asp Leu Ser Leu Arg
1               5                   10                  15

Cys Tyr Asp Pro Asp Ala Asp Pro Glu Gly Arg Phe Lys Ala Arg Gln
                20                  25                  30

Cys
```

<210> SEQ ID NO 184
<211> LENGTH: 32
<212> TYPE: PRT
<213> ORGANISM: Homo sapiens

<400> SEQUENCE: 184

```
His Ser Asp Leu Asp Ala Glu Leu Arg Arg Leu Phe Arg Glu Arg Cys
1               5                   10                  15

His Ser Asp Leu Asp Ala Glu Leu Arg Arg Leu Phe Arg Glu Arg Cys
                20                  25                  30
```

<210> SEQ ID NO 185
<211> LENGTH: 33
<212> TYPE: PRT
<213> ORGANISM: Homo sapiens

<400> SEQUENCE: 185

```
Cys Asp Glu Leu Val Arg Thr His His Ile Leu Ile Asp Leu Arg His
1               5                   10                  15

Cys Asp Leu Asp Ala Glu Leu Arg Arg Leu Phe Arg Glu Arg Tyr Arg
                20                  25                  30
```

Cys

<210> SEQ ID NO 186
<211> LENGTH: 30
<212> TYPE: PRT
<213> ORGANISM: Homo sapiens

<400> SEQUENCE: 186

Cys Val Asn Ser Val Gly Val Arg Arg Thr Asp Lys Gly Asp Leu Ser
1               5                   10                  15

Leu Arg Cys Asp Glu Leu Val Arg Thr His His Ile Leu Ile
            20                  25                  30

<210> SEQ ID NO 187
<211> LENGTH: 30
<212> TYPE: PRT
<213> ORGANISM: Homo sapiens

<400> SEQUENCE: 187

Val Arg Arg Thr Asp Lys Gly Asp Leu Ser Leu Arg Cys Asp Glu Leu
1               5                   10                  15

Val Arg Thr His His Ile Leu Ile Asp Leu Arg His Arg Pro
            20                  25                  30

<210> SEQ ID NO 188
<211> LENGTH: 33
<212> TYPE: PRT
<213> ORGANISM: Homo sapiens

<400> SEQUENCE: 188

Cys Val Glu Arg Thr Leu Ile Tyr Tyr Leu Asp Glu Ile Pro Pro Lys
1               5                   10                  15

Cys His His Ile Leu Ile Asp Leu Arg His Arg Pro Thr Ala Gly Ala
            20                  25                  30

Cys

<210> SEQ ID NO 189
<211> LENGTH: 33
<212> TYPE: PRT
<213> ORGANISM: Homo sapiens

<400> SEQUENCE: 189

Cys His His Ile Leu Ile Asp Leu Arg His Arg Pro Thr Ala Gly Ala
1               5                   10                  15

Cys His Ser Asp Leu Asp Ala Glu Leu Arg Arg Leu Phe Arg Glu Arg
            20                  25                  30

Cys

<210> SEQ ID NO 190
<211> LENGTH: 33
<212> TYPE: PRT
<213> ORGANISM: Homo sapiens

<400> SEQUENCE: 190

Cys Val Asn Ser Val Gly Val Arg Arg Thr Asp Lys Gly Asp Leu Ser
1               5                   10                  15

Cys Pro Asp Ala Asp Pro Glu Gly Arg Phe Lys Ala Arg Gln Ala Asn
            20                  25                  30

Cys

```
<210> SEQ ID NO 191
<211> LENGTH: 33
<212> TYPE: PRT
<213> ORGANISM: Homo sapiens

<400> SEQUENCE: 191

Cys Val His Tyr Glu Gln Pro Thr Ile Gln Ile Glu Leu Arg Gln Asn
1               5                   10                  15

Cys His His Ile Leu Ile Asp Leu Arg His Arg Pro Thr Ala Gly Ala
            20                  25                  30

Cys

<210> SEQ ID NO 192
<211> LENGTH: 30
<212> TYPE: PRT
<213> ORGANISM: Homo sapiens

<400> SEQUENCE: 192

Val Gly Val Arg Arg Thr Asp Lys Gly Asp Leu Ser Leu Arg Cys Asp
1               5                   10                  15

Glu Leu Val Arg Thr His His Ile Leu Ile Asp Leu Arg His
            20                  25                  30

<210> SEQ ID NO 193
<211> LENGTH: 33
<212> TYPE: PRT
<213> ORGANISM: Homo sapiens

<400> SEQUENCE: 193

Cys Ala Gly Ala Phe Asn His Ser Asp Leu Asp Ala Glu Leu Arg Arg
1               5                   10                  15

Cys His His Ile Leu Ile Asp Leu Arg His Arg Pro Thr Ala Gly Ala
            20                  25                  30

Cys

<210> SEQ ID NO 194
<211> LENGTH: 33
<212> TYPE: PRT
<213> ORGANISM: Homo sapiens

<400> SEQUENCE: 194

Cys Ser Val Gly Val Arg Arg Thr Asp Lys Gly Asp Leu Ser Leu Arg
1               5                   10                  15

Cys Pro Asp Ala Asp Pro Glu Gly Arg Phe Lys Ala Arg Gln Ala Asn
            20                  25                  30

Cys

<210> SEQ ID NO 195
<211> LENGTH: 33
<212> TYPE: PRT
<213> ORGANISM: Homo sapiens

<400> SEQUENCE: 195

Cys Val Arg Pro Ser Glu His Ala Leu Val Asp Asn Asp Gly Leu Tyr
1               5                   10                  15

Cys Ser Val Gly Val Arg Arg Thr Asp Lys Gly Asp Leu Ser Leu Arg
            20                  25                  30

Cys
```

```
<210> SEQ ID NO 196
<211> LENGTH: 33
<212> TYPE: PRT
<213> ORGANISM: Homo sapiens

<400> SEQUENCE: 196

Cys Asp Ala Glu Leu Arg Arg Leu Phe Arg Glu Arg Tyr Arg Leu His
1               5                   10                  15

Cys His Ser Asp Leu Asp Ala Glu Leu Arg Arg Leu Phe Arg Glu Arg
            20                  25                  30

Cys

<210> SEQ ID NO 197
<211> LENGTH: 33
<212> TYPE: PRT
<213> ORGANISM: Homo sapiens

<400> SEQUENCE: 197

Cys Ser Val Gly Val Arg Arg Thr Asp Lys Gly Asp Leu Ser Leu Arg
1               5                   10                  15

Cys Asn Asp Gly Leu Tyr Asp Pro Asp Ala Asp Pro Glu Gly Arg Phe
            20                  25                  30

Cys

<210> SEQ ID NO 198
<211> LENGTH: 33
<212> TYPE: PRT
<213> ORGANISM: Homo sapiens

<400> SEQUENCE: 198

Cys Val Asn Ser Val Gly Val Arg Arg Thr Asp Lys Gly Asp Leu Ser
1               5                   10                  15

Cys Gly Leu Tyr Asp Pro Asp Ala Asp Pro Glu Gly Arg Phe Lys Ala
            20                  25                  30

Cys

<210> SEQ ID NO 199
<211> LENGTH: 33
<212> TYPE: PRT
<213> ORGANISM: Homo sapiens

<400> SEQUENCE: 199

Cys Asp Leu Asp Ala Glu Leu Arg Arg Leu Phe Arg Glu Arg Tyr Arg
1               5                   10                  15

Cys His Ser Asp Leu Asp Ala Glu Leu Arg Arg Leu Phe Arg Glu Arg
            20                  25                  30

Cys

<210> SEQ ID NO 200
<211> LENGTH: 33
<212> TYPE: PRT
<213> ORGANISM: Homo sapiens

<400> SEQUENCE: 200

Cys Asp Glu Leu Val Arg Thr His His Ile Leu Ile Asp Leu Arg His
1               5                   10                  15

Cys His His Ile Leu Ile Asp Leu Arg His Arg Pro Thr Ala Gly Ala
            20                  25                  30

Cys
```

<210> SEQ ID NO 201
<211> LENGTH: 33
<212> TYPE: PRT
<213> ORGANISM: Homo sapiens

<400> SEQUENCE: 201

Cys Ala Gly Ala Phe Asn His Ser Asp Leu Asp Ala Glu Leu Arg Arg
1               5                   10                  15

Cys Asp Leu Asp Ala Glu Leu Arg Arg Leu Phe Arg Glu Arg Tyr Arg
                20                  25                  30

Cys

<210> SEQ ID NO 202
<211> LENGTH: 33
<212> TYPE: PRT
<213> ORGANISM: Homo sapiens

<400> SEQUENCE: 202

Cys Asp Ala Glu Leu Arg Arg Leu Phe Arg Glu Arg Tyr Arg Leu His
1               5                   10                  15

Cys Asp Glu Leu Val Arg Thr His His Ile Leu Ile Asp Leu Arg His
                20                  25                  30

Cys

<210> SEQ ID NO 203
<211> LENGTH: 33
<212> TYPE: PRT
<213> ORGANISM: Homo sapiens

<400> SEQUENCE: 203

Cys Val His Tyr Glu Gln Pro Thr Ile Gln Ile Glu Leu Arg Gln Asn
1               5                   10                  15

Cys Asp Leu Asp Ala Glu Leu Arg Arg Leu Phe Arg Glu Arg Tyr Arg
                20                  25                  30

Cys

<210> SEQ ID NO 204
<211> LENGTH: 33
<212> TYPE: PRT
<213> ORGANISM: Homo sapiens

<400> SEQUENCE: 204

Cys His His Ile Leu Ile Asp Leu Arg His Arg Pro Thr Ala Gly Ala
1               5                   10                  15

Cys Val His Tyr Glu Gln Pro Thr Ile Gln Ile Glu Leu Arg Gln Asn
                20                  25                  30

Cys

<210> SEQ ID NO 205
<211> LENGTH: 33
<212> TYPE: PRT
<213> ORGANISM: Homo sapiens

<400> SEQUENCE: 205

Cys Gly Val Arg Arg Thr Asp Lys Gly Asp Leu Ser Leu Arg Ala Asp
1               5                   10                  15

Cys Gly Val Arg Arg Thr Asp Lys Gly Asp Leu Ser Leu Arg Ala Asp
                20                  25                  30

Cys

```
<210> SEQ ID NO 206
<211> LENGTH: 33
<212> TYPE: PRT
<213> ORGANISM: Homo sapiens

<400> SEQUENCE: 206

Cys Gly Leu Asp Leu Arg Val Arg Gly Glu Pro Leu Gln Val Glu Arg
1               5                   10                  15

Cys His His Ile Leu Ile Asp Leu Arg His Arg Pro Thr Ala Gly Ala
            20                  25                  30

Cys

<210> SEQ ID NO 207
<211> LENGTH: 33
<212> TYPE: PRT
<213> ORGANISM: Homo sapiens

<400> SEQUENCE: 207

Cys Asp Leu Asp Ala Glu Leu Arg Arg Leu Phe Arg Glu Arg Tyr Arg
1               5                   10                  15

Cys Asp Glu Leu Val Arg Thr His His Ile Leu Ile Asp Leu Arg His
            20                  25                  30

Cys
```